US012473321B2

(12) United States Patent
Butler et al.

(10) Patent No.: US 12,473,321 B2
(45) Date of Patent: Nov. 18, 2025

(54) COMPOSITIONS AND METHODS FOR PHOSPHORAMIDITE AND OLIGONUCLEOTIDE SYNTHESIS

(71) Applicant: WAVE LIFE SCIENCES LTD., Singapore (SG)

(72) Inventors: David Charles Donnell Butler, Medford, MA (US); Pachamuthu Kandasamy, Lexington, MA (US); Subramanian Marappan, Acton, MA (US); Ik-Hyeon Paik, Needham, MA (US); Jayakanthan Kumarasamy, Arlington, MA (US); Gopal Reddy Bommineni, Belmont, MA (US)

(73) Assignee: WAVE LIFE SCIENCES LTD., Singapore (SG)

( * ) Notice: Subject to any disclaimer, the term of this patent is extended or adjusted under 35 U.S.C. 154(b) by 0 days.

(21) Appl. No.: 18/522,146

(22) Filed: Nov. 28, 2023

(65) Prior Publication Data

US 2024/0368207 A1 Nov. 7, 2024

Related U.S. Application Data

(62) Division of application No. 16/463,328, filed as application No. PCT/US2017/062996 on Nov. 22, 2017, now Pat. No. 11,873,316.

(60) Provisional application No. 62/426,079, filed on Nov. 23, 2016.

(51) Int. Cl.

*C07H 1/06* (2006.01)
*C07H 19/10* (2006.01)
*C07H 19/207* (2006.01)
*C07H 21/00* (2006.01)

(52) U.S. Cl.

CPC ............... *C07H 1/06* (2013.01); *C07H 19/10* (2013.01); *C07H 19/207* (2013.01); *C07H 21/00* (2013.01)

(58) Field of Classification Search

None

See application file for complete search history.

(56) References Cited

U.S. PATENT DOCUMENTS

| | | | |
|---|---|---|---|
| 4,725,677 | A | 2/1988 | Koster et al. |
| 5,846,466 | A | 12/1998 | Abe et al. |
| 5,869,696 | A | 2/1999 | Reddy et al. |
| 6,133,438 | A | 10/2000 | Cook et al. |
| 6,867,294 | B1 | 3/2005 | Sanghvi et al. |
| 7,030,230 | B2 | 4/2006 | Ross et al. |
| 7,057,062 | B2 | 6/2006 | Song et al. |
| 7,101,993 | B1 | 9/2006 | Cook et al. |
| 7,897,758 | B2 | 3/2011 | Wolter et al. |
| 8,431,693 | B2 | 4/2013 | Manoharan et al. |
| 8,470,987 | B2 | 6/2013 | Wada et al. |
| 8,822,671 | B2 | 9/2014 | Shimizu et al. |
| 8,859,755 | B2 | 10/2014 | Wada et al. |
| 9,394,333 | B2 | 7/2016 | Wada et al. |
| 9,598,458 | B2 | 3/2017 | Shimizu et al. |
| 9,605,019 | B2 | 3/2017 | Verdine et al. |
| 9,617,547 | B2 | 4/2017 | Gemba |
| 9,695,211 | B2 | 7/2017 | Wada et al. |
| 9,744,183 | B2 | 8/2017 | Verdine et al. |
| 9,982,257 | B2 | 5/2018 | Butler et al. |
| 10,144,933 | B2 | 12/2018 | Gemba et al. |
| 10,149,905 | B2 | 12/2018 | Gemba et al. |
| 10,160,969 | B2 | 12/2018 | Meena et al. |
| 10,167,309 | B2 | 1/2019 | Shimizu et al. |
| 10,280,192 | B2 | 5/2019 | Verdine et al. |
| 10,307,434 | B2 | 6/2019 | Verdine et al. |
| 10,322,173 | B2 | 6/2019 | Gemba et al. |
| 10,329,318 | B2 | 6/2019 | Wada et al. |
| 10,428,019 | B2 | 10/2019 | Wada et al. |
| 10,450,568 | B2 | 10/2019 | Butler et al. |
| 10,479,995 | B2 | 11/2019 | Vargeese et al. |
| 10,590,413 | B2 | 3/2020 | Butler et al. |
| 10,696,711 | B2 | 6/2020 | Shimizu et al. |
| 10,724,035 | B2 | 7/2020 | Vargeese et al. |
| 10,815,482 | B2 | 10/2020 | Meena et al. |
| 11,013,757 | B2 | 5/2021 | Zhang et al. |
| 11,136,346 | B2 | 10/2021 | Shimizu et al. |
| 11,407,775 | B2 | 8/2022 | Butler et al. |
| 11,596,646 | B2 | 3/2023 | Zhang et al. |
| 11,597,927 | B2 | 3/2023 | Vargeese et al. |
| 11,603,532 | B2 | 3/2023 | Vargeese et al. |
| 11,608,355 | B2 | 3/2023 | Bowman et al. |
| 11,634,710 | B2 | 4/2023 | Frank-Kamenetsky et al. |
| 11,643,657 | B2 | 5/2023 | Butler et al. |

(Continued)

FOREIGN PATENT DOCUMENTS

| | | |
|---|---|---|
| CN | 102675386 A | 9/2012 |
| CN | 102516337 B | 7/2014 |

(Continued)

OTHER PUBLICATIONS

U.S. Appl. No. 18/316,932, filed May 12, 2023, Butler et al.

(Continued)

*Primary Examiner* — Layla D Berry

(74) *Attorney, Agent, or Firm* — Choate, Hall & Stewart LLP; Xiaodong Li; Yuxiang Chen

(57) ABSTRACT

The present disclosure, among other things, provides technologies for oligonucleotide synthesis. In some embodiments, the present disclosure provides phosphoramidites and methods for synthesis thereof. In some embodiments, provided methods provides higher yields and/or purities. In some embodiments, provided methods remove byproducts without contact with an aqueous solution.

10 Claims, No Drawings

Specification includes a Sequence Listing.

(56) References Cited

U.S. PATENT DOCUMENTS

| | | | |
|---|---|---|---|
| 11,718,638 | B2 | 8/2023 | Butler et al. |
| 11,739,325 | B2 | 8/2023 | Vargeese et al. |
| 11,873,316 | B2 | 1/2024 | Butler et al. |
| 2003/0017451 | A1 | 1/2003 | Wang et al. |
| 2003/0032794 | A1 | 2/2003 | Koch et al. |
| 2003/0232978 | A1 | 12/2003 | Seeberger et al. |
| 2007/0196852 | A1 | 8/2007 | Heindl et al. |
| 2011/0178284 | A1 | 7/2011 | Wada et al. |
| 2011/0294124 | A1 | 12/2011 | Wada et al. |
| 2013/0178612 | A1 | 7/2013 | Wada et al. |
| 2013/0236536 | A1 | 9/2013 | Phiasivongsa et al. |
| 2015/0166999 | A1 | 6/2015 | Gemba |
| 2015/0179540 | A1 | 6/2015 | Yasui |
| 2016/0331835 | A1 | 11/2016 | Gemba et al. |
| 2016/0331836 | A1 | 11/2016 | Gemba et al. |
| 2016/0333349 | A1 | 11/2016 | Gemba et al. |
| 2016/0347784 | A1 | 12/2016 | Verdine et al. |
| 2017/0029445 | A1 | 2/2017 | Shimizu et al. |
| 2017/0029457 | A1 | 2/2017 | Verdine et al. |
| 2017/0037399 | A1 | 2/2017 | Meena et al. |
| 2017/0275621 | A1 | 9/2017 | Butler et al. |
| 2018/0111958 | A1 | 4/2018 | Wada et al. |
| 2018/0216107 | A1 | 8/2018 | Frank-Kamenetsky et al. |
| 2018/0216108 | A1 | 8/2018 | Vargeese et al. |
| 2018/0222936 | A1 | 8/2018 | Verdine et al. |
| 2019/0127733 | A1 | 5/2019 | Butler et al. |
| 2019/0249173 | A1 | 8/2019 | Vargeese et al. |
| 2019/0264267 | A1 | 8/2019 | Yang et al. |
| 2019/0390197 | A1 | 12/2019 | Butler et al. |
| 2020/0080083 | A1 | 3/2020 | Vargeese et al. |
| 2020/0362337 | A1 | 11/2020 | Dodart et al. |
| 2021/0115444 | A1 | 4/2021 | Meena et al. |
| 2021/0198305 | A1 | 7/2021 | Vargeese et al. |
| 2021/0254062 | A1 | 8/2021 | Zhang et al. |
| 2022/0098585 | A1 | 3/2022 | Brown et al. |
| 2022/0127301 | A1 | 4/2022 | Shimizu et al. |
| 2022/0145300 | A1 | 5/2022 | Liu et al. |
| 2022/0162598 | A1 | 5/2022 | Vargeese et al. |
| 2022/0186217 | A1 | 6/2022 | Zhang et al. |
| 2022/0195429 | A1 | 6/2022 | Vargeese et al. |
| 2022/0306573 | A1 | 9/2022 | Zhang et al. |
| 2022/0307019 | A1 | 9/2022 | Yokota et al. |
| 2022/0401467 | A1 | 12/2022 | Zhang et al. |
| 2023/0089442 | A1 | 3/2023 | Kandasamy et al. |
| 2023/0136645 | A1 | 5/2023 | Butler et al. |
| 2023/0145795 | A1 | 5/2023 | Byrne et al. |
| 2023/0203087 | A1 | 6/2023 | Kandasamy et al. |
| 2023/0220384 | A1 | 7/2023 | Monian et al. |
| 2023/0295617 | A1 | 9/2023 | Vargeese et al. |
| 2023/0295619 | A1 | 9/2023 | Maguire et al. |
| 2023/0329201 | A1 | 10/2023 | Yang et al. |
| 2023/0348524 | A1 | 11/2023 | Bowman et al. |
| 2023/0392137 | A1 | 12/2023 | Monian et al. |
| 2024/0026358 | A1 | 1/2024 | Monian et al. |
| 2024/0109931 | A1 | 4/2024 | Vargeese et al. |
| 2024/0117347 | A1 | 4/2024 | Butler et al. |
| 2024/0132894 | A1 | 4/2024 | Vargeese et al. |
| 2024/0150756 | A1 | 5/2024 | Frank-Kamenetsky et al. |
| 2024/0174710 | A1 | 5/2024 | Butler et al. |
| 2024/0175016 | A1 | 5/2024 | Liu et al. |
| 2024/0175018 | A1 | 5/2024 | Vargeese et al. |
| 2024/0229026 | A1 | 7/2024 | Butler et al. |
| 2025/0051778 | A1 | 2/2025 | Byrne et al. |
| 2025/0066775 | A1 | 2/2025 | Vargeese et al. |

FOREIGN PATENT DOCUMENTS

| | | | |
|---|---|---|---|
| CN | 104684893 | A | 6/2015 |
| CN | 103819501 | B | 11/2015 |
| CN | 108779132 | A | 11/2018 |
| CN | 108779139 | A | 11/2018 |
| JP | 2003-238586 | A | 8/2003 |
| JP | 2005-89441 | A | 4/2005 |
| JP | 2006-292394 | A | 10/2006 |
| JP | 2011-121881 | A | 6/2011 |
| JP | 2011-184318 | A | 9/2011 |
| JP | 2015-523316 | A | 8/2015 |
| JP | 2015-528002 | A | 9/2015 |
| WO | WO-97/09443 | A1 | 3/1987 |
| WO | WO-89/09780 | A1 | 10/1989 |
| WO | WO-1995/15333 | A1 | 6/1995 |
| WO | WO-1995/31434 | A1 | 11/1995 |
| WO | WO-1997/40458 | A2 | 10/1997 |
| WO | WO-98/016535 | A1 | 4/1998 |
| WO | WO-2004/055037 | A2 | 7/2004 |
| WO | WO-2005/014609 | A2 | 2/2005 |
| WO | WO-2005/023828 | A1 | 3/2005 |
| WO | WO-2005/028494 | A1 | 3/2005 |
| WO | WO-2005/070859 | A1 | 8/2005 |
| WO | WO-2005/085272 | A1 | 9/2005 |
| WO | WO-2005/092909 | A1 | 10/2005 |
| WO | WO-2005/097817 | A2 | 10/2005 |
| WO | WO-2009/143369 | A2 | 11/2009 |
| WO | WO-2010/064146 | A2 | 6/2010 |
| WO | WO-2011/005761 | A1 | 1/2011 |
| WO | WO-2011/034072 | A1 | 3/2011 |
| WO | WO-2011/108682 | A1 | 9/2011 |
| WO | WO-2012/039448 | A1 | 3/2012 |
| WO | WO-2012/073857 | A1 | 6/2012 |
| WO | WO-2013/012758 | A1 | 1/2013 |
| WO | WO-2014/010250 | A1 | 1/2014 |
| WO | WO-2014/010718 | A1 | 1/2014 |
| WO | WO-2014/012081 | A2 | 1/2014 |
| WO | WO-2015/107425 | A2 | 7/2015 |
| WO | WO-2015/108046 | A1 | 7/2015 |
| WO | WO-2015/108047 | A1 | 7/2015 |
| WO | WO-2015/108048 | A1 | 7/2015 |
| WO | WO-2015/168461 | A2 | 11/2015 |
| WO | WO-2016/079181 | A1 | 5/2016 |
| WO | WO-2017/015555 | A1 | 1/2017 |
| WO | WO-2017/015575 | A1 | 1/2017 |
| WO | WO-2017/062862 | A2 | 4/2017 |
| WO | WO-2017/157672 | A1 | 9/2017 |
| WO | WO-2017/160741 | A1 | 9/2017 |
| WO | WO-2017/192664 | A1 | 11/2017 |
| WO | WO-2017/192679 | A1 | 11/2017 |
| WO | WO-2017/210647 | A1 | 12/2017 |
| WO | WO-2018/022473 | A1 | 2/2018 |
| WO | WO-2018/067973 | A1 | 4/2018 |
| WO | WO-2018/098264 | A1 | 5/2018 |
| WO | WO-2018/223056 | A1 | 12/2018 |
| WO | WO-2018/223073 | A1 | 12/2018 |
| WO | WO-2018/223081 | A1 | 12/2018 |
| WO | WO-2018/237194 | A1 | 12/2018 |
| WO | WO-2019/002237 | A1 | 1/2019 |
| WO | WO-2019/032607 | A1 | 2/2019 |
| WO | WO-2019/032612 | A1 | 2/2019 |
| WO | WO-2019/055951 | A1 | 3/2019 |
| WO | WO-2019/075357 | A1 | 4/2019 |
| WO | WO-2019/200185 | A1 | 10/2019 |
| WO | WO-2019/217784 | A1 | 11/2019 |
| WO | WO-2020/118246 | A1 | 6/2020 |
| WO | WO-2020/160336 | A1 | 8/2020 |
| WO | WO-2020/191252 | A1 | 9/2020 |
| WO | WO-2020/196662 | A1 | 10/2020 |
| WO | WO-2020/219981 | A2 | 10/2020 |
| WO | WO-2020/219983 | A2 | 10/2020 |
| WO | WO-2020/227691 | A2 | 11/2020 |
| WO | WO-2021/071788 | A2 | 4/2021 |
| WO | WO-2021/071858 | A1 | 4/2021 |
| WO | WO-2021/178237 | A2 | 9/2021 |
| WO | WO-2021/234459 | A2 | 11/2021 |
| WO | WO-2021/237223 | A1 | 11/2021 |
| WO | WO-2022/046667 | A1 | 3/2022 |
| WO | WO-2022/046723 | A1 | 3/2022 |
| WO | WO-2022/099159 | A1 | 5/2022 |
| WO | WO-2024/035946 | A1 | 2/2023 |
| WO | WO-2023/049475 | A1 | 3/2023 |
| WO | WO-2023/049477 | A2 | 3/2023 |
| WO | WO-2023/075766 | A1 | 5/2023 |
| WO | WO-2023/076352 | A2 | 5/2023 |
| WO | WO-2023/154528 | A1 | 8/2023 |
| WO | WO-2023/168014 | A2 | 9/2023 |

(56) References Cited

FOREIGN PATENT DOCUMENTS

| | | | |
|---|---|---|---|
| WO | WO-2023/201095 | A2 | 10/2023 |
| WO | WO-2023/220440 | A1 | 11/2023 |
| WO | WO-2025/030155 | A1 | 2/2025 |

OTHER PUBLICATIONS

U.S. Appl. No. 18/613,034, filed Mar. 21, 2024, Vargeese et al.
U.S. Appl. No. 18/695,346, filed Mar. 25, 2024, Monian et al.
U.S. Appl. No. 18/695,348, filed Mar. 25, 2024, Acker et al.
U.S. Appl. No. 18/704,629, filed Apr. 25, 2024, Byrne et al.
Almer, et al. A New Approach to Stereospecific Synthesis of P-chiral Phosphorothioates. Preparation of Diastereomeric Dithymidyl-(3'-5') Phosphorothioates, Chem. Commun., (3): 290-1 (2004).
Arai, K. et al., Synthesis and properties of novel 2'-O-alkoxymethyl-modified nucleic acids, Bioorganic & Medicinal Chemistry Letters, 21(21): 6285-6287 (2011).
Bobkov, G.V. et al., Phosphoramidite building blocks for efficient incorporation of 2'-O-aminoethoxy(and propoxy)methyl nucleosides into oligonucleotides, Tetrahedron, 64: 6238-6251 (2008).
Bradley, D. et al., Drying of Organic Solvents: Quantitative Evaluation of the Efficiency of Several Desiccants, J. Org. Chem., 75:8351-8354 (2010).
Chem Station, I tried collecting small silica gel material, blog, 15 pages, posted May 16, 2012, <https://www.chem-station.com/blog/2012/05/post-386.html>.
Cramer, H., Different Approaches to Oligonucleotide Synthesis, WAVE Life Sciences, Presented at the 7th Annual Oligo Networking Event, Roche Basel, Switzerland, 31 pages (Mar. 26, 2019).
Current Protocols in Nucleic Acid Chemistry, Edited by Beaucage, S.L. et al., Chapter 2: Protection of Nucleosides for Oligonucleotide Synthesis, 2.0.1.-2.16.31 (2012).
Deleavey, G.F. and Damha, M.J., Designing chemically modified oligonucleotides for targeted gene silencing. Chem. Biol., 19: 937-54 (2012).
Ellington, A. and Pollard, J.D., Introduction to the synthesis and purification of oligonucleotides, Curr. Protoc. Nucleic Acid Chem., Appendix 3:Appendix 3C, (2001).
Giebel FilTec, Fundamentals for the regeneration of silica gel, Giebel Adsorber, 5 pages (Jan. 1, 2009), <https://blog.giebel-adsorber.de/wp-content/uploads/2020/02/Silicagel_Fundamentals-Regeneration-Of-Silicagel_EN.pdf>.
Hargreaves, J.S. et al., The Degradation of dG Phosphoramidites in Solution, Nucleosides, Nucleotides and Nucleic Acids, 24(10): 691-707 (2015).
International Search Report for PCT/US2017/022135, 3 pages (Jun. 6, 2017).
International Search Report for PCT/US2017/062996, 4 pages (mailed Mar. 9, 2018).
Iwamoto et al., Stereocontrolled Synthesis of H-phosphonate DNA, Nucleic Acids Symposium Series, (50): 159-60 (2006).
Iwamoto, N. et al., Control of phosphorothioate stereochemistry substantially increases the efficacy of antisense oligonucleotides, Nature Biotechnology, 1-7 pages (2017). All Supplemental Data, 8-53 pages (2017).
Iwamoto, N. et al., Optimization of Therapeutic Phosphorothioate Oligonucleotides by P-Chirality Control, WAVE Life Sciences, PSJ Congress: The Pharmaceutical Society of Japan, (Mar. 25, 2015-Mar. 28, 2016).
Iwamoto, N. et al., Stereocontrolled solid-phase synthesis of oligonucleoside H-phosphonates by an oxazaphospholidine approach, Angewandte Chemie International Edition, 48(3):496-499 (2009).
Koshkin, A.A. et al., LNA (Locked Nucleic Acids): Synthesis of the Adenine, Cytosine, Guanine, 5-Methylcytosine, Thymine and Uracil Bicyclonucleoside Monomers, Oligomerisation, and Unprecedented Nucleic Acid Recognition, Tetrahedron 54: 3607-3630 (1998).
Krotz, A.H. et al., Phosphorothioate Oligonucleotides with Low Phosphate Diester Content: Greater than 99.9% Sulfurization Efficiency with "Aged" Solutions of Phenylacetyl Disulfide (PADS), Organic Process Research & Development, 8: 852-858 (2004).
Krotz, A.H. et al., Solution Stability and Degradation Pathway of Deoxyriboncleoside Phosphoramidites in Acetonitrile, Nucleosides, Nucleotides and Nucleic Acids, 23(5): 767-775 (2004).
Leviten, M., Wave's Purity Progress, Biocentury, 1-6 (Sep. 28, 2017).
Meena, Control of Human RNase H Mediated Cleavage by Stereopure Phosphorothioate Oligonucleotides, WAVE Life Sciences, TIDES Meeting, 23 pages (May 3-6, 2015).
Meena, Development of Allele Specific Antisense Oligonucleotides, WAVE Life Sciences, ACS Central Regional Meeting (CERM), Covington, KY (May 19, 2016).
Meena, Development of Allele Specific Antisense Oligonucleotides, WAVE Life Sciences, TIDES Meeting (May 11, 2016).
Meena, et al., Discovery and Early Clinical Development of the First Allele-Specific Stereopure ASO Drug Candidate with Disease—Modifying Potential for the Treatment of Huntington's Disease, WAVE Life Sciences, Poster, 1 page (2016).
Meena, et al., Therapeutic Implications of Controlling P-Chirality in Phosphorothioate Oligonucleotides, TIDES Poster (May 12-15, 2014).
Nawrot et al., DNA Oligonucleotides Containing Stereodefined Phosphorothioate Linkages in Selected Positions, Current Protocols in Nucleic Acid Chemistry, UNIT 4.34: 4.34.1-4.34.15 (2009).
Nukaga, Y. et al., Stereocontrolled Solid-Phase Synthesis of Phosphate/Phosphorothioate (PO/PS) Chimeric Oligodeoxyribonucleotides on an Automated Synthesizer Using an Oxazaphospholidine-Phosphoramidite Method, J. Org. Chem., A-J, 10 pages (Publication Date (Web): Mar. 3, 2016).
Nukaga, Y. et al., Stereocontrolled Solid-Phase Synthesis of Phosphorothioate Oligoribonucleotides Using 2'-O-(2-Cyanoethoxymethyl)-nucleoside 3'-O-Oxazaphospholiidine Monomers, Journal of Organic Chemistry, 77(18):7913-7922 (2012).
Oka, N. and Wada, T., Stereocontrolled synthesis of oligonucleotide analogs containing chiral internucleotidic phosphorus atoms, Chemical Society Reviews, 40(12):5829-5843 (2011).
Oka, N. et al., Solid-Phase Synthesis of Stereoregular Oligodeoxyribonucleoside Phosphorothioates Using Bicyclic Oxazaphospholidine Derivatives as Monomer Units, Journal of the American Chemical Society, 130(47):16031-16037 (2008).
Oka, N. et al., Solid-Phase Synthesis of Stereoregular Oligodeoxyribonucleoside Phosphorothioates Using Bicyclic Oxazaphospholidine Derivatives as Monomer Units, Journal of the American Chemical Society, 130(47):16031-16037 (2008). Supporting Information, 57 pages.
Pubchem, Substance Record for SID 174316404, Available Date: Mar. 31, 2014 (retrieved on Feb. 26, 2018). Retrieved from the Internet: <URL: https://pubchem.ncbi.nlm.nih.gov/substance/174316404>.
Pubchem, Substance Record for SID 174316700, Available Date: Mar. 31, 2014 (retrieved on Feb. 26, 2018). Retrieved from the Internet: <URL: https://pubchem.ncbi.nlm.nih.gov/substance/174316700>.
Pubchem, Substance Record for SID 174316999, Available Date: Mar. 31, 2014 {retrieved on Feb. 26, 2018). Retrieved from the Internet: <URL: https://pubchem.ncbi.nlm.nih.gov/substance/174316999>.
Schultz, R.G. and Gryaznov, S.M., Oligo-24-fluoro-24-deoxynucleotide N3'->P5' phosphoramidates: synthesis and properties, Nucleic Acids Res., 24(15): 2966-2973 (1996).
Silicycle, How can the cols. be cleaned or regenerated, website, 2 pages (Jun. 14, 2021), <https://www.silicycle.com/faq/hplc/how-can-the-columns-be-cleaned-or-regenerated>.
Singh, S.K. et al., Synthesis of Novel Bicyclo[2.2.1] Ribonucleosides: 2'-Amino- and 2'-Thio-LNA Monomeric Nucleosides, J. Org. Chem., 63: 6078-6079 (1998).
Sorensen, M.D., Functionalized LNA (locked nucleic acid): high-affinity hybridization of oligonucleotides containing N-acylated and N-alkylated 2'-amino-LNA monomers, Chem. Comm., 2130-2131 (2003).
Stec, W.J. et al., Deoxyribonucleoside 3'-O-(2-Thio- and 2-Oxo-"spiro"-4,4-pentamethylene-1,3,2-oxathiaphospholane)s: Monomers for Stereocontrolled Synthesis of Oligo(deoxyribonucleoside

(56) References Cited

OTHER PUBLICATIONS phosphorothioate)s and Chimeric PS/PO Oligonucleotides, J. Am. Chem. Soc., 120(29): 7156-7167 (1998).
Stevens, W.C. et al., General methods for flash chromatography using disposable columns, Molecular Diversity, Kluwer Academic Publishers, DO, 13(2): 247-252 (2009).
Swayze, E.E. and Bhat, B., The medicinal chemistry of oligonucleotides, Crooke, S.T. (ed) Antisense Drug Technology: Principles, Strategies, and Applications, CRC Press, Boca Raton, FL: 143-82 (2007).
Tian, J. et al., Advancing high-throughput gene synthesis technology, Mol. BioSyst., 5: 714-722 (2009).
U.S. Food and Drug Administration, Development of New Stereoisomeric Drugs, 8 pages (May 1, 1992). URL: http://www.fda.gov/Drugs/GuidanceComplianceRegulatoryInformation/Guidances/ucm122883.htm [Retrieved Jun. 15, 2016].
Verhagen et al., A Conformationally locked Aminomethyl C-Glycoside and Studies on Its N-Pyren-1-ylcarbonyl Derivative Inserted into Oligodeoxynucleotides, European Journal of Organic Chemistry, 2538-2548 (2006).
Verma, S. and Eckstein, F., Modified oligonucleotides: synthesis and strategy for users, Annu. Rev. Biochem., 67:99-134 (1998).
Wan et al., Synthesis of Second Generation Antisense Oligonucleotides Containing Chiral Phosphorothioate Linkages and Evaluation of their Biophysical Properties and Biological Activity, 10th Annual Meeting of the Oligonucleotide Therapeutics Society, abstract received by Applicant Oct. 7, 2014, poster setup prior to presentation (first known to Applicant late Oct. 12, 2014, PST), poster presentation Oct. 13, 2014.
Wan, Q. et al., Thermal pretreatment of silica composite filler materials, Journal of Thermal Analysis and Calorimetry, Kluwer Academic Publishers, Dordrecht, NL, 99(1): 237-243 (2009).
Wan, W. B. et al., Synthesis, biophysical properties and biological activity of second generation antisense oligonucleotides containing chiral phosphorothioate linkages, Nucleic Acids Research, 42(22):13456-13468 (2014).
Wan, W.B. and Seth, P.P., The Medicinal Chemistry of Therapeutic Oligonucleotides, J. Med. Chem., 59: 9645-9667 (2016).
Wan, W.B. et al., Synthesis, biophysical properties and biological activity of second generation antisense oligonucleotides containing chiral phosphorothioate linkages, Nucleic Acid Research, 42: 13456-13468 (2014). Supplementary Information, 14 pages.
Wilk, A. et al., Deoxyribonucleoside Cyclic N-Acylphosphoramidites as a New Class of Monomers for the Stereocontrolled Synthesis of Oligothymidylyl- and Oligodeoxycytidylyl-Phosphorothioates, Journal of the American Chemical Society, 122(10): 2149-2156 (2000).
Written Opinion for PCT/US2017/022135, 11 pages (Jun. 6, 2017).
Written Opinion for PCT/US2017/062996, 9 pages (mailed Mar. 9, 2018).
Yu, D. et al., Stereo-enriched phosphorothioate oligonucleotides: synthesis, biophysical and biological properties, Bioorg. Medic. Chem., 8(1):275-284 (2000).
Zhuravlev, L. T. et al., Structurally bound water and surface characterization of amorphous silica, Pure & Applied Chemistry, 61(11): 1969-1976 (1989).
U.S. Appl. No. 18/836,993, filed Aug. 8, 2024, Kandasamy et al.
U.S. Appl. No. 18/843,171, filed Aug. 30, 2024, Hu et al.
U.S. Appl. No. 18/856,553, filed Oct. 11, 2024, Lu et al.
U.S. Appl. No. 18/864,860, filed Nov. 11, 2024, Shivalila et al.
U.S. Appl. No. 18/864,863, filed Nov. 11, 2024, Liu et al.
U.S. Appl. No. 18/942,334, filed Nov. 8, 2024, Yang et al.
U.S. Appl. No. 18/953,020, filed Nov. 19, 2024, Meena et al.
U.S. Appl. No. 19/008,522, filed Jan. 2, 2025, Vargeese et al.
U.S. Appl. No. 19/085,460, filed Mar. 20, 2025, Bowman et al.
U.S. Appl. No. 19/102,669, filed Feb. 10, 2025, Lake et al.
Anonymous, Nucleoside phosphoramidite, Wikipedia, accessed Feb. 6, 2011. <https://en.wikipedia.org/wiki/Nucleoside_phosphoramidite>.
Li, N-S and Piccirilli, J. A., Synthesis of the Phosphoramidite Derivatives of 2'-Deoxy-2'-C-α-methylcytidine and 2'-Deoxy-2'-C-α-hydroxymethylcytidine: Analogues for Chemical Dissection of RNA's 2'-Hydroxyl Group, J. Org. Chem., 69:4751-4759 (2004).
Sandahl, A. F. et al., On-demand synthesis of phosphoramidites, Nat. Comm., 12(2760):1-7 (2021).

SEQUENCE LISTING

```
Sequence total quantity: 16
SEQ ID NO: 1            moltype = RNA  length = 20
FEATURE                 Location/Qualifiers
misc_feature            1..20
                        note = Description of Artificial Sequence: Synthetic
                         oligonucleotide
source                  1..20
                        mol_type = other RNA
                        organism = synthetic construct
SEQUENCE: 1
ggcacaaggg cacagacttc                                                20

SEQ ID NO: 2            moltype = DNA  length = 20
FEATURE                 Location/Qualifiers
misc_feature            1..20
                        note = Description of Combined DNA/RNA Molecule: Synthetic
                         oligonucleotide
```

-continued

```
modified_base          4
                       mod_base = OTHER
                       note = uracil
source                 1..20
                       mol_type = other DNA
                       organism = synthetic construct
SEQUENCE: 2
gggtcctccc cacagaggga                                             20

SEQ ID NO: 3           moltype = DNA  length = 20
FEATURE                Location/Qualifiers
misc_feature           1..20
                       note = Description of Combined DNA/RNA Molecule: Synthetic
                        oligonucleotide
modified_base          2
                       mod_base = OTHER
                       note = uracil
source                 1..20
                       mol_type = other DNA
                       organism = synthetic construct
SEQUENCE: 3
gtgcacacag tagatgaggg                                             20

SEQ ID NO: 4           moltype = RNA  length = 20
FEATURE                Location/Qualifiers
misc_feature           1..20
                       note = Description of Artificial Sequence: Synthetic
                        oligonucleotide
source                 1..20
                       mol_type = other RNA
                       organism = synthetic construct
SEQUENCE: 4
tcaaggaaga tggcatttct                                             20

SEQ ID NO: 5           moltype = RNA  length = 20
FEATURE                Location/Qualifiers
misc_feature           1..20
                       note = Description of Artificial Sequence: Synthetic
                        oligonucleotide
source                 1..20
                       mol_type = other RNA
                       organism = synthetic construct
SEQUENCE: 5
ggcacaaggg cacagacttc                                             20

SEQ ID NO: 6           moltype = RNA  length = 20
FEATURE                Location/Qualifiers
misc_feature           1..20
                       note = Description of Artificial Sequence: Synthetic
                        oligonucleotide
source                 1..20
                       mol_type = other RNA
                       organism = synthetic construct
SEQUENCE: 6
gcacaagggc acagacttcc                                             20

SEQ ID NO: 7           moltype = RNA  length = 20
FEATURE                Location/Qualifiers
misc_feature           1..20
                       note = Description of Artificial Sequence: Synthetic
                        oligonucleotide
source                 1..20
                       mol_type = other RNA
                       organism = synthetic construct
SEQUENCE: 7
cacaagggca cagacttcca                                             20

SEQ ID NO: 8           moltype = DNA  length = 20
FEATURE                Location/Qualifiers
misc_feature           1..20
                       note = Description of Combined DNA/RNA Molecule: Synthetic
                        oligonucleotide
modified_base          2
                       mod_base = OTHER
                       note = uracil
source                 1..20
                       mol_type = other DNA
                       organism = synthetic construct
SEQUENCE: 8
```

-continued

```
ataaattgtc atcaccagaa                                              20

SEQ ID NO: 9             moltype = DNA  length = 20
FEATURE                  Location/Qualifiers
misc_feature             1..20
                         note = Description of Combined DNA/RNA Molecule: Synthetic
                          oligonucleotide
modified_base            3
                         mod_base = OTHER
                         note = uracil
source                   1..20
                         mol_type = other DNA
                         organism = synthetic construct
SEQUENCE: 9
aataaattgt catcaccaga                                              20

SEQ ID NO: 10            moltype = DNA  length = 20
FEATURE                  Location/Qualifiers
misc_feature             1..20
                         note = Description of Artificial Sequence: Synthetic
                          oligonucleotide
source                   1..20
                         mol_type = other DNA
                         organism = synthetic construct
SEQUENCE: 10
gcacacagta gatgagggag                                              20

SEQ ID NO: 11            moltype = DNA  length = 20
FEATURE                  Location/Qualifiers
misc_feature             1..20
                         note = Description of Combined DNA/RNA Molecule: Synthetic
                          oligonucleotide
modified_base            1
                         mod_base = OTHER
                         note = uracil
source                   1..20
                         mol_type = other DNA
                         organism = synthetic construct
SEQUENCE: 11
tgcacacagt agatgaggga                                              20

SEQ ID NO: 12            moltype = DNA  length = 20
FEATURE                  Location/Qualifiers
misc_feature             1..20
                         note = Description of Combined DNA/RNA Molecule: Synthetic
                          oligonucleotide
modified_base            4
                         mod_base = OTHER
                         note = uracil
source                   1..20
                         mol_type = other DNA
                         organism = synthetic construct
SEQUENCE: 12
gggtcctccc cacagaggga                                              20

SEQ ID NO: 13            moltype = RNA  length = 20
FEATURE                  Location/Qualifiers
misc_feature             1..20
                         note = Description of Artificial Sequence: Synthetic
                          oligonucleotide
source                   1..20
                         mol_type = other RNA
                         organism = synthetic construct
SEQUENCE: 13
tcaaggaaga tggcatttct                                              20

SEQ ID NO: 14            moltype = RNA  length = 20
FEATURE                  Location/Qualifiers
misc_feature             1..20
                         note = Description of Artificial Sequence: Synthetic
                          oligonucleotide
source                   1..20
                         mol_type = other RNA
                         organism = synthetic construct
SEQUENCE: 14
tcaaggaaga tggcatttct                                              20

SEQ ID NO: 15            moltype = RNA  length = 20
FEATURE                  Location/Qualifiers
```

-continued

```
misc_feature          1..20
                      note = Description of Artificial Sequence: Synthetic
                       oligonucleotide
source                1..20
                      mol_type = other RNA
                      organism = synthetic construct
SEQUENCE: 15
tcaaggaaga tggcatttct                                              20

SEQ ID NO: 16         moltype = RNA  length = 20
FEATURE               Location/Qualifiers
misc_feature          1..20
                      note = Description of Artificial Sequence: Synthetic
                       oligonucleotide
source                1..20
                      mol_type = other RNA
                      organism = synthetic construct
SEQUENCE: 16
tcaaggaaga tggcatttct                                              20
```

COMPOSITIONS AND METHODS FOR PHOSPHORAMIDITE AND OLIGONUCLEOTIDE SYNTHESIS

CROSS-REFERENCE TO RELATED APPLICATIONS

This application is a Division of U.S. application Ser. No. 16/463,328, filed May 22, 2019, and issued as U.S. Pat. No. 11,873,316 Jan. 16, 2024, which is a U.S. National Stage Application of International PCT Application No. PCT/US2017/062996, filed Nov. 22, 2017, which claims priority to U.S. Provisional Application No. 62/426,079, filed Nov. 23, 2016, the entirety of each of which is incorporated herein by reference.

SEQUENCE LISTING

The instant application contains a Sequence Listing which has been submitted electronically in XML format and is hereby incorporated by reference in its entirety. Said XML copy, created on Jul. 3, 2024, is named SL.xml and is 25,137 bytes in size.

BACKGROUND

Oligonucleotides are useful for many purposes, including treating various diseases. There is a need for efficient synthetic methods for oligonucleotides.

SUMMARY

Phosphoramidites are important reagents for oligonucleotide synthesis. Many technologies for preparing phosphoramidites suffer from low yields and/or purities, which may significantly increase the cost of oligonucleotide preparation. In some embodiments, the present disclosure encompasses the recognition of a source of a problem with many technologies for phosphoramidite preparation.

Many conventional methods for phosphoramidite preparation utilize a material amount (e.g., containing water in an amount of equal to or more than 2, 3, 4, 5, 6, 7, 8, 9, 10, 11, 12, 13, 14, 15, 16, 17, 18, 19, 20, 25, 30, 35, 40, 45, 50, 55, 60, 65, 70, 75, 80, 85, 90, 95, or 100 fold in mole (equivalents) of desired phosphoramidite products; molar ratios between water and desired phosphoramidite products (equivalents) are generally more than 2, 5, 10, 50, or 100) of an aqueous solvent (optionally comprising one or more solutes) to wash crude preparations of phosphoramidite products in order, e.g., to quench certain unreacted reagents (e.g., a phosphorochloridite (Cl—P(—O—)—N—)), to remove one or more unreacted reagents (e.g., a base), to remove one or more reaction byproducts formed during synthesis of phosphoramidite (e.g., one or more salts), etc. In many conventional methods, after washes, aqueous solvents/solutions are typically extracted using organic solvents, often halogenated solvents such as chloroform, in order to recover desired phosphoramidite products.

Among other things, the present disclosure recognizes that exposure to a material amount of aqueous solvents and/or extraction processes can decrease yields and/or purity of desired phosphoramidite products. In some embodiments, the present disclosure encompasses certain surprising findings, including that replacing exposure to aqueous washes and/or extractions with filtration to remove solid reaction products can unexpectedly increase yields and/or purity of phosphoramidite products. In some embodiments, filtration can increase yields by 10%, 20%, 30%, 40%, 50%, 60%, 70%, 80%, 90% or more relative to aqueous washes/extractions. In some embodiments, filtration can be performed under vacuum and/or under inert gas. In some embodiments, it is observed that phosphoramidite decomposition is greatly decreased using filtration when compared to contact with aqueous washes and extractions. In some embodiments, removal of extraction processes, particularly those employing halogenated solvents such as chloroform, additionally avoid generation of organic wastes, providing substantial environmental and economic benefits.

In some embodiments, the present disclosure provides a method for preparing a phosphoramidite, comprising steps of:

a) providing a preparation comprising a phosphoramidite product and one or more reaction byproducts of the product's synthesis; and b) performing a filtration step on the preparation to provide a filtrate, wherein the filtrate contains a reduced level of the one or more reaction byproducts relative to the product as compared to that level present in the preparation prior to the filtration step.

In some embodiments, in a method of preparing a phosphoramidite that includes a step of separating a phosphoramidite product from one or more reaction byproducts of the product's synthesis, the present disclosure provides improvement comprising: subjecting a preparation comprising the phosphoramidite product and the one or more reaction byproducts to filtration without adding a material amount of water to the preparation after the phosphoramidite product has been formed.

In some embodiments, in a method of preparing a phosphoramidite that includes a step of separating a phosphoramidite product from one or more reaction byproducts of the product's synthesis, the present disclosure provides improvement comprising: subjecting a preparation comprising the phosphoramidite product and the one or more reaction byproducts to filtration without adding a material amount of any aqueous or halogenated solvent to the preparation after the phosphoramidite product has been formed.

In some embodiments, in a method of preparing a phosphoramidite that includes a step of separating a phosphoramidite product from one or more reaction byproducts of the product's synthesis, the present disclosure provides improvement comprising: subjecting a preparation comprising the phosphoramidite product and the one or more reaction byproducts to filtration without adding a material amount of any aqueous solvent, or performing any extraction from an aqueous solvent, after the phosphoramidite product has been formed.

In some embodiments, technologies (compounds, compositions, methods, etc.) provided in the present disclosure greatly decreased decomposition of desired phosphoramidite products during their isolation after formation. In some embodiments, presently provided methods surprisingly delivered in high yields and purity phosphoramidites that cannot be prepared in satisfactory yields and/or purity by conventional methods comprising use of a material amount of aqueous solvents. For example, in some embodiments, the present disclosure provides G phosphoramidite monomers without $O^6$ protection for oligonucleotide synthesis. Among other things, such provided technologies, which remove steps for $O^6$ protection and de-protection, significantly decrease cost of oligonucleotide preparation, including stereoselective oligonucleotide preparation which can provide powerful therapeutics but can be expensive. In some embodiments, the present disclosure provides a compound of formula I, described infra. In some embodiments, provided compounds are phosphoramidites useful for oligonucleotide preparation, including stereoselective preparation of chirally controlled oligonucleotide compositions.

In some embodiments, the present disclosure provides methods for oligonucleotide synthesis using provided phosphoramidites, e.g., those of formula I. In some embodiments, provided methods can be used for preparing chirally controlled oligonucleotide compositions.

In some embodiments, the present disclosure provides the following example embodiments:

1. A method for preparing a phosphoramidite, comprising steps of:
   a) providing a preparation comprising a phosphoramidite product and one or more reaction byproducts of the product's synthesis; and
   b) performing a filtration step on the preparation to provide a filtrate, wherein the filtrate contains a reduced level of the one or more reaction byproducts relative to the product as compared to that level present in the preparation prior to the filtration step.

2. The method of embodiment 1, wherein the preparation comprises a solution and one or more solids.

3. The method of embodiment 2, wherein the solution comprises the phosphoramidite product.

4. The method of any one of the preceding embodiments, wherein the solution comprises one or more reaction byproducts.

5. The method of any one of the preceding embodiments, wherein one or more solids comprise one or more reaction byproducts.

6. The method of any one of the preceding embodiments, wherein the preparation is formed by a reaction comprising the use of a base.

7. The method of any one of the preceding embodiments, wherein a reaction byproduct is a salt of the base.

8. The method of any one of the preceding embodiments, wherein one or more solids comprise a reaction product which is a salt of the base.

9. The method of any one of the preceding embodiments, wherein the base is $N(R)_3$, wherein each R is independently hydrogen, or an optionally substituted group selected from $C_{1-30}$ aliphatic, $C_{1-30}$ heteroaliphatic having 1-10 heteroatoms independently selected from oxygen, nitrogen, sulfur, phosphorus and silicon, $C_{6-30}$ aryl, a 5-30 membered heteroaryl ring having 1-10 heteroatoms independently selected from oxygen, nitrogen, sulfur, phosphorus and silicon, and a 3-30 membered heterocyclic ring having 1-10 heteroatoms independently selected from oxygen, nitrogen, sulfur, phosphorus and silicon.

10. The method of any one of the preceding embodiments, wherein the base is $Et_3N$.

11. The method of any one of embodiments 1-9, wherein the base is DIEA.

12. The method of any one of the preceding embodiments, wherein the preparation is formed by a reaction between a compound comprising a nucleobase moiety and a compound comprising an amino alcohol moiety.

13. The method of any one of the preceding embodiments, wherein the preparation is formed by a reaction comprising a nucleoside and a phosphorochloridite.

14. The method of any one of the preceding embodiments, wherein the nucleoside is protected.

15. The method of any one of the preceding embodiments, wherein the nucleoside is transiently protected.

16. The method of any one of the preceding embodiments, comprising providing a silylating reagent.

17. The method of any one of the preceding embodiments, comprising providing a silylating reagent having the structure of $(R)_3SiCl$, wherein each R is optionally substituted alkyl or aryl.

18. The method of any one of the preceding embodiments, wherein the silylating reagent is selected from chlorotrimethylsilane, chlorotriethylsilane, tert-tutyldimethylsilyl chloride, chloro-decyl-dimethylsilane, and chlorodimethylphenethylsilane.

19. The method of any one of the preceding embodiments, wherein the silylating reagent is chlorotrimethylsilane.

20. The method of any one of the preceding embodiments, wherein the silylating reagent protects a nucleobase.

21. The method of any one of the preceding embodiments, wherein the silylating reagent transiently protects a nucleobase.

22. The method of any one of the preceding embodiments, wherein the silylating reagent protects guanine.

23. The method of any one of the preceding embodiments, wherein the silylating reagent protects $O^6$ of guanine.

24. The method of any one of the preceding embodiments, wherein the silylating reagent transiently protects guanine.

25. The method of any one of the preceding embodiments, wherein the silylating reagent transiently protects $O^6$ of guanine.

26. The method of any one of the preceding embodiments, wherein protection by the silylating reagent is performed before reacting a nucleobase-containing compound with an amino alcohol- or chiral auxiliary-containing compound.

27. The method of any one of the preceding embodiments, wherein removal of the silyl protection group does not require a specific deprotection step.

28. The method of any one of the preceding embodiments, wherein the silylating step is performed with the phosphoramidite formation step within one pot.

29. The method of any one of the preceding embodiments, wherein the de-protection/de-silylating step is performed with the phosphoramidite formation step within one pot.

30. The method of any one of the preceding embodiments, wherein the nucleoside has the structure of formula I-a:

BA-SU—H, I-a wherein:

BA is an optionally substituted group selected from $C_{1-30}$ cycloaliphatic, $C_{6-30}$ aryl, $C_{3-30}$ heterocyclyl having 1-10 heteroatoms independently selected from oxygen, nitrogen, sulfur, phosphorus and silicon, $C_{5-30}$ heteroaryl having 1-10 heteroatoms independently selected from oxygen, nitrogen, sulfur, phosphorus and silicon, a natural nucleobase moiety, and a modified nucleobase moiety;

SU is -L-O— or

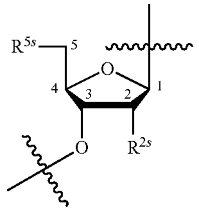

, wherein SU is connected to the phosphorus atom in formula I through the oxygen atom;

L is a covalent bond, or a bivalent, optionally substituted, linear or branched group selected from $C_{1-30}$ aliphatic and $C_{1-30}$ heteroaliphatic group having 1-10 heteroatoms independently selected from oxygen, nitrogen, sulfur, phosphorus and silicon, wherein one or more methylene units are optionally and independently replaced by an optionally substituted $C_{1-6}$ alkylene, $C_{1-6}$ alkenylene, —C≡C—, —C(R')$_2$—, -Cy-, —O—, —S—, —S—S—, —N(R')—, —C(O)—, —C(S)—, —C(NR')—, —C(O)N(R')—, —N(R')C(O)N(R')—, —N(R')C(O)—, —N(R')C(O)O—, —OC(O)N(R')—, —S(O)—, —S(O)$_2$—, —S(O)$_2$N(R')—, —N(R')S(O)$_2$—, —SC(O)—, —C(O)S—, —OC(O)—, or —C(O)O—;

$R^{5s}$ is R' or —OR';

$R^{2s}$ is —F, —CN, —$N_3$, —NO, —$NO_2$, —R'—OR', —SR', —N(R')$_2$, —O-L-OR', —O-L-SR', or —O-L-N(R')$_2$, or $R^{2s}$ is L connecting C2 with C1, C2, C3, C4 or C5;

-Cy- is an optionally substituted bivalent ring selected from 3-30 membered carbocyclylene, 6-30 membered arylene, 5-30 membered heteroarylene having 1-10 heteroatoms independently selected from oxygen, nitrogen and sulfur, and 3-30 membered heterocyclylene having 1-10 heteroatoms independently selected from oxygen, nitrogen, sulfur, phosphorus and silicon;

Ring A is an optionally substituted multivalent, monocyclic, bicyclic or polycyclic, saturated, partially unsaturated, or aryl 3-30 membered ring having, in addition to the intervening atoms, 0-10 heteroatoms independently selected from oxygen, nitrogen, sulfur, phosphorus and silicon;

each $R^s$ is independently R' or -L-R';

t is 0-5;

each R' is independently —R, —C(O)R, —$CO_2$R, or —$SO_2$R, or:

two or more R' are taken together with their intervening atoms to form an optionally substituted monocyclic, bicyclic or polycyclic, saturated, partially unsaturated, or aryl 3-30 membered ring having, in addition to the intervening atoms, 0-10 heteroatoms independently selected from oxygen, nitrogen, sulfur, phosphorus and silicon; and each R is independently hydrogen, or an optionally substituted group selected from $C_{1-30}$ aliphatic, $C_{1-30}$ heteroaliphatic having 1-10 heteroatoms independently selected from oxygen, nitrogen, sulfur, phosphorus and silicon, $C_{6-30}$ aryl, a 5-30 membered heteroaryl ring having 1-10 heteroatoms independently selected from oxygen, nitrogen, sulfur, phosphorus and silicon, and a 3-30 membered heterocyclic ring having 1-10 heteroatoms independently selected from oxygen, nitrogen, sulfur, phosphorus and silicon.

31. The method of any one of the preceding embodiments, wherein the phosphorochloridite has the structure of formula I-b:

I-b

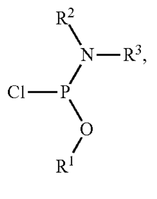

wherein:

each of $R^1$, $R^2$, and $R^3$ is independently R', or two or three of $R^1$, $R^2$, and $R^3$ are taken together with their intervening atoms to form:

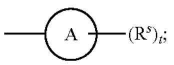

Ring A is an optionally substituted multivalent, monocyclic, bicyclic or polycyclic, saturated, partially unsaturated, or aryl 3-30 membered ring having, in addition to the intervening atoms, 0-10 heteroatoms independently selected from oxygen, nitrogen, sulfur, phosphorus and silicon;

each $R^s$ is independently R' or -L-R';

t is 0-5;

L is a covalent bond, or a bivalent, optionally substituted, linear or branched group selected from $C_{1-30}$ aliphatic and $C_{1-30}$ heteroaliphatic group having 1-10 heteroatoms independently selected from oxygen, nitrogen, sulfur, phosphorus and silicon, wherein one or more methylene units are optionally and independently replaced by an optionally substituted $C_{1-6}$ alkylene, $C_{1-6}$ alkenylene, —C≡C—, —C(R')$_2$—, -Cy-, —O—, —S—, —S—S—, —N(R')—, —C(O)—, —C(S)—, —C(NR')—, —C(O)N(R')—, —N(R')C(O)N(R')—, —N(R')C(O)—, —N(R')C(O)O—, —OC(O)N(R')—, —S(O)—, —S(O)$_2$—, —S(O)$_2$N(R')—, —N(R')S(O)$_2$—, —SC(O)—, —C(O)S—, —OC(O)—, or —C(O)O—;

-Cy- is an optionally substituted bivalent ring selected from 3-30 membered carbocyclylene, 6-30 membered arylene, 5-30 membered heteroarylene having 1-10 heteroatoms independently selected from oxygen, nitrogen and sulfur, and 3-30 membered heterocyclylene having 1-10 heteroatoms independently selected from oxygen, nitrogen, sulfur, phosphorus and silicon;

each R' is independently —R, —C(O)R, —$CO_2$R, or —$SO_2$R, or:

two or more R' are taken together with their intervening atoms to form an optionally substituted monocyclic, bicyclic or polycyclic, saturated, partially unsaturated, or aryl 3-30 membered ring having, in addition to the intervening atoms, 0-10 heteroatoms independently selected from oxygen, nitrogen, sulfur, phosphorus and silicon; and each R is independently hydrogen, or an optionally substituted group selected from $C_{1-30}$ aliphatic, $C_{1-30}$ heteroaliphatic having 1-10 heteroatoms independently selected from oxygen, nitrogen, sulfur, phosphorus and silicon, $C_{6-30}$ aryl, a 5-30 membered heteroaryl ring having 1-10 heteroatoms independently selected from oxygen, nitrogen, sulfur, phosphorus and silicon, and a 3-30 membered heterocyclic ring having 1-10 heteroatoms independently selected from oxygen, nitrogen, sulfur, phosphorus and silicon.

32. The method of any one of the preceding embodiments, wherein the phosphoramidite has the structure of formula I:

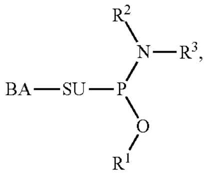

I wherein:

BA is an optionally substituted group selected from $C_{1-30}$ cycloaliphatic, $C_{6-30}$ aryl, $C_{3-30}$ heterocyclyl having 1-10 heteroatoms independently selected from oxygen, nitrogen, sulfur, phosphorus and silicon, $C_{5-30}$ heteroaryl having 1-10 heteroatoms independently selected from oxygen, nitrogen, sulfur, phosphorus and silicon, a natural nucleobase moiety and a modified nucleobase moiety;

SU is -L-O— or

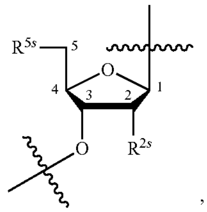

, wherein SU is connected to the phosphorus atom in formula I through the oxygen atom;

L is a covalent bond, or a bivalent, optionally substituted, linear or branched group selected from $C_{1-30}$ aliphatic and $C_{1-30}$ heteroaliphatic group having 1-10 heteroatoms independently selected from oxygen, nitrogen, sulfur, phosphorus and silicon, wherein one or more methylene units are optionally and independently replaced by an optionally substituted $C_{1-6}$ alkylene, $C_{1-6}$ alkenylene, —C≡C—, —$C(R')_2$—, -Cy-, —O—, —S—, —S—S—, —N(R')—, —C(O)—, —C(S)—, —C(NR')—, —C(O)N(R')—, —N(R')C(O)N(R')—, —N(R')C(O)—, —N(R')C(O)O—, —OC(O)N(R')—, —S(O)—, —$S(O)_2$—, —$S(O)_2N(R')$—, —$N(R')S(O)_2$—, —SC(O)—, —C(O)S—, —OC(O)—, or —C(O)O—;

$R^{5s}$ is R' or —OR';

$R^{2s}$ is —F, —CN, —$N_3$, —NO, —$NO_2$, —R'—OR', —SR', —$N(R')_2$, —O-L-OR', —O-L-SR', or —O-L-N$(R')_2$, or $R^{2s}$ is L connecting C2 with C1, C2, C3, C4 or C5;

-Cy- is an optionally substituted bivalent ring selected from 3-30 membered carbocyclylene, 6-30 membered arylene, 5-30 membered heteroarylene having 1-10 heteroatoms independently selected from oxygen, nitrogen and sulfur, and 3-30 membered heterocyclylene having 1-10 heteroatoms independently selected from oxygen, nitrogen, sulfur, phosphorus and silicon;

each of $R^1$, $R^2$, and $R^3$ is independently R', or two or three of $R^1$, $R^2$, and $R^3$ are taken together with their intervening atoms to form:

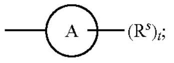

Ring A is an optionally substituted multivalent, monocyclic, bicyclic or polycyclic, saturated, partially unsaturated, or aryl 3-30 membered ring having, in addition to the intervening atoms, 0-10 heteroatoms independently selected from oxygen, nitrogen, sulfur, phosphorus and silicon;

each $R^s$ is independently R' or -L-R';

t is 0-5;

each R' is independently —R, —C(O)R, —$CO_2R$, or —$SO_2R$, or:

two or more R' are taken together with their intervening atoms to form an optionally substituted monocyclic, bicyclic or polycyclic, saturated, partially unsaturated, or aryl 3-30 membered ring having, in addition to the intervening atoms, 0-10 heteroatoms independently selected from oxygen, nitrogen, sulfur, phosphorus and silicon; and each R is independently hydrogen, or an optionally substituted group selected from $C_{1-30}$ aliphatic, $C_{1-30}$ heteroaliphatic having 1-10 heteroatoms independently selected from oxygen, nitrogen, sulfur, phosphorus and silicon, $C_{6-30}$ aryl, a 5-30 membered heteroaryl ring having 1-10 heteroatoms independently selected from oxygen, nitrogen, sulfur, phosphorus and silicon, and a 3-30 membered heterocyclic ring having 1-10 heteroatoms independently selected from oxygen, nitrogen, sulfur, phosphorus and silicon.

33. The method of any one of the preceding embodiments, wherein BA is an optionally substituted group selected from $C_{1-30}$ cycloaliphatic, $C_{6-30}$ aryl, $C_{3-30}$ heterocyclyl, $C_{5-30}$ heteroaryl, and a natural nucleobase moiety.

34. The method of any one of the preceding embodiments, wherein BA is an optionally substituted group, which group is formed by removing a —H from

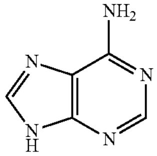

,

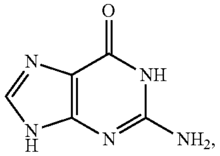

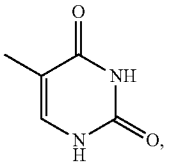

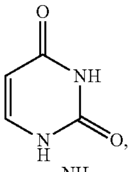

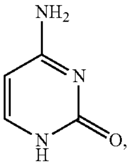

or

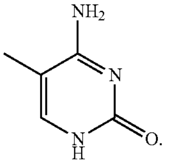

35. The method of any one of the preceding embodiments, wherein BA is an optionally substituted group which group is selected from

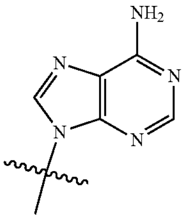
,
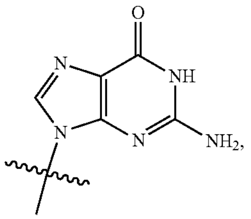 [SMILES: *n1cnc2c(=O)[nH]c(N)nc21]

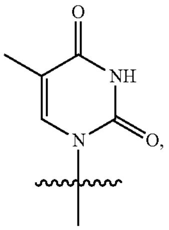
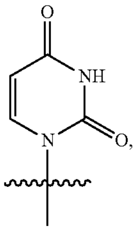
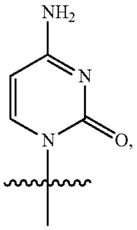
and
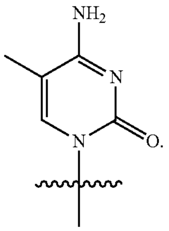

36. The method of any one of the preceding embodiments, wherein BA is a protected nucleobase selected from

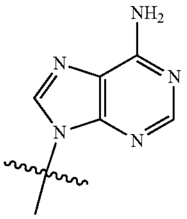
,
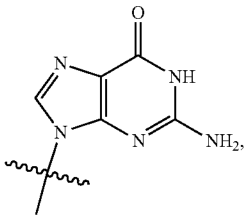 [SMILES: *n1cnc2c(=O)[nH]c(N)nc21]
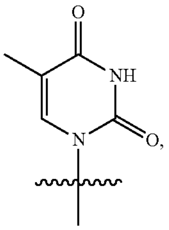
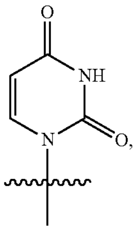
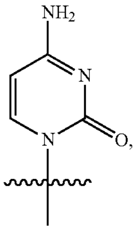
and
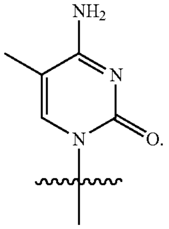

37. The method of any one of the preceding embodiments, wherein BA is protected

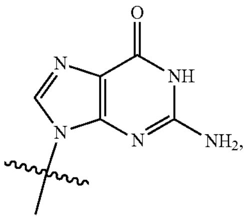

wherein $O^6$ is protected.

38. The method of any one of the preceding embodiments, wherein BA is

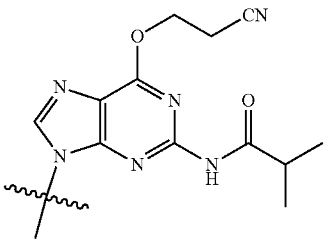
.

39. The method of any one of embodiments 1-36, wherein BA is protected

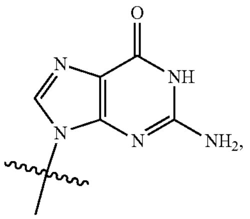

wherein $O^6$ is not protected.

40. The method of any one of embodiments 1-36, wherein BA is

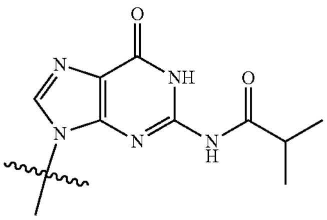
.

41. The method of any one of the preceding embodiments, wherein BA is a modified base.

42. The method of any one of the preceding embodiments, wherein SU is a modified or unmodified sugar moiety.

43. The method of any one of the preceding embodiments, wherein SU is -L-O—.

44. The method of any one of the preceding embodiments, wherein SU is -L-O—, and L is optionally substituted 5-10 membered heterocyclylene having one oxygen atom.

45. The method of any one of the preceding embodiments, wherein SU is -L-O—, and L is optionally substituted 5-membered heterocyclylene having one oxygen atom.

46. The method of any one of embodiments 1-44, wherein SU is -L-O—, and L is optionally substituted 7-10 membered bicyclic heterocyclylene having two oxygen atoms.

47. The method of any one of the preceding embodiments, wherein SU is

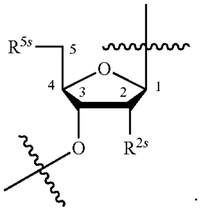

.

48. The method of any one of the preceding embodiments, wherein $R^{5s}$ is —OR'.

49. The method of any one of the preceding embodiments, wherein $R^{5s}$ is —ODMTr.

50. The method of any one of the preceding embodiments, wherein $R^{2s}$ is —H.

51. The method of any one of embodiments 1-49, wherein $R^{2s}$ is —F.

52. The method of any one of embodiments 1-49, wherein $R^{2s}$ is —OR'.

53. The method of any one of embodiments 1-49, wherein $R^{2s}$ is —O-L-OR'.

54. The method of any one of embodiments 1-49 and 52-53, wherein $R^{2s}$ is —OMe.

55. The method of any one of embodiments 1-49 and 52-53, wherein $R^{2s}$ is —$OCH_2CH_2OMe$.

56. The method of any one of embodiments 1-49, wherein $R^{2s}$ is L connecting C2 with C1, C2, C3, C4 or C5.

57. The method of any one of embodiments 1-49 and 56, wherein $R^{2s}$ is L connecting $C_2$ with C4.

58. The method of any one of embodiments 1-49 and 56-57, wherein L is (C2)-O-(optionally substituted methylene)-.

59. The method of any one of embodiments 1-49 and 56-58, wherein L is (C2)-O-(unsubstituted methylene)-.

60. The method of any one of embodiments 1-49 and 56-58, wherein L is (C2)-O-(optionally substituted methylene)-, wherein the methylene group is substituted with methyl.

61. The method of any one of embodiments 1-49 and 56-58, wherein L is (C2)-O-(optionally substituted methylene)-, wherein the methylene group is substituted with ethyl.

62. The method of embodiment 60 or 61, wherein the carbon atom of the methylene group is S.

63. The method of embodiment 60 or 61, wherein the carbon atom of the methylene group is R.

64. The method of any one of the preceding embodiments, wherein $R^1$, $R^2$, and $R^3$ are taken together with their intervening nitrogen, phosphorus and oxygen atoms to form

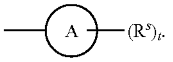

65. The method of any one of the preceding embodiments, wherein Ring A comprises a ring system having the backbone structure of

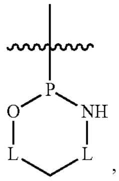

, or

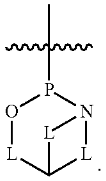

.

66. The method of any one of the preceding embodiments, wherein Ring A comprises a ring system having the backbone structure of

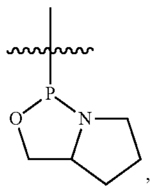

,

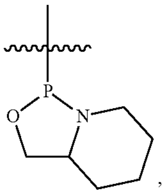

,

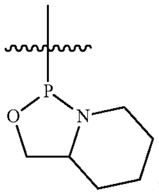

, or

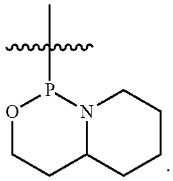

.

67. The method of any one of the preceding embodiments, wherein t is 0.

68. The method of any one of embodiments 1-67, wherein t is 1-5.

69. The method of any one of the preceding embodiments, wherein one $R^s$ is R' or -L-R' wherein -L- is a bivalent, optionally substituted $C_{1-30}$ heteroaliphatic group.

70. The method of any one of the preceding embodiments, wherein one $R^s$ is —$CH_2Si(Ph)_2CH_3$.

71. The method of any one of the preceding embodiments, wherein

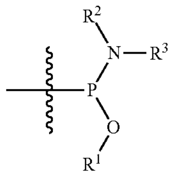

comprises one or more chiral elements and is asymmetric.

72. The method of any one of the preceding embodiments, wherein when used in oligonucleotide synthesis, the phosphoramidite can deliver diastereoselectivity greater than about 50%, 60%, 70%, 80%, 90%, 91%, 92%, 93%, 94%, 95%, 96%, 97%, 98% or 99% at the newly formed P-chiral center, optionally with greater than about 50%, 60%, 70%, 80%, 90%, 91%, 92%, 93%, 94%, 95%, 96%, 97%, 98% or 99% yield.

73. The method of any one of the preceding embodiments, wherein the oligonucleotide synthesis method is one described in WO/2011/005761, WO/2013/012758, WO/2014/012081, WO/2015/107425, WO/2010/064146, WO/2014/010250, WO/2011/108682, WO/2012/039448, or WO/2012/073857.

74. The method of any one of the preceding embodiments, wherein

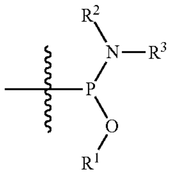

is

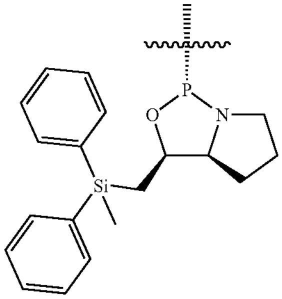

or

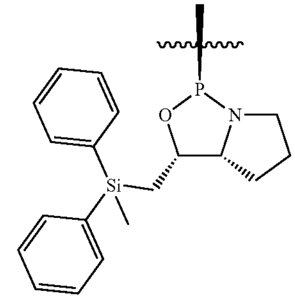

.

75. The method of any one of embodiments 1-73, wherein

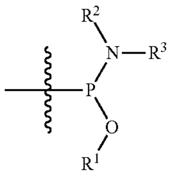

is

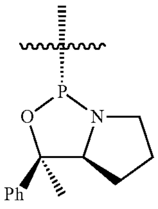

or

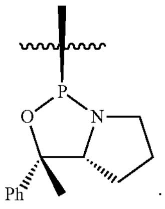

.

76. The method of any one of the preceding embodiments, wherein the phosphoramidite is one described in WO/2011/005761, WO/2013/012758, WO/2014/012081, WO/2015/107425, WO/2010/064146, WO/2014/010250, WO/2011/108682, WO/2012/039448, or WO/2012/073857.

77. The method of any one of the preceding embodiments, wherein the phosphoramidite is selected from:

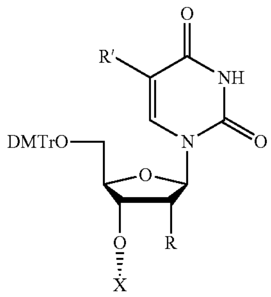

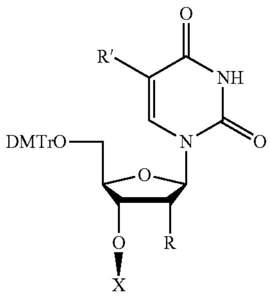

X =

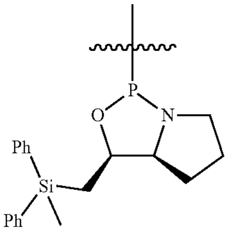

17: R′ = H, R = H
18: R′ = H, R = OMe
19: R′ = H, R = $OCH_2CH_2OMe$
20: R′ = H, R = F
21: R′ = Me, R = H
22: R′ = Me, R = OMe
23: R′ = Me, R = $OCH_2CH_2OMe$
24: R′ = Me, R = F

X =

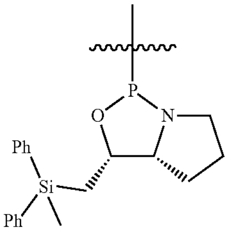

25: R′ = H, R = H
26: R′ = H, R = OMe
27: R′ = H, R = $OCH_2CH_2OMe$
28: R′ = H, R = F
29: R′ = Me, R = H
30: R′ = Me, R = OMe
31: R′ = Me, R = $OCH_2CH_2OMe$
32: R′ = Me, R = F

X =

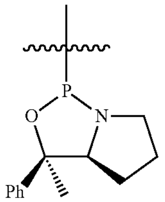

33: R′ = H, R = H
34: R′ = H, R = OMe
35: R′ = H, R = $OCH_2CH_2OMe$
36: R′ = H, R = F
37: R′ = Me, R = H
38: R′ = Me, R = OMe
39: R′ = Me, R = $OCH_2CH_2OMe$
40: R′ = Me, R = F

-continued

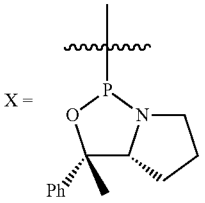

41: R′ = H, R = H
42: R′ = H, R = OMe
43: R′ = H, R = $OCH_2CH_2OMe$
44: R′ = H, R = F
45: R′ = Me, R = H
46: R′ = Me, R = OMe
47: R′ = Me, R = $OCH_2CH_2OMe$
48: R′ = Me, R = F

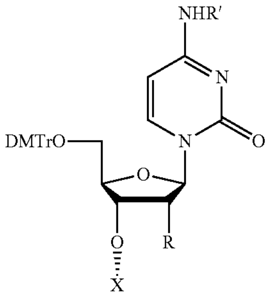

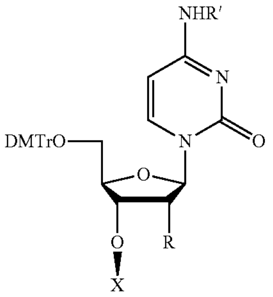

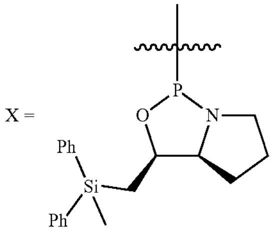

53: R′ = Ac, R = H
54: R′ = Ac, R = OMe
55: R′ = Ac, R = $OCH_2CH_2OMe$
56: R′ = Ac, R = F
53a: R′ = iBu, R = H
54a: R′ = iBu, R = OMe
55a: R′ = iBu, R = $OCH_2CH_2OMe$
56a: R′ = iBu, R = F

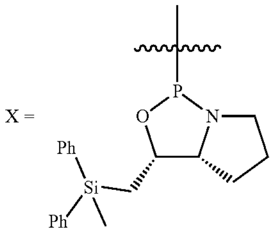

57: R′ = Ac, R = H
58: R′ = Ac, R = OMe
59: R′ = Ac, R = $OCH_2CH_2OMe$
60: R′ = Ac, R = F
57a: R′ = iBu, R = H
58a: R′ = iBu, R = OMe
59a: R′ = iBu, R = $OCH_2CH_2OMe$
60a: R′ = iBu, R = F

-continued

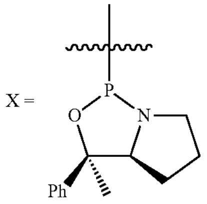

61: R′ = Ac, R = H
62: R′ = Ac, R = OMe
63: R′ = Ac, R = $OCH_2CH_2OMe$
64: R′ = Ac, R = F
61a: R′ = iBu, R = H
62a: R′ = iBu, R = OMe
63a: R′ = iBu, R = $OCH_2CH_2OMe$
64a: R′ = iBu, R = F

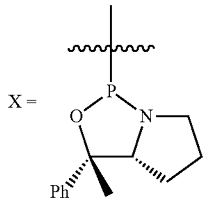

65: R′ = Ac, R = H
66: R′ = Ac, R = OMe
67: R′ = Ac, R = $OCH_2CH_2OMe$
68: R′ = Ac, R = F
65a: R′ = iBu, R = H
66a: R′ = iBu, R = OMe
67a: R′ = iBu, R = $OCH_2CH_2OMe$
68a: R′ = iBu, R = F

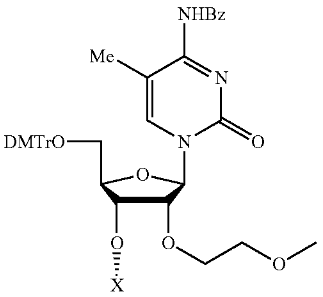

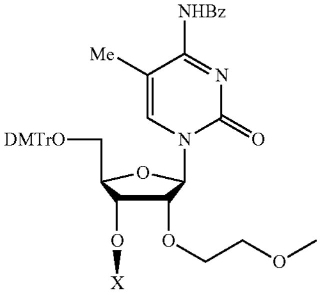

55b

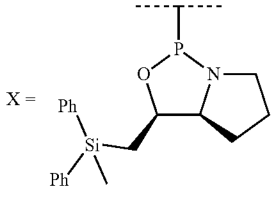

-continued
59b
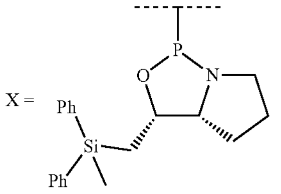
63b
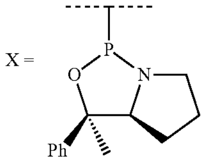
67b
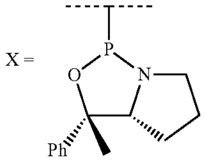
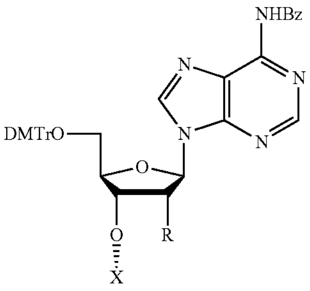
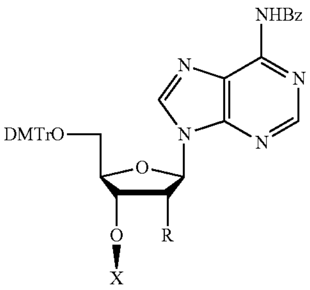
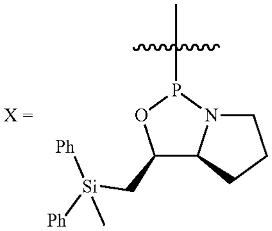
73: R = H
74: R = OMe
75: R = $OCH_2CH_2OMe$
76: R = F
-continued
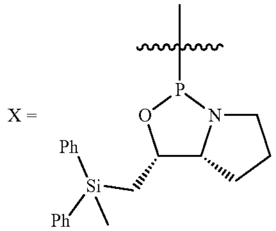
77: R = H
78: R = OMe
79: R = $OCH_2CH_2OMe$
80: R = F
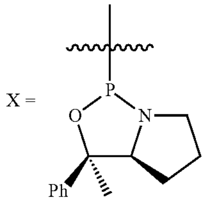
81: R = H
82: R = OMe
83: R = $OCH_2CH_2OMe$
84: R = F
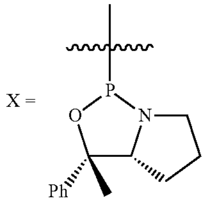
85: R = H
86: R = OMe
87: R = $OCH_2CH_2OMe$
88: R = F
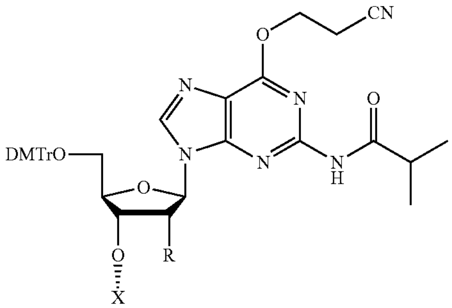
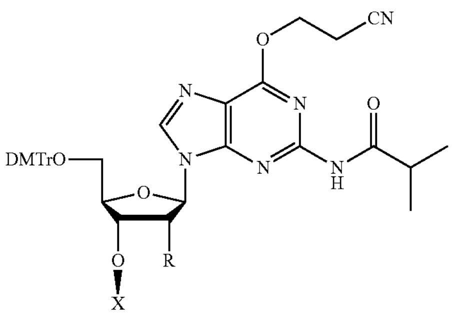

-continued
X = 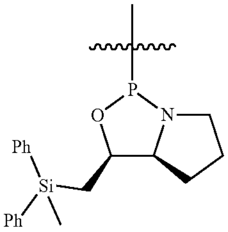
93: R = H
94: R = OMe
95: R = $OCH_2CH_2OMe$
96: R = F
X = 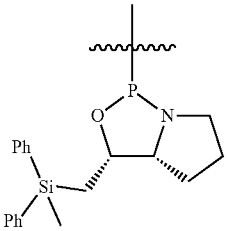
97: R = H
98: R = OMe
99: R = $OCH_2CH_2OMe$
100: R = F
X = 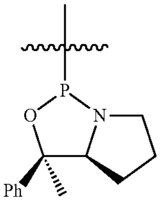
101: R = H
102: R = OMe
103: R = $OCH_2CH_2OMe$
104: R = F
X = 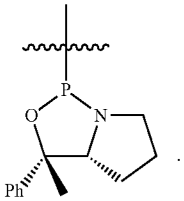
105: R = H
106: R = OMe
107: R = $OCH_2CH_2OMe$
108: R = F
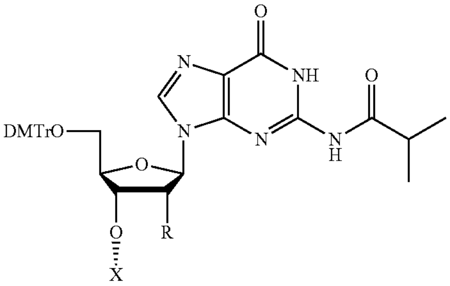
-continued
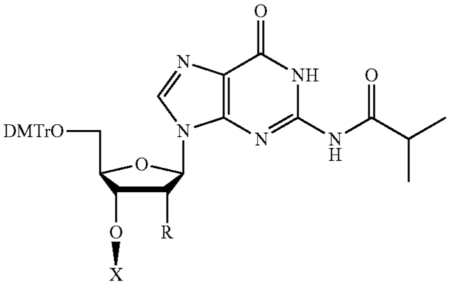
X = 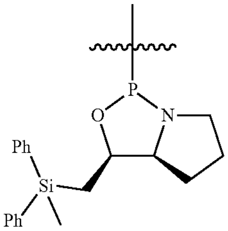
113: R = H
114: R = OMe
115: R = $OCH_2CH_2OMe$
116: R = F
X = 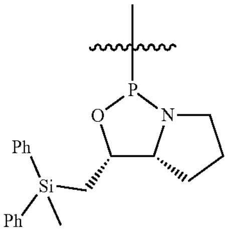
117: R = H
118: R = OMe
119: R = $OCH_2CH_2OMe$
120: R = F
X = 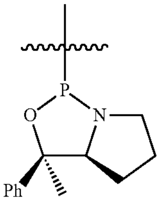
121: R = H
122: R = OMe
123: R = $OCH_2CH_2OMe$
124: R = F
X = 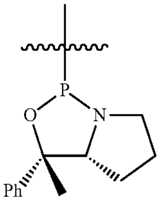
125: R = H
126: R = OMe
127: R = $OCH_2CH_2OMe$
128: R = F
78. The method of any one of the preceding embodiments, wherein the phosphoramidite is selected from

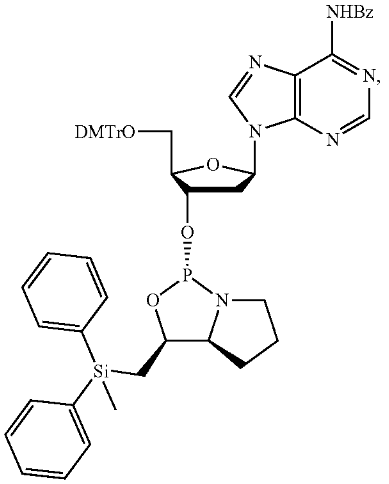
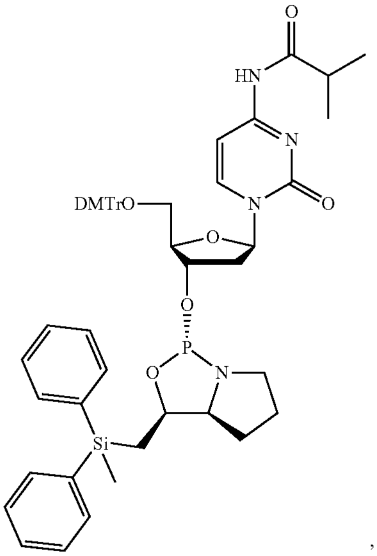
,
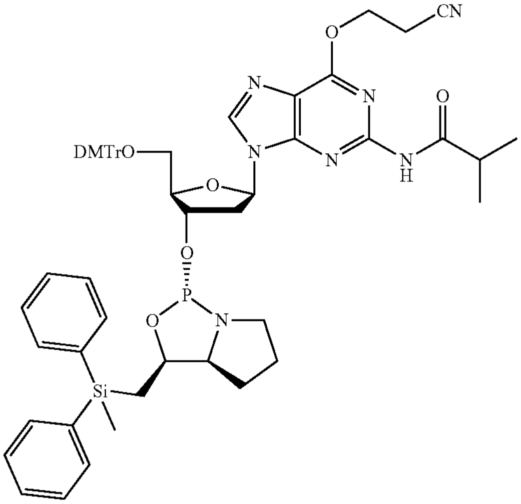
,
-continued
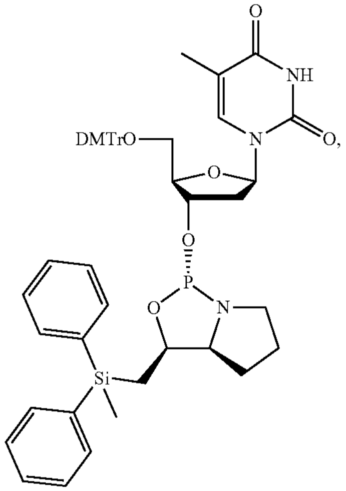
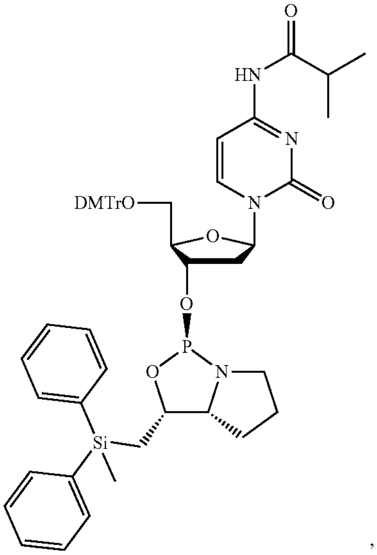
,
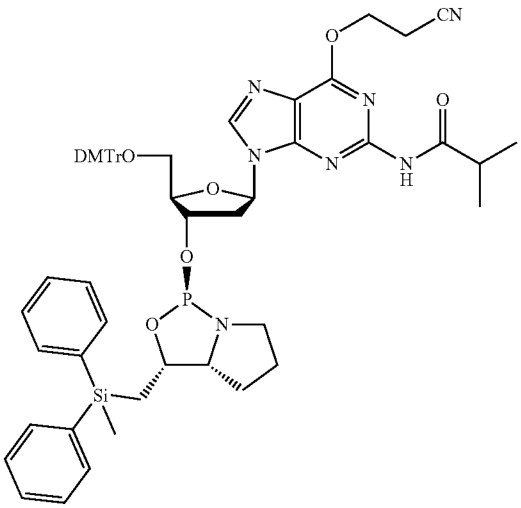
, -continued
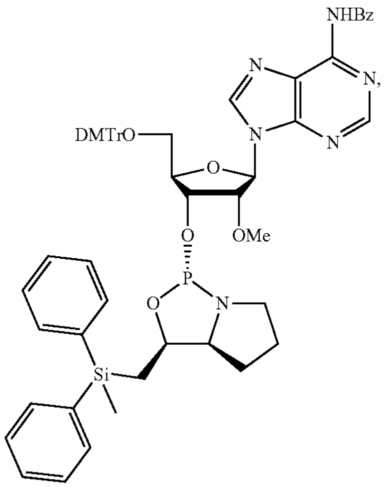
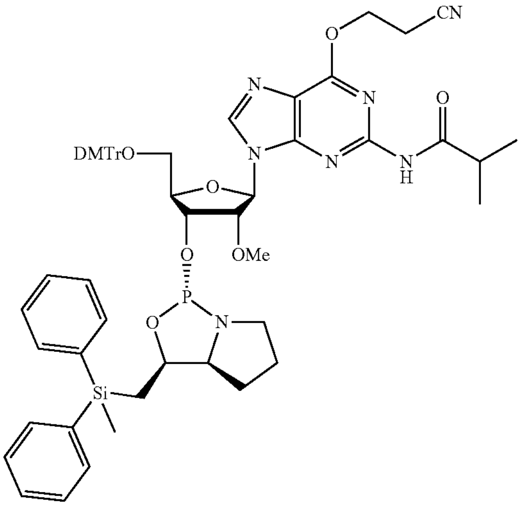
,
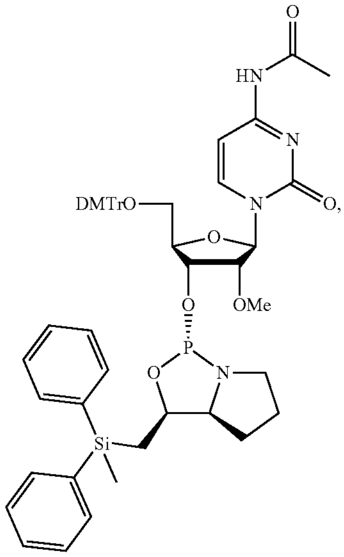
and
-continued
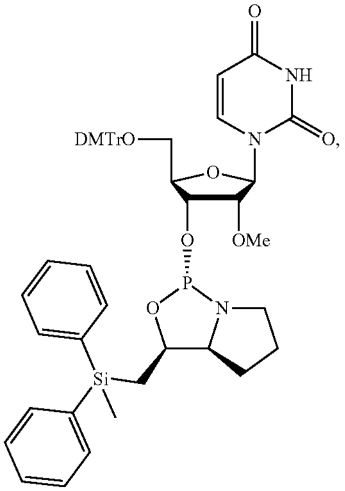
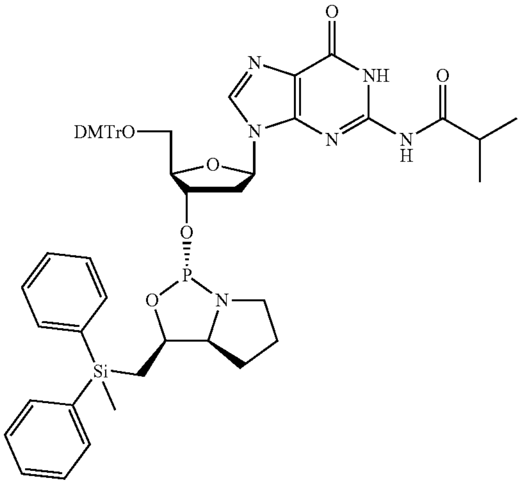
,
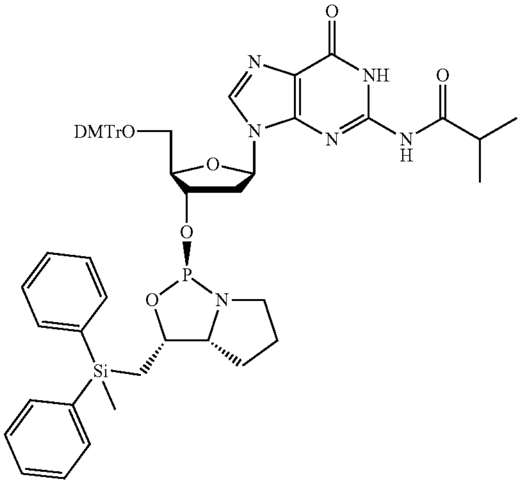
.
79. The method of any one of embodiments 1-73, wherein the phosphoramidite is

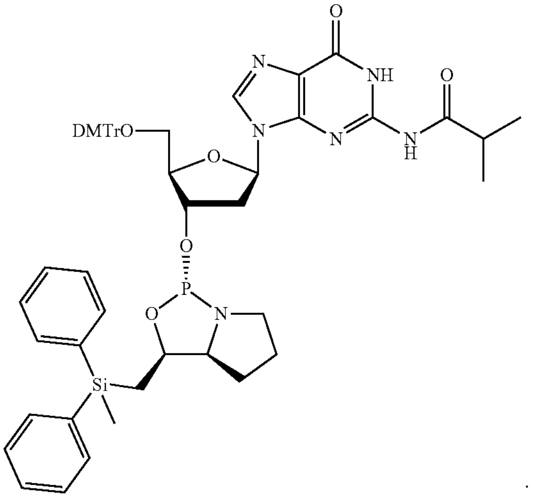

80. The method of any one of embodiments 1-73, wherein the phosphoramidite is

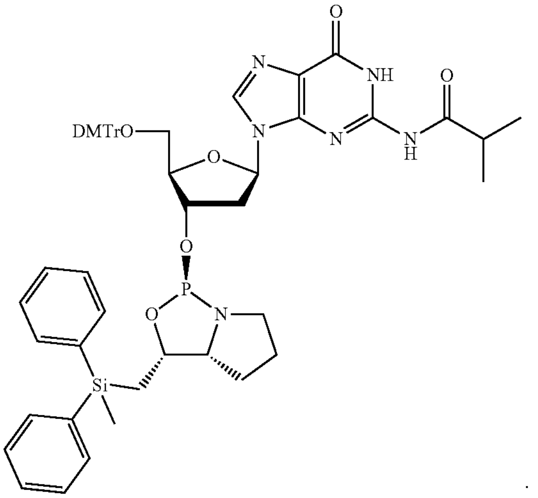

81. The method of any one of embodiments 1-73, wherein the phosphoramidite is

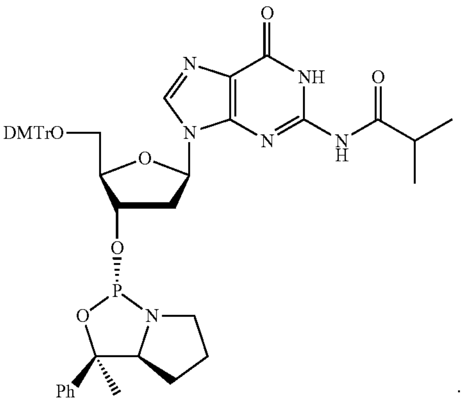

82. The method of any one of embodiments 1-73, wherein the phosphoramidite is

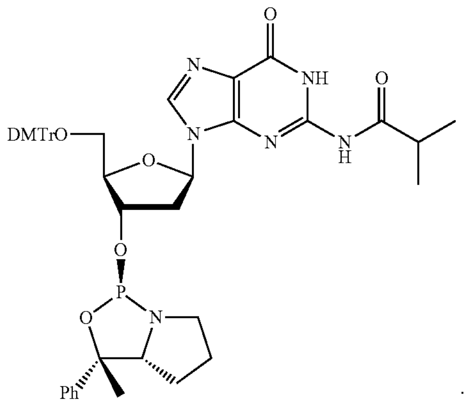

83. The method of any one of the preceding embodiments, wherein the reaction forming the preparation prior to filtration is a multi-step reaction.

84. The method of any one of the preceding embodiments, wherein the reaction forming the preparation prior to filtration comprises the use of a reduced temperature.

85. The method of any one of the preceding embodiments, wherein the reaction forming the preparation prior to filtration uses a solvent comprising THF.

86. The method of any one of the preceding embodiments, wherein the reaction forming the preparation prior to filtration uses THE as solvent.

87. The method of any one of the preceding embodiments, wherein the reaction forming the preparation prior to filtration comprises reacting residual phosphorochloridite with water.

88. The method of embodiment 87, comprising removing the excess water.

89. The method of embodiment 88, comprising removing the excess water by adding a desiccant.

90. The method of embodiment 89, wherein the desiccant is $Na_2SO_4$.

91. The method of embodiment 89, wherein the desiccant is $MgSO_4$.

92. The method of any one of the preceding embodiments, wherein no solution comprising the phosphoramidite product is contacted with water of more than 100, 90, 80, 70, 60, 50, 40, 30, 20, 10, 9, 8, 7, 6, 5, 4, 3, 2, or 1 mole equivalent of the phosphoramidite.

93. The method of any one of the preceding embodiments, wherein no solution comprising the phosphoramidite product is contacted with water of more than 100, 90, 80, 70, 60, 50, 40, 30, 20, 10, 9, 8, 7, 6, 5, 4, 3, or 2 mole equivalents of the phosphoramidite.

94. The method of any one of the preceding embodiments, wherein no solution comprising the phosphoramidite product is contacted with water of more than 100, 90, 80, 70, 60, 50, 40, 30, 20, 10, 9, 8, 7, 6, or 5 mole equivalents of the phosphoramidite.

95. The method of any one of the preceding embodiments, wherein no solution comprising the phosphoramidite product is contacted with water of more than 100, 90, 80, 70, 60, 50, 40, 30, 20, or 10 mole equivalents of the phosphoramidite.

96. The method of any one of the preceding embodiments, wherein one or more steps are performed under an inert gas.

97. The method of any one of the preceding embodiments, wherein the preparation is formed under an inert gas.

98. The method of any one of the preceding embodiments, wherein the filtration is performed under an inert gas.

99. The method of any one of embodiments 96-97, wherein the inert gas is argon.

100. The method of any one of the preceding embodiments, wherein the filtration is performed under vacuum.

101. The method of any one of the preceding embodiments, wherein no chloroform solvent is used.

102. The method of any one of the preceding embodiments, wherein no halogenated solvent is used.

103. The method of any one of the preceding embodiments, comprising purifying the phosphoramidite product using chromatography.

104. The method of any one of the preceding embodiments, comprising purifying the phosphoramidite product using silica gel column chromatography.

105. The method of embodiment 104, wherein the silica gel is treated with an anhydrous solvent.

106. The method of embodiment 104, wherein the anhydrous solvent is an alcohol.

107. The method of embodiment 104, wherein the silica gel is treated with an anhydrous solvent prior loading of a compound to be purified.

108. The method of any one of embodiments 105-107, wherein the solvent is acetonitrile.

109. The method of any one of embodiments 105-107, wherein the solvent is ethyl acetate.

110. The method of any one of embodiments 105-107, wherein the solvent is methanol.

111. The method of any one of embodiments 101-110, wherein the mobile phase comprising a base.

112. The method of any one of embodiments 101-111, wherein the mobile phase comprising triethylamine.

113. The method of any one of the preceding embodiments, the purified phosphoramidite product has a purity of 80%, 85%, 90%, 91%, 92%, 93%, 94%, 95%, 96%, 97%, 98%, 99% or more.

114. The method of any one of the preceding embodiments, the purified phosphoramidite product has a purity of 90%, 91%, 92%, 93%, 94%, 95%, 96%, 97%, 98%, 99% or more.

115. The method of any one of the preceding embodiments, the purified phosphoramidite product has a purity of 95%, 96%, 97%, 98%, 99% or more.

116. In a method of preparing a phosphoramidite that includes a step of separating a phosphoramidite product from one or more reaction byproducts of the product's synthesis, the improvement comprising:

subjecting a preparation comprising the phosphoramidite product and the one or more reaction byproducts to filtration without adding a material amount of water to the preparation after the phosphoramidite product has been formed.

117. The improvement of embodiment 116, comprising subjecting a preparation comprising the phosphoramidite product and the one or more reaction byproducts to filtration without adding a material amount of water or halogenated solvent to the preparation after the phosphoramidite product has been formed.

118. In a method of preparing a phosphoramidite that includes a step of separating a phosphoramidite product from one or more reaction byproducts of the product's synthesis, the improvement comprising:

subjecting a preparation comprising the phosphoramidite product and the one or more reaction byproducts to filtration without adding a material amount of any aqueous or halogenated solvent to the preparation after the phosphoramidite product has been formed.

119. In a method of preparing a phosphoramidite that includes a step of separating a phosphoramidite product from one or more reaction byproducts of the product's synthesis, the improvement comprising:

subjecting a preparation comprising the phosphoramidite product and the one or more reaction byproducts to filtration without adding a material amount of any aqueous solvent, or performing any extraction from an aqueous solvent, after the phosphoramidite product has been formed.

120. The improvement of embodiment 119, wherein the extraction is performed using a halogenated solvent.

121. The improvement of any one of embodiments 116-120, wherein the filtration removes part of all of a reaction byproduct.

122. The improvement of any one of embodiments 116-120, wherein the filtration removes part of all of a reaction byproduct as a solid.

123. The improvement of any one of embodiments 116-122, wherein the halogenated solvent is chloroform.

124. The improvement of any one of embodiments 116-123, wherein the improvement comprises less degradation of the phosphoramidite product.

125. The improvement of any one of embodiments 116-124, wherein the improvement comprises improving the yield of the purified phosphoramidite product by 10%, 20%, 30%, 40%, 50%, 60%, 70%, 80%, 90% or more relative to the yield prior to the improvement.

126. The improvement of any one of embodiments 116-124, wherein the improvement comprises improving the yield of the purified phosphoramidite product by 20%, 30%, 40%, 50%, 60%, 70%, 80%, 90% or more relative to the yield prior to the improvement.

127. The improvement of any one of embodiments 116-124, wherein the improvement comprises improving the yield of the purified phosphoramidite product by 30%, 40%, 50%, 60%, 70%, 80%, 90% or more relative to the yield prior to the improvement.

128. The improvement of any one of embodiments 116-124, wherein the purified phosphoramidite has a purity of 80%, 85%, 90%, 91%, 92%, 93%, 94%, 95%, 96%, 97%, 98%, 99% or more.

129. The improvement of any one of embodiments 116-124, wherein the purified phosphoramidite has a purity of 85%, 90%, 91%, 92%, 93%, 94%, 95%, 96%, 97%, 98%, 99% or more.

130. The improvement of any one of embodiments 116-124, wherein the purified phosphoramidite has a purity of 90%, 91%, 92%, 93%, 94%, 95%, 96%, 97%, 98%, 99% or more.

131. The improvement of any one of embodiments 116-124, wherein the purified phosphoramidite has a purity of 95%, 96%, 97%, 98%, 99% or more.

132. The improvement of any one of embodiments 116-131, wherein a material amount is about or more than 1, 2, 3, 4, 5, 6, 7, 8, 9, 10, 11, 12, 13, 14, 15, 16, 17, 18, 19, 20, 25, 30, 35, 40, 45, 50, 55, 60, 65, 70, 75, 80, 85, 90, 95, 100 mole equivalents of the phosphoramidite product.

133. The improvement of any one of embodiments 116-131, wherein a material amount is 1 or more mole equivalents of the phosphoramidite product.

134. The improvement of any one of embodiments 116-131, wherein a material amount is 2 or more mole equivalents of the phosphoramidite product.

135. The improvement of any one of embodiments 116-131, wherein a material amount is 5 or more mole equivalents of the phosphoramidite product.

136. The improvement of any one of embodiments 116-131, wherein a material amount is 10 or more mole equivalents of the phosphoramidite product.

137. The improvement of any one of embodiments 116-136, wherein a material amount is about or more than 0.5%, 1%, 2%, 3%, 4%, 5%, 6%, 7%, 8%, 9%, 10%, 15%, 20%, 30%, 40%, 50%, 60%, 70%, 80%, 90%, 100%, 200% or more (v/v) of the preparation comprising the phosphoramidite product and the one or more reaction byproducts.

138. The improvement of 137, wherein a material amount is about or more than 1% (v/v) of the preparation comprising the phosphoramidite product and the one or more reaction byproducts.

139. The improvement of 137, wherein a material amount is about or more than 5% (v/v) of the preparation comprising the phosphoramidite product and the one or more reaction byproducts.

140. The improvement of 137, wherein a material amount is about or more than 10% (v/v) of the preparation comprising the phosphoramidite product and the one or more reaction byproducts.

141. The improvement of 137, wherein a material amount is about or more than 20% (v/v) of the preparation comprising the phosphoramidite product and the one or more reaction byproducts.

142. The improvement of 137, wherein a material amount is about or more than 50% (v/v) of the preparation comprising the phosphoramidite product and the one or more reaction byproducts.

143. The improvement of 137, wherein a material amount is about or more than 100% (v/v) of the preparation comprising the phosphoramidite product and the one or more reaction byproducts.

144. The improvement of any one of embodiments 116-132, wherein the improved method is a method of any one of embodiments 1-112.

145. The improvement of any one of embodiments 116-132, wherein the improved method is a method of any one of embodiments 1-112.

146. A compound having the structure of formula I:

I

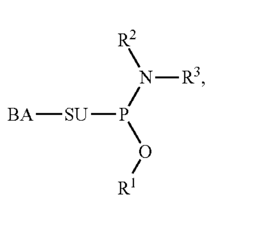

or a salt thereof, wherein:

BA is optionally protected

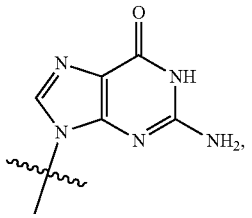

wherein $O^6$ is not protected;

SU is -L-O— or

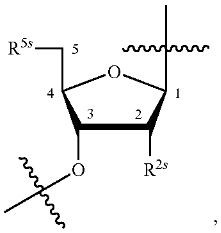

, wherein SU is connected to the phosphorus atom in formula I through the oxygen atom;

L is a covalent bond, or a bivalent, optionally substituted, linear or branched group selected from $C_{1-30}$ aliphatic and $C_{1-30}$ heteroaliphatic group having 1-10 heteroatoms independently selected from oxygen, nitrogen, sulfur, phosphorus and silicon, wherein one or more methylene units are optionally and independently replaced by an optionally substituted $C_{1-6}$ alkylene, $C_{1-6}$ alkenylene, —C≡C—, —C(R')$_2$—, -Cy-, —O—, —S—, —S—S—, —N(R')—, —C(O)—, —C(S)—, —C(NR')—, —C(O)N(R')—, —N(R')C(O)N(R')—, —N(R')C(O)—, —N(R')C(O)O—, —OC(O)N(R')—, —S(O)—, —S(O)$_2$—, —S(O)$_2$N(R')—, —N(R')S(O)$_2$—, —SC(O)—, —C(O)S—, —OC(O)—, or —C(O)O—;

$R^{5s}$ is R' or —OR';

$R^{2s}$ is —F, —CN, —$N_3$, —NO, —$NO_2$, —R'—OR', —SR', —N(R')$_2$, —O-L-OR', —O-L-SR', or —O-L-N(R')$_2$, or $R^{2s}$ is L connecting C2 with C1, C2, C3, C4 or C5;

-Cy- is an optionally substituted bivalent ring selected from 3-30 membered carbocyclylene, 6-30 membered arylene, 5-30 membered heteroarylene having 1-10 heteroatoms independently selected from oxygen, nitrogen and sulfur, and 3-30 membered heterocyclylene having 1-10 heteroatoms independently selected from oxygen, nitrogen, sulfur, phosphorus and silicon;

each of $R^1$, $R^2$, and $R^3$ is independently R', wherein two or three of $R^1$, $R^2$, and $R^3$ are taken together with their intervening atoms to form:

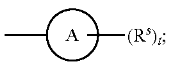

Ring A is an optionally substituted multivalent, monocyclic, bicyclic or polycyclic, saturated, partially unsaturated, or aryl 3-30 membered ring having, in addition to the intervening atoms, 0-10 heteroatoms independently selected from oxygen, nitrogen, sulfur, phosphorus and silicon;

each $R^s$ is independently R' or -L-R';

t is 0-5;

each R' is independently —R, —C(O)R, —$CO_2$R, or —$SO_2$R, or:

two or more R' are taken together with their intervening atoms to form an optionally substituted monocyclic, bicyclic or polycyclic, saturated, partially unsaturated, or aryl 3-30 membered ring having, in addition to the intervening atoms, 0-10 heteroatoms independently selected from oxygen, nitrogen, sulfur, phosphorus and silicon; and each R is independently hydrogen, or an optionally substituted group selected from $C_{1-30}$ aliphatic, $C_{1-30}$ heteroaliphatic having 1-10 heteroatoms independently selected from oxygen, nitrogen, sulfur, phosphorus and silicon, $C_{6-30}$ aryl, a 5-30 membered heteroaryl ring having 1-10 heteroatoms independently selected from oxygen, nitrogen, sulfur, phosphorus and silicon, and a 3-30 membered heterocyclic ring having 1-10 heteroatoms independently selected from oxygen, nitrogen, sulfur, phosphorus and silicon.

147. The compound of embodiment 146, wherein BA is protected

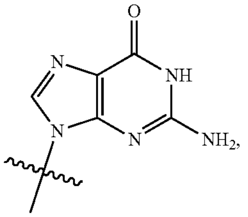

wherein $O^6$ is not protected.

148. A compound having the structure of formula I:

I

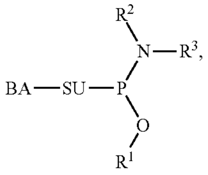

or a salt thereof, wherein:

BA is optionally substituted

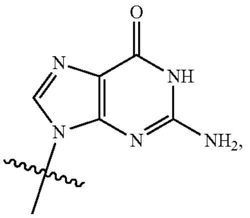

wherein $O^6$ is not substituted;

SU is -L-O— or

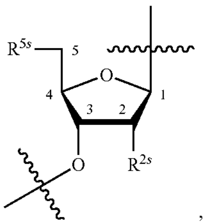

, wherein SU is connected to the phosphorus atom in formula I through the oxygen atom;

L is a covalent bond, or a bivalent, optionally substituted, linear or branched group selected from $C_{1-30}$ aliphatic and $C_{1-30}$ heteroaliphatic group having 1-10 heteroatoms independently selected from oxygen, nitrogen, sulfur, phosphorus and silicon, wherein one or more methylene units are optionally and independently replaced by an optionally substituted $C_{1-6}$ alkylene, $C_{1-6}$ alkenylene, —C≡C—, —$C(R')_2$—, -Cy-, —O—, —S—, —S—S—, —N(R')—, —C(O)—, —C(S)—, —C(NR')—, —C(O)N(R')—, —N(R')C(O)N(R')—, —N(R')C(O)—, —N(R')C(O)O—, —OC(O)N(R')—, —S(O)—, —$S(O)_2$—, —$S(O)_2N(R')$—, —$N(R')S(O)_2$—, —SC(O)—, —C(O)S—, —OC(O)—, or —C(O)O—;

$R^{5s}$ is R' or —OR';

$R^{2s}$ is —F, —CN, —$N_3$, —NO, —$N_{02}$, —R'—OR', —SR', —$N(R')_2$, —O-L-OR', —O-L-SR', or —O-L-N$(R')_2$, or $R^{2s}$ is L connecting C2 with C1, C2, C3, C4 or C5;

Cy- is an optionally substituted bivalent ring selected from 3-30 membered carbocyclylene, 6-30 membered arylene, 5-30 membered heteroarylene having 1-10 heteroatoms independently selected from oxygen, nitrogen and sulfur, and 3-30 membered heterocyclylene having 1-10 heteroatoms independently selected from oxygen, nitrogen, sulfur, phosphorus and silicon;

each of $R^1$, $R^2$, and $R^3$ is independently R', wherein two or three of $R^1$, $R^2$, and $R^3$ are taken together with their intervening atoms to form:

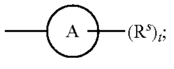

Ring A is an optionally substituted multivalent, monocyclic, bicyclic or polycyclic, saturated, partially unsaturated, or aryl 3-30 membered ring having, in addition to the intervening atoms, 0-10 heteroatoms independently selected from oxygen, nitrogen, sulfur, phosphorus and silicon;

each $R^s$ is independently R' or -L-R';

t is 0-5;

each R' is independently —R, —C(O)R, —$CO_2R$, or —$SO_2R$, or:

two or more R' are taken together with their intervening atoms to form an optionally substituted monocyclic, bicyclic or polycyclic, saturated, partially unsaturated, or aryl 3-30 membered ring having, in addition to the intervening atoms, 0-10 heteroatoms independently selected from oxygen, nitrogen, sulfur, phosphorus and silicon; and each R is independently hydrogen, or an optionally substituted group selected from $C_{1-30}$ aliphatic, $C_{1-30}$ heteroaliphatic having 1-10 heteroatoms independently selected from oxygen, nitrogen, sulfur, phosphorus and silicon, $C_{6-30}$ aryl, a 5-30 membered heteroaryl ring having 1-10 heteroatoms independently selected from oxygen, nitrogen, sulfur, phosphorus and silicon, and a 3-30 membered heterocyclic ring having 1-10 heteroatoms independently selected from oxygen, nitrogen, sulfur, phosphorus and silicon.

149. The compound of embodiment 148, wherein BA is substituted

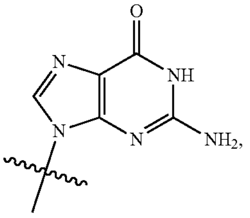

wherein $O^6$ is not substituted.

150. A compound having the structure of formula I:

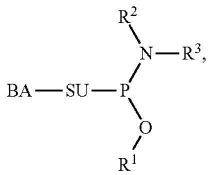

I or a salt thereof, wherein:

BA is

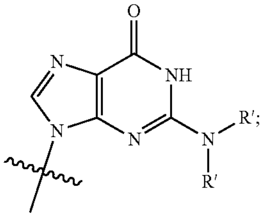

SU is -L-O— or

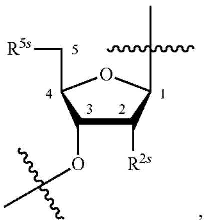

, wherein SU is connected to the phosphorus atom in formula I through the oxygen atom;

L is a covalent bond, or a bivalent, optionally substituted, linear or branched group selected from $C_{1-30}$ aliphatic and $C_{1-30}$ heteroaliphatic group having 1-10 heteroatoms independently selected from oxygen, nitrogen, sulfur, phosphorus and silicon, wherein one or more methylene units are optionally and independently replaced by an optionally substituted $C_{1-6}$ alkylene, $C_{1-6}$ alkenylene, —C≡C—, —C(R')$_2$—, -Cy-, —O—, —S—, —S—S—, —N(R')—, —C(O)—, —C(S)—, —C(NR')—, —C(O)N(R')—, —N(R')C(O)N(R')—, —N(R')C(O)—, —N(R')C(O)O—, —OC(O)N(R')—, —S(O)—, —S(O)$_2$—, —S(O)$_2$N(R')—, —N(R')S(O)$_2$—, —SC(O)—, —C(O)S—, —OC(O)—, or —C(O)O—;

$R^{5s}$ is R' or —OR';

$R^{2s}$ is —F, —CN, —$N_3$, —NO, —$NO_2$, —R'—OR', —SR', —N(R')$_2$, —O-L-OR', —O-L-SR', or —O-L-N(R')$_2$, or $R^{2s}$ is L connecting C2 with C1, C2, C3, C4 or C5;

Cy- is an optionally substituted bivalent ring selected from 3-30 membered carbocyclylene, 6-30 membered arylene, 5-30 membered heteroarylene having 1-10 heteroatoms independently selected from oxygen, nitrogen and sulfur, and 3-30 membered heterocyclylene having 1-10 heteroatoms independently selected from oxygen, nitrogen, sulfur, phosphorus and silicon;

each of $R^1$, $R^2$, and $R^3$ is independently R', wherein two or three of $R^1$, $R^2$, and $R^3$ are taken together with their intervening atoms to form:

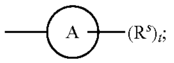

Ring A is an optionally substituted multivalent, monocyclic, bicyclic or polycyclic, saturated, partially unsaturated, or aryl 3-30 membered ring having, in addition to the intervening atoms, 0-10 heteroatoms independently selected from oxygen, nitrogen, sulfur, phosphorus and silicon;

each $R^s$ is independently R' or -L-R';

t is 0-5;

each R' is independently —R, —C(O)R, —$CO_2$R, or —$SO_2$R, or:

two or more R' are taken together with their intervening atoms to form an optionally substituted monocyclic, bicyclic or polycyclic, saturated, partially unsaturated, or aryl 3-30 membered ring having, in addition to the intervening atoms, 0-10 heteroatoms independently selected from oxygen, nitrogen, sulfur, phosphorus and silicon; and each R is independently hydrogen, or an optionally substituted group selected from $C_{1-30}$ aliphatic, $C_{1-30}$ heteroaliphatic having 1-10 heteroatoms independently selected from oxygen, nitrogen, sulfur, phosphorus and silicon, $C_{6-30}$ aryl, a 5-30 membered heteroaryl ring having 1-10 heteroatoms independently selected from oxygen, nitrogen, sulfur, phosphorus and silicon, and a 3-30 membered heterocyclic ring having 1-10 heteroatoms independently selected from oxygen, nitrogen, sulfur, phosphorus and silicon.

151. The compound of embodiment 150, wherein BA is

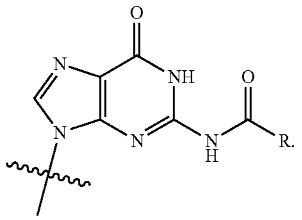

152. The compound of any one of embodiments 146-150, wherein BA is

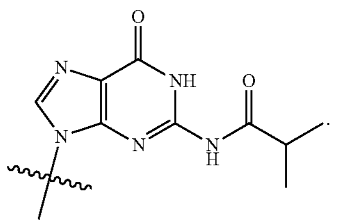 [SMILES: *n1cnc2c(=O)[nH]c(NC(=O)C(C)C)nc21]

153. A compound or a salt thereof, wherein the compound is an oligonucleotide comprising one or more base moieties BA, wherein BA is optionally protected

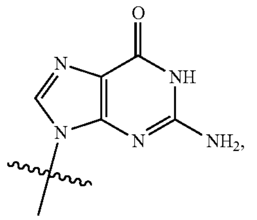

wherein $O^6$ is not protected.

154. The compound of embodiment 153, wherein BA is protected

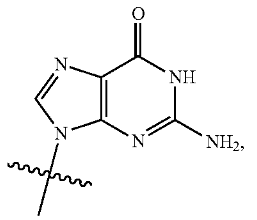

wherein $O^6$ is not protected.

155. A compound or a salt thereof, wherein the compound is an oligonucleotide comprising one or more base moieties BA, wherein BA is optionally substituted

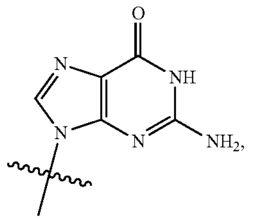

wherein $O^6$ is not substituted.

156. The compound of embodiment 155, wherein BA is substituted

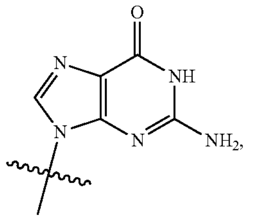

wherein $O^6$ is not protected.

157. The compound of any one of embodiments 153-155, wherein the oligonucleotide comprises one or more moieties having the structure of BA-SU—, wherein:

SU is -L-O— or

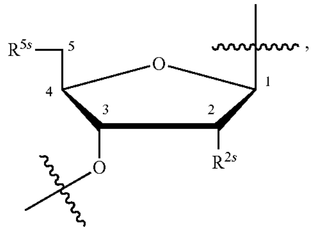

wherein SU is connected to a phosphorus atom through the 3'-oxygen atom;

L is a covalent bond, or a bivalent, optionally substituted, linear or branched group selected from $C_{1-30}$ aliphatic and $C_{1-30}$ heteroaliphatic group having 1-10 heteroatoms independently selected from oxygen, nitrogen, sulfur, phosphorus and silicon, wherein one or more methylene units are optionally and independently replaced by an optionally substituted $C_{1-6}$ alkylene, $C_{1-6}$ alkenylene, —C≡C—, —C(R')$_2$—, -Cy-, —O—, —S—, —S—S—, —N(R')—, —C(O)—, —C(S)—, —C(NR')—, —C(O)N(R')—, —N(R')C(O)N(R')—, —N(R')C(O)—, —N(R')C(O)O—, —OC(O)N(R')—, —S(O)—, —S(O)$_2$—, —S(O)$_2$N(R')—, —N(R')S(O)$_2$—, —SC(O)—, —C(O)S—, —OC(O)—, or —C(O)O—;

$R^{5s}$ is R' or —OR';

$R^{2s}$ is —F, —CN, —$N_3$, —NO, —$N_{02}$, —R'—OR', —SR', —N(R')$_2$, —O-L-OR', —O-L-SR', or —O-L-N(R')$_2$, or $R^{2s}$ is L connecting C2 with C1, C2, C3, C4 or C5;

-Cy- is an optionally substituted bivalent ring selected from 3-30 membered carbocyclylene, 6-30 membered arylene, 5-30 membered heteroarylene having 1-10 heteroatoms independently selected from oxygen, nitrogen and sulfur, and 3-30 membered heterocyclylene having 1-10 heteroatoms independently selected from oxygen, nitrogen, sulfur, phosphorus and silicon;

each R' is independently —R, —C(O)R, —$CO_2$R, or —$SO_2$R, or:

two or more R' are taken together with their intervening atoms to form an optionally substituted monocyclic, bicyclic or polycyclic, saturated, partially unsaturated, or aryl 3-30 membered ring having, in addition to the intervening atoms, 0-10 heteroatoms independently selected from oxygen, nitrogen, sulfur, phosphorus and silicon; and each R is independently hydrogen, or an optionally substituted group selected from $C_{1-30}$ aliphatic, $C_{1-30}$ heteroaliphatic having 1-10 heteroatoms independently selected from oxygen, nitrogen, sulfur, phosphorus and silicon, $C_{6-30}$ aryl, a 5-30 membered heteroaryl ring having 1-10 heteroatoms independently selected from oxygen, nitrogen, sulfur, phosphorus and silicon, and a 3-30 membered heterocyclic ring having 1-10 heteroatoms independently selected from oxygen, nitrogen, sulfur, phosphorus and silicon.

158. The compound of any one of embodiments 153-157, wherein the oligonucleotide comprises one or more moieties having the structure of

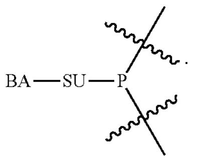

159. The compound of any one of embodiments 153-158, wherein the oligonucleotide comprises one or more moieties having the structure of

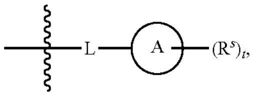

wherein:

L is a covalent bond, or a bivalent, optionally substituted, linear or branched group selected from $C_{1-30}$ aliphatic and $C_{1-30}$ heteroaliphatic group having 1-10 heteroatoms independently selected from oxygen, nitrogen, sulfur, phosphorus and silicon, wherein one or more methylene units are optionally and independently replaced by an optionally substituted $C_{1-6}$ alkylene, $C_{1-6}$ alkenylene, —C≡C—, —$C(R')_2$—, -Cy-, —O—, —S—, —S—S—, —N(R')—, —C(O)—, —C(S)—, —C(NR')—, —C(O)N(R')—, —N(R')C(O)N(R')—, —N(R')C(O)—, —N(R')C(O)O—, —OC(O)N(R')—, —S(O)—, —$S(O)_2$—, —$S(O)_2N(R')$—, —$N(R')S(O)_2$—, —SC(O)—, —C(O)S—, —OC(O)—, or —C(O)O—;

-Cy- is an optionally substituted bivalent ring selected from 3-30 membered carbocyclylene, 6-30 membered arylene, 5-30 membered heteroarylene having 1-10 heteroatoms independently selected from oxygen, nitrogen and sulfur, and 3-30 membered heterocyclylene having 1-10 heteroatoms independently selected from oxygen, nitrogen, sulfur, phosphorus and silicon;

Ring A is an optionally substituted multivalent, monocyclic, bicyclic or polycyclic, saturated, partially unsaturated, or aryl 3-30 membered ring having, in addition to the intervening atoms, 0-10 heteroatoms independently selected from oxygen, nitrogen, sulfur, phosphorus and silicon;

each $R^s$ is independently R' or -L-R';

t is 0-5;

each R' is independently —R, —C(O)R, —$CO_2$R, or —$SO_2$R, or:

two or more R' are taken together with their intervening atoms to form an optionally substituted monocyclic, bicyclic or polycyclic, saturated, partially unsaturated, or aryl 3-30 membered ring having, in addition to the intervening atoms, 0-10 heteroatoms independently selected from oxygen, nitrogen, sulfur, phosphorus and silicon; and each R is independently hydrogen, or an optionally substituted group selected from $C_{1-30}$ aliphatic, $C_{1-30}$ heteroaliphatic having 1-10 heteroatoms independently selected from oxygen, nitrogen, sulfur, phosphorus and silicon, $C_{6-30}$ aryl, a 5-30 membered heteroaryl ring having 1-10 heteroatoms independently selected from oxygen, nitrogen, sulfur, phosphorus and silicon, and a 3-30 membered heterocyclic ring having 1-10 heteroatoms independently selected from oxygen, nitrogen, sulfur, phosphorus and silicon.

160. The compound of any one of embodiments 153-159, wherein L is connected to a linkage phosphorus.

161. The compound of any one of embodiments 153-160, wherein

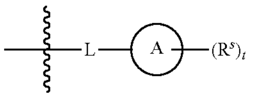

is asymmetric.

162. The compound of any one of embodiments 153-161, wherein

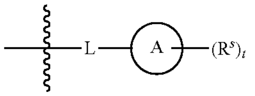

is a P-modification (not a nucleoside unit of the oligonucleotide).

163. The compound of any one of embodiments 153-162, wherein L is —O-L'-, wherein the L' is optionally substituted —CH2- or —C(Rs)2.

164. The compound of any one of embodiments 153-163, wherein L is —O-L'-, wherein L' is optionally substituted —CH2- or —C(Rs)2 and is bonded to Ring A.

165. The compound of any one of embodiments 153-164, wherein L is

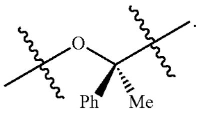 [SMILES: *O[C@](*)(C)c1ccccc1]

166. The compound ofany one of embodiments 153-164, wherein L is

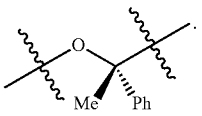 [SMILES: *O[C@@](*)(C)c1ccccc1]

167. The compound of any one of embodiments 153-164, wherein L is

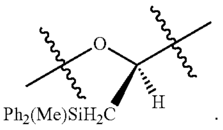

168. The compound of any one of embodiments 153-164, wherein L is

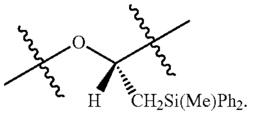

169. The compound of any one of embodiments 153-168, wherein Ring A is optionally substituted

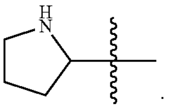 [SMILES: *C1CCCN1]

170. The compound of any one of embodiments 153-169, wherein Ring A is

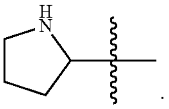

171. The compound of any one of embodiments 153-169, wherein Ring A is

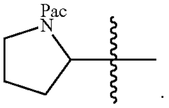

172. The compound of any one of embodiments 153-164, wherein

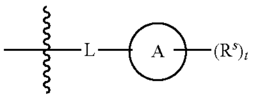

is optionally substituted P

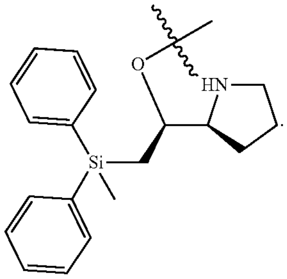 [SMILES: *O[C@H](C[Si](C)(c1ccccc1)c1ccccc1)[C@@H]1CCCN1]

173. The compound of any one of embodiments 153-164, wherein

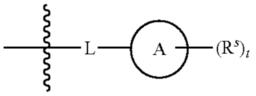

is optionally substituted

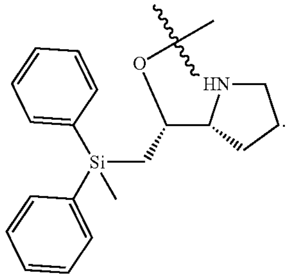 [SMILES: *O[C@@H](C[Si](C)(c1ccccc1)c1ccccc1)[C@H]1CCCN1]

174. The compound of any one of embodiments 153-164, wherein

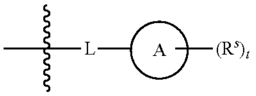

is optionally substituted

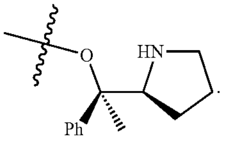 [SMILES: *O[C@](C)(c1ccccc1)[C@@H]1CCCN1]

175. The compound of any one of embodiments 153-164, wherein

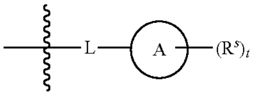

is optionally substituted

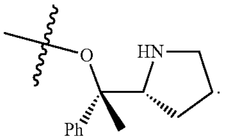 [SMILES: *O[C@@](C)(c1ccccc1)[C@H]1CCCN1]

176. The compound of any one of embodiments 153-164, wherein

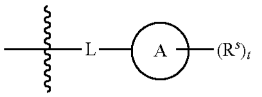

is

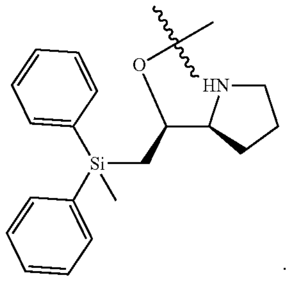 [SMILES: *O[C@H](C[Si](C)(c1ccccc1)c1ccccc1)[C@@H]1CCCN1]

177. The compound of any one of embodiments 153-164, wherein

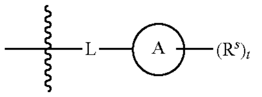

is

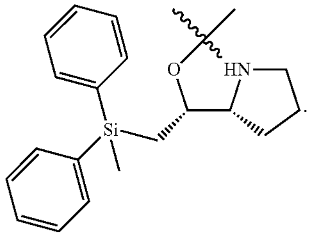 [SMILES: *O[C@@H](C[Si](C)(c1ccccc1)c1ccccc1)[C@H]1CCCN1]

178. The compound of any one of embodiments 153-164, wherein

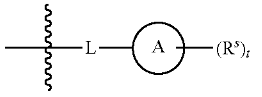

is

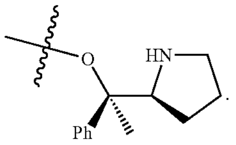 [SMILES: *O[C@](C)(c1ccccc1)[C@@H]1CCCN1]

179. The compound of any one of embodiments 153-164, wherein

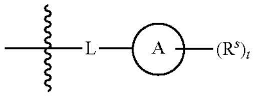

is

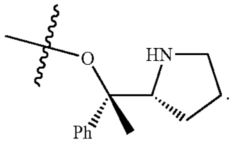 [SMILES: *O[C@@](C)(c1ccccc1)[C@H]1CCCN1]

180. The compound of any one of embodiments 172-179, wherein the amino group is protected.

181. The compound of any one of embodiments 172-179, wherein the amino group is protected by Pac-.

182. The compound of any one of embodiments 153-179, wherein the amino group is protected by Pac-.

183. The compound of any one of embodiments 153-182, wherein BA is

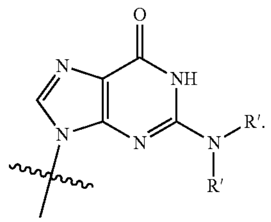

184. The compound of any one of embodiments 153-183, wherein BA is

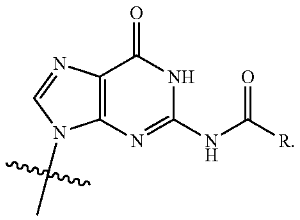

185. The compound of any one of embodiments 153-184, wherein BA is

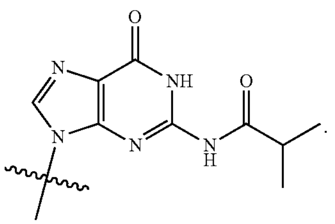 [SMILES: *n1cnc2c(=O)[nH]c(NC(=O)C(C)C)nc21]

186. The compound of any one of embodiments 153-185, wherein the oligonucleotide comprises about or more than 5, 6, 7, 8, 9, 10, 11, 12, 14, 14, 15, 16, 17, 18, 19, 20, 21, 22, 23, 24, 25, 26, 27, 28, 29, 30, 40, 50 bases.

187. The compound of any one of embodiments 153-186, wherein the oligonucleotide comprises about or more than 5, 6, 7, 8, 9, 10, 11, 12, 14, 14, 15, 16, 17, 18, 19, 20, 21, 22, 23, 24, 25, 26, 27, 28, 29, 30, 40, 50 chiral linkage phosphorus.

188. The compound of any one of embodiments 153-187, wherein the oligonucleotide comprises about or more than 5, 6, 7, 8, 9, 10, 11, 12, 14, 14, 15, 16, 17, 18, 19, 20, 21, 22, 23, 24, 25, 26, 27, 28, 29, 30, 40, 50 chirally controlled internucleotidic linkages.

189. The compound of any one of embodiments 153-188, wherein the oligonucleotide is connected to a solid support.

190. The compound of any one of embodiments 146-189, wherein SU is a modified or unmodified sugar moiety.

191. The compound of any one of embodiments 146-190, wherein SU is -L-O—.

192. The compound of any one of embodiments 146-190, wherein SU is -L-O—, and L is optionally substituted 5-10 membered heterocyclylene having one oxygen atom.

193. The compound of any one of embodiments 146-190, wherein SU is -L-O—, and L is optionally substituted 5-membered heterocyclylene having one oxygen atom.

194. The compound of any one of embodiments 146-190, wherein SU is -L-O—, and L is optionally substituted 7-10 membered bicyclic heterocyclylene having two oxygen atoms.

195. The compound of any one of embodiments 146-190, wherein SU is

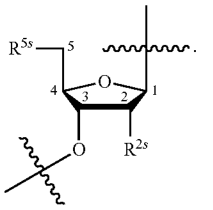

196. The compound of any one of embodiments 146-195, wherein R5s is —OR'.

197. The compound of any one of embodiments 146-196, wherein R5s is —ODMTr.

198. The compound of any one of embodiments 146-197, wherein R2s is —H.

199. The compound of any one of embodiments 146-197, wherein R2s is —F.

200. The compound of any one of embodiments 146-197, wherein R2s is —OR'.

201. The compound of embodiment 200, wherein R' is optionally substituted $C_{1-6}$ aliphatic.

202. The compound of embodiment 200 or 201, wherein R' is methyl.

203. The compound of any one of embodiments 146-197, wherein R2s is —O-L-OR'.

204. The compound of embodiment 203, wherein R2s is —$OCH_2CH_2OMe$.

205. The compound of any one of embodiments 146-197, wherein R2s is L connecting C2 with C1, C2, C3, C4 or C5.

206. The compound of any one of embodiments 146-197, wherein R2s is L connecting C2 with C4.

207. The compound of any one of embodiments 146-206, wherein L is (C2)-O-(optionally substituted methylene)-.

208. The compound of any one of embodiments 146-206, wherein L is (C2)-O-(unsubstituted methylene)-.

209. The compound of any one of embodiments 146-206, wherein L is (C2)-O-(optionally substituted methylene)-, wherein the methylene group is substituted with methyl.

210. The compound of any one of embodiments 146-207, wherein L is (C2)-O-(optionally substituted methylene)-, wherein the methylene group is substituted with ethyl.

211. The compound of embodiment 209 or 210, wherein the carbon atom of the methylene group is S.

212. The compound of embodiment 209 or 210, wherein the carbon atom of the methylene group is R.

213. The compound of any one of embodiments 146-212, wherein R1, R2, and R3 are taken together with their intervening nitrogen, phosphorus and oxygen atoms to form

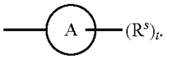

214. The compound of embodiment 213, wherein

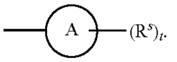

is asymmetric.

215. The compound of any one of embodiments 146-214, wherein Ring A comprises a ring system having the backbone structure of

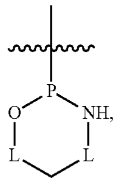

or

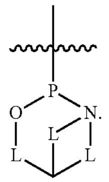

216. The compound of any one of embodiments 146-215, wherein Ring A comprises a ring system having the backbone structure of

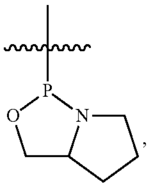

,

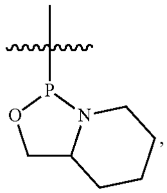

,

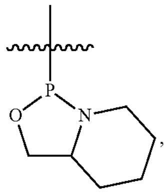

, or

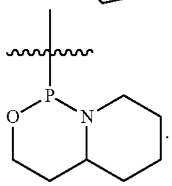

217. The compound of any one of embodiments 146-216, wherein Ring A comprises a ring system having the backbone structure of

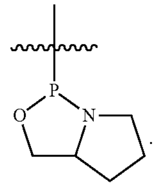 [SMILES: *P1OCC2CCCN21]

218. The compound of any one of embodiments 146-217, wherein t is 0.
219. The compound of any one of embodiments 146-217, wherein t is 1-5.
220. The compound of any one of embodiments 146-219, wherein one Rs is R' or -L-R' wherein -L- is a bivalent, optionally substituted C1-30 heteroaliphatic group.
221. The compound of any one of embodiments 146-220, wherein at least one Rs is not hydrogen.
222. The compound of any one of embodiments 146-220, wherein a Rs is —CH2Si(Ph)2CH3.
223. The compound of any one of embodiments 146-220, wherein a Rs is optionally substituted phenyl.
224. The compound of any one of embodiments 146-220, wherein a Rs is phenyl.
225. The compound of any one of embodiments 146-220, wherein a Rs is —H.
226. The compound of any one of embodiments 146-220, wherein a Rs is optionally substituted C1-6 aliphatic.
227. The compound of any one of embodiments 146-220, wherein a Rs is methyl.
228. The compound of any one of embodiments 146-227, wherein when used in oligonucleotide synthesis, the phosphoramidite can deliver diastereoselectivity greater than about 50%, 60%, 70%, 80%, 90%, 91%, 92%, 93%, 94%, 95%, 96%, 97%, 98% or 99% at the newly formed P-chiral center, optionally with greater than about 50%, 60%, 70%, 80%, 90%, 91%, 92%, 93%, 94%, 95%, 96%, 97%, 98% or 99% yield.
229. The compound of any one of embodiments 146-228, wherein the oligonucleotide synthesis method is one described in WO/2011/005761, WO/2013/012758, WO/2014/012081, WO/2015/107425, WO/2010/064146, WO/2014/010250, WO/2011/108682, WO/2012/039448, or WO/2012/073857.
230. The compound of any one of embodiments 146-221, wherein

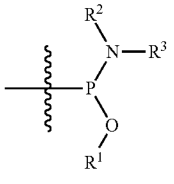

is

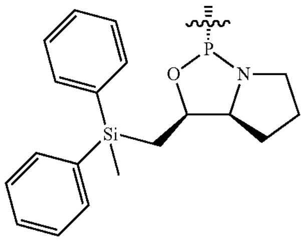

or

-continued

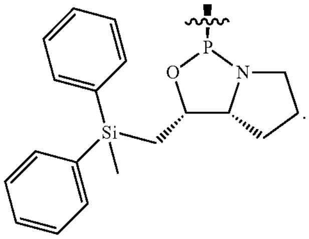

231. The compound of any one of embodiments 146-221, wherein

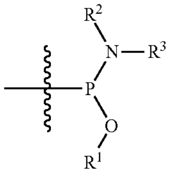

is

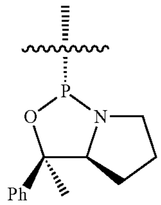

or

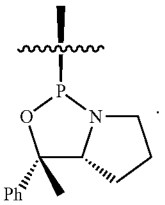

232. The compound of any one of embodiments 146-195, wherein the compound is a phosphoramidite from:

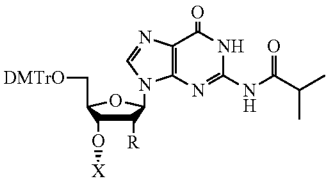

X =

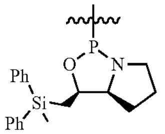

113: R = H
114: R = OMe
115: R = $OCH_2CH_2OMe$
116: R = F

X =

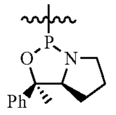

121: R = H
122: R = OMe
123: R = $OCH_2CH_2OMe$
124: R = F

-continued

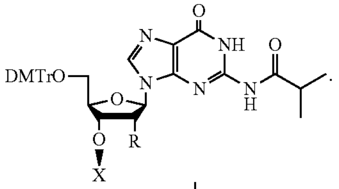

X = 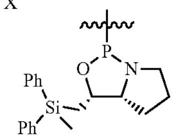

117: R = H
118: R = OMe
119: R = $OCH_2CH_2OMe$
120: R = F

X = 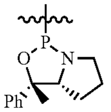

125: R = H
126: R = OMe
127: R = $OCH_2CH_2OMe$
128: R = F

233. The compound of any one of embodiments 146-195, wherein the compound is selected from compounds 113-128.

234. The compound of any one of embodiments 146-195, wherein the compound is

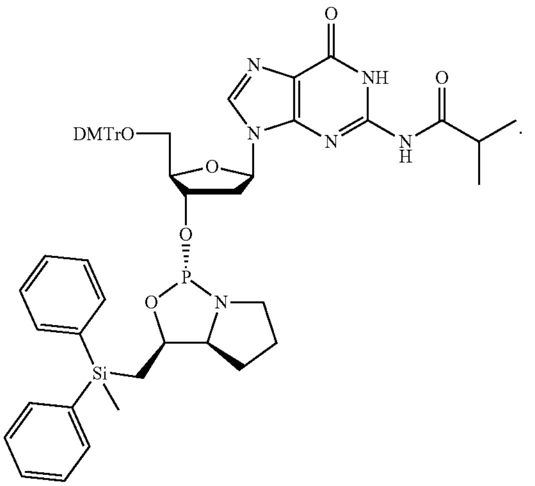

235. The compound of any one of embodiments 146-195, wherein the compound is

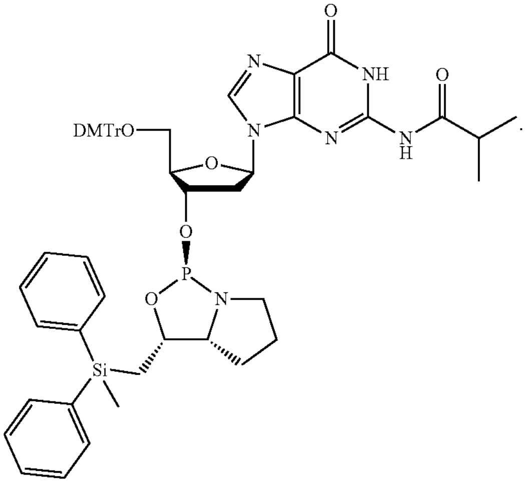

236. The compound of any one of embodiments 146-195, wherein the compound is

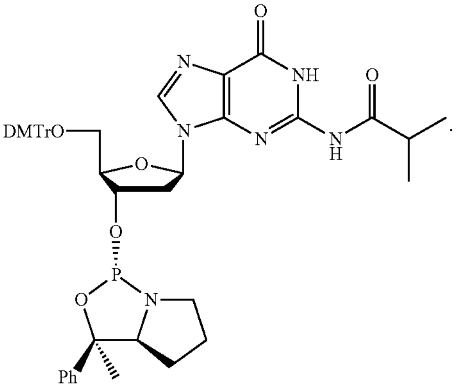

237. The compound of any one of embodiments 146-195, wherein the compound is

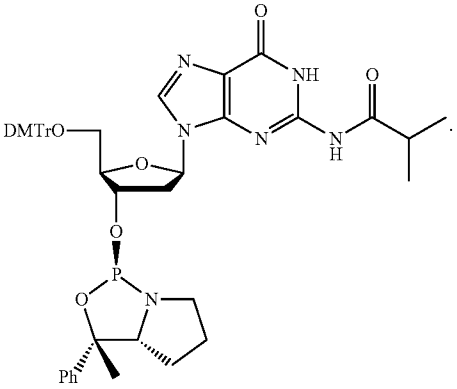

238. The compound of any one of embodiments 146-195, wherein the compound is

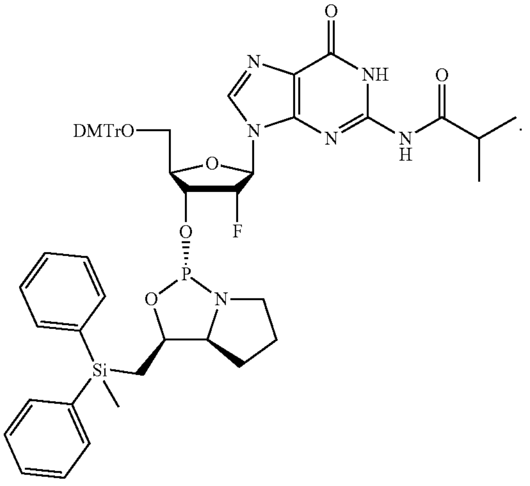

239. The compound of any one of embodiments 146-195, wherein the compound is

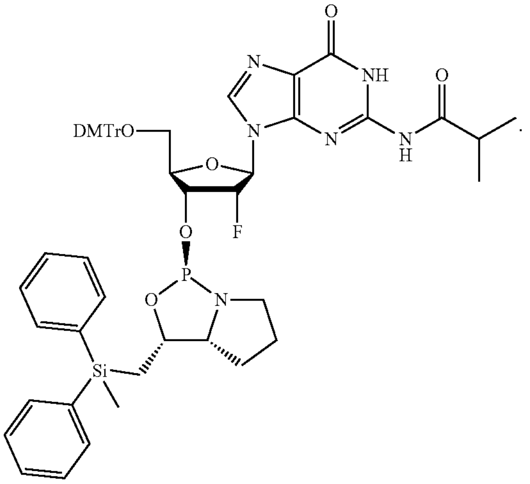

240. The compound of any one of embodiments 146-195, wherein the compound is

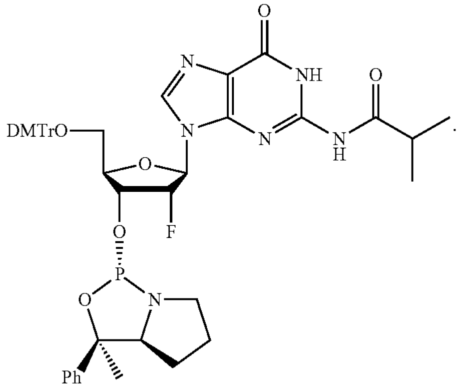

241. The compound of any one of embodiments 146-195, wherein the compound is

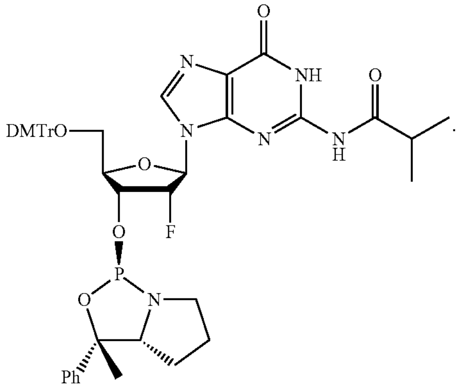

242. The compound of any one of embodiments 146-195, wherein the compound is

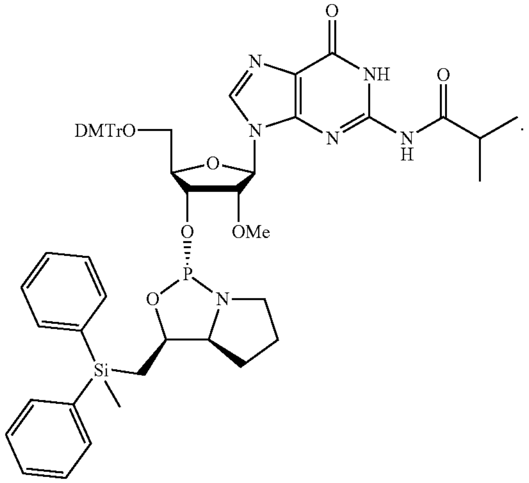

243. The compound of any one of embodiments 146-195, wherein the compound is

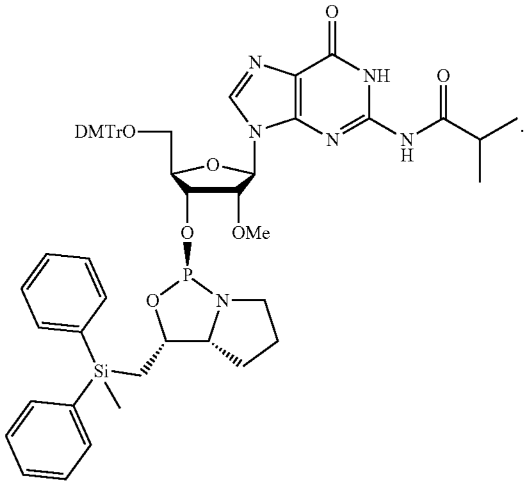

244. The compound of any one of embodiments 146-195, wherein the compound is

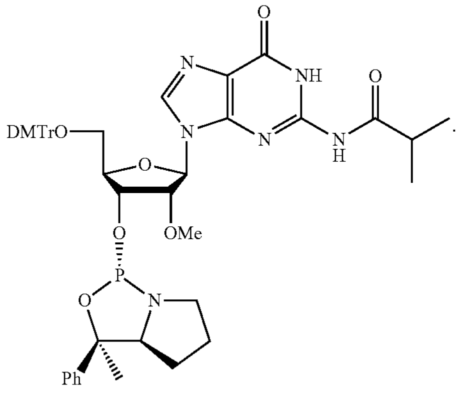

245. The compound of any one of embodiments 146-195, wherein the compound is

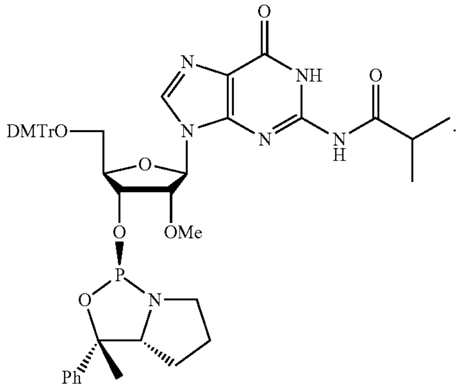

246. The compound of any one of embodiments 146-195, wherein the compound is

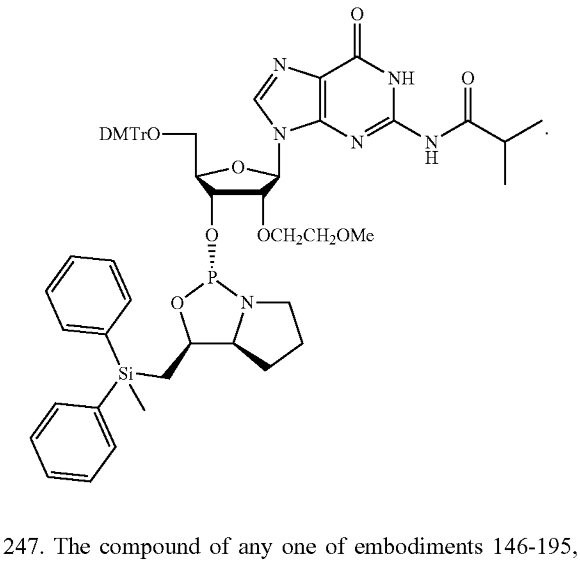

247. The compound of any one of embodiments 146-195, wherein the compound is

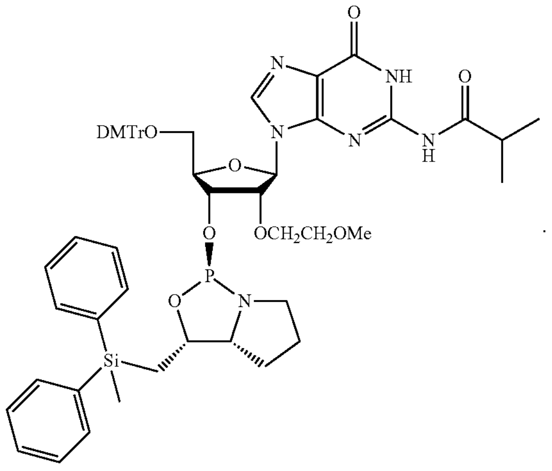

248. The compound of any one of embodiments 146-195, wherein the compound is

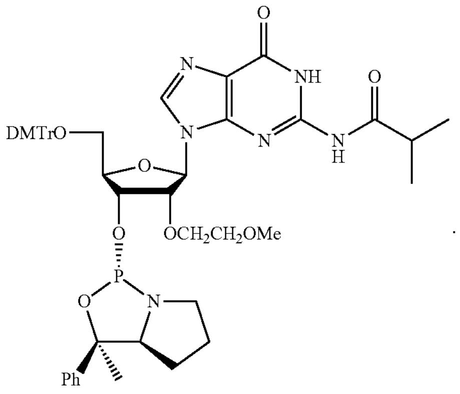

249. The compound of any one of embodiments 146-195, wherein the compound is

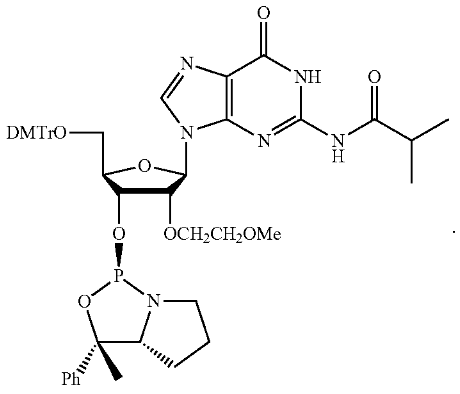

250. The compound of any one of embodiments 146-249, having a purity of at least 10%, 20%, 30%, 40%, 50%, 60%, 70%, 80%, 90%, 95%, 96%, 97%, 98%, 99% or 99.5%.

251. The compound of any one of embodiments 146-249, having a purity of at least 90%.

252. The compound of any one of embodiments 146-249, having a purity of at least 95%.

253. The compound of any one of embodiments 146-249, having a purity of at least 99%.
254. A method for preparing an oligonucleotide, comprising reacting a compound of any one of embodiments 1-253 to incorporate a nucleoside into an oligonucleotide.
255. A method for preparing an oligonucleotide, comprising providing a compound of any one of embodiments 1-253.
256. The method of any one of embodiments 254-255, wherein the oligonucleotide is WV-1510, WV-2378, WV-2380, WV-2417, WV-2418, WV-2601, WV-2602, WV-1092, WV-2528, WV-2531, WV-3047, or WV-3153.
257. The method of any one of embodiments 254-255, wherein the oligonucleotide is WV-2380, WV-2417, WV-2418, or WV-2603.
258. The method of any one of embodiments 254-255, wherein the oligonucleotide is WV-2601, WV-2602, WV-3473, WV-2528, WV-2531, WV-3047, or WV-3153.
259. The method of any one of embodiments 254-255, wherein the oligonucleotide is capable of hybridizing with a transcript of dystrophin, Malat1, myostatin, Huntingtin, a myostatin receptor, c-Myc, ActRIIB, ActRIIA, SMN2, K-Ras, beta-catenin, dystrophia myotonica protein kinase (DMPK), C9orf72, alpha-ENaC, beta-ENaC, ApoE4, ApoC3, FGF23, an epidermal growth factor receptor, Vascular Endothelial Growth Factor Receptor-2 (VEGFR-2), Proprotein convertase subtilisin/kexin type 9 (PCSK9), SMAD7 or KRT14 (Keratin 14), estrogen receptor (ER) and ERBB2, calcium signal transducer 2 (TACSTD2) or a mutant thereof.
260. The method of embodiment 259, wherein the oligonucleotide is capable of hybridizing with a transcript of dystrophin or a mutant thereof.
261. The method of embodiment 260, wherein the oligonucleotide is capable of hybridizing with a transcript of mutant dystrophin, and causes skip of one or more exons to produce a protein with higher activity than the protein produced absent skip of the one or more exons.
262. The method of embodiment 259, wherein the oligonucleotide is capable of hybridizing with a transcript of Huntingtin or a mutant thereof.
263. The method of embodiment 262, wherein the oligonucleotide is capable of hybridizing with a transcript of a mutant Huntingtin comprising expanded CAG repeats.
264. The method of any one of embodiments 254-263, wherein the method provides a chirally controlled oligonucleotide composition of the oligonucleotide.
265. A product or intermediate oligonucleotide of any one of embodiments 254-264, wherein the oligonucleotide is an oligonucleotide compound of any one of embodiments 153-227.

DETAILED DESCRIPTION OF CERTAIN EMBODIMENTS

1. Definitions

As used herein, the following definitions shall apply unless otherwise indicated. For purposes of this disclosure, the chemical elements are identified in accordance with the Periodic Table of the Elements, CAS version, Handbook of Chemistry and Physics, $75^{th}$ Ed. Additionally, general principles of organic chemistry are described in "Organic Chemistry", Thomas Sorrell, University Science Books, Sausalito: 1999, and "March's Advanced Organic Chemistry", $5^{th}$ Ed., Ed.: Smith, M. B. and March, J., John Wiley & Sons, New York: 2001, the entire contents of which are hereby incorporated by reference.

Aliphatic: As used herein, "aliphatic" means a straight-chain (i.e., unbranched) or branched, substituted or unsubstituted hydrocarbon chain that is completely saturated or that contains one or more units of unsaturation, or a substituted or unsubstituted monocyclic, bicyclic, or polycyclic hydrocarbon ring that is completely saturated or that contains one or more units of unsaturation, or combinations thereof. Unless otherwise specified, aliphatic groups contain 1-100 aliphatic carbon atoms. In some embodiments, aliphatic groups contain 1-20 aliphatic carbon atoms. In other embodiments, aliphatic groups contain 1-10 aliphatic carbon atoms. In other embodiments, aliphatic groups contain 1-9 aliphatic carbon atoms. In other embodiments, aliphatic groups contain 1-8 aliphatic carbon atoms. In other embodiments, aliphatic groups contain 1-7 aliphatic carbon atoms. In other embodiments, aliphatic groups contain 1-6 aliphatic carbon atoms. In still other embodiments, aliphatic groups contain 1-5 aliphatic carbon atoms, and in yet other embodiments, aliphatic groups contain 1, 2, 3, or 4 aliphatic carbon atoms. Suitable aliphatic groups include, but are not limited to, linear or branched, substituted or unsubstituted alkyl, alkenyl, alkynyl groups and hybrids thereof.

Alkyl: As used herein, the term "alkyl" is given its ordinary meaning in the art and may include saturated aliphatic groups, including straight-chain alkyl groups, branched-chain alkyl groups, cycloalkyl (alicyclic) groups, alkyl substituted cycloalkyl groups, and cycloalkyl substituted alkyl groups. In some embodiments, alkyl has 1-100 carbon atoms. In certain embodiments, a straight chain or branched chain alkyl has about 1-20 carbon atoms in its backbone (e.g., $C_1$-$C_{20}$ for straight chain, $C_2$-$C_{20}$ for branched chain), and alternatively, about 1-10. In some embodiments, cycloalkyl rings have from about 3-10 carbon atoms in their ring structure where such rings are monocyclic, bicyclic, or polycyclic, and alternatively about 5, 6 or 7 carbons in the ring structure. In some embodiments, an alkyl group may be a lower alkyl group, wherein a lower alkyl group comprises 1-4 carbon atoms (e.g., $C_1$-$C_4$ for straight chain lower alkyls).

Alkenyl: As used herein, the term "alkenyl" refers to an alkyl group, as defined herein, having one or more double bonds.

Alkynyl: As used herein, the term "alkynyl" refers to an alkyl group, as defined herein, having one or more triple bonds.

Aryl: The term "aryl" used alone or as part of a larger moiety as in "aralkyl," "aralkoxy," or "aryloxyalkyl," refers to monocyclic, bicyclic or polycyclic ring systems having a total of five to thirty ring members, wherein at least one ring in the system is aromatic. In some embodiments, an aryl group is a monocyclic, bicyclic or polycyclic ring system having a total of five to fourteen ring members, wherein at least one ring in the system is aromatic, and wherein each ring in the system contains 3 to 7 ring members. In some embodiments, an aryl group is a biaryl group. The term "aryl" may be used interchangeably with the term "aryl ring." In certain embodiments of the present disclosure, "aryl" refers to an aromatic ring system which includes, but not limited to, phenyl, biphenyl, naphthyl, binaphthyl, anthracyl and the like, which may bear one or more substituents. Also included within the scope of the term "aryl," as it is used herein, is a group in which an aromatic ring is fused to one or more non-aromatic rings, such as indanyl, phthalimidyl, naphthimidyl, phenanthridinyl, or tetrahydronaphthyl, and the like. In some embodiments, an aryl group has a radical or point of attachment on an aromatic ring.

Chiral control: As used herein, "chiral control" refers to an ability to control the stereochemical designation of a chiral linkage phosphorus in a chiral internucleotidic linkage within an oligonucleotide. In some embodiments, a control is achieved through a chiral element that is absent from the sugar and base moieties of an oligonucleotide, for example, in some embodiments, a control is achieved through use of one or more chiral auxiliaries during oligonucleotide preparation as exemplified in the present disclosure. In contrast to chiral control, a person having ordinary skill in the art appreciates that conventional oligonucleotide synthesis which does not use chiral auxiliaries cannot control stereochemistry at a chiral internucleotidic linkage if such conventional oligonucleotide synthesis is used to form the chiral internucleotidic linkage. In some embodiments, the stereochemical designation of each chiral linkage phosphorus in a chiral internucleotidic linkage within an oligonucleotide is controlled.

Chirally controlled oligonucleotide composition: The terms "chirally controlled oligonucleotide composition", "chirally controlled nucleic acid composition", and the like, as used herein, refers to a composition that comprises a plurality of oligonucleotides (or nucleic acids) which share 1) a common base sequence, 2) a common pattern of backbone linkages, and 3) a common pattern of backbone phosphorus modifications, wherein the plurality of oligonucleotides share the same stereochemistry at one or more chiral internucleotidic linkages (chirally controlled internucleotidic linkages), and the level of the plurality of oligonucleotides in the composition is pre-determined. In some embodiments, each chiral internucleotidic linkage is a chiral controlled internucleotidic linkage, and the composition is a completely chirally controlled oligonucleotide composition. In some embodiments, not all chiral internucleotidic linkages are chiral controlled internucleotidic linkages, and the composition is a partially chirally controlled oligonucleotide composition. In some embodiments, a chirally controlled oligonucleotide composition comprises predetermined levels of individual oligonucleotide or nucleic acids types. For instance, in some embodiments a chirally controlled oligonucleotide composition comprises one oligonucleotide type. In some embodiments, a chirally controlled oligonucleotide composition comprises more than one oligonucleotide type. In some embodiments, a chirally controlled oligonucleotide composition comprises multiple oligonucleotide types.

Cycloaliphatic: The term "cycloaliphatic," as used herein, refers to saturated or partially unsaturated aliphatic monocyclic, bicyclic, or polycyclic ring systems having, e.g., from 3 to 30, members, wherein the aliphatic ring system is optionally substituted. Cycloaliphatic groups include, without limitation, cyclopropyl, cyclobutyl, cyclopentyl, cyclopentenyl, cyclohexyl, cyclohexenyl, cycloheptyl, cycloheptenyl, cyclooctyl, cyclooctenyl, norbornyl, adamantyl, and cyclooctadienyl. In some embodiments, the cycloalkyl has 3-6 carbons. The terms "cycloaliphatic" may also include aliphatic rings that are fused to one or more aromatic or nonaromatic rings, such as decahydronaphthyl or tetrahydronaphthyl, where the radical or point of attachment is on the aliphatic ring. In some embodiments, a carbocyclic group is bicyclic. In some embodiments, a carbocyclic group is tricyclic. In some embodiments, a carbocyclic group is polycyclic. In some embodiments, "cycloaliphatic" (or "carbocycle" or "cycloalkyl") refers to a monocyclic $C_3$-$C_6$ hydrocarbon, or a $C_8$-$C_{10}$ bicyclic hydrocarbon that is completely saturated or that contains one or more units of unsaturation, but which is not aromatic, that has a single point of attachment to the rest of the molecule, or a $C_9$-$C_{16}$ tricyclic hydrocarbon that is completely saturated or that contains one or more units of unsaturation, but which is not aromatic, that has a single point of attachment to the rest of the molecule.

Halogen: The term "halogen" means F, Cl, Br, or I.

Heteroaliphatic: The term "heteroaliphatic" is given its ordinary meaning in the art and refers to aliphatic groups as described herein in which one or more carbon atoms is replaced with a heteroatom (e.g., oxygen, nitrogen, sulfur, silicon, phosphorus, and the like).

Heteroalkyl: The term "heteroalkyl" is given its ordinary meaning in the art and refers to alkyl groups as described herein in which one or more carbon atoms is replaced with a heteroatom (e.g., oxygen, nitrogen, sulfur, silicon, phosphorus, and the like). Examples of heteroalkyl groups include, but are not limited to, alkoxy, poly(ethylene glycol)-, alkyl-substituted amino, tetrahydrofuranyl, piperidinyl, morpholinyl, etc.

Heteroaryl: The terms "heteroaryl" and "heteroar-," used alone or as part of a larger moiety, e.g., "heteroaralkyl," or "heteroaralkoxy," refer to monocyclic, bicyclic or polycyclic ring systems having a total of five to thirty ring members, wherein at least one ring in the system is aromatic and at least one aromatic ring atom is a heteroatom. In some embodiments, a heteroaryl group is a group having 5 to 10 ring atoms (i.e., monocyclic, bicyclic or polycyclic), in some embodiments 5, 6, 9, or 10 ring atoms. In some embodiments, a heteroaryl group has 6, 10, or 14 $\pi$ electrons shared in a cyclic array; and having, in addition to carbon atoms, from one to five heteroatoms. Heteroaryl groups include, without limitation, thienyl, furanyl, pyrrolyl, imidazolyl, pyrazolyl, triazolyl, tetrazolyl, oxazolyl, isoxazolyl, oxadiazolyl, thiazolyl, isothiazolyl, thiadiazolyl, pyridyl, pyridazinyl, pyrimidinyl, pyrazinyl, indolizinyl, purinyl, naphthyridinyl, and pteridinyl. In some embodiments, a heteroaryl is a heterobiaryl group, such as bipyridyl and the like. The terms "heteroaryl" and "heteroar-", as used herein, also include groups in which a heteroaromatic ring is fused to one or more aryl, cycloaliphatic, or heterocyclyl rings, where the radical or point of attachment is on the heteroaromatic ring. Non-limiting examples include indolyl, isoindolyl, benzothienyl, benzofuranyl, dibenzofuranyl, indazolyl, benzimidazolyl, benzthiazolyl, quinolyl, isoquinolyl, cinnolinyl, phthalazinyl, quinazolinyl, quinoxalinyl, 4H-quinolizinyl, carbazolyl, acridinyl, phenazinyl, phenothiazinyl, phenoxazinyl, tetrahydroquinolinyl, tetrahydroisoquinolinyl, and pyrido[2,3-b]-1,4-oxazin-3(4H)-one. A heteroaryl group may be monocyclic, bicyclic or polycyclic. The term "heteroaryl" may be used interchangeably with the terms "heteroaryl ring," "heteroaryl group," or "heteroaromatic," any of which terms include rings that are optionally substituted. The term "heteroaralkyl" refers to an alkyl group substituted by a heteroaryl group, wherein the alkyl and heteroaryl portions independently are optionally substituted.

Heteroatom: The term "heteroatom" means an atom that is not carbon or hydrogen. In some embodiments, a heteroatom is oxygen, sulfur, nitrogen, phosphorus, or silicon (including any oxidized form of nitrogen, sulfur, phosphorus, or silicon; the quaternized form of any basic nitrogen or a substitutable nitrogen of a heterocyclic ring (for example, N as in 3,4-dihydro-2H-pyrrolyl), NH (as in pyrrolidinyl) or $NR^+$ (as in N-substituted pyrrolidinyl); etc.).

Heterocyclyl: As used herein, the terms "heterocycle," "heterocyclyl," "heterocyclic radical," and "heterocyclic ring" are used interchangeably and refer to a monocyclic, bicyclic or polycyclic ring moiety (e.g., 3-30 membered)

that is saturated or partially unsaturated and has one or more heteroatom ring atoms. In some embodiments, a heterocyclyl group is a stable 5- to 7-membered monocyclic or 7- to 10-membered bicyclic heterocyclic moiety that is either saturated or partially unsaturated, and having, in addition to carbon atoms, one or more, preferably one to four, heteroatoms, as defined above. When used in reference to a ring atom of a heterocycle, the term "nitrogen" includes substituted nitrogen. As an example, in a saturated or partially unsaturated ring having 0-3 heteroatoms selected from oxygen, sulfur or nitrogen, the nitrogen may be N (as in 3,4-dihydro-2H-pyrrolyl), NH (as in pyrrolidinyl), or $^{+}NR$ (as in N-substituted pyrrolidinyl). A heterocyclic ring can be attached to its pendant group at any heteroatom or carbon atom that results in a stable structure and any of the ring atoms can be optionally substituted. Examples of such saturated or partially unsaturated heterocyclic radicals include, without limitation, tetrahydrofuranyl, tetrahydrothienyl, pyrrolidinyl, piperidinyl, pyrrolinyl, tetrahydroquinolinyl, tetrahydroisoquinolinyl, decahydroquinolinyl, oxazolidinyl, piperazinyl, dioxanyl, dioxolanyl, diazepinyl, oxazepinyl, thiazepinyl, morpholinyl, and quinuclidinyl. The terms "heterocycle," "heterocyclyl," "heterocyclyl ring," "heterocyclic group," "heterocyclic moiety," and "heterocyclic radical," are used interchangeably herein, and also include groups in which a heterocyclyl ring is fused to one or more aryl, heteroaryl, or cycloaliphatic rings, such as indolinyl, 3H-indolyl, chromanyl, phenanthridinyl, or tetrahydroquinolinyl. A heterocyclyl group may be monocyclic, bicyclic or polycyclic. The term "heterocyclylalkyl" refers to an alkyl group substituted by a heterocyclyl, wherein the alkyl and heterocyclyl portions independently are optionally substituted.

Oligonucleotide type: As used herein, the phrase "oligonucleotide type" is used to define an oligonucleotide that has a particular base sequence, pattern of backbone linkages (i.e., pattern of internucleotidic linkage types, for example, phosphate, phosphorothioate, etc.), pattern of backbone chiral centers (i.e. pattern of linkage phosphorus stereochemistry (Rp/Sp)), and pattern of backbone phosphorus modifications (e.g., pattern of "$-XLR^1$" groups in formula I). In some embodiments, oligonucleotides of a common designated "type" are structurally identical to one another.

Partially unsaturated: As used herein, the term "partially unsaturated" refers to a moiety that includes at least one double or triple bond. The term "partially unsaturated" is intended to encompass groups having multiple sites of unsaturation, but is not intended to include aryl or heteroaryl moieties.

Pharmaceutical composition: As used herein, the term "pharmaceutical composition" refers to an active agent, formulated together with one or more pharmaceutically acceptable carriers. In some embodiments, active agent is present in unit dose amount appropriate for administration in a therapeutic regimen that shows a statistically significant probability of achieving a predetermined therapeutic effect when administered to a relevant population. In some embodiments, pharmaceutical compositions may be specially formulated for administration in solid or liquid form, including those adapted for the following: oral administration, for example, drenches (aqueous or non-aqueous solutions or suspensions), tablets, e.g., those targeted for buccal, sublingual, and systemic absorption, boluses, powders, granules, pastes for application to the tongue; parenteral administration, for example, by subcutaneous, intramuscular, intravenous or epidural injection as, for example, a sterile solution or suspension, or sustained-release formulation; topical application, for example, as a cream, ointment, or a controlled-release patch or spray applied to the skin, lungs, or oral cavity; intravaginally or intrarectally, for example, as a pessary, cream, or foam; sublingually; ocularly; transdermally; or nasally, pulmonary, and to other mucosal surfaces.

Pharmaceutically acceptable: As used herein, the phrase "pharmaceutically acceptable" refers to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

Pharmaceutically acceptable carrier: As used herein, the term "pharmaceutically acceptable carrier" means a pharmaceutically-acceptable material, composition or vehicle, such as a liquid or solid filler, diluent, excipient, or solvent encapsulating material, involved in carrying or transporting the subject compound from one organ, or portion of the body, to another organ, or portion of the body. Each carrier must be "acceptable" in the sense of being compatible with the other ingredients of the formulation and not injurious to the patient. Some examples of materials which can serve as pharmaceutically-acceptable carriers include: sugars, such as lactose, glucose and sucrose; starches, such as corn starch and potato starch; cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; alginic acid; pyrogen-free water; isotonic saline; Ringer's solution; ethyl alcohol; pH buffered solutions; polyesters, polycarbonates and/or polyanhydrides; and other nontoxic compatible substances employed in pharmaceutical formulations.

Pharmaceutically acceptable salt: The term "pharmaceutically acceptable salt", as used herein, refers to salts of such compounds that are appropriate for use in pharmaceutical contexts, i.e., salts which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art. For example, S. M. Berge, et al. describes pharmaceutically acceptable salts in detail in J. Pharmaceutical Sciences, 66: 1-19 (1977). In some embodiments, pharmaceutically acceptable salts include, but are not limited to, nontoxic acid addition salts, which are salts of an amino group formed with inorganic acids such as hydrochloric acid, hydrobromic acid, phosphoric acid, sulfuric acid and perchloric acid or with organic acids such as acetic acid, maleic acid, tartaric acid, citric acid, succinic acid or malonic acid or by using other methods used in the art such as ion exchange. In some embodiments, pharmaceutically acceptable salts include, but are not limited to, adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. In some embodiments, pharmaceutically acceptable salts include, but are not limited to, nontoxic base addition salts, such as those formed by acidic groups of provided compounds (e.g., phosphate linkage groups of oligonucleotides, phosphorothioate linkage groups of oligonucleotides, etc.) with bases. Representative alkali or alkaline earth metal salts include salts of sodium, lithium, potassium, calcium, magnesium, and the like. In some embodiments, pharmaceutically acceptable salts are ammonium salts. In some embodiments, pharmaceutically acceptable salts include, when appropriate, nontoxic ammonium, quaternary ammonium, and amine cations formed using counterions such as halide, hydroxide, carboxylate, sulfate, phosphate, nitrate, alkyl having from 1 to 6 carbon atoms, sulfonate and aryl sulfonate.

Predetermined: By predetermined (or pre-determined) is meant deliberately selected, for example as opposed to randomly occurring or achieved without control. Those of ordinary skill in the art, reading the present specification, will appreciate that the present disclosure provides technologies that permit selection of particular chemistry and/or stereochemistry features to be incorporated into oligonucleotide compositions, and further permits controlled preparation of oligonucleotide compositions having such chemistry and/or stereochemistry features. Such provided compositions are "predetermined" as described herein. Compositions that may contain certain oligonucleotides because they happen to have been generated through a process that cannot be controlled to intentionally generate the particular chemistry and/or stereochemistry features is not a "predetermined" composition. In some embodiments, a predetermined composition is one that can be intentionally reproduced (e.g., through repetition of a controlled process). In some embodiments, a predetermined level of a plurality of oligonucleotides in a composition means that the absolute amount, and/or the relative amount (ratio, percentage, etc.) of the plurality of oligonucleotides in the composition is controlled.

Protecting Group: The phrase "protecting group," as used herein, refers to temporary substituents which protect a potentially reactive functional group from undesired chemical transformations. Examples of such protecting groups include esters of carboxylic acids, silyl ethers of alcohols, and acetals and ketals of aldehydes and ketones, respectively. A "Si protecting group" is a protecting group comprising a Si atom, such as Si-trialkyl (e.g., trimethylsilyl, tributylsilyl, t-butyldimethylsilyl), Si-triaryl, Si-alkyl-diphenyl (e.g., t-butyldiphenylsilyl), or Si-aryl-dialkyl (e.g., Si-phenyldialkyl). Generally, a Si protecting group is attached to an oxygen atom. The field of protecting group chemistry has been reviewed (Greene, T. W.; Wuts, P. G. M. Protective Groups in Organic Synthesis, 2nd ed.; Wiley: New York, 1991). Such protecting groups (and associated protected moieties) are described in detail below.

Protected hydroxyl groups are well known in the art and include those described in detail in Protecting Groups in Organic Synthesis, T. W. Greene and P. G. M. Wuts, 3rd edition, John Wiley & Sons, 1999, the entirety of which is incorporated herein by reference. Examples of suitably protected hydroxyl groups further include, but are not limited to, esters, carbonates, sulfonates, allyl ethers, ethers, silyl ethers, alkyl ethers, arylalkyl ethers, and alkoxyalkyl ethers. Examples of suitable esters include formates, acetates, proprionates, pentanoates, crotonates, and benzoates. Specific examples of suitable esters include formate, benzoyl formate, chloroacetate, trifluoroacetate, methoxyacetate, triphenylmethoxyacetate, p-chlorophenoxyacetate, 3-phenylpropionate, 4-oxopentanoate, 4,4-(ethylenedithio) pentanoate, pivaloate (trimethylacetate), crotonate, 4-methoxy-crotonate, benzoate, p-benznylbenzoate, 2,4,6-trimethylbenzoate. Examples of suitable carbonates include 9-fluorenylmethyl, ethyl, 2,2,2-trichloroethyl, 2-(trimethylsilyl)ethyl, 2-(phenylsulfonyl)ethyl, vinyl, allyl, and p-nitrobenzyl carbonate. Examples of suitable silyl ethers include trimethylsilyl, triethylsilyl, t-butyldimethylsilyl, t-butyldiphenylsilyl, triisopropylsilyl ether, and other trialkylsilyl ethers. Examples of suitable alkyl ethers include methyl, benzyl, p-methoxybenzyl, 3,4-dimethoxybenzyl, trityl, t-butyl, and allyl ether, or derivatives thereof. Alkoxyalkyl ethers include acetals such as methoxymethyl, methylthiomethyl, (2-methoxyethoxy)methyl, benzyloxymethyl, beta-(trimethylsilyl)ethoxymethyl, and tetrahydropyran-2-yl ether. Examples of suitable arylalkyl ethers include benzyl, p-methoxybenzyl (MPM), 3,4-dimethoxybenzyl, O-nitrobenzyl, p-nitrobenzyl, p-halobenzyl, 2,6-dichlorobenzyl, p-cyanobenzyl, 2- and 4-picolyl ethers.

Protected amines are well known in the art and include those described in detail in Greene (1999). Suitable mono-protected amines further include, but are not limited to, aralkylamines, carbamates, allyl amines, amides, and the like. Examples of suitable mono-protected amino moieties include t-butyloxycarbonylamino (—NHBOC), ethyloxycarbonylamino, methyloxycarbonylamino, trichloroethyloxycarbonylamino, allyloxycarbonylamino (—NHAlloc), benzyloxocarbonylamino (—NHCBZ), allylamino, benzylamino (—NHBn), fluorenylmethylcarbonyl (—NHFmoc), formamido, acetamido, chloroacetamido, dichloroacetamido, trichloroacetamido, phenylacetamido, trifluoroacetamido, benzamido, t-butyldiphenylsilyl, and the like. Suitable di-protected amines include amines that are substituted with two substituents independently selected from those described above as mono-protected amines, and further include cyclic imides, such as phthalimide, maleimide, succinimide, and the like. Suitable di-protected amines also include pyrroles and the like, 2,2,5,5-tetramethyl-[1,2,5] azadisilolidine and the like, and azide.

Protected aldehydes are well known in the art and include those described in detail in Greene (1999). Suitable protected aldehydes further include, but are not limited to, acyclic acetals, cyclic acetals, hydrazones, imines, and the like. Examples of such groups include dimethyl acetal, diethyl acetal, diisopropyl acetal, dibenzyl acetal, bis(2-nitrobenzyl) acetal, 1,3-dioxanes, 1,3-dioxolanes, semicarbazones, and derivatives thereof.

Protected carboxylic acids are well known in the art and include those described in detail in Greene (1999). Suitable protected carboxylic acids further include, but are not limited to, optionally substituted $C_{1-6}$ aliphatic esters, optionally substituted aryl esters, silyl esters, activated esters, amides, hydrazides, and the like. Examples of such ester groups include methyl, ethyl, propyl, isopropyl, butyl, isobutyl, benzyl, and phenyl ester, wherein each group is optionally substituted. Additional suitable protected carboxylic acids include oxazolines and ortho esters.

Protected thiols are well known in the art and include those described in detail in Greene (1999). Suitable protected thiols further include, but are not limited to, disulfides, thioethers, silyl thioethers, thioesters, thiocarbonates, and thiocarbamates, and the like. Examples of such groups include, but are not limited to, alkyl thioethers, benzyl and substituted benzyl thioethers, triphenylmethyl thioethers, and trichloroethoxycarbonyl thioester, to name but a few.

Substitution: As described herein, compounds of the disclosure may contain optionally substituted and/or substituted moieties. In general, the term "substituted," whether preceded by the term "optionally" or not, means that one or more hydrogens of the designated moiety are replaced with a suitable substituent. Unless otherwise indicated, an "optionally substituted" group may have a suitable substituent at each substitutable position of the group, and when more than one position in any given structure may be substituted with more than one substituent selected from a specified group, the substituent may be either the same or different at every position. Combinations of substituents envisioned by this disclosure are preferably those that result in the formation of stable or chemically feasible compounds. The term "stable," as used herein, refers to compounds that are not substantially altered when subjected to conditions to allow for their production, detection, and, in certain embodiments, their recovery, purification, and use for one or more of the purposes disclosed herein.

Suitable monovalent substituents include halogen; $-(CH_2)_{0-4}R^{\circ}$; $-(CH_2)_{0-4}OR^{\circ}$; $-O(CH_2)_{0-4}R^{\circ}$, $-O-(CH_2)_{0-4}C(O)OR^{\circ}$; $-(CH_2)_{0-4}CH(OR^{\circ})_2$; $-(CH_2)_{0-4}Ph$, which may be substituted with $R^{\circ}$; $-(CH_2)_{0-4}O(CH_2)_{0-1}Ph$ which may be substituted with $R^{\circ}$; $-CH{=}CHPh$, which may be substituted with $R^{\circ}$; $-(CH_2)_{0-4}O(CH_2)_{0-1}$-pyridyl which may be substituted with $R^{\circ}$; $-NO_2$; $-CN$; $-N_3$; $-(CH_2)_{0-4}N(R^{\circ})_2$; $-(CH_2)_{0-4}N(R^{\circ})C(O)R^{\circ}$; $-N(R^{\circ})C(S)R^{\circ}$; $-(CH_2)_{0-4}N(R^{\circ})C(O)NR^{\circ}_2$; $-N(R^{\circ})C(S)NR^{\circ}_2$; $-(CH_2)_{0-4}N(R^{\circ})C(O)OR^{\circ}$; $-N(R^{\circ})N(R^{\circ})C(O)R^{\circ}$; $-N(R^{\circ})N(R^{\circ})C(O)NR^{\circ}_2$; $-N(R^{\circ})N(R^{\circ})C(O)OR^{\circ}$; $-(CH_2)_{0-4}C(O)R^{\circ}$; $-C(S)R^{\circ}$; $-(CH_2)_{0-4}C(O)OR^{\circ}$; $-(CH_2)_{0-4}C(O)SR^{\circ}$; $-(CH_2)_{0-4}C(O)OSiR^{\circ}_3$; $-(CH_2)_{0-4}OC(O)R^{\circ}$; $-OC(O)(CH_2)_{0-4}SR$, $-SC(S)SR^{\circ}$; $-(CH_2)_{0-4}SC(O)R^{\circ}$; $-(CH_2)_{0-4}C(O)NR^{\circ}_2$; $-C(S)NR^{\circ}_2$; $-C(S)SR^{\circ}$; $-SC(S)SR^{\circ}$, $-(CH_2)_{0-4}OC(O)NR^{\circ}_2$; $-C(O)N(OR^{\circ})R^{\circ}$; $-C(O)C(O)R^{\circ}$; $-C(O)CH_2C(O)R^{\circ}$; $-C(NOR^{\circ})R^{\circ}$; $-(CH_2)_{0-4}SSR^{\circ}$; $-(CH_2)_{0-4}S(O)_2R^{\circ}$; $-(CH_2)_{0-4}S(O)_2OR^{\circ}$; $-(CH_2)_{0-4}OS(O)_2R^{\circ}$; $-S(O)_2NR^{\circ}_2$; $-(CH_2)_{0-4}S(O)R^{\circ}$; $-N(R^{\circ})S(O)_2NR^{\circ}_2$; $-N(R^{\circ})S(O)_2R^{\circ}$; $-N(OR^{\circ})R^{\circ}$; $-C(NH)NR^{\circ}_2$; $-P(O)_2R^{\circ}$; $-P(O)R^{\circ}_2$; $-OP(O)R^{\circ}_2$; $-OP(O)(OR^{\circ})_2$; $-SiR^{\circ}_3$; $-OSiR^{\circ}_3$; $-(C_{1-4}$ straight or branched alkylene)$O-N(R^{\circ})_2$; or $-(C_{1-4}$ straight or branched alkylene)$C(O)O-N(R^{\circ})_2$, wherein each $R^{\circ}$ may be substituted as defined below and is independently hydrogen, $C_{1-20}$ aliphatic, $C_{1-20}$ heteroaliphatic having 1-5 heteroatoms independently selected from nitrogen, oxygen, sulfur, silicon and phosphorus, $-CH_2-(C_{6-14}$ aryl), $-O(CH_2)_{0-1}(C_{6-14}$ aryl), $-CH_2$-(5-14 membered heteroaryl ring), a 5-20 membered, monocyclic, bicyclic, or polycyclic, saturated, partially unsaturated or aryl ring having 0-5 heteroatoms independently selected from nitrogen, oxygen, sulfur, silicon and phosphorus, or, notwithstanding the definition above, two independent occurrences of $R^{\circ}$, taken together with their intervening atom(s), form a 5-20 membered, monocyclic, bicyclic, or polycyclic, saturated, partially unsaturated or aryl ring having 0-5 heteroatoms independently selected from nitrogen, oxygen, sulfur, silicon and phosphorus, which may be substituted as defined below.

Suitable monovalent substituents on $R^{\circ}$ (or the ring formed by taking two independent occurrences of $R^{\circ}$ together with their intervening atoms), are independently halogen, $-(CH_2)_{0-2}R^{\bullet}$, -(halo$R^{\bullet}$), $-(CH_2)_{0-2}OH$, $-(CH_2)_{0-2}OR^{\bullet}$, $-(CH_2)_{0-2}CH(OR^{\bullet})_2$; $-O$(halo$R^{\bullet}$), $-CN$, $-N_3$, $-(CH_2)_{0-2}C(O)R^{\bullet}$, $-(CH_2)_{0-2}C(O)OH$, $-(CH_2)_{0-2}C(O)OR^{\bullet}$, $-(CH_2)_{0-2}SR^{\bullet}$, $-(CH_2)_{0-2}SH$, $-(CH_2)_{0-2}NH_2$, $-(CH_2)_{0-2}NHR^{\bullet}$, $-(CH_2)_{0-2}NR^{\bullet}_2$, $-NO_2$, $-SiR^{\bullet}_3$, $-OSiR^{\bullet}_3$, $-C(O)SR^{\bullet}$, $-(C_{1-4}$ straight or branched alkylene)$C(O)OR^{\bullet}$, or $-SSR^{\bullet}$ wherein each $R^{\bullet}$ is unsubstituted or where preceded by "halo" is substituted only with one or more halogens, and is independently selected from $C_{1-4}$ aliphatic, $-CH_2Ph$, $-O(CH_2)_{0-1}Ph$, or a 5-6-membered saturated, partially unsaturated, or aryl ring having 0-4 heteroatoms independently selected from nitrogen, oxygen, and sulfur. Suitable divalent substituents on a saturated carbon atom of $R^{\circ}$ include $=O$ and $=S$.

Suitable divalent substituents include the following: $=O$, $=S$, $=NNR^*_2$, $=NNHC(O)R^*$, $=NNHC(O)OR^*$, $=NNHS(O)_2R^*$, $=NR^*$, $=NOR^*$, $-O(C(R^*_2))_{2-3}O-$, or $-S(C(R^*_2))_{2-3}S-$, wherein each independent occurrence of $R^*$ is selected from hydrogen, $C_{1-6}$ aliphatic which may be substituted as defined below, or an unsubstituted 5-6-membered saturated, partially unsaturated, or aryl ring having 0-4 heteroatoms independently selected from nitrogen, oxygen, and sulfur. Suitable divalent substituents that are bound to vicinal substitutable carbons of an "optionally substituted" group include: $-O(CR^*_2)_{2-3}O-$, wherein each independent occurrence of $R^*$ is selected from hydrogen, $C_{1-6}$ aliphatic which may be substituted as defined below, or an unsubstituted 5-6-membered saturated, partially unsaturated, or aryl ring having 0-4 heteroatoms independently selected from nitrogen, oxygen, and sulfur.

Suitable substituents on the aliphatic group of $R^*$ include halogen, $-R^{\bullet}$, -(halo$R^{\bullet}$), $-OH$, $-OR^{\bullet}$, $-O$(halo$R^{\bullet}$), $-CN$, $-C(O)OH$, $-C(O)OR^{\bullet}$, $-NH_2$, $-NHR^{\bullet}$, $-NR^{\bullet}_2$, or $-NO_2$, wherein each $R^{\bullet}$ is unsubstituted or where preceded by "halo" is substituted only with one or more halogens, and is independently $C_{1-4}$ aliphatic, $-CH_2Ph$, $-O(CH_2)_{0-1}Ph$, or a 5-6-membered saturated, partially unsaturated, or aryl ring having 0-4 heteroatoms independently selected from nitrogen, oxygen, and sulfur.

In some embodiments, suitable substituents on a substitutable nitrogen include $-R^{\dagger}$, $-NR^{\dagger}_2$, $-C(O)R^{\dagger}$, $-C(O)OR^{\dagger}$, $-C(O)C(O)R^{\dagger}$, $-C(O)CH_2C(O)R^{\dagger}$, $-S(O)_2R^{\dagger}$, $-S(O)_2NR^{\dagger}_2$, $-C(S)NR^{\dagger}_2$, $-C(NH)NR^{\dagger}_2$, or $-N(R^{\dagger})S(O)_2R^{\dagger}$; wherein each RT is independently hydrogen, $C_{1-6}$ aliphatic which may be substituted as defined below, unsubstituted $-OPh$, or an unsubstituted 5-6-membered saturated, partially unsaturated, or aryl ring having 0-4 heteroatoms independently selected from nitrogen, oxygen, and sulfur, or, notwithstanding the definition above, two independent occurrences of Rt, taken together with their intervening atom(s) form an unsubstituted 3-12-membered saturated, partially unsaturated, or aryl mono- or bicyclic ring having 0-4 heteroatoms independently selected from nitrogen, oxygen, and sulfur.

Suitable substituents on the aliphatic group of $R^{\dagger}$ are independently halogen, $-R^{\bullet}$, -(halo$R^{\bullet}$), $-OH$, $-OR^{\bullet}$, $-O$(halo$R^{\bullet}$), $-CN$, $-C(O)OH$, $-C(O)OR^{\bullet}$, $-NH_2$, $-NHR^{\bullet}$, $-NR'_2$, or $-NO_2$, wherein each $R^{\bullet}$ is unsubstituted or where preceded by "halo" is substituted only with one or more halogens, and is independently $C_{1-4}$ aliphatic, $-CH_2Ph$, $-O(CH_2)_{0-1}Ph$, or a 5-6-membered saturated, partially unsaturated, or aryl ring having 0-4 heteroatoms independently selected from nitrogen, oxygen, and sulfur.

Unsaturated: The term "unsaturated" as used herein, means that a moiety has one or more units of unsaturation.

2. Detailed Description of Certain Embodiments

Phosphoramidites have a variety of applications; for example, nucleoside phosphoramidites are widely used as monomers for oligonucleotide synthesis. Many technologies for preparing phosphoramidites, however, suffer from low yields and/or purity.

Among other things, the present disclosure encompasses the recognition that in some instances, a low yield and/or purity can be due to the purification process when a phosphoramidite product is separated from other substances, e.g., reaction byproducts formed during formation of the phosphoramidite product, e.g., work-ups after formation of the phosphoramidite product. In some embodiments, work-ups in typical conventional preparations comprise washing a preparation comprising a phosphoramidite product and one or more reaction byproducts of the product's synthesis using a material amount of an aqueous solvent (optionally having one or more solute, e.g., $NaHCO_3$, NaCl, etc.), followed by extraction(s) of the resulting aqueous phase using an organic extraction solvent in order to recover phosphoramidite lost during the washes. In some embodiments, extractions are performed with a halogenated solvent. In some embodiments, a halogenated solvent is chloroform.

Among other things, the present disclosure recognizes that exposure to material amounts of water and/or extractions with organic solvents increase degradation of phosphoramidite products, lower yields and/or purity, and/or produce excessive waste, all of which increase production cost of phosphoramidites and oligonucleotides synthesized therefrom. Without wishing to be bound by any particular theory, the present disclosure proposes that, in some instances, phosphoramidites may be lost due to exposure to air and/or water during aqueous work-ups and/or extractions. Among other things, the present disclosure provides technologies that enable the removal of exposure to material amounts of water and/or extractions, thereby significantly improving yields and/or purity of phosphoramidite products. In some embodiments, provided technologies use filtration to remove (a fraction of, most of, or all of) one or more reaction byproducts. In some embodiments, reaction byproducts removed by filtration in provided methods were removed (partially, mostly, or completely) by the aqueous work-ups and/or extractions. As demonstrated by Applicant, provided technologies, among other things, significantly improve yields and/or purity of phosphoramidites, thereby lowering cost and improving efficiency. Such lowered cost and improved efficiency may be particularly important for preparation of chirally controlled oligonucleotide compositions, the preparation of which requires multiple-step preparation of chiral phosphoramidites, for example, those illustrated in the present disclosure.

Preparation of a phosphoramidite starts with formation of the phosphoramidite through reactions that provide a preparation comprising a phosphoramidite product and one or more reaction byproducts of the product's synthesis. In some embodiments, the preparation comprises a solution and one or more solids. In some embodiments, the solution comprises the desired phosphoramidite products, while the one or more solids are mostly reaction products to be separated from the desired phosphoramidite products. In some embodiments, the solution also comprises one or more reaction byproducts, including one or more that exist in the solids, as the solution is a saturated solution for one or more compounds in the solids.

In some embodiments, provided technologies comprise providing a silylating reagent. In some embodiments, a silylating reagent has the structure of $(R)_3SiX$, wherein each R is independently as described in the present disclosure, and X is halogen. In some embodiments, a silylating reagent has the structure of $(R)_3SiCl$, wherein each R is independently as described in the present disclosure. In some embodiments, a silylating reagent has the structure of $(R)_3SiCl$, wherein each R is independently as described in the present disclosure and is not —H. In some embodiments, each R is independently optionally substituted aliphatic or aryl. In some embodiments, each R is independently optionally substituted alkyl or aryl. As appreciated by those skilled in the art, various silylating reagents can be used in accordance with the present disclosure. In some embodiments, a silylating reagent is chlorotrimethylsilane. In some embodiments, a silylating reagent is chlorotriethylsilane. In some embodiments, a silylating reagent is tert-tutyldimethylsilyl chlorid. In some embodiments, a silylating reagent is chlorodecyl-dimethylsilane. In some embodiments, a silylating reagent is chlorodimethylphenethylsilane. In some embodiments, a silylating reagent is chloro triisopropylsilane. In some embodiments, a silylating reagent protects a functional group of a compound, e.g., a starting material. In some embodiments, a silylating reagent protects a nucleobase. In some embodiments, a silylating reagent protects G. In some embodiments, a silylating reagent protects $O^6$ of G. In some embodiments, the present disclosure provides methods, comprising using a silylating reagent to protect, in some embodiments, transiently protect, a compound, e.g., protection of a nucleobase, such as $O^6$ of G. In some embodiments, provided technologies comprises protecting a nucleobase using a silylating reagent. In some embodiments, such a step is performed before reacting a nucleobase-containing compound with an amino alcohol- or chiral auxiliary-containing compound. In some embodiments, a protection by a silylating reagent is transient in that, as shown in the Examples, a final phosphoramidite product comprises no silyl protection group. In some embodiments, no specific de-protection step is performed for removing a silyl protection group. In some embodiments, protection, de-protection, and phosphoramidite formation are all performed in one pot.

In some embodiments, rather than using a material amount of aqueous solutions to dissolve and remove byproducts in solids, the present disclosure provides filtration to effectively remove byproducts in solids.

After filtration, a provided filtrate contains a reduced level of one or more reaction byproducts relative to a phosphoramidite product as compared to that level present in the preparation prior to the filtration step. In some embodiments, a reduced level is measured by molar ratio. In some embodiments, as readily appreciated by a person having ordinary skill in the art, a reduced level is due to removal of the solids, which comprise mostly byproducts, and retention of the solution as a filtrate, which contains most of the desired phosphoramidite product.

In some embodiments, a phosphoramidite product forms in the presence of a base. In some embodiments, a base is used to neutralize an acid generated during formation of a phosphoramidite. In some embodiments, after formation of a phosphoramidite product, a base is converted into a salt thereof. In some embodiments, a salt precipitates out as a solid. In some embodiments, one or more solids in a provided method comprise a salt of a base.

In some embodiments, a base has the formula of $N(R)_3$, wherein each R is independently hydrogen, or an optionally substituted group selected from $C_{1-30}$ aliphatic, $C_{1-30}$ heteroaliphatic having 1-10 heteroatoms independently selected from oxygen, nitrogen, sulfur, phosphorus and silicon, $C_{6-30}$ aryl, a 5-30 membered heteroaryl ring having 1-10 heteroatoms independently selected from oxygen, nitrogen, sulfur, phosphorus and silicon, and a 3-30 membered heterocyclic ring having 1-10 heteroatoms independently selected from oxygen, nitrogen, sulfur, phosphorus and silicon. In some embodiments, R is hydrogen, or optionally substituted $C_{1-6}$ aliphatic. In some embodiments, a base is $Et_3N$. In some embodiments, a base is DIEA. In some embodiments, a base is DIPEA.

In some embodiments, a salt is formed between a base and HCl. In some embodiments, a salt is $N(R)_3HCl$. As readily appreciated by a person having ordinary skill in the art, other salts may form depending on the reagents and/or methods used for forming a phosphoramidite.

Various reactions can be used to form phosphoramidites, for example, those described in US 2011/0294124, US 2015/0211006, US 2015/0197540, and WO 2015/107425, each of which is incorporated herein by reference. In some embodiments, phosphoramidites are formed by reactions between nucleosides and phosphorochloridites. In some embodiments, phosphoramidites are formed by reactions between nucleosides and amino alcohols, such as chiral reagents described in US 2011/0294124, US 2015/0211006, US 2015/0197540, and WO 2015/107425, each of which is incorporated herein by reference. In some embodiments, nucleosides and/or amino alcohols are optionally derivatized, protected, and/or activated for formation of phosphoramidites. In some embodiments, phosphoramidites are formed by reactions between compounds comprising nucleoside moieties and compounds comprising amino alcohol moieties. In some embodiments, as illustrated in the present disclosure and US 2011/0294124, US 2015/0211006, US 2015/0197540, WO 2015/107425, etc., chiral auxiliaries are amino alcohols. As readily appreciated by a person having ordinary skill in the art, phosphoramidites may be protected, for example, as protected for oligonucleotide synthesis.

In some embodiments, a provided nucleoside has the structure of formula I-a:

BA-SU—H, I-a wherein:

- BA is an optionally substituted group selected from $C_{1-30}$ cycloaliphatic, $C_{6-30}$ aryl, $C_{3-30}$ heterocyclyl having 1-10 heteroatoms independently selected from oxygen, nitrogen, sulfur, phosphorus and silicon, $C_{5-30}$ heteroaryl having 1-10 heteroatoms independently selected from oxygen, nitrogen, sulfur, phosphorus and silicon, a natural nucleobase moiety, and a modified nucleobase moiety;
- SU is -L-O— or

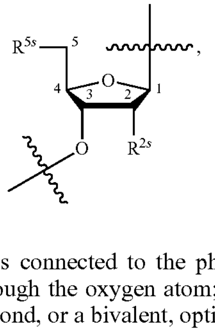

wherein SU is connected to the phosphorus atom in formula I through the oxygen atom;

- L is a covalent bond, or a bivalent, optionally substituted, linear or branched group selected from $C_{1-30}$ aliphatic and $C_{1-30}$ heteroaliphatic group having 1-10 heteroatoms independently selected from oxygen, nitrogen, sulfur, phosphorus and silicon, wherein one or more methylene units are optionally and independently replaced by an optionally substituted $C_{1-6}$ alkylene, $C_{1-6}$ alkenylene, —C≡C—, —C(R')$_2$—, -Cy-, —O—, —S—, —S—S—, —N(R')—, —C(O)—, —C(S)—, —C(NR')—, —C(O)N(R')—, —N(R')C(O)N(R')—, —N(R')C(O)—, —N(R')C(O)O—, —OC(O)N(R')—, —S(O)—, —S(O)$_2$—, —S(O)$_2$N(R')—, —N(R')S(O)$_2$—, —SC(O)—, —C(O)S—, —OC(O)—, or —C(O)O—;
- $R^{5s}$ is R' or —OR';
- $R^{2s}$ is —F, —CN, —$N_3$, —NO, —$NO_2$, —R'—OR', —SR', —N(R')$_2$, —O-L-OR', —O-L-SR', or —O-L-N(R')$_2$, or $R^{2s}$ is L connecting $C_2$ with $C_1$, $C_2$, $C_3$, $C_4$ or $C_5$;
  - Cy- is an optionally substituted bivalent ring selected from 3-30 membered carbocyclylene, 6-30 membered arylene, 5-30 membered heteroarylene having 1-10 heteroatoms independently selected from oxygen, nitrogen and sulfur, and 3-30 membered heterocyclylene having 1-10 heteroatoms independently selected from oxygen, nitrogen, sulfur, phosphorus and silicon;
- Ring A is an optionally substituted multivalent, monocyclic, bicyclic or polycyclic, saturated, partially unsaturated, or aryl 3-30 membered ring having, in addition to the intervening atoms, 0-10 heteroatoms independently selected from oxygen, nitrogen, sulfur, phosphorus and silicon;
- each $R^s$ is independently R' or -L-R';
- t is 0-5;
- each R' is independently —R, —C(O)R, —$CO_2$R, or —$SO_2$R, or:
  - two or more R' are taken together with their intervening atoms to form an optionally substituted monocyclic, bicyclic or polycyclic, saturated, partially unsaturated, or aryl 3-30 membered ring having, in addition to the intervening atoms, 0-10 heteroatoms independently selected from oxygen, nitrogen, sulfur, phosphorus and silicon; and
- each R is independently hydrogen, or an optionally substituted group selected from $C_{1-30}$ aliphatic, $C_{1-30}$ heteroaliphatic having 1-10 heteroatoms independently selected from oxygen, nitrogen, sulfur, phosphorus and silicon, $C_{6-30}$ aryl, a 5-30 membered heteroaryl ring having 1-10 heteroatoms independently selected from oxygen, nitrogen, sulfur, phosphorus and silicon, and a 3-30 membered heterocyclic ring having 1-10 heteroatoms independently selected from oxygen, nitrogen, sulfur, phosphorus and silicon.

In some embodiments, a provided phosphorochloridite has the structure of formula I-b:

I-b

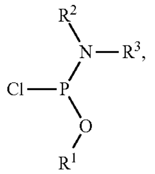

wherein:

- each of $R^1$, $R^2$, and $R^3$ is independently R', or two or three of $R^1$, $R^2$, and $R^3$ are taken together with their intervening atoms to form:

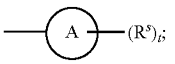

Ring A is an optionally substituted multivalent, monocyclic, bicyclic or polycyclic, saturated, partially unsaturated, or aryl 3-30 membered ring having, in addition to the intervening atoms, 0-10 heteroatoms independently selected from oxygen, nitrogen, sulfur, phosphorus and silicon;

each $R^s$ is independently R' or -L-R';

t is 0-5;

L is a covalent bond, or a bivalent, optionally substituted, linear or branched group selected from $C_{1-30}$ aliphatic and $C_{1-30}$ heteroaliphatic group having 1-10 heteroatoms independently selected from oxygen, nitrogen, sulfur, phosphorus and silicon, wherein one or more methylene units are optionally and independently replaced by an optionally substituted $C_{1-6}$ alkylene, $C_{1-6}$ alkenylene, —C≡C—, —C(R')$_2$—, -Cy-, —O—, —S—, —S—S—, —N(R')—, —C(O)—, —C(S)—, —C(NR')—, —C(O)N(R')—, —N(R')C(O)N(R')—, —N(R')C(O)—, —N(R')C(O)O—, —OC(O)N(R')—, —S(O)—, —S(O)$_2$—, —S(O)$_2$N(R')—, —N(R')S(O)$_2$—, —SC(O)—, —C(O)S—, —OC(O)—, or —C(O)O—;

Cy- is an optionally substituted bivalent ring selected from 3-30 membered carbocyclylene, 6-30 membered arylene, 5-30 membered heteroarylene having 1-10 heteroatoms independently selected from oxygen, nitrogen and sulfur, and 3-30 membered heterocyclylene having 1-10 heteroatoms independently selected from oxygen, nitrogen, sulfur, phosphorus and silicon;

each R' is independently —R, —C(O)R, —$CO_2$R, or —$SO_2$R, or:

two or more R' are taken together with their intervening atoms to form an optionally substituted monocyclic, bicyclic or polycyclic, saturated, partially unsaturated, or aryl 3-30 membered ring having, in addition to the intervening atoms, 0-10 heteroatoms independently selected from oxygen, nitrogen, sulfur, phosphorus and silicon; and each R is independently hydrogen, or an optionally substituted group selected from $C_{1-30}$ aliphatic, $C_{1-30}$ heteroaliphatic having 1-10 heteroatoms independently selected from oxygen, nitrogen, sulfur, phosphorus and silicon, $C_{6-30}$ aryl, a 5-30 membered heteroaryl ring having 1-10 heteroatoms independently selected from oxygen, nitrogen, sulfur, phosphorus and silicon, and a 3-30 membered heterocyclic ring having 1-10 heteroatoms independently selected from oxygen, nitrogen, sulfur, phosphorus and silicon.

In some embodiments, a provided phosphoramidite has the structure of formula I:

I

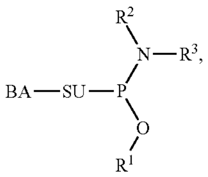

wherein:

BA is an optionally substituted group selected from $C_{1-30}$ cycloaliphatic, $C_{6-30}$ aryl, $C_{3-30}$ heterocyclyl having 1-10 heteroatoms independently selected from oxygen, nitrogen, sulfur, phosphorus and silicon, $C_{5-30}$ heteroaryl having 1-10 heteroatoms independently selected from oxygen, nitrogen, sulfur, phosphorus and silicon, a natural nucleobase moiety, and a modified nucleobase moiety;

SU is -L-O— or

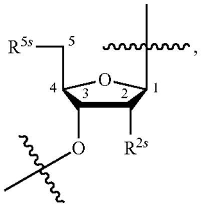

wherein SU is connected to the phosphorus atom in formula I through the oxygen atom;

L is a covalent bond, or a bivalent, optionally substituted, linear or branched group selected from $C_{1-30}$ aliphatic and $C_{1-30}$ heteroaliphatic group having 1-10 heteroatoms independently selected from oxygen, nitrogen, sulfur, phosphorus and silicon, wherein one or more methylene units are optionally and independently replaced by an optionally substituted $C_{1-6}$ alkylene, $C_{1-6}$ alkenylene, —C≡C—, —C(R')$_2$—, -Cy-, —O—, —S—, —S—S—, —N(R')—, —C(O)—, —C(S)—, —C(NR')—, —C(O)N(R')—, —N(R')C(O)N(R')—, —N(R')C(O)—, —N(R')C(O)O—, —OC(O)N(R')—, —S(O)—, —S(O)$_2$—, —S(O)$_2$N(R')—, —N(R')S(O)$_2$—, —SC(O)—, —C(O)S—, —OC(O)—, or —C(O)O—;

$R^{5s}$ is R' or —OR';

$R^{2s}$ is —F, —CN, —$N_3$, —NO, —$NO_2$, —R'—OR', —SR', —N(R')$_2$, —O-L-OR', —O-L-SR', or —O-L-N(R')$_2$, or $R^{2s}$ is L connecting $C_2$ with $C_1$, $C_2$, $C_3$, $C_4$ or $C_5$;

Cy- is an optionally substituted bivalent ring selected from 3-30 membered carbocyclylene, 6-30 membered arylene, 5-30 membered heteroarylene having 1-10 heteroatoms independently selected from oxygen, nitrogen and sulfur, and 3-30 membered heterocyclylene having 1-10 heteroatoms independently selected from oxygen, nitrogen, sulfur, phosphorus and silicon;

each of $R^1$, $R^2$, and $R^3$ is independently R', or two or three of $R^1$, $R^2$, and $R^3$ are taken together with their intervening atoms to form:

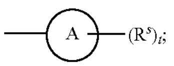

Ring A is an optionally substituted multivalent, monocyclic, bicyclic or polycyclic, saturated, partially unsaturated, or aryl 3-30 membered ring having, in addition to the intervening atoms, 0-10 heteroatoms independently selected from oxygen, nitrogen, sulfur, phosphorus and silicon;

each $R^s$ is independently R' or -L-R';

t is 0-5;

each R' is independently —R, —C(O)R, —$CO_2$R, or —$SO_2$R, or:

two or more R' are taken together with their intervening atoms to form an optionally substituted monocyclic, bicyclic or polycyclic, saturated, partially unsaturated, or aryl 3-30 membered ring having, in addition to the intervening atoms, 0-10 heteroatoms independently selected from oxygen, nitrogen, sulfur, phosphorus and silicon; and each R is independently hydrogen, or an optionally substituted group selected from $C_{1-30}$ aliphatic, $C_{1-30}$ heteroaliphatic having 1-10 heteroatoms independently selected from oxygen, nitrogen, sulfur, phosphorus and silicon, $C_{6-30}$ aryl, a 5-30 membered heteroaryl ring having 1-10 heteroatoms independently selected from oxygen, nitrogen, sulfur, phosphorus and silicon, and a 3-30 membered heterocyclic ring having 1-10 heteroatoms independently selected from oxygen, nitrogen, sulfur, phosphorus and silicon.

In some embodiments, BA is optionally substituted $C_{1-30}$ cycloaliphatic. In some embodiments, BA is optionally substituted $C_{6-30}$ aryl. In some embodiments, BA is optionally substituted $C_{3-30}$ heterocyclyl. In some embodiments, BA is optionally substituted $C_{5-30}$ heteroaryl. In some embodiments, BA is an optionally substituted natural base moiety. In some embodiments, BA is an optionally substituted modified base moiety. BA is an optionally substituted group selected from $C_{1-30}$ cycloaliphatic, $C_{6-30}$ aryl, $C_{3-30}$ heterocyclyl, and $C_{5-30}$ heteroaryl. In some embodiments, BA is an optionally substituted group selected from $C_{1-30}$ cycloaliphatic, $C_{6-30}$ aryl, $C_{3-30}$ heterocyclyl, $C_{5-30}$ heteroaryl, and a natural nucleobase moiety.

In some embodiments, BA is connected to SU through an aromatic ring. In some embodiments, BA is connected to SU through a heteroatom. In some embodiments, BA is connected to SU through a ring heteroatom of an aromatic ring. In some embodiments, BA is connected to SU through a ring nitrogen atom of an aromatic ring.

In some embodiments, BA is a natural nucleobase moiety. In some embodiments, BA is an optionally substituted natural nucleobase moiety. In some embodiments, BA is a substituted natural nucleobase moiety.

In some embodiments, BA is an optionally substituted group, which group is formed by removing a —H from

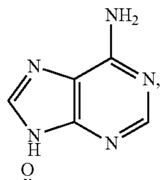
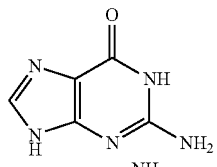
,
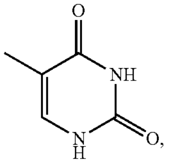
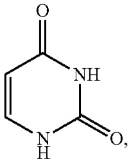
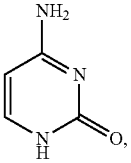
and
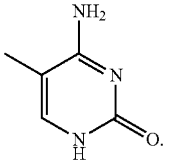

In some embodiments, BA is an optionally substituted group which group is selected

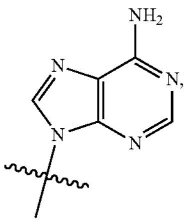
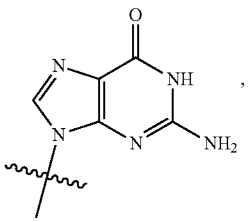
,
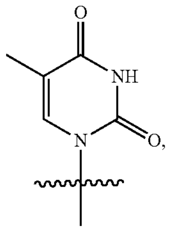
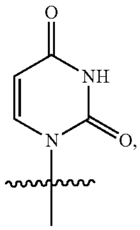
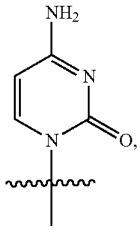
and
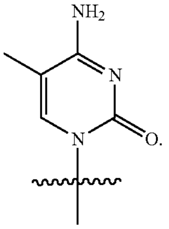

In some embodiments, BA is an optionally substituted group, which group is formed by removing a —H from

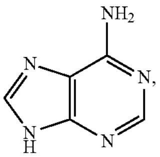
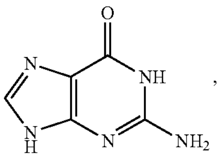
,
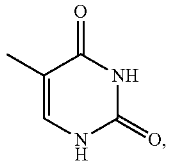
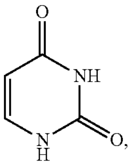
and
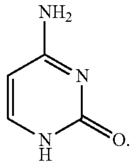

In some embodiments, BA is an optionally substituted group which group is selected from

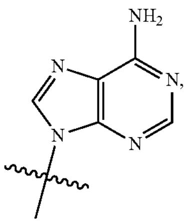
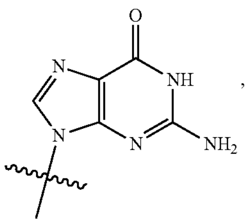
,

-continued

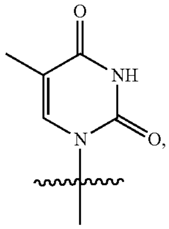
,
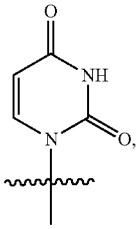
, and
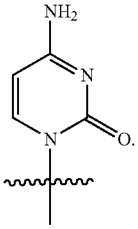
.

In some embodiments, BA is

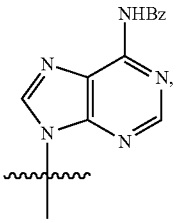
,
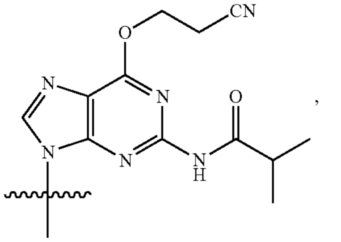
,
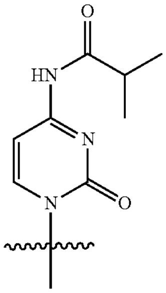
,
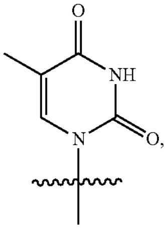
,
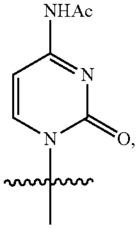
,
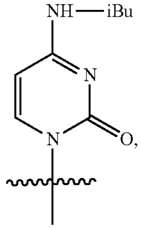
,
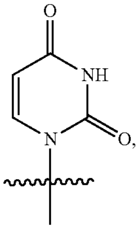
, or
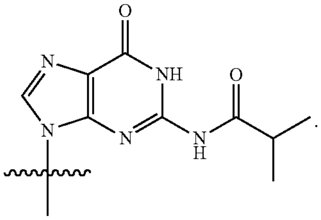
.

In some embodiments, BA is

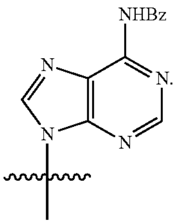
.

In some embodiments, BA is

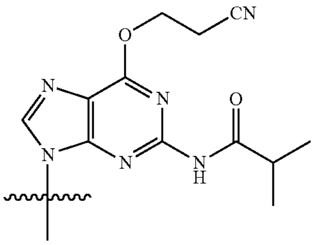
or
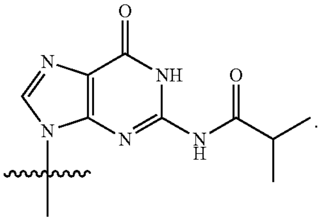
.

In some embodiments, BA is an optionally substituted purine base residue. In some embodiments, BA is a protected purine base residue. In some embodiments, BA is an optionally substituted adenine residue. In some embodiments, BA is a protected adenine residue. In some embodiments, BA is an optionally substituted guanine residue. In some embodiments, BA is a protected guanine residue. In some embodiments, provided technologies provide surprisingly improved yields and/or purity for preparation of purine phosphoramidites, which can be particularly challenging to prepare and often suffer from low yields and/or purity.

In some embodiments, BA is a protected base residue as used in oligonucleotide preparation. In some embodiments, BA is a base residue illustrated in US 2011/0294124, US 2015/0211006, US 2015/0197540, and WO 2015/107425, each of which is incorporated herein by reference.

Those skilled in the art appreciate that a variety of modified nucleobases are suitable for use in accordance with the present disclosure in formula I. Example modified bases include but are not limited to those limited in WO/2011/005761, WO/2013/012758, WO/2014/012081, WO/2015/107425, WO/2010/064146, WO/2014/010250, WO/2011/108682, WO/2012/039448, and WO/2012/073857, the modified nucleobases of each of which are hereby incorporated by reference.

In some embodiments, BA is a substituted nucleobase so that the phosphoramidite is properly protected with one or more protecting groups and can be used for oligonucleotide synthesis. Suitable protecting groups for nucleobases are widely known in the art, including those useful for oligonucleotide synthesis, and can be used in accordance with the present disclosure. In some embodiments, a protecting group is acetyl (Ac), phenylacetyl, benzoyl (Bz), isobutyryl (iBu), phenoxyacetyl (Pac), isopropyl-Pac, tertbutyl-Pac, alkyl-Pac, dimethylformamidine (DMF), or dialkylformamidine. In some embodiments, a protecting group is phthalimido, 9-fludrenylmethoxycarbonyl (FMOC), triphenylmethylsulfenyl, t-BOC, 4,4'-dimethoxytrityl (DMTr), 4-methoxytrityl (MMTr), 9-phenylxanthin-9-yl (Pixyl), trityl (Tr), or 9-(p-methoxyphenyl)xanthin-9-yl (MOX). For additional suitable protecting groups, see Green and Wuts, Protective Groups in Organic Synthesis, 2nd Ed., John Wiley & Sons, New York, 1991, and WO/2011/005761, WO/2013/012758, WO/2014/012081, WO/2015/107425, WO/2010/064146, WO/2014/010250, WO/2011/108682, WO/2012/039448, and WO/2012/073857, the protecting groups of each of which are hereby incorporated by reference.

In some embodiments, the present disclosure encompasses the recognition that, surprisingly, guanine-containing phosphoramidites can be prepared with satisfactory yields and purity without $O^6$ protection. In some embodiments, BA is

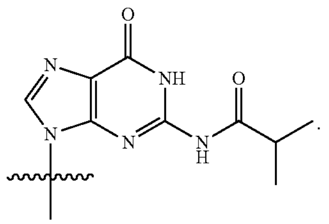 [SMILES: *n1cnc2c(=O)[nH]c(NC(=O)C(C)C)nc21]

In some embodiments, the present disclosure provides a compound of formula I or a salt thereof, wherein:

BA is optionally protected

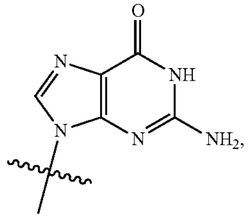

wherein $O^6$ is not protected;

SU is -L-O— or

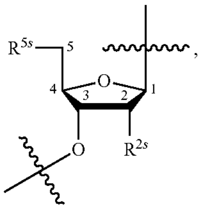

wherein SU is connected to the phosphorus atom in formula I through the oxygen atom;

L is a covalent bond, or a bivalent, optionally substituted, linear or branched group selected from $C_{1-30}$ aliphatic and $C_{1-30}$ heteroaliphatic group having 1-10 heteroatoms independently selected from oxygen, nitrogen, sulfur, phosphorus and silicon, wherein one or more methylene units are optionally and independently replaced by an optionally substituted $C_{1-6}$ alkylene, $C_{1-6}$ alkenylene, —C≡C—, —C(R')$_2$—, -Cy-, —O—, —S—, —S—S—, —N(R')—, —C(O)—, —C(S)—, —C(NR')—, —C(O)N(R')—, —N(R')C(O)N(R')—, —N(R')C(O)—, —N(R')C(O)O—, —OC(O)N(R')—, —S(O)—, —S(O)$_2$—, —S(O)$_2$N(R')—, —N(R')S(O)$_2$—, —SC(O)—, —C(O)S—, —OC(O)—, or —C(O)O—;

$R^{5s}$ is R' or —OR';

$R^{2s}$ is —F, —CN, —$N_3$, —NO, —$NO_2$, —R'—OR', —SR', —N(R')$_2$, —O-L-OR', —O-L-SR', or —O-L-N(R')$_2$, or $R^{2s}$ is L connecting $C_2$ with $C_1$, $C_2$, $C_3$, $C_4$ or $C_5$;

Cy- is an optionally substituted bivalent ring selected from 3-30 membered carbocyclylene, 6-30 membered arylene, 5-30 membered heteroarylene having 1-10 heteroatoms independently selected from oxygen, nitrogen and sulfur, and 3-30 membered heterocyclylene having 1-10 heteroatoms independently selected from oxygen, nitrogen, sulfur, phosphorus and silicon;

each of $R^1$, $R^2$, and $R^3$ is independently R', wherein two or three of $R^1$, $R^2$, and $R^3$ are taken together with their intervening atoms to form:

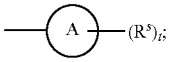

Ring A is an optionally substituted multivalent, monocyclic, bicyclic or polycyclic, saturated, partially unsaturated, or aryl 3-30 membered ring having, in addition to the intervening atoms, 0-10 heteroatoms independently selected from oxygen, nitrogen, sulfur, phosphorus and silicon;

each $R^s$ is independently R' or -L-R';

t is 0-5;

each R' is independently —R, —C(O)R, —$CO_2$R, or —$SO_2$R, or:

two or more R' are taken together with their intervening atoms to form an optionally substituted monocyclic, bicyclic or polycyclic, saturated, partially unsaturated, or aryl 3-30 membered ring having, in addition to the intervening atoms, 0-10 heteroatoms independently selected from oxygen, nitrogen, sulfur, phosphorus and silicon; and each R is independently hydrogen, or an optionally substituted group selected from $C_{1-30}$ aliphatic, $C_{1-30}$ heteroaliphatic having 1-10 heteroatoms independently selected from oxygen, nitrogen, sulfur, phosphorus and silicon, $C_{6-30}$ aryl, a 5-30 membered heteroaryl ring having 1-10 heteroatoms independently selected from oxygen, nitrogen, sulfur, phosphorus and silicon, and a 3-30 membered heterocyclic ring having 1-10 heteroatoms independently selected from oxygen, nitrogen, sulfur, phosphorus and silicon.

In some embodiments, BA is protected

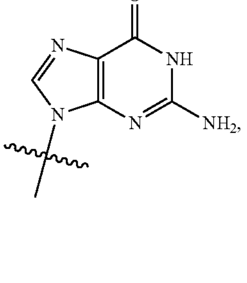

wherein $O^6$ is not protected.

In some embodiments, the present disclosure provides a compound of formula I or a salt thereof, wherein:

BA is optionally substituted

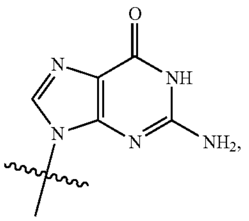

wherein $O^6$ is not substituted;

SU is -L-O— or

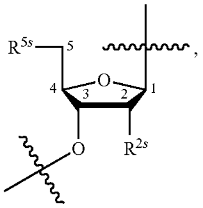

wherein SU is connected to the phosphorus atom in formula I through the oxygen atom;

L is a covalent bond, or a bivalent, optionally substituted, linear or branched group selected from $C_{1-30}$ aliphatic and $C_{1-30}$ heteroaliphatic group having 1-10 heteroatoms independently selected from oxygen, nitrogen, sulfur, phosphorus and silicon, wherein one or more methylene units are optionally and independently replaced by an optionally substituted $C_{1-6}$ alkylene, $C_{1-6}$ alkenylene, —C≡C—, —C(R')$_2$—, -Cy-, —O—, —S—, —S—S—, —N(R')—, —C(O)—, —C(S)—, —C(NR')—, —C(O)N(R')—, —N(R')C(O)N(R')—, —N(R')C(O)—, —N(R')C(O)O—, —OC(O)N(R')—, —S(O)—, —S(O)$_2$—, —S(O)$_2$N(R')—, —N(R')S(O)$_2$—, —SC(O)—, —C(O)S—, —OC(O)—, or —C(O)O—;

$R^{5s}$ is R' or —OR';

$R^{2s}$ is —F, —CN, —$N_3$, —NO, —$NO_2$, —R'—OR', —SR', —N(R')$_2$, —O-L-OR', —O-L-SR', or —O-L-N(R')$_2$, or $R^{2s}$ is L connecting $C_2$ with $C_1$, $C_2$, $C_3$, $C_4$ or $C_5$;

Cy- is an optionally substituted bivalent ring selected from 3-30 membered carbocyclylene, 6-30 membered arylene, 5-30 membered heteroarylene having 1-10 heteroatoms independently selected from oxygen, nitrogen and sulfur, and 3-30 membered heterocyclylene having 1-10 heteroatoms independently selected from oxygen, nitrogen, sulfur, phosphorus and silicon;

each of $R^1$, $R^2$, and $R^3$ is independently R', wherein two or three of $R^1$, $R^2$, and $R^3$ are taken together with their intervening atoms to form:

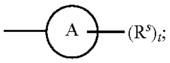

Ring A is an optionally substituted multivalent, monocyclic, bicyclic or polycyclic, saturated, partially unsaturated, or aryl 3-30 membered ring having, in addition to the intervening atoms, 0-10 heteroatoms independently selected from oxygen, nitrogen, sulfur, phosphorus and silicon;

each $R^s$ is independently R' or -L-R';

t is 0-5;

each R' is independently —R, —C(O)R, —$CO_2$R, or —$SO_2$R, or:

two or more R' are taken together with their intervening atoms to form an optionally substituted monocyclic, bicyclic or polycyclic, saturated, partially unsaturated, or aryl 3-30 membered ring having, in addition to the intervening atoms, 0-10 heteroatoms independently selected from oxygen, nitrogen, sulfur, phosphorus and silicon; and each R is independently hydrogen, or an optionally substituted group selected from $C_{1-30}$ aliphatic, $C_{1-30}$ heteroaliphatic having 1-10 heteroatoms independently selected from oxygen, nitrogen, sulfur, phosphorus and silicon, $C_{6-30}$ aryl, a 5-30 membered heteroaryl ring having 1-10 heteroatoms independently selected from oxygen, nitrogen, sulfur, phosphorus and silicon, and a 3-30 membered heterocyclic ring having 1-10 heteroatoms independently selected from oxygen, nitrogen, sulfur, phosphorus and silicon.

In some embodiments, BA is substituted

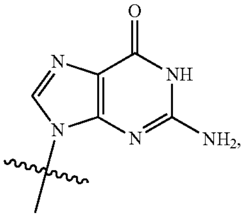

wherein $O^6$ is not substituted.

In some embodiments, the present disclosure provides a compound of formula I or a salt thereof, wherein:

BA is

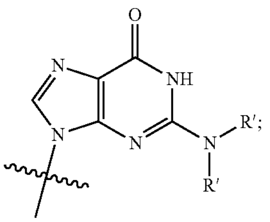

SU is -L-O— or

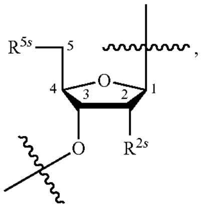

wherein SU is connected to the phosphorus atom in formula I through the oxygen atom;

L is a covalent bond, or a bivalent, optionally substituted, linear or branched group selected from $C_{1-30}$ aliphatic and $C_{1-30}$ heteroaliphatic group having 1-10 heteroatoms independently selected from oxygen, nitrogen, sulfur, phosphorus and silicon, wherein one or more methylene units are optionally and independently replaced by an optionally substituted $C_{1-6}$ alkylene, $C_{1-6}$ alkenylene, —C≡C—, —$C(R')_2$—, -Cy-, —O—, —S—, —S—S—, —N(R')—, —C(O)—, —C(S)—, —C(NR')—, —C(O)N(R')—, —N(R')C(O)N(R')—, —N(R')C(O)—, —N(R')C(O)O—, —OC(O)N(R')—, —S(O)—, —$S(O)_2$—, —$S(O)_2N(R')$—, —$N(R')S(O)_2$—, —SC(O)—, —C(O)S—, —OC(O)—, or —C(O)O—;

$R^{5s}$ is R' or —OR';

$R^{2s}$ is —F, —CN, —$N_3$, —NO, —$N_{02}$, —R'—OR', —SR', —$N(R')_2$, —O-L-OR', —O-L-SR', or —O-L-$N(R')_2$, or $R^{2s}$ is L connecting $C_2$ with $C_1$, $C_2$, $C_3$, $C_4$ or $C_5$;

Cy- is an optionally substituted bivalent ring selected from 3-30 membered carbocyclylene, 6-30 membered arylene, 5-30 membered heteroarylene having 1-10 heteroatoms independently selected from oxygen, nitrogen and sulfur, and 3-30 membered heterocyclylene having 1-10 heteroatoms independently selected from oxygen, nitrogen, sulfur, phosphorus and silicon;

each of $R^1$, $R^2$, and $R^3$ is independently R', wherein two or three of $R^1$, $R^2$, and $R^3$ are taken together with their intervening atoms to form:

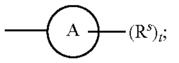

Ring A is an optionally substituted multivalent, monocyclic, bicyclic or polycyclic, saturated, partially unsaturated, or aryl 3-30 membered ring having, in addition to the intervening atoms, 0-10 heteroatoms independently selected from oxygen, nitrogen, sulfur, phosphorus and silicon;

each $R^s$ is independently R' or -L-R';

t is 0-5;

each R' is independently —R, —C(O)R, —$CO_2R$, or —$SO_2R$, or:

two or more R' are taken together with their intervening atoms to form an optionally substituted monocyclic, bicyclic or polycyclic, saturated, partially unsaturated, or aryl 3-30 membered ring having, in addition to the intervening atoms, 0-10 heteroatoms independently selected from oxygen, nitrogen, sulfur, phosphorus and silicon; and each R is independently hydrogen, or an optionally substituted group selected from $C_{1-30}$ aliphatic, $C_{1-30}$ heteroaliphatic having 1-10 heteroatoms independently selected from oxygen, nitrogen, sulfur, phosphorus and silicon, $C_{6-30}$ aryl, a 5-30 membered heteroaryl ring having 1-10 heteroatoms independently selected from oxygen, nitrogen, sulfur, phosphorus and silicon, and a 3-30 membered heterocyclic ring having 1-10 heteroatoms independently selected from oxygen, nitrogen, sulfur, phosphorus and silicon.

In some embodiments, BA is

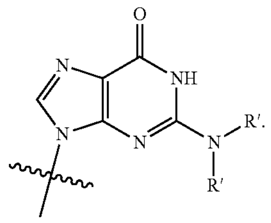

In some embodiments, BA is

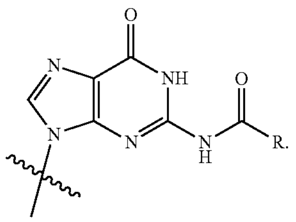

In some embodiments, BA is

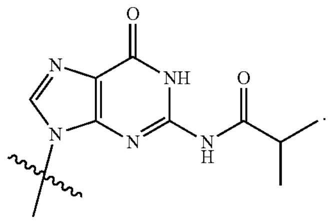 [SMILES: *n1cnc2c(=O)[nH]c(NC(=O)C(C)C)nc21]

In some embodiments, a provided compound is a phosphoramidite. In some embodiments, a provided phosphoramidite is selected from:

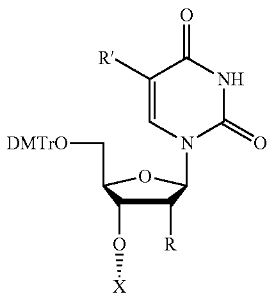

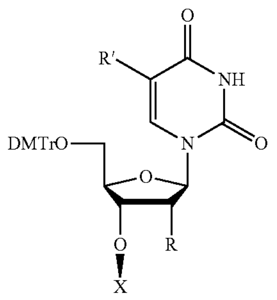

-continued

X =

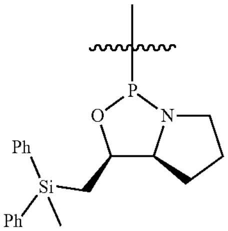

17: R′ = H, R = H
18: R′ = H, R = OMe
19: R′ = H, R = $OCH_2CH_2OMe$
20: R′ = H, R = F
21: R′ = Me, R = H
22: R′ = Me, R = OMe
23: R′ = Me, R = $OCH_2CH_2OMe$
24: R′ = Me, R = F

X =

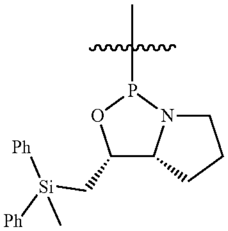

25: R′ = H, R = H
26: R′ = H, R = OMe
27: R′ = H, R = $OCH_2CH_2OMe$
28: R′ = H, R = F
29: R′ = Me, R = H
30: R′ = Me, R = OMe
31: R′ = Me, R = $OCH_2CH_2OMe$
32: R′ = Me, R = F

X =

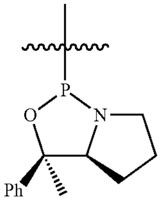

33: R′ = H, R = H
34: R′ = H, R = OMe
35: R′ = H, R = $OCH_2CH_2OMe$
36: R′ = H, R = F
37: R′ = Me, R = H
38: R′ = Me, R = OMe
39: R′ = Me, R = $OCH_2CH_2OMe$
40: R′ = Me, R = F

X =

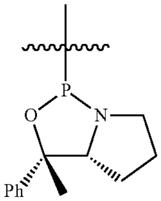

41: R′ = H, R = H
42: R′ = H, R = OMe
43: R′ = H, R = $OCH_2CH_2OMe$
44: R′ = H, R = F
45: R′ = Me, R = H
46: R′ = Me, R = OMe
47: R′ = Me, R = $OCH_2CH_2OMe$
48: R′ = Me, R = F

-continued

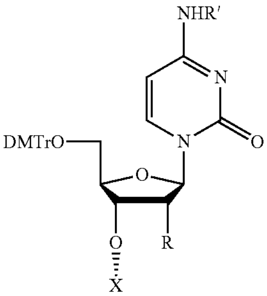

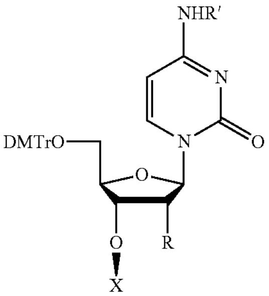

X =

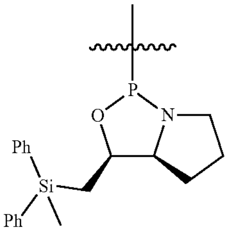

53: R′ = Ac, R = H
54: R′ = Ac, R = OMe
55: R′ = Ac, R = $OCH_2CH_2OMe$
56: R′ = Ac, R = F
53a: R′ = iBu, R = H
54a: R′ = iBu, R = OMe
55a: R′ = iBu, R = $OCH_2CH_2OMe$
56a: R′ = iBu, R = F

X =

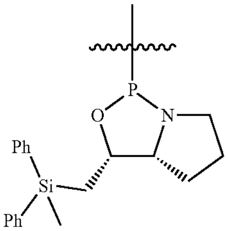

57: R′ = Ac, R = H
58: R′ = Ac, R = OMe
59: R′ = Ac, R = $OCH_2CH_2OMe$
60: R′ = Ac, R = F
57a: R′ = iBu, R = H
58a: R′ = iBu, R = OMe
59a: R′ = iBu, R = $OCH_2CH_2OMe$
60a: R′ = iBu, R = F

X =

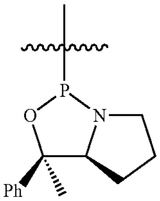

61: R′ = Ac, R = H
62: R′ = Ac, R = OMe
63: R′ = Ac, R = $OCH_2CH_2OMe$
64: R′ = Ac, R = F
61a: R′ = iBu, R = H
62a: R′ = iBu, R = OMe
63a: R′ = iBu, R = $OCH_2CH_2OMe$
64a: R′ = iBu, R = F

-continued
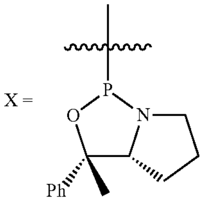
65: R′ = Ac, R = H
66: R′ = Ac, R = OMe
67: R′ = Ac, R = $OCH_2CH_2OMe$
68: R′ = Ac, R = F
65a: R′ = iBu, R = H
66a: R′ = iBu, R = OMe
67a: R′ = iBu, R = $OCH_2CH_2OMe$
68a: R′ = iBu, R = F
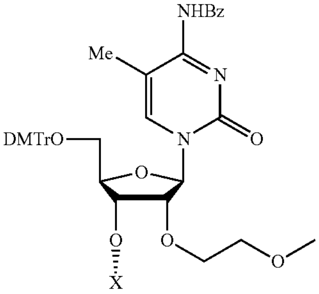
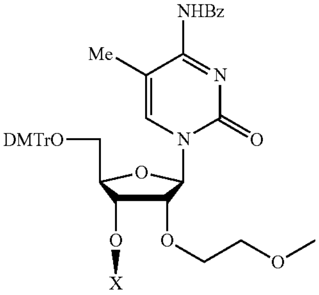
55b
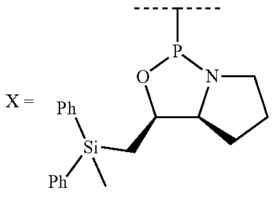
59b
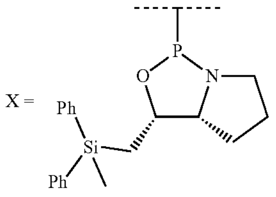
63b
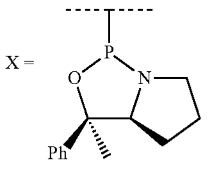
-continued
67b
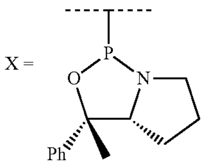
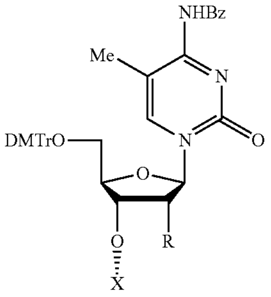
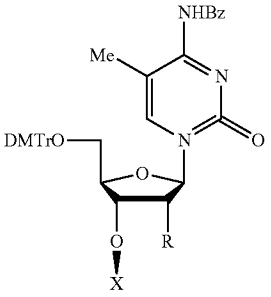
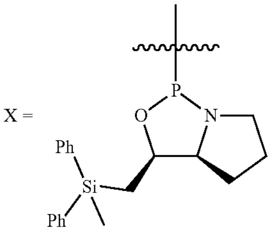
73: R = H
74: R = OMe
75: R = $OCH_2CH_2OMe$
76: R = F
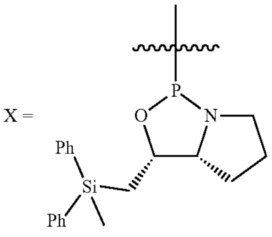
77: R = H
78: R = OMe
79: R = $OCH_2CH_2OMe$
80: R = F
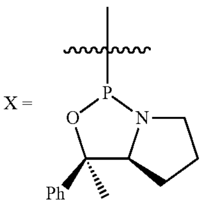
81: R = H
82: R = OMe
83: R = $OCH_2CH_2OMe$
84: R = F -continued
X =
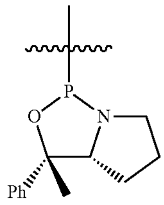
85: R = H
86: R = OMe
87: R = $OCH_2CH_2OMe$
88: R = F
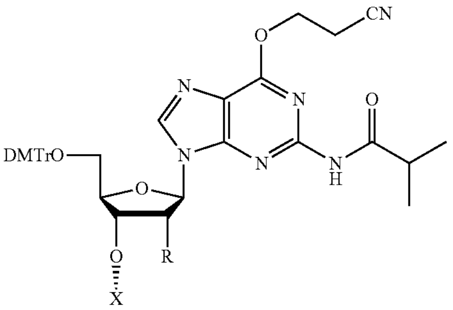
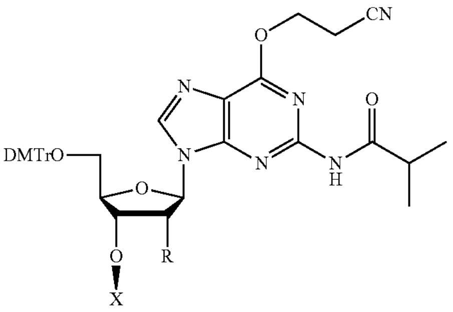
X =
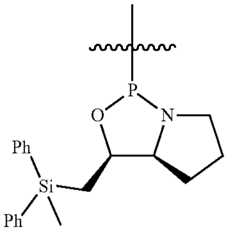
93: R = H
94: R = OMe
95: R = $OCH_2CH_2OMe$
96: R = F
X =
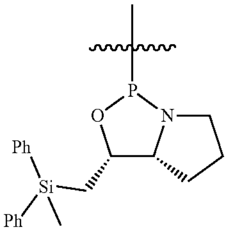
97: R = H
98: R = OMe
99: R = $OCH_2CH_2OMe$
100: R = F
-continued
X =
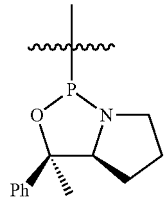
101: R = H
102: R = OMe
103: R = $OCH_2CH_2OMe$
104: R = F
X =
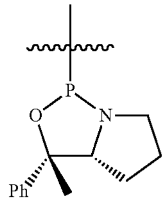
105: R = H
106: R = OMe
107: R = $OCH_2CH_2OMe$
108: R = F
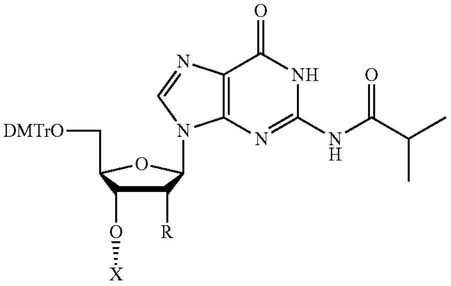
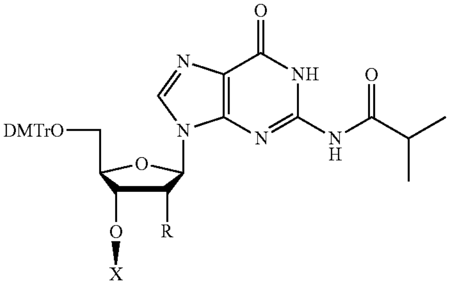
X =
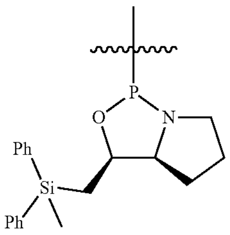
113: R = H
114: R = OMe
115: R = $OCH_2CH_2OMe$
116: R = F -continued
X = 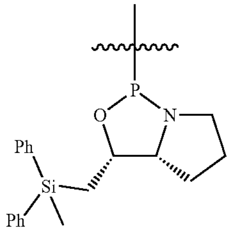
117: R = H
118: R = OMe
119: R = $OCH_2CH_2OMe$
120: R = F
X = 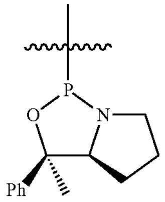
121: R = H
122: R = OMe
123: R = $OCH_2CH_2OMe$
124: R = F
X = 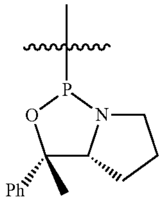
125: R = H
126: R = OMe
127: R = $OCH_2CH_2OMe$
128: R = F
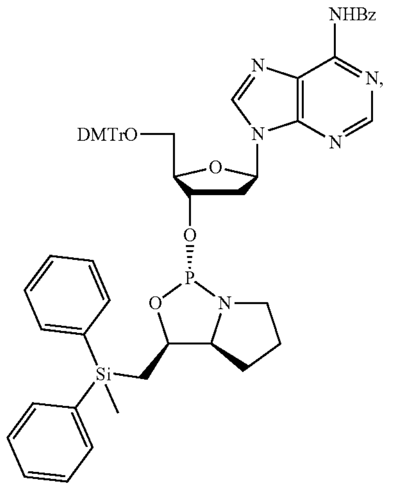
-continued
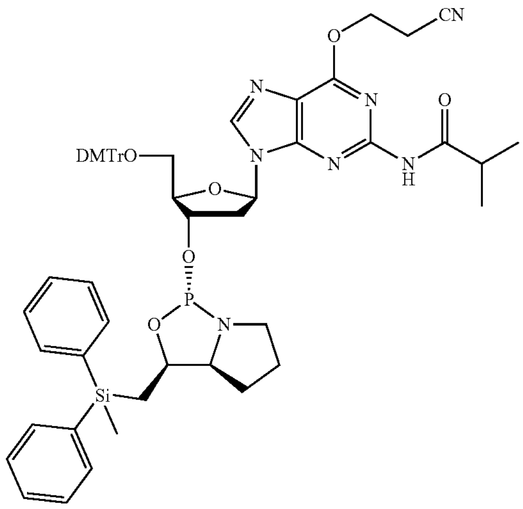
,
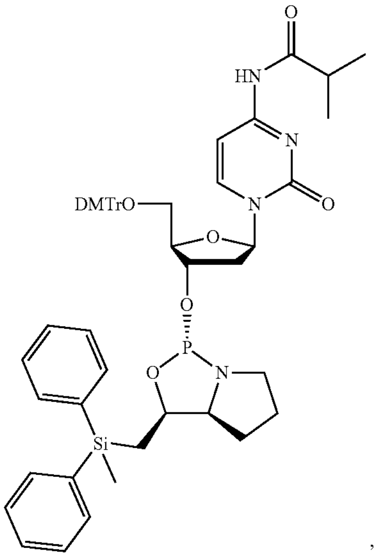
,
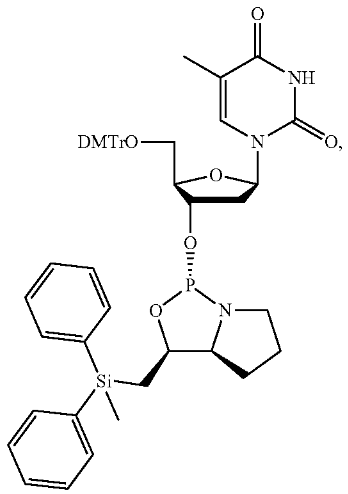

-continued
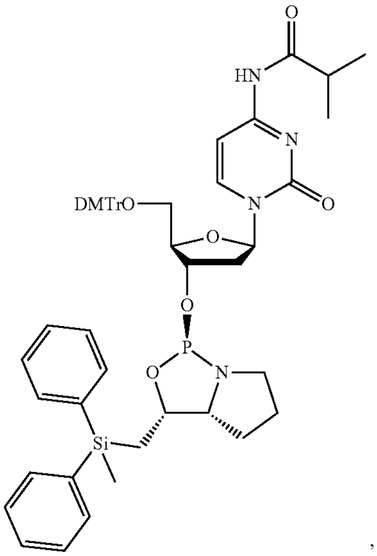
,
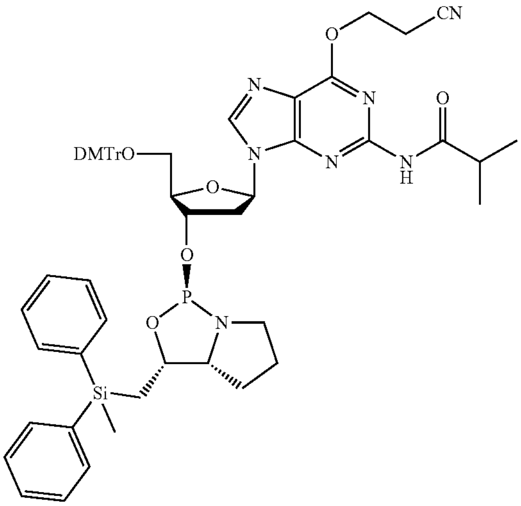
,
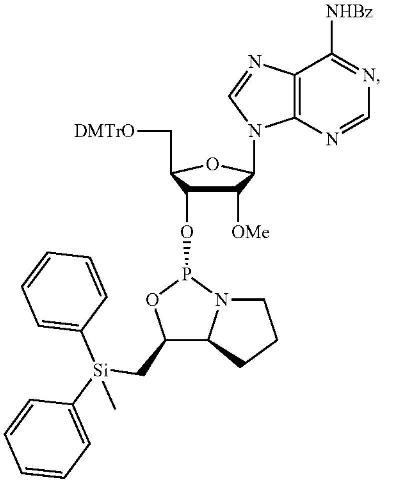
-continued
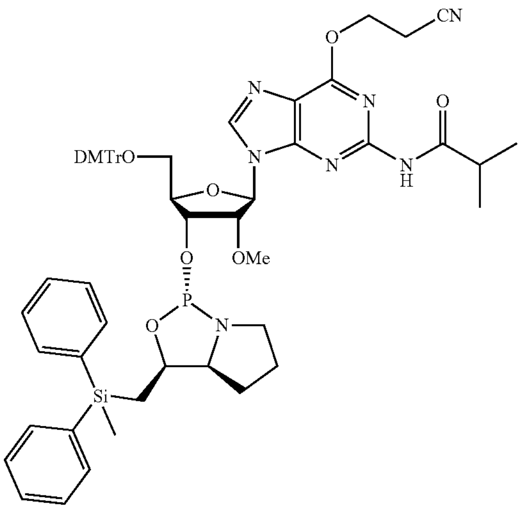
,
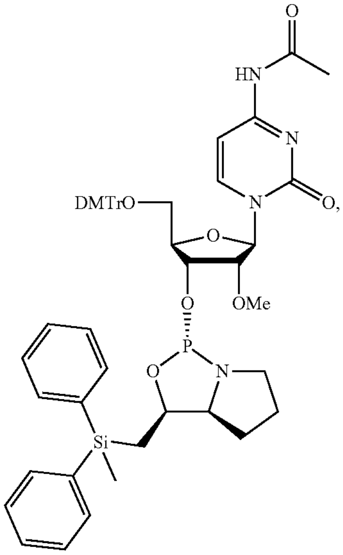
and
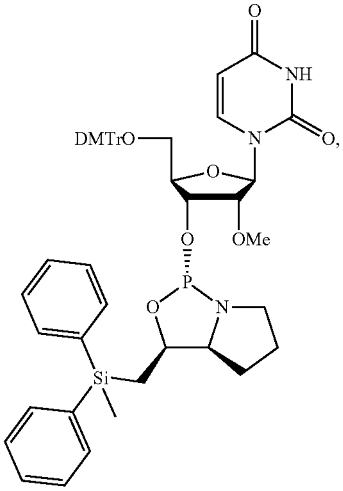

-continued

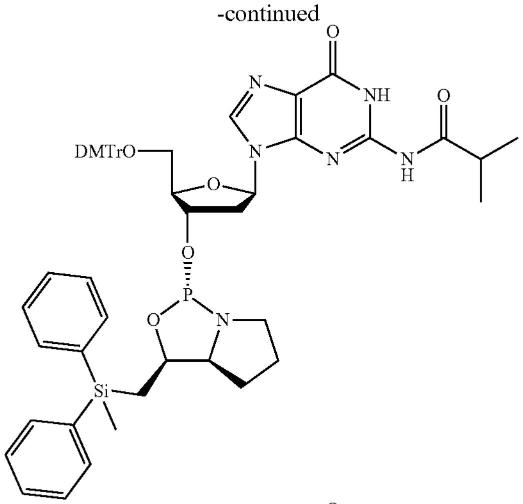

,

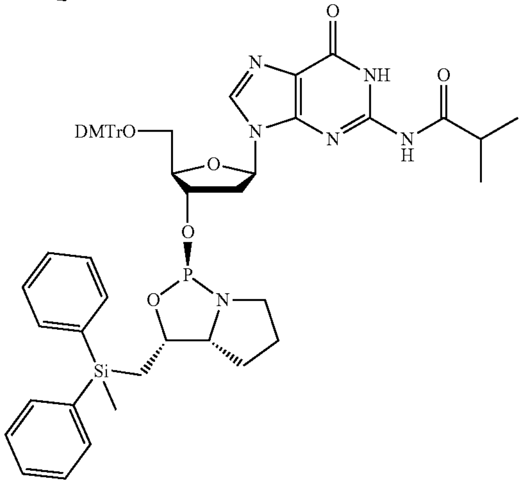

.

In some embodiments, a provided phosphoramidite is selected from compounds 17-48, 53-56, 53a-56a, 57-60, 57a-60a, 61-64, 61a-64a, 65-68, 65a-68a, 73-88, 93-108, and 113-128. In some embodiments, a provided nucleoside is selected from compounds 9-16, 49-52, 49a-52a, 69-72, 89-92, and 109-112. In some embodiments, a provided phosphorochloridite is selected from compound 5-8. In some embodiments, a chiral auxiliary useful for preparing provided phosphorochloridite and/or phosphoramidite is selected from compounds 1-4.

In some embodiments, a provided phosphoramidite is selected from compounds 17-20. In some embodiments, a provided phosphoramidite is selected from compounds 21-24. In some embodiments, a provided phosphoramidite is selected from compounds 25-28. In some embodiments, a provided phosphoramidite is selected from compounds 29-32. In some embodiments, a provided phosphoramidite is selected from compounds 33-36. In some embodiments, a provided phosphoramidite is selected from compounds 37-40. In some embodiments, a provided phosphoramidite is selected from compounds 41-44. In some embodiments, a provided phosphoramidite is selected from compounds 45-48. In some embodiments, a provided phosphoramidite is selected from compounds 53-56. In some embodiments, a provided phosphoramidite is selected from compounds 53a-56a. In some embodiments, a provided phosphoramidite is selected from compounds 57-60. In some embodiments, a provided phosphoramidite is selected from compounds 57a-60a. In some embodiments, a provided phosphoramidite is selected from compounds 61-64. In some embodiments, a provided phosphoramidite is selected from compounds 61a-64a. In some embodiments, a provided phosphoramidite is selected from compounds 65-68. In some embodiments, a provided phosphoramidite is selected from compounds 65a-68a. In some embodiments, a provided phosphoramidite is selected from compounds 73-76. In some embodiments, a provided phosphoramidite is selected from compounds 77-80. In some embodiments, a provided phosphoramidite is selected from compounds 81-84. In some embodiments, a provided phosphoramidite is selected from compounds 85-88. In some embodiments, a provided phosphoramidite is selected from compounds 93-96. In some embodiments, a provided phosphoramidite is selected from compounds 97-100. In some embodiments, a provided phosphoramidite is selected from compounds 101-104. In some embodiments, a provided phosphoramidite is selected from compounds 105-108. In some embodiments, a provided phosphoramidite is selected from compounds 113-116. In some embodiments, a provided phosphoramidite is selected from compounds 117-120. In some embodiments, a provided phosphoramidite is selected from compounds 121-124. In some embodiments, a provided phosphoramidite is selected from compounds 125-128. In some embodiments, a provided phosphoramidite is selected from compounds 113-128. In some embodiments, a provided phosphoramidite is compound 113. In some embodiments, a provided phosphoramidite is compound 114. In some embodiments, a provided phosphoramidite is compound 115. In some embodiments, a provided phosphoramidite is compound 116. In some embodiments, a provided phosphoramidite is compound 117. In some embodiments, a provided phosphoramidite is compound 118. In some embodiments, a provided phosphoramidite is compound 119. In some embodiments, a provided phosphoramidite is compound 120. In some embodiments, a provided phosphoramidite is compound 121. In some embodiments, a provided phosphoramidite is compound 122. In some embodiments, a provided phosphoramidite is compound 123. In some embodiments, a provided phosphoramidite is compound 124. In some embodiments, a provided phosphoramidite is compound 125. In some embodiments, a provided phosphoramidite is compound 126. In some embodiments, a provided phosphoramidite is compound 127. In some embodiments, a provided phosphoramidite is compound 128.

In some embodiments, SU is a sugar moiety as used in oligonucleotides. In some embodiments, SU is a modified sugar moiety as used in oligonucleotides. In some embodiments, a modified sugar moiety is a 2'-OMe, 2'-F, or 2'-MOE sugar moiety. In some embodiments, a modified sugar moiety is a sugar moiety a LNA sugar moiety or a cET sugar moiety.

In some embodiments, SU is a sugar moiety or modified sugar moiety in natural or unnatural nucleosides, nucleotides, and/or oligonucleotides.

The most common naturally occurring nucleotides are comprised of ribose sugars linked to the nucleobases adenosine (A), cytosine (C), guanine (G), and thymine (T) or uracil (U). Also contemplated are modified nucleotides wherein a phosphate group or linkage phosphorus in the nucleotides can be linked to various positions of a sugar or modified sugar. As non-limiting examples, the phosphate group or linkage phosphorus can be linked to the 2', 3', 4' or 5' hydroxyl moiety of a sugar or modified sugar. Nucleotides that incorporate modified nucleobases as described herein are also contemplated in this context. In some embodiments, nucleotides or modified nucleotides comprising an unprotected —OH moiety are used in accordance with methods of the present disclosure.

In some embodiments, SU is -L-O—. In some embodiments, L is -Cy-. In some embodiments, L is optionally substituted 3-30 membered carbocyclylene. In some embodiments, L is optionally substituted 6-30 membered arylene. In some embodiments, L is optionally substituted 5-30 membered heteroarylene having 1-10 heteroatoms independently selected from oxygen, nitrogen and sulfur. In some embodiments, L is optionally substituted 5-30 membered heteroarylene having 1-5 heteroatoms independently selected from oxygen, nitrogen and sulfur. In some embodiments, L is optionally substituted 3-30 membered heterocyclylene having 1-10 heteroatoms independently selected from oxygen, nitrogen, sulfur, phosphorus and silicon. In some embodiments, L is optionally substituted 3-30 membered heterocyclylene having 1-5 heteroatoms independently selected from oxygen, nitrogen, sulfur, phosphorus and silicon. In some embodiments, L is optionally substituted 5-30 membered heterocyclylene having 1-10 heteroatoms independently selected from oxygen, nitrogen, sulfur, phosphorus and silicon. In some embodiments, L is optionally substituted 5-30 membered heterocyclylene having 1-5 heteroatoms independently selected from oxygen, nitrogen, sulfur, phosphorus and silicon. In some embodiments, L is optionally substituted 5-10 membered heterocyclylene having one oxygen atom. In some embodiments, L is optionally substituted 5-membered heterocyclylene having one oxygen atom. In some embodiments, L is optionally substituted 6-membered heterocyclylene having one oxygen atom. In some embodiments, L is optionally substituted 5-10 membered bicyclic heterocyclylene having one or two oxygen atoms. In some embodiments, L is optionally substituted 7-10 membered bicyclic heterocyclylene having one or two oxygen atoms. In some embodiments, L is optionally substituted 7-10 membered bicyclic heterocyclylene having two oxygen atoms. In some embodiments, L is optionally substituted 7-membered bicyclic heterocyclylene having two oxygen atoms.

In some embodiments, SU is a sugar moiety used in oligonucleotide synthesis. A person of ordinary skill in the art understands that phosphoramidites with a variety of sugar moieties can benefit from improved yields and/or purity when provided technologies are utilized for their preparation. In some embodiments, SU is an optionally substituted saturated monocyclic, bicyclic or polycyclic saturated aliphatic ring wherein one or more methylene units are replaced with —O—. In some embodiments, SU is a ribose or deoxyribose moiety found in natural DNA or RNA molecules.

In some embodiments, SU is

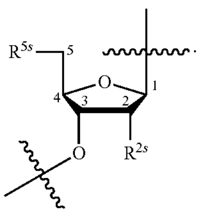

In some embodiments, SU is a modified sugar having the structure of:

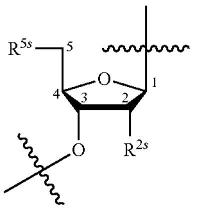

wherein $R^{5s}$ is —OR'; and $R^{2s}$ is —F, —CN, —$N_3$, —NO, —$NO_2$, —R', —OR', —SR', —$N(R')_2$, —O-L-OR', —O-L-SR', or —O-L-$N(R')_2$, or $R^{2s}$ is L connecting $C_2$ with $C_1$, $C_2$, $C_3$, $C_4$ or $C_5$. In some embodiments, $R^{2s}$ is —H. In some embodiments, $R^{2s}$ is —F. In some embodiments, $R^{2s}$ is —OMe. In some embodiments, $R^{2s}$ is —$OCH_2CH_2OMe$. In some embodiments, $R^{2s}$ is L connecting C2 with C1, C2, C3, C4 or C5. In some embodiments, $R^{2s}$ is L connecting C2 with and C4. In some embodiments, L is optionally substituted (C2)-O—$CH_2$—. In some embodiments, L is (C2)-O—$CH_2$—. In some embodiments, a sugar moiety, e.g., of an oligonucleotide, has the structure of

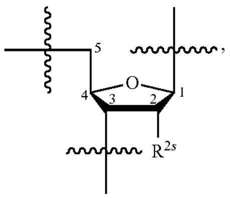

wherein $R^{2s}$ is as described in the present disclosure. In some embodiments, C1 is bonded to a nucleobase, and each of C3 and C5 is independently bonded to an internucleotidic linkage, a 5'-end group, or a 3'-end group. In some embodiments, an oligonucleotide comprises one or more natural DNA sugar moiety (

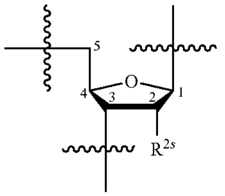

$R^{2S}$ wherein $R^{2s}$ is —H) and one or more modified sugar moiety (e.g.,

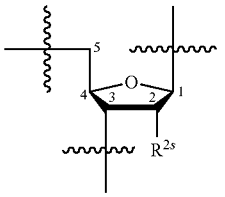

wherein $R^{2s}$ is not —H or —OH). In some embodiments, an oligonucleotide comprises one or more

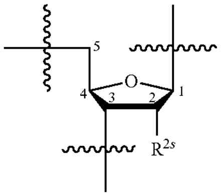

$R^{2s}$ wherein $R^{2s}$ is —H, and one or more

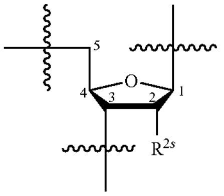

$R^{2s}$ wherein $R^{2s}$ is L connecting C2 with C1, C2, C3, C4 or C5. In some embodiments, an oligonucleotide comprises one or more

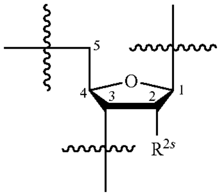

wherein $R^{2s}$ is —H, and one or more

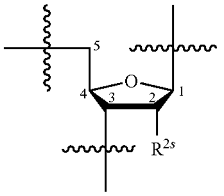

wherein $R^{2s}$ is L connecting C2 with C4, wherein L is optionally substituted —O—$CH_2$—. In some embodiments, an oligonucleotide comprises one or more

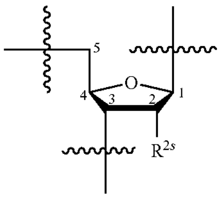

wherein $R^{2s}$ is —H, and one or more

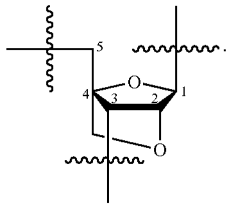 [SMILES: *C[C@]12CO[C@@H](C1*)[C@H](*)O2]

In some embodiments, a modified sugar contains one or more substituents at the 2' position (e.g., $R^{2s}$) including one of the following: —F, —CN, —$N_3$, —NO, —$NO_2$, —OR', —SR', or —$N(R')_2$, wherein each R' is independently as defined above and described herein; —O—($C_{1-10}$ alkyl), —S—($C_{1-10}$ alkyl), —NH—($C_{1-10}$ alkyl), or —N($C_{1-10}$ alkyl)$_2$; —O—($C_{2-10}$ alkenyl), —S—($C_{2-10}$ alkenyl), —NH—($C_{2-10}$ alkenyl), or —N($C_{2-10}$ alkenyl)$_2$; —O—($C_{2-10}$ alkynyl), —S—($C_{2-10}$ alkynyl), —NH—($C_{2-10}$ alkynyl), or —N($C_{2-10}$ alkynyl)$_2$; or —O($C_{1-10}$ alkylene)-O—($C_{1-10}$ alkyl), —O—($C_{1-10}$ alkylene)-NH—($C_{1-10}$ alkyl) or —O—($C_{1-10}$ alkylene)-NH($C_{1-10}$ alkyl)$_2$, —NH—($C_{1-10}$ alkylene)-O—($C_{1-10}$ alkyl), or —N($C_{1-10}$ alkyl)-($C_{1-10}$ alkylene)-O—($C_{1-10}$ alkyl), wherein the alkyl, alkylene, alkenyl and alkynyl may be substituted or unsubstituted. Examples of substituents include, and are not limited to, —$O(CH_2)_nOCH_3$, and —$O(CH_2)_nNH_2$, wherein n is from 1 to about 10, MOE, DMAOE, and DMAEOE.

Also contemplated herein are modified sugars described in WO 2001/088198; and Martin et al., *Helv. Chim. Acta,* 1995, 78, 486-504. In some embodiments, a modified sugar comprises one or more groups selected from a substituted silyl group, an RNA cleaving group, a reporter group, a fluorescent label, an intercalator, a group for improving the pharmacokinetic properties of a nucleic acid, a group for improving the pharmacodynamic properties of a nucleic acid, or other substituents having similar properties. In some embodiments, modifications are made at one or more of the the 2', 3', 4', 5', or 6' positions of the sugar or modified sugar, including the 3' position of the sugar on the 3'-terminal nucleotide or in the 5' position of the 5'-terminal nucleotide.

In some embodiments, the 2'-OH of a ribose is replaced with a group including one of the following: —H, —F; —$CF_3$, —CN, —$N_3$, —NO, —$NO_2$, —OR', —SR', or —$N(R')_2$, wherein each R' is independently as defined above and described herein; —O—($C_1$-$C_{10}$ alkyl), —S—($C_1$-$C_{10}$ alkyl), —NH—($C_1$-$C_{10}$ alkyl), or —N($C_1$-$C_{10}$ alkyl)$_2$; —O—($C_2$-$C_{10}$ alkenyl), —S—($C_2$-$C_{10}$ alkenyl), —NH—($C_2$-$C_{10}$ alkenyl), or —N($C_2$-$C_{10}$ alkenyl)$_2$; —O—($C_2$-$C_{10}$ alkynyl), —S—($C_2$-$C_{10}$ alkynyl), —NH—($C_2$-$C_{10}$ alkynyl), or —N($C_2$-$C_{10}$ alkynyl)$_2$; or —O—($C_1$-$C_{10}$ alkylene)-O—($C_1$-$C_{10}$ alkyl), —O—($C_1$-$C_{10}$ alkylene)-NH—($C_1$-$C_{10}$ alkyl) or —O—($C_1$-$C_{10}$ alkylene)-NH($C_1$-$C_{10}$ alkyl)$_2$, —NH—($C_1$-$C_{10}$ alkylene)-O—($C_1$-$C_{10}$ alkyl), or —N($C_1$-$C_{10}$ alkyl)-($C_1$-$C_{10}$ alkylene)-O—($C_1$-$C_{10}$ alkyl), wherein the alkyl, alkylene, alkenyl and alkynyl may be substituted or unsubstituted. In some embodiments, the 2'-OH is replaced with —H (deoxyribose). In some embodiments, the 2'-OH is replaced with —F. In some embodiments, the 2'-OH is replaced with —OR'. In some embodiments, the 2'-OH is replaced with —OMe. In some embodiments, the 2'-OH is replaced with —$OCH_2CH_2OMe$.

Modified sugars also include sugar moieties of locked nucleic acids (LNAs). In some embodiments, two substituents on sugar carbon atoms are taken together to form a bivalent moiety. In some embodiments, two substituents are on two different sugar carbon atoms. In some embodiments, a formed bivalent moiety has the structure of -L- as defined herein. In some embodiments, $R^{2s}$ is -L-. In some embodiments, -L- is $—O—CH_2—$, wherein $—CH_2—$ is optionally substituted. In some embodiments, -L- is $—O—CH_2—$. In some embodiments, -L- is —O—CH(Et)-. In some embodiments, -L- is between $C_2$ and $C_4$ of a sugar moiety. In some embodiments, a locked nucleic acid has the structure indicated below. A locked nucleic acid of the structure below is indicated, wherein Ba represents a nucleobase or modified nucleobase as described herein, and wherein $R^{2s}$ is $—OCH_2C4'$-.

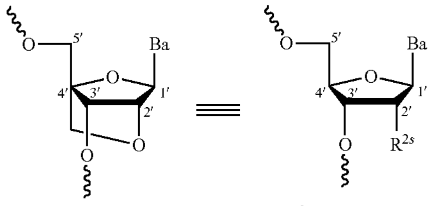

C2'OCH$_2$C4' = LNA (Locked Nucleic Acid)

$R^{2s}$ = OCH$_2$C4'

In some embodiments, a modified sugar is an ENA. In some embodiments, a modified sugar is any of those found in an XNA (xenonucleic acid), for instance, arabinose, anhydrohexitol, threose, 2'fluoroarabinose, or cyclohexene. In some embodiments, a modified sugar is a sugar in tricyclo-DNA (tcDNA). In some embodiments, an oligonucleotide comprises a LNA sugar or a tcDNA sugar.

Modified sugars include sugar mimetics such as cyclobutyl or cyclopentyl moieties in place of the pentofuranosyl sugar. Representative United States patents that teach the preparation of such modified sugar structures include, but are not limited to, U.S. Pat. Nos. 4,981,957; 5,118,800; 5,319,080; and 5,359,044. Some modified sugars that are contemplated include sugars in which the oxygen atom within the ribose ring is replaced by nitrogen, sulfur, selenium, or carbon. In some embodiments, a modified sugar is a modified ribose wherein the oxygen atom within the ribose ring is replaced with nitrogen, and wherein the nitrogen is optionally substituted with an alkyl group (e.g., methyl, ethyl, isopropyl, etc.).

Non-limiting examples of modified sugars include glycerol, which form glycerol nucleic acid (GNA) analogues. One example of a GNA analogue is shown below and is described in Zhang, R et al., *J. Am. Chem. Soc.*, 2008, 130, 5846-5847; Zhang L, et al., *J. Am. Chem. Soc.*, 2005, 127, 4174-4175 and Tsai C H et al., *PNAS*, 2007, 14598-14603 ($X=O^-$):

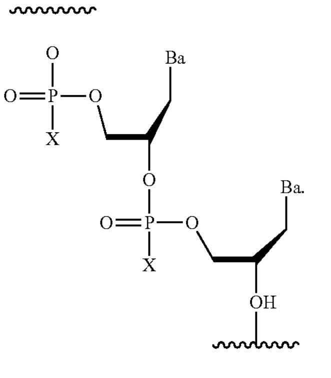

Another example of a GNA derived analogue, flexible nucleic acid (FNA) based on the mixed acetal aminal of formyl glycerol, is described in Joyce G F et al., *PNAS*, 1987, 84, 4398-4402 and Heuberger B D and Switzer C, *J. Am. Chem. Soc.*, 2008, 130, 412-413, and is shown below:

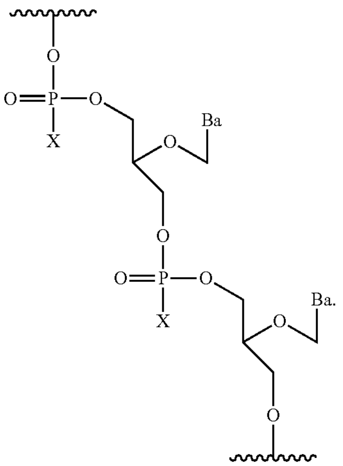

Additional non-limiting examples of modified sugars include hexopyranosyl (6' to 4'), pentopyranosyl (4' to 2'), pentopyranosyl (4' to 3'), or tetrofuranosyl (3' to 2') sugars. In some embodiments, a hexopyranosyl (6' to 4') sugar is of any one in the following formulae:

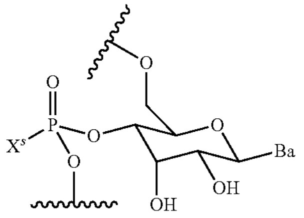

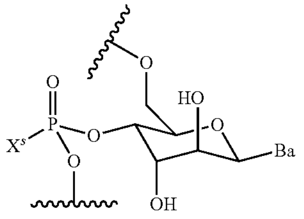

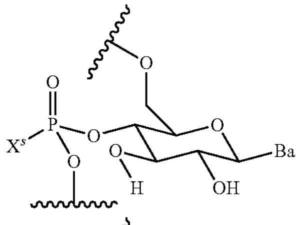

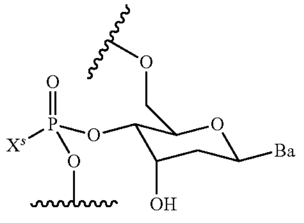

-continued

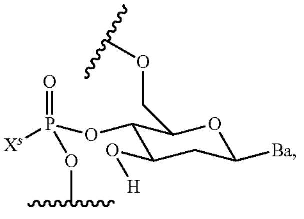

wherein $X^s$ corresponds to a P-modification group and Ba is defined as BA.

In some embodiments, a pentopyranosyl (4' to 2') sugar is of any one in the following formulae:

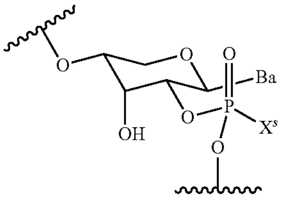

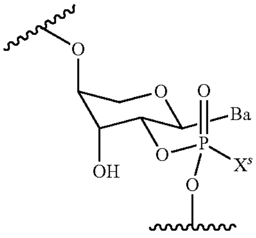

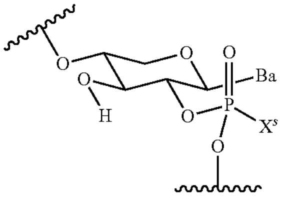

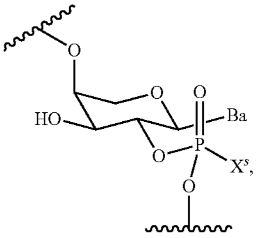

wherein $X^s$ corresponds to a P-modification group and Ba is defined as BA.

In some embodiments, a pentopyranosyl (4' to 3') sugar is of any one in the following formulae:

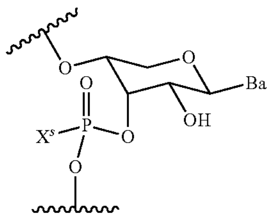

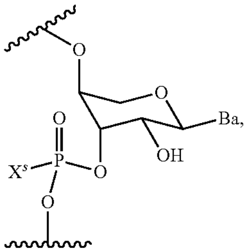

wherein $X^s$ corresponds to a P-modification group and Ba is defined as BA.

In some embodiments, a tetrofuranosyl (3' to 2') sugar is of either in the following formulae:

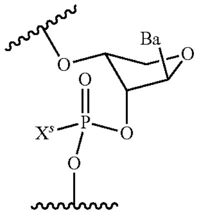

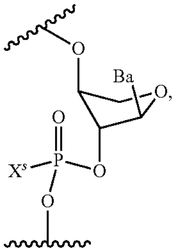

wherein $X^s$ corresponds to a P-modification group and Ba is defined as BA.

In some embodiments, a modified sugar is of any one in the following formulae:

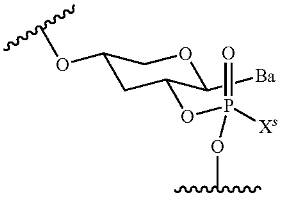

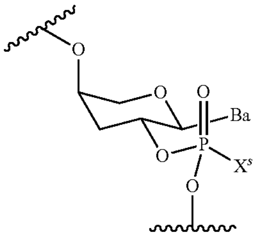

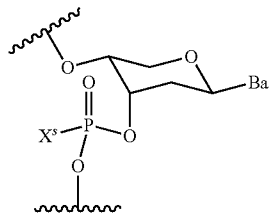

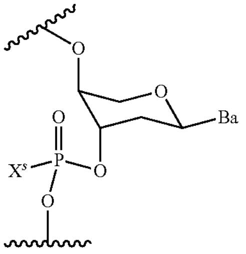

-continued
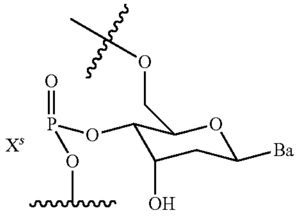
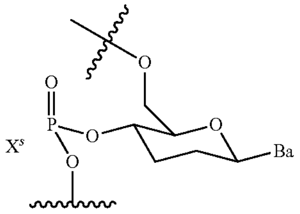
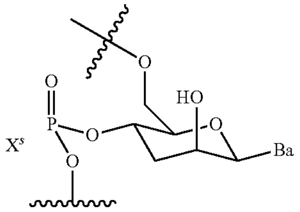
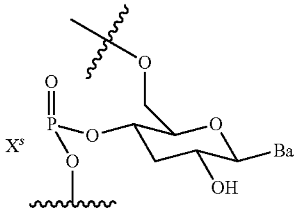
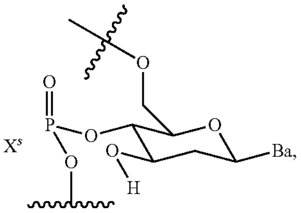
wherein $X^s$ corresponds to a P-modification group and Ba is defined as BA.
In some embodiments, a sugar mimetic is as illustrated below, $X^s$ corresponds to a P-modification group and Ba is defined as BA, and $X^1$ is selected from —S—, —Se—, —$CH_2$—, —NMe-, —NEt- or —NiPr—.
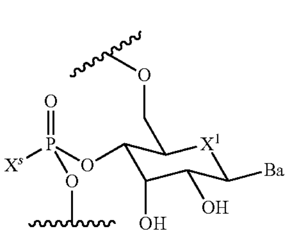
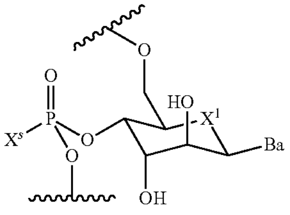
-continued
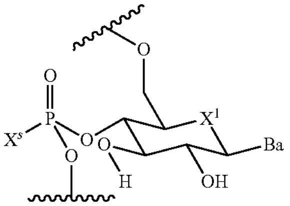
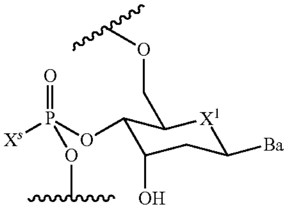
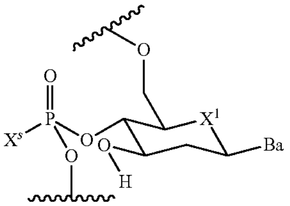
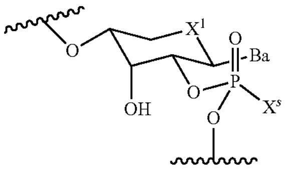
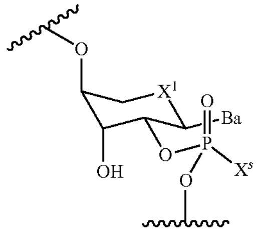
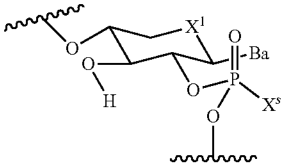
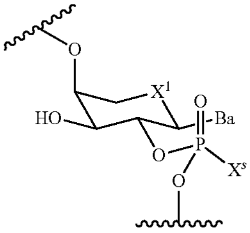
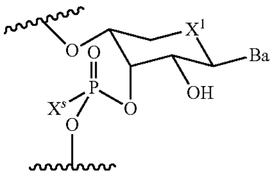

-continued

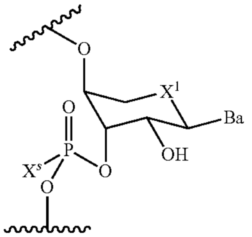

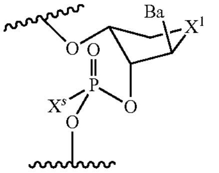

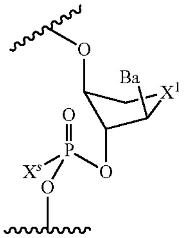

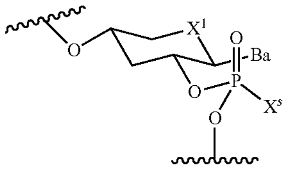

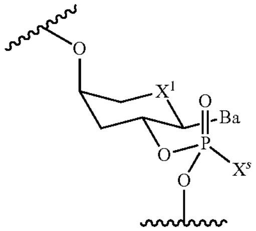

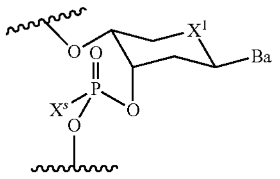

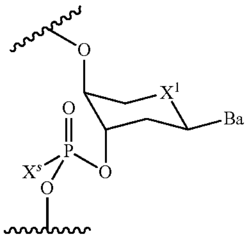

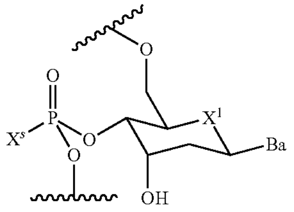

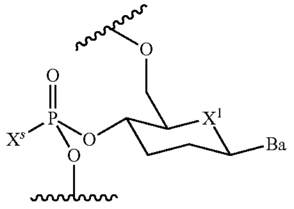

-continued

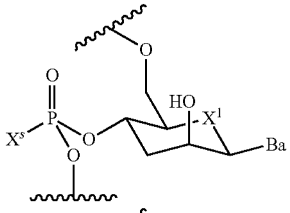

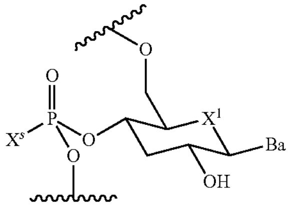

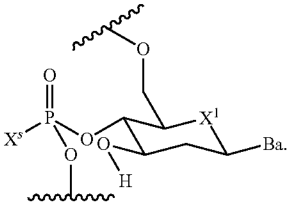

In some embodiments, at least 1%, 2%, 3%, 4%, 5%, 6%, 7%, 8%, 9%, 10%, 11%, 12%, 13%, 14% 5, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50% or more (e.g., 55%, 60%, 65%, 70%, 75%, 80%, 85%, 90%, 95% or more), inclusive, of the sugars in a chirally controlled oligonucleotide composition are modified. In some embodiments, only purine residues are modified (e.g., about 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50% or more [e.g., 55%, 60%, 65%, 70%, 75%, 80%, 85%, 90%, 95% or more] of the purine residues are modified). In some embodiments, only pyrimidine residues are modified (e.g., about 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50% or more [e.g., 55%, 60%, 65%, 70%, 75%, 80%, 85%, 90%, 95% or more] of the pyridimine residues are modified). In some embodiments, both purine and pyrimidine residues are modified.

Modified sugars and sugar mimetics can be prepared by methods known in the art, including, but not limited to: A. Eschenmoser, Science (1999), 284:2118; M. Bohringer et al, Helv. Chim. Acta (1992), 75:1416-1477; M. Egli et al, J. Am. Chem. Soc. (2006), 128(33):10847-56; A. Eschenmoser in *Chemical Synthesis: Gnosis to Prognosis*, C. Chatgilialoglu and V. Sniekus, Ed., (Kluwer Academic, Netherlands, 1996), p. 293; K.-U. Schoning et al, Science (2000), 290:1347-1351; A. Eschenmoser et al, Helv. Chim. Acta (1992), 75:218; J. Hunziker et al, Helv. Chim. Acta (1993), 76:259; G. Otting et al, Helv. Chim. Acta (1993), 76:2701; K. Groebke et al, Helv. Chim. Acta (1998), 81:375; and A. Eschenmoser, Science (1999), 284:2118. Modifications to the 2' modifications can be found in Verma, S. et al. Annu. Rev. Biochem. 1998, 67, 99-134 and all references therein. Specific modifications to the ribose can be found in the following references: 2'-fluoro (Kawasaki et. al., J. Med. Chem., 1993, 36, 831-841), 2'-MOE (Martin, P. *Helv. Chim. Acta* 1996, 79, 1930-1938), "LNA" (Wengel, *J. Acc. Chem. Res.* 1999, 32, 301-310). In some embodiments, a modified sugar is any of those described in PCT Publication No. WO2012/030683, incorporated herein by reference, and depicted in the FIGS. 26-30 of the present application. In some embodiments, a modified sugar is any modified sugar described in any of: Gryaznov, S; Chen, J.-K. J. Am. Chem. Soc. 1994, 116, 3143; Hendrix et al. 1997 Chem. Eur. J. 3: 110; Hyrup et al. 1996 Bioorg. Med. Chem. 4: 5; Jepsen et al. 2004 Oligo. 14: 130-146; Jones et al. J. Org. Chem. 1993, 58, 2983; Koizumi et al. 2003 Nuc. Acids Res. 12: 3267-3273; Koshkin et al. 1998 Tetrahedron 54: 3607-3630; Kumar et al. 1998 Bioo. Med. Chem. Let. 8: 2219-2222; Lauritsen et al. 2002 Chem. Comm. 5: 530-531; Lauritsen et al. 2003 Bioo. Med. Chem. Lett. 13: 253-256; Mesmaeker et al. Angew. Chem., Int. Ed. Engl. 1994, 33, 226; Morita et al. 2001 Nucl. Acids Res. Supp. 1: 241-242; Morita et al. 2002 Bioo. Med. Chem. Lett. 12: 73-76; Morita et al. 2003 Bioo. Med. Chem. Lett. 2211-2226; Nielsen et al. 1997 Chem. Soc. Rev. 73; Nielsen et al. 1997 J. Chem. Soc. Perkins Transl. 1: 3423-3433; Obika et al. 1997 Tetrahedron Lett. 38 (50): 8735-8; Obika et al. 1998 Tetrahedron Lett. 39: 5401-5404; Pallan et al. 2012 Chem. Comm. 48: 8195-8197; Petersen et al. 2003 TRENDS Biotech. 21: 74-81; Rajwanshi et al. 1999 Chem. Commun. 1395-1396; Schultz et al. 1996 Nucleic Acids Res. 24: 2966; Seth et al. 2009 J. Med. Chem. 52: 10-13; Seth et al. 2010 J. Med. Chem. 53: 8309-8318; Seth et al. 2010 J. Org. Chem. 75: 1569-1581; Seth et al. 2012 Bioo. Med. Chem. Lett. 22: 296-299; Seth et al. 2012 Mol. Ther-Nuc. Acids. 1, e47; Seth, Punit P; Siwkowski, Andrew; Allerson, Charles R; Vasquez, Guillermo; Lee, Sam; Prakash, Thazha P; Kinberger, Garth; Migawa, Michael T; Gaus, Hans; Bhat, Balkrishen; et al. From Nucleic Acids Symposium Series (2008), 52(1), 553-554; Singh et al. 1998 Chem. Comm. 1247-1248; Singh et al. 1998 J. Org. Chem. 63: 10035-39; Singh et al. 1998 J. Org. Chem. 63: 6078-6079; Sorensen 2003 Chem. Comm. 2130-2131; Ts'o et al. Ann. N. Y. Acad. Sci. 1988, 507, 220; Van Aerschot et al. 1995 Angew. Chem. Int. Ed. Engl. 34: 1338; Vasseur et al. J. Am. Chem. Soc. 1992, 114, 4006; WO 20070900071; WO 20070900071; or WO 2016/079181.

Example sugars are also described in US 20110294124, US 20120316224, US 20140194610, US 20150211006, US 20150197540, WO 2015107425, PCT/US2016/043542, and PCT/US2016/043598, each of which is incorporated herein by reference. In some embodiments, a modified sugar moiety is an optionally substituted pentose or hexose moiety. In some embodiments, a modified sugar moiety is an optionally substituted pentose moiety. In some embodiments, a modified sugar moiety is an optionally substituted hexose moiety. In some embodiments, a modified sugar moiety is an optionally substituted ribose or hexitol moiety. In some embodiments, a modified sugar moiety is an optionally substituted ribose moiety. In some embodiments, a modified sugar moiety is an optionally substituted hexitol moiety.

In some embodiments, an example modified internucleotidic linkage and/or sugar is selected from:

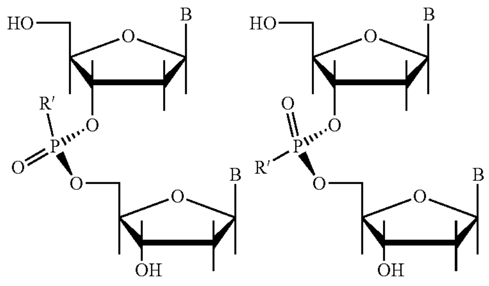

S $R' = -OC_2H$ $R' = -CH_3$

R

Np(Et)N

NpN

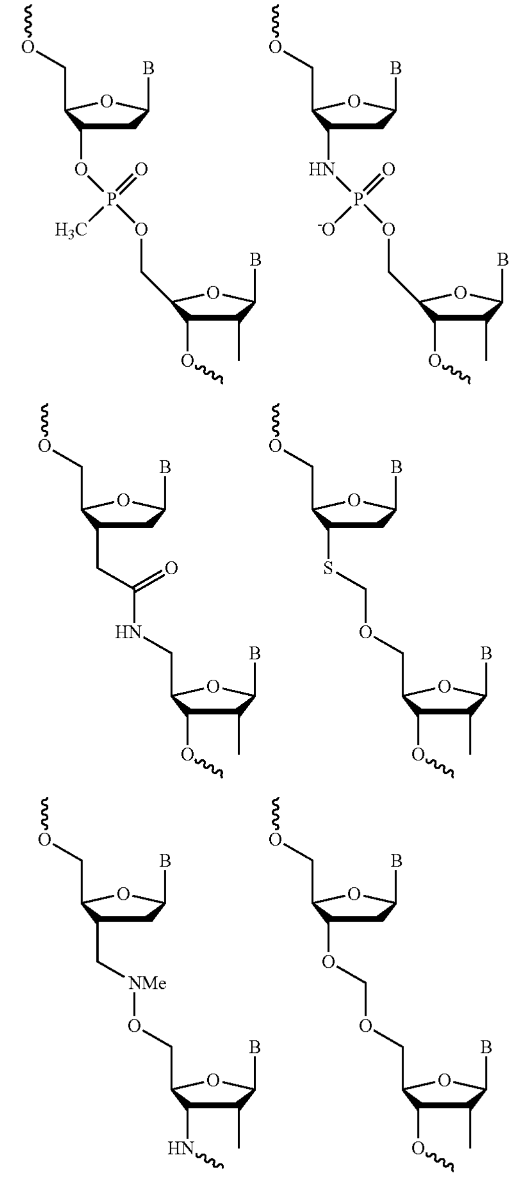

-continued
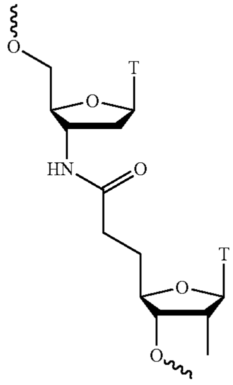
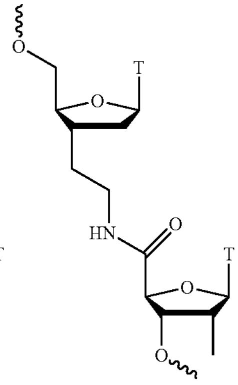
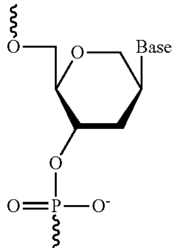
HNA
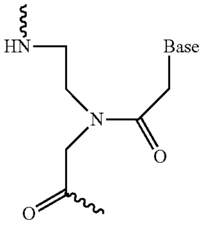
PNA
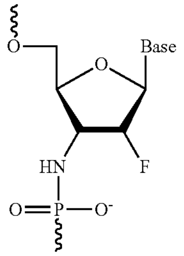
2′-Fluoro N3′-P5′-phosphoramidate LNA
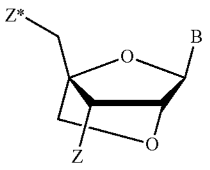
beta-D-oxy-LNA
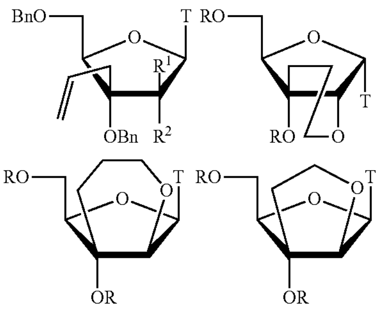
2′-O,3′-C-linked bicyclic
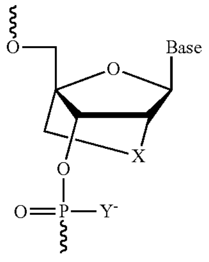
LNA: X = O, Y = O
2′-Thio-LNA: X = S, Y = O
2′-Phosphorothioate-LNA: X = O, Y = S
-continued
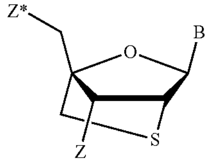
PS-LNA
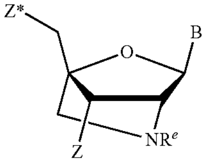
beta-D-thio-LNA
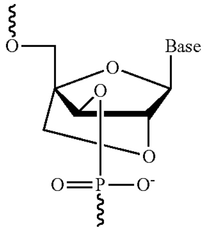
beta-D-amino-LNA
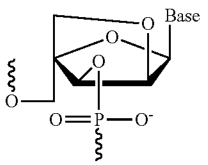
xylo-LNA [c]
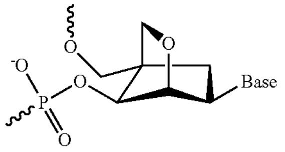
alpha-L-LNA
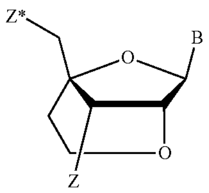
ENA
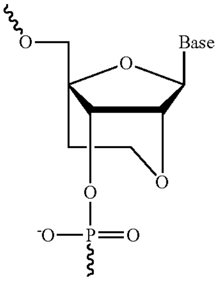
beta-D-ENA
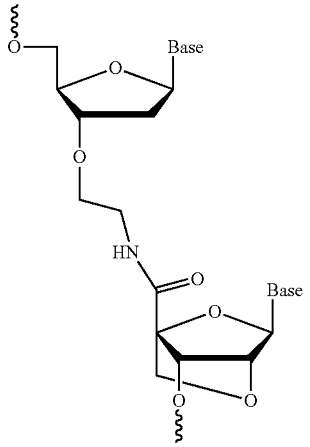
amide-linked LNA
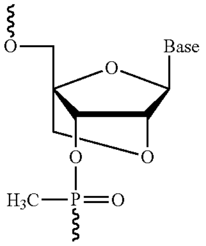
methylphosphonate-LNA
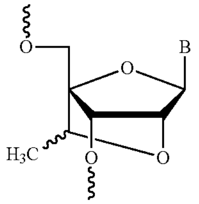
(R, S)-cEt
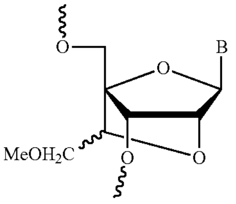
(R, S)-cMOE
(R, S)-cMOE -continued

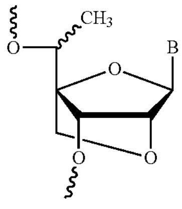

(R, S)-5'-Me-LNA

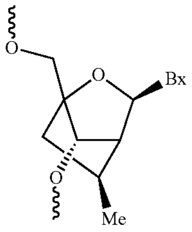

S-Me cLNA

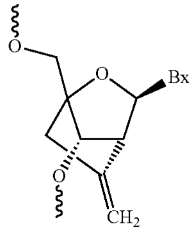

Methylene-cLNA

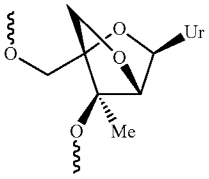

3'-Me-alpha-L-LNA

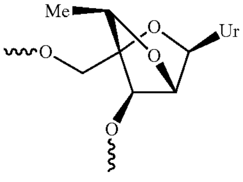

R-6'-Me-alpha-L-LNA

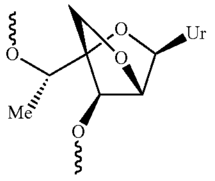

S-5'-Me-alpha-L-LNA

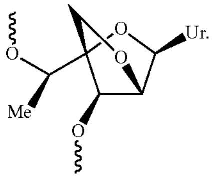

R-5'-Me-alpha-L-LNA

In some embodiments, $R^1$ is R as defined and described. In some embodiments, $R^2$ is R. In some embodiments, $R^e$ is R. In some embodiments, $R^e$ is H, $CH_3$, Bn, $COCF_3$, benzoyl, benzyl, pyren-1-ylcarbonyl, pyren-1-ylmethyl, 2-aminoethyl. In some embodiments, an example modified internucleotidic linkage and/or sugar is selected from those described in Ts'o et al. Ann. N. Y. Acad. Sci. 1988, 507, 220; Gryaznov, S.; Chen, J.-K. J. Am. Chem. Soc. 1994, 116, 3143; Mesmaeker et al. Angew. Chem., Int. Ed. Engl. 1994, 33, 226; Jones et al. J. Org. Chem. 1993, 58, 2983; Vasseur et al. J. Am. Chem. Soc. 1992, 114, 4006; Van Aerschot et al. 1995 Angew. Chem. Int. Ed. Engl. 34: 1338; Hendrix et al. 1997 Chem. Eur. J. 3: 110; Koshkin et al. 1998 Tetrahedron 54: 3607-3630; Hyrup et al. 1996 Bioorg. Med. Chem. 4: 5; Nielsen et al. 1997 Chem. Soc. Rev. 73; Schultz et al. 1996 Nucleic Acids Res. 24: 2966; Obika et al. 1997 Tetrahedron Lett. 38 (50): 8735-8; Obika et al. 1998 Tetrahedron Lett. 39: 5401-5404; Singh et al. 1998 Chem. Comm. 1247-1248; Kumar et al. 1998 Bioo. Med. Chem. Let. 8: 2219-2222; Nielsen et al. 1997 J. Chem. Soc. Perkins Transl. 1: 3423-3433; Singh et al. 1998 J. Org. Chem. 63: 6078-6079; Seth et al. 2010 J. Org. Chem. 75: 1569-1581; Singh et al. 1998 J. Org. Chem. 63: 10035-39; Sorensen 2003 Chem. Comm. 2130-2131; Petersen et al. 2003 TRENDS Biotech. 21: 74-81; Rajwanshi et al. 1999 Chem. Commun. 1395-1396; Jepsen et al. 2004 Oligo. 14: 130-146; Morita et al. 2001 Nucl. Acids Res. Supp. 1: 241-242; Morita et al. 2002 Bioo. Med. Chem. Lett. 12: 73-76; Morita et al. 2003 Bioo. Med. Chem. Lett. 2211-2226; Koizumi et al. 2003 Nuc. Acids Res. 12: 3267-3273; Lauritsen et al. 2002 Chem. Comm. 5: 530-531; Lauritsen et al. 2003 Bioo. Med. Chem. Lett. 13: 253-256; WO 20070900071; Seth et al., Nucleic Acids Symposium Series (2008), 52(1), 553-554; Seth et al. 2009 J. Med. Chem. 52: 10-13; Seth et al. 2012 Mol. Ther-Nuc. Acids. 1, e47; Pallan et al. 2012 Chem. Comm. 48: 8195-8197; Seth et al. 2010 J. Med. Chem. 53: 8309-8318; Seth et al. 2012 Bioo. Med. Chem. Lett. 22: 296-299; WO 2016/079181; U.S. Pat. Nos. 6,326,199; 6,066,500; and 6,440,739, the base and sugar modifications of each of which is herein incorporated by reference.

In some embodiments, one or more hydroxyl group in a sugar moiety is optionally and independently replaced with halogen, —R'—N(R')$_2$, —OR', or —SR', wherein each R' is independently as defined above and described herein.

In some embodiments, SU is

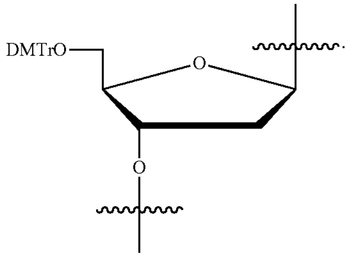

In some embodiments, SU is

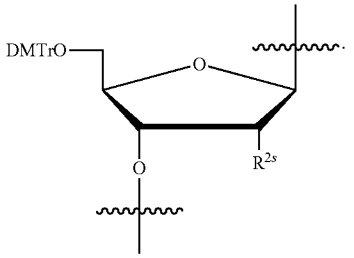

In some embodiments, SU is

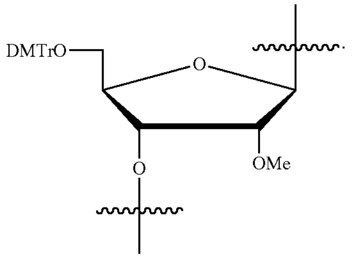

In some embodiments, SU is

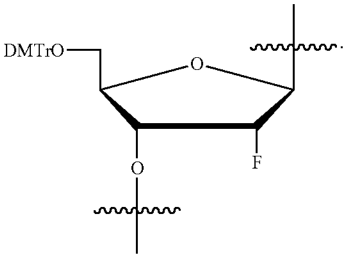

In some embodiments, SU is

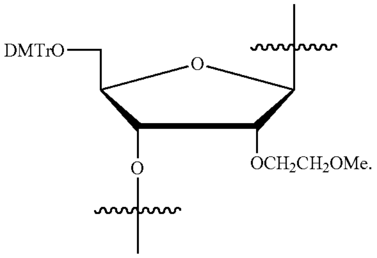

In some embodiments, L is a covalent bond. In some embodiments, L is not a covalent bond. In some embodiments, L is a bivalent, optionally substituted, linear or branched group selected from $C_{1-30}$ aliphatic and $C_{1-30}$ heteroaliphatic group having 1-10 heteroatoms independently selected from oxygen, nitrogen, sulfur, phosphorus and silicon, wherein one or more methylene units are optionally and independently replaced by an optionally substituted $C_{1-6}$ alkylene, $C_{1-6}$ alkenylene, —C≡C—, —C(R')$_2$—, -Cy-, —O—, —S—, —S—S—, —N(R')—, —C(O)—, —C(S)—, —C(NR')—, —C(O)N(R')—, —N(R')C(O)N(R')—, —N(R')C(O)—, —N(R')C(O)O—, —OC(O)N(R')—, —S(O)—, —S(O)$_2$—, —S(O)$_2$N(R')—, —N(R')S(O)$_2$—, —SC(O)—, —C(O)S—, —OC(O)—, or —C(O)O—. In some embodiments, L is a bivalent, optionally substituted, linear or branched $C_{1-30}$ aliphatic group, wherein one or more methylene units are optionally and independently replaced by an optionally substituted $C_{1-6}$ alkylene, $C_{1-6}$ alkenylene, —C≡C—, —C(R')$_2$—, -Cy-, —O—, —S—, —S—S—, —N(R')—, —C(O)—, —C(S)—, —C(NR')—, —C(O)N(R')—, —N(R')C(O)N(R')—, —N(R')C(O)—, —N(R')C(O)O—, —OC(O)N(R')—, —S(O)—, —S(O)$_2$—, —S(O)$_2$N(R')—, —N(R')S(O)$_2$—, —SC(O)—, —C(O)S—, —OC(O)—, or —C(O)O—. In some embodiments, L is a bivalent, optionally substituted, linear or branched $C_{1-30}$ heteroaliphatic group, wherein one or more methylene units are optionally and independently replaced by an optionally substituted $C_{1-6}$ alkylene, $C_{1-6}$ alkenylene, —C≡C—, —C(R')$_2$—, -Cy-, —O—, —S—, —S—S—, —N(R')—, —C(O)—, —C(S)—, —C(NR')—, —C(O)N(R')—, —N(R')C(O)N(R')—, —N(R')C(O)—, —N(R')C(O)O—, —OC(O)N(R')—, —S(O)—, —S(O)$_2$—, —S(O)$_2$N(R')—, —N(R')S(O)$_2$—, —SC(O)—, —C(O)S—, —OC(O)—, or —C(O)O—. In some embodiments, L is a bivalent, optionally substituted, linear or branched $C_{1-30}$ heteroaliphatic group. In some embodiments, L comprises one or more Si.

In some embodiments, $R^{5s}$ is R'. In some embodiments, $R^{5s}$ is —OR'. In some embodiments, $R^{5s}$ is a protected hydroxyl group suitable for oligonucleotide synthesis. In some embodiments, $R^{5s}$ is —OR', wherein R' is optionally substituted $C_{1-6}$ aliphatic. In some embodiments, $R^{5s}$ is DMTrO—. Example protecting groups are widely known in the art for use in accordance with the present disclosure. For additional examples, see Greene, T. W.; Wuts, P. G. M. Protective Groups in Organic Synthesis, 2nd ed.; Wiley: New York, 1991, and WO/2011/005761, WO/2013/012758, WO/2014/012081, WO/2015/107425, WO/2010/064146, WO/2014/010250, WO/2011/108682, WO/2012/039448, and WO/2012/073857, the protecting groups of each of which are hereby incorporated by reference.

In some embodiments, $R^{2s}$ is —H. In some embodiments, $R^{2s}$ is —F. In some embodiments, $R^{2s}$ is —CN. In some embodiments, $R^{2s}$ is —$N_3$. In some embodiments, $R^{2s}$ is —NO. In some embodiments, $R^{2s}$ is —$NO_2$. In some embodiments, $R^{2s}$ is —R'. In some embodiments, $R^{2s}$ is —OR'. In some embodiments, $R^{2s}$ is —OR', wherein R' is optionally substituted $C_{1-6}$ aliphatic. In some embodiments, $R^{2s}$ is —OMe. In some embodiments, $R^{2s}$ is —SR'. In some embodiments, $R^{2s}$ is —N(R')$_2$. In some embodiments, $R^{2s}$ is —O-L-OR'. In some embodiments, $R^{2s}$ is —O-L-OR', wherein L is optionally substituted $C_{1-6}$ alkylene, and R' is optionally substituted $C_1$-6 aliphatic. In some embodiments, $R^{2s}$ is —O-(optionally substituted $C_{1-6}$ alkylene)-OR'. In some embodiments, $R^{2s}$ is —O-(optionally substituted $C_{1-6}$ alkylene)-OR', wherein R' is optionally substituted $C_{1-6}$ alkyl. In some embodiments, $R^{2s}$ is —$OCH_2CH_2OMe$. In some embodiments, $R^{2s}$ is —O-L-SR'. In some embodiments, $R^{2s}$ is —O-L-N(R')$_2$. In some embodiments, $R^{2s}$ is L connecting $C_2$ with $C_1$, $C_2$, $C_3$, $C_4$ or $C_5$. In some embodiments, $R^{2s}$ is L connecting $C_2$ with $C_1$. In some embodiments, $R^{2s}$ is L connecting $C_2$ with $C_2$. In some embodiments, $R^{2s}$ is L connecting $C_2$ with $C_3$. In some embodiments, $R^{2s}$ is L connecting $C_2$ with $C_4$. In some embodiments, $R^{2s}$ is L connecting $C_2$ with $C_5$. In some embodiments, $R^{2s}$ (C2)-O-(optionally substituted methylene)-(C4). In some embodiments, $R^{2s}$ (C2)-O-(methylene)-(C4). In some embodiments, $R^{2s}$ (C2)-O-(methylmethylene)-(C4). In some embodiments, $R^{2s}$ (C2)-O—((R)-methylmethylene)-($C_4$). In some embodiments, $R^{2s}$ (C2)-O—((S)-methylmethylene)-(C4). In some embodiments, $R^{2s}$ (C2)-O-(ethylmethylene)-(C4). In some embodiments, $R^{2s}$(C2)-O—((R)-ethylmethylene)-(C4). In some embodiments, $R^{2s}$ (C2)-O—((S)-ethylmethylene)-($C_4$). In some embodiments, $R^{2s}$ comprises a chiral carbon in R configuration. In some embodiments, $R^{2s}$ comprises a chiral carbon in S configuration.

In some embodiments, $C_1$ is connected to BA.

In some embodiments, -Cy- is an optionally substituted bivalent 3-30 membered carbocyclylene. In some embodiments, -Cy- is an optionally substituted bivalent 6-30 membered arylene. In some embodiments, -Cy- is an optionally substituted bivalent 5-30 membered heteroarylene having 1-10 heteroatoms independently selected from oxygen, nitrogen and sulfur. In some embodiments, -Cy- is an optionally substituted bivalent 3-30 membered heterocyclylene having 1-10 heteroatoms independently selected from oxygen, nitrogen, sulfur, phosphorus and silicon. In some embodiments, -Cy- is an optionally substituted bivalent 5-30 membered heteroarylene having 1-5 heteroatoms independently selected from oxygen, nitrogen and sulfur. In some embodiments, -Cy- is an optionally substituted bivalent 3-30 membered heterocyclylene having 1-5 heteroatoms independently selected from oxygen, nitrogen, sulfur, phosphorus and silicon.

In some embodiments, $R^1$ is R'. In some embodiments, $R^2$ is R'. In some embodiments, $R^3$ is R'.

In some embodiments, each of $R^1$, $R^2$, and $R^3$ is independently R', or two or three of $R^1$, $R^2$, and $R^3$ are taken together with their intervening atoms to form

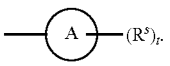

In some embodiments, valence of Ring A is t+1. In some embodiments, Ring A is bivalent. In some embodiments, Ring A is trivalent. In some embodiments, Ring A is polyvalent having a valence greater than 3.

In some embodiments, $R^1$ is R. In some embodiments, $R^1$ is R, wherein R is not hydrogen. In some embodiments, $R^1$ is optionally substituted $C_{1-10}$ aliphatic. In some embodiments, $R^1$ is optionally substituted $C_{1-10}$ alkyl. In some embodiments, $R^1$ is optionally substituted methyl. In some embodiments, $R^1$ is optionally substituted ethyl. In some embodiments, $R^1$ is $—O(CH_2)_2CN$.

In some embodiments, $R^2$ is R. In some embodiments, $R^2$ is R, wherein R is not hydrogen. In some embodiments, $R^2$ is optionally substituted $C_{1-10}$ aliphatic. In some embodiments, $R^2$ is optionally substituted $C_{1-10}$ alkyl. In some embodiments, $R^2$ is optionally substituted methyl. In some embodiments, $R^2$ is optionally substituted ethyl. In some embodiments, $R^2$ is isopropyl.

In some embodiments, $R^3$ is R. In some embodiments, $R^3$ is R, wherein R is not hydrogen. In some embodiments, $R^3$ is optionally substituted $C_{1-10}$ aliphatic. In some embodiments, $R^3$ is optionally substituted $C_{1-10}$ alkyl. In some embodiments, $R^3$ is optionally substituted methyl. In some embodiments, $R^3$ is optionally substituted ethyl. In some embodiments, $R^3$ is isopropyl.

In some embodiments, $R^2$ and $R^3$ are the same. In some embodiments, $R^2$ and $R^3$ are different.

In some embodiments, $R^1$ and $R^2$ are taken together with their intervening atoms to form

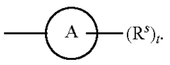

In some embodiments, $R^1$ and $R^3$ are taken together with their intervening atoms to form

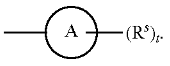

In some embodiments, $R^2$ and $R^3$ are taken together with their intervening atoms to form

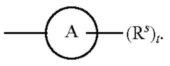

In some embodiments, $R^1$, $R^2$ and $R^3$ are taken together with their intervening atoms to form

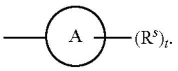

In some embodiments, Ring A is an optionally substituted multivalent, monocyclic, bicyclic or polycyclic, saturated, partially unsaturated, or aryl 3-30 membered ring having, in addition to the intervening nitrogen, phosphorus and oxygen atoms, 0-10 heteroatoms independently selected from oxygen, nitrogen, sulfur, phosphorus and silicon. In some embodiments, Ring A is an optionally substituted multivalent, monocyclic, bicyclic or polycyclic, saturated, partially unsaturated, or aryl 3-30 membered ring having, in addition to the intervening nitrogen, phosphorus and oxygen atoms, 0-10 heteroatoms independently selected from oxygen, nitrogen, and sulfur.

In some embodiments, Ring A is an optionally substituted multivalent, monocyclic, bicyclic or polycyclic, saturated, partially unsaturated, or aryl 3-30 membered ring having, in addition to the intervening nitrogen, phosphorus and oxygen atoms, 0 heteroatom.

In some embodiments, Ring A is an optionally substituted multivalent monocyclic saturated 5-7 membered ring having the intervening nitrogen, phosphorus and oxygen atoms and no additional heteroatoms. In some embodiments, Ring A is an optionally substituted multivalent monocyclic saturated 5-membered ring having the intervening nitrogen, phosphorus and oxygen atoms and no additional heteroatoms. In some embodiments, Ring A is an optionally substituted multivalent monocyclic saturated 6-membered ring having the intervening nitrogen, phosphorus and oxygen atoms and no additional heteroatoms. In some embodiments, Ring A is an optionally substituted multivalent monocyclic saturated 7-membered ring having the intervening nitrogen, phosphorus and oxygen atoms and no additional heteroatoms.

In some embodiments, Ring A is an optionally substituted multivalent, bicyclic, saturated, partially unsaturated, or aryl 5-30 membered ring having, in addition to the intervening nitrogen, phosphorus and oxygen atoms, 0-10 heteroatoms independently selected from oxygen, nitrogen, sulfur, phosphorus and silicon. In some embodiments, Ring A is an optionally substituted multivalent, bicyclic, saturated, partially unsaturated, or aryl 5-30 membered ring having, in addition to the intervening nitrogen, phosphorus and oxygen atoms, 0-10 heteroatoms independently selected from oxygen, nitrogen, and sulfur. In some embodiments, Ring A is a multivalent, bicyclic and saturated 8-10 membered bicyclic ring having the intervening nitrogen, phosphorus and oxygen atoms and no additional heteroatoms. In some embodiments, Ring A is a multivalent, bicyclic and saturated 8-membered bicyclic ring having the intervening nitrogen, phosphorus and oxygen atoms and no additional heteroatoms. In some embodiments, Ring A is a multivalent, bicyclic and saturated 9-membered bicyclic ring having the intervening nitrogen, phosphorus and oxygen atoms and no additional heteroatoms. In some embodiments, Ring A is a multivalent, bicyclic and saturated 10-membered bicyclic ring having the intervening nitrogen, phosphorus and oxygen atoms and no additional heteroatoms. In some embodiments, Ring A is bicyclic and comprises a 5-membered ring fused to a 5-membered ring. In some embodiments, Ring A is bicyclic and comprises a 5-membered ring fused to a 6-membered ring. In some embodiments, the 5-membered ring comprises the intervening nitrogen, phosphorus and oxygen atoms as ring atoms. In some embodiments, Ring A comprises a ring system having the backbone structure of

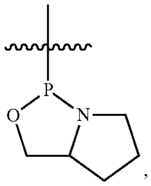, 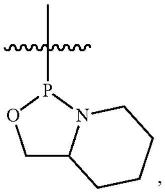, 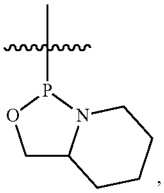, or 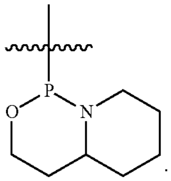.

In some embodiments, Ring A is an optionally substituted multivalent, polycyclic, saturated, partially unsaturated, or aryl 3-30 membered ring having, in addition to the intervening nitrogen, phosphorus and oxygen atoms, 0-10 heteroatoms independently selected from oxygen, nitrogen, sulfur, phosphorus and silicon. In some embodiments, Ring A is an optionally substituted multivalent, polycyclic, saturated, partially unsaturated, or aryl 3-30 membered ring having, in addition to the intervening nitrogen, phosphorus and oxygen atoms, 0-10 heteroatoms independently selected from oxygen, nitrogen, and sulfur.

In some embodiments, Ring A is monocyclic, bicyclic or polycyclic and comprises an optionally substituted 5-10 membered monocyclic ring whose ring atoms comprise the intervening nitrogen, phosphorus and oxygen atoms. In some embodiments, Ring A is monocyclic, bicyclic or polycyclic and comprises an optionally substituted 5-9 membered monocyclic ring whose ring atoms comprise the intervening nitrogen, phosphorus and oxygen atoms. In some embodiments, Ring A is monocyclic, bicyclic or polycyclic and comprises an optionally substituted 5-8 membered monocyclic ring whose ring atoms comprise the intervening nitrogen, phosphorus and oxygen atoms. In some embodiments, Ring A is monocyclic, bicyclic or polycyclic and comprises an optionally substituted 5-7 membered monocyclic ring whose ring atoms comprise the intervening nitrogen, phosphorus and oxygen atoms. In some embodiments, Ring A is monocyclic, bicyclic or polycyclic and comprises an optionally substituted 5-6 membered monocyclic ring whose ring atoms comprise the intervening nitrogen, phosphorus and oxygen atoms.

In some embodiments, Ring A is monocyclic, bicyclic or polycyclic and comprises an optionally substituted 5-membered monocyclic ring whose ring atoms comprise the intervening nitrogen, phosphorus and oxygen atoms. In some embodiments, Ring A is monocyclic, bicyclic or polycyclic and comprises an optionally substituted 6-membered monocyclic ring whose ring atoms comprise the intervening nitrogen, phosphorus and oxygen atoms. In some embodiments, Ring A is monocyclic, bicyclic or polycyclic and comprises an optionally substituted 7-membered monocyclic ring whose ring atoms comprise the intervening nitrogen, phosphorus and oxygen atoms. In some embodiments, Ring A is monocyclic, bicyclic or polycyclic and comprises an optionally substituted 8-membered monocyclic ring whose ring atoms comprise the intervening nitrogen, phosphorus and oxygen atoms. In some embodiments, Ring A is monocyclic, bicyclic or polycyclic and comprises an optionally substituted 9-membered monocyclic ring whose ring atoms comprise the intervening nitrogen, phosphorus and oxygen atoms. In some embodiments, Ring A is monocyclic, bicyclic or polycyclic and comprises an optionally substituted 10-membered monocyclic ring whose ring atoms comprise the intervening nitrogen, phosphorus and oxygen atoms.

In some embodiments, Ring A is monocyclic, bicyclic or polycyclic and comprises an optionally substituted 5-membered ring whose ring atoms consist of the intervening nitrogen, phosphorus and oxygen atoms and carbon atoms. In some embodiments, Ring A is monocyclic, bicyclic or polycyclic and comprises an optionally substituted 6-membered ring whose ring atoms consist of the intervening nitrogen, phosphorus and oxygen atoms and carbon atoms. In some embodiments, Ring A is monocyclic, bicyclic or polycyclic and comprises an optionally substituted 7-membered ring whose ring atoms consist of the intervening nitrogen, phosphorus and oxygen atoms and carbon atoms. In some embodiments, Ring A is monocyclic, bicyclic or polycyclic and comprises an optionally substituted 8-membered ring whose ring atoms consist of the intervening nitrogen, phosphorus and oxygen atoms and carbon atoms. In some embodiments, Ring A is monocyclic, bicyclic or polycyclic and comprises an optionally substituted 9-membered ring whose ring atoms consist of the intervening nitrogen, phosphorus and oxygen atoms and carbon atoms. In some embodiments, Ring A is monocyclic, bicyclic or polycyclic and comprises an optionally substituted 10-membered ring whose ring atoms consist of the intervening nitrogen, phosphorus and oxygen atoms and carbon atoms.

In some embodiments, Ring A comprises a ring system having the backbone structure of

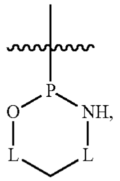 or 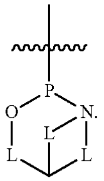

In some embodiments, $R^s$ is R'. In some embodiments, $R^s$ is R. In some embodiments, $R^s$ is optionally substituted $C_{1-30}$ heteroaliphatic. In some embodiments, $R^s$ comprises one or more silicon atoms. In some embodiments, $R^s$ is $—CH_2Si(Ph)_2CH_3$.

In some embodiments, $R^s$ is -L-R'. In some embodiments, $R^s$ is -L-R' wherein -L- is a bivalent, optionally substituted $C_{1-30}$ heteroaliphatic group. In some embodiments, $R^s$ is $—CH_2Si(Ph)_2CH_3$.

In some embodiments, t is 0. In some embodiments, t is 1-5. In some embodiments, t is 1. In some embodiments, t is 2. In some embodiments, t is 3. In some embodiments, t is 4. In some embodiments, t is 5.

In some embodiments, R' is —R. In some embodiments, R' is —C(O)R. In some embodiments, R' is $—CO_2R$. In some embodiments, R' is $—SO_2R$. In some embodiments, two or more R' are taken together with their intervening atoms to form an optionally substituted monocyclic, bicyclic or polycyclic, saturated, partially unsaturated, or aryl 3-30 membered ring having, in addition to the intervening atoms, 0-10 heteroatoms independently selected from oxygen, nitrogen, sulfur, phosphorus and silicon. In some embodiments, R' is hydrogen. In some embodiments, R' is not hydrogen.

In some embodiments, R is hydrogen. In some embodiments, R is not hydrogen. In some embodiments, R is an optionally substituted group selected from $C_{1-30}$ aliphatic, $C_{1-30}$ heteroaliphatic having 1-10 heteroatoms independently selected from oxygen, nitrogen, sulfur, phosphorus and silicon, $C_{6-30}$ aryl, a 5-30 membered heteroaryl ring having 1-10 heteroatoms independently selected from oxygen, nitrogen, sulfur, phosphorus and silicon, and a 3-30 membered heterocyclic ring having 1-10 heteroatoms independently selected from oxygen, nitrogen, sulfur, phosphorus and silicon.

In some embodiments, R is hydrogen or an optionally substituted group selected from $C_{1-20}$ aliphatic, phenyl, a 3-7 membered saturated or partially unsaturated carbocyclic ring, an 8-10 membered bicyclic saturated, partially unsaturated or aryl ring, a 5-6 membered monocyclic heteroaryl ring having 1-4 heteroatoms independently selected from nitrogen, oxygen, and sulfur, a 4-7 membered saturated or partially unsaturated heterocyclic ring having 1-3 heteroatoms independently selected from nitrogen, oxygen, and sulfur, a 7-10 membered bicyclic saturated or partially unsaturated heterocyclic ring having 1-5 heteroatoms independently selected from nitrogen, oxygen, and sulfur, or an 8-10 membered bicyclic heteroaryl ring having 1-5 heteroatoms independently selected from nitrogen, oxygen, and sulfur.

In some embodiments, R is optionally substituted $C_{1-30}$ aliphatic. In some embodiments, R is optionally substituted $C_{1-20}$ aliphatic. In some embodiments, R is optionally substituted $C_{1-15}$ aliphatic. In some embodiments, R is optionally substituted $C_{1-10}$ aliphatic. In some embodiments, R is optionally substituted $C_{1-6}$ aliphatic. In some embodiments, R is optionally substituted $C_{1-6}$ alkyl. In some embodiments, R is optionally substituted hexyl, pentyl, butyl, propyl, ethyl or methyl. In some embodiments, R is optionally substituted hexyl. In some embodiments, R is optionally substituted pentyl. In some embodiments, R is optionally substituted butyl. In some embodiments, R is optionally substituted propyl. In some embodiments, R is optionally substituted ethyl. In some embodiments, R is optionally substituted methyl. In some embodiments, R is hexyl. In some embodiments, R is pentyl. In some embodiments, R is butyl. In some embodiments, R is propyl. In some embodiments, R is ethyl. In some embodiments, R is methyl. In some embodiments, R is isopropyl. In some embodiments, R is n-propyl. In some embodiments, R is tert-butyl. In some embodiments, R is sec-butyl. In some embodiments, R is n-butyl.

In some embodiments, R is optionally substituted $C_{3-30}$ cycloaliphatic. In some embodiments, R is optionally substituted $C_{3-20}$ cycloaliphatic. In some embodiments, R is optionally substituted $C_{3-10}$ cycloaliphatic. In some embodiments, R is optionally substituted cyclohexyl. In some embodiments, R is cyclohexyl. In some embodiments, R is optionally substituted cyclopentyl. In some embodiments, R is cyclopentyl.

In some embodiments, R is an optionally substituted 3-30 membered saturated or partially unsaturated carbocyclic ring. In some embodiments, R is an optionally substituted 3-7 membered saturated or partially unsaturated carbocyclic ring. In some embodiments, R is an optionally substituted 3-membered saturated or partially unsaturated carbocyclic ring. In some embodiments, R is an optionally substituted 4-membered saturated or partially unsaturated carbocyclic ring. In some embodiments, R is an optionally substituted 5-membered saturated or partially unsaturated carbocyclic ring. In some embodiments, R is an optionally substituted 6-membered saturated or partially unsaturated carbocyclic ring. In some embodiments, R is an optionally substituted 7-membered saturated or partially unsaturated carbocyclic ring. In some embodiments, R is optionally substituted cycloheptyl. In some embodiments, R is cycloheptyl. In some embodiments, R is optionally substituted cyclohexyl. In some embodiments, R is cyclohexyl. In some embodiments, R is optionally substituted cyclopentyl. In some embodiments, R is cyclopentyl. In some embodiments, R is optionally substituted cyclobutyl. In some embodiments, R is cyclobutyl. In some embodiments, R is optionally substituted cyclopropyl. In some embodiments, R is cyclopropyl.

In some embodiments, R is $C_{1-30}$ heteroaliphatic having 1-10 heteroatoms independently selected from oxygen, nitrogen, sulfur, phosphorus and silicon. In some embodiments, R is $C_{1-20}$ heteroaliphatic having 1-10 heteroatoms. In some embodiments, R is $C_{1-20}$ heteroaliphatic having 1-10 heteroatoms independently selected from oxygen, nitrogen, sulfur, phosphorus or silicon, optionally including one or more oxidized forms of nitrogen, sulfur, phosphorus or selenium. In some embodiments, R is $C_{1-30}$ heteroaliphatic comprising 1-10 groups independently selected from

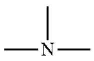,

—N═, ≡N, —S—, —S(O)—, —S(O)$_2$—, —O—, ═O,

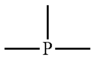, 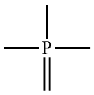, and 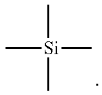.

In some embodiments, R is optionally substituted $C_{6-30}$ aryl. In some embodiments, R is optionally substituted phenyl. In some embodiments, R is phenyl. In some embodiments, R is substituted phenyl.

In some embodiments, R is an optionally substituted 8-10 membered bicyclic saturated, partially unsaturated or aryl ring. In some embodiments, R is an optionally substituted 8-10 membered bicyclic saturated ring. In some embodiments, R is an optionally substituted 8-10 membered bicyclic partially unsaturated ring. In some embodiments, R is an optionally substituted 8-10 membered bicyclic aryl ring. In some embodiments, R is optionally substituted naphthyl.

In some embodiments, R is optionally substituted 5-30 membered heteroaryl ring having 1-10 heteroatoms independently selected from oxygen, nitrogen, sulfur, phosphorus and silicon. In some embodiments, R is optionally substituted 5-30 membered heteroaryl ring having 1-10 heteroatoms independently selected from oxygen, nitrogen, and sulfur. In some embodiments, R is optionally substituted 5-30 membered heteroaryl ring having 1-5 heteroatoms independently selected from oxygen, nitrogen, sulfur, phosphorus and silicon. In some embodiments, R is optionally substituted 5-30 membered heteroaryl ring having 1-5 heteroatoms independently selected from oxygen, nitrogen, and sulfur.

In some embodiments, R is an optionally substituted 5-6 membered monocyclic heteroaryl ring having 1-4 heteroatoms independently selected from nitrogen, oxygen, and sulfur. In some embodiments, R is a substituted 5-6 membered monocyclic heteroaryl ring having 1-4 heteroatoms independently selected from nitrogen, oxygen, and sulfur. In some embodiments, R is an unsubstituted 5-6 membered monocyclic heteroaryl ring having 1-4 heteroatoms independently selected from nitrogen, oxygen, and sulfur.

In some embodiments, R is an optionally substituted 5-membered monocyclic heteroaryl ring having 1-4 heteroatoms independently selected from nitrogen, oxygen or sulfur. In some embodiments, R is an optionally substituted 6-membered monocyclic heteroaryl ring having 1-4 heteroatoms independently selected from nitrogen, oxygen, and sulfur.

In some embodiments, R is an optionally substituted 5-membered monocyclic heteroaryl ring having one heteroatom selected from nitrogen, oxygen, and sulfur. In some embodiments, R is selected from optionally substituted pyrrolyl, furanyl, or thienyl.

In some embodiments, R is an optionally substituted 5-membered heteroaryl ring having two heteroatoms independently selected from nitrogen, oxygen, and sulfur. In certain embodiments, R is an optionally substituted 5-membered heteroaryl ring having one nitrogen atom, and an additional heteroatom selected from sulfur or oxygen. Example R groups include but are not limited to optionally substituted pyrazolyl, imidazolyl, thiazolyl, isothiazolyl, oxazolyl or isoxazolyl.

In some embodiments, R is an optionally substituted 5-membered heteroaryl ring having three heteroatoms independently selected from nitrogen, oxygen, and sulfur. Example R groups include but are not limited to optionally substituted triazolyl, oxadiazolyl or thiadiazolyl.

In some embodiments, R is an optionally substituted 5-membered heteroaryl ring having four heteroatoms independently selected from nitrogen, oxygen, and sulfur. Example R groups include but are not limited to optionally substituted tetrazolyl, oxatriazolyl and thiatriazolyl.

In some embodiments, R is an optionally substituted 6-membered heteroaryl ring having 1-4 nitrogen atoms. In some embodiments, R is an optionally substituted 6-membered heteroaryl ring having 1-3 nitrogen atoms. In other embodiments, R is an optionally substituted 6-membered heteroaryl ring having 1-2 nitrogen atoms. In some embodiments, R is an optionally substituted 6-membered heteroaryl ring having four nitrogen atoms. In some embodiments, R is an optionally substituted 6-membered heteroaryl ring having three nitrogen atoms. In some embodiments, R is an optionally substituted 6-membered heteroaryl ring having two nitrogen atoms. In certain embodiments, R is an optionally substituted 6-membered heteroaryl ring having one nitrogen atom. Example R groups include but are not limited to optionally substituted pyridinyl, pyrimidinyl, pyrazinyl, pyridazinyl, triazinyl, or tetrazinyl.

In some embodiments, R is 3-30 membered heterocyclic ring having 1-10 heteroatoms independently selected from oxygen, nitrogen, sulfur, phosphorus and silicon. In some embodiments, R is 3-30 membered heterocyclic ring having 1-10 heteroatoms independently selected from oxygen, nitrogen, and sulfur. In some embodiments, R is 3-30 membered heterocyclic ring having 1-5 heteroatoms independently selected from oxygen, nitrogen, sulfur, phosphorus and silicon. In some embodiments, R is 3-30 membered heterocyclic ring having 1-5 heteroatoms independently selected from oxygen, nitrogen, and sulfur.

In some embodiments, R is an optionally substituted 3-7 membered saturated or partially unsaturated heterocyclic ring having 1-3 heteroatoms independently selected from nitrogen, oxygen, and sulfur. In some embodiments, R is a substituted 3-7 membered saturated or partially unsaturated heterocyclic ring having 1-3 heteroatoms independently selected from nitrogen, oxygen, and sulfur. In some embodiments, R is an unsubstituted 3-7 membered saturated or partially unsaturated heterocyclic ring having 1-3 heteroatoms independently selected from nitrogen, oxygen, and sulfur. In certain embodiments, R is an optionally substituted 5-7 membered partially unsaturated monocyclic ring having 1-3 heteroatoms independently selected from nitrogen, oxygen, and sulfur. In certain embodiments, R is an optionally substituted 5-6 membered partially unsaturated monocyclic ring having 1-3 heteroatoms independently selected from nitrogen, oxygen, and sulfur. In certain embodiments, R is an optionally substituted 5-membered partially unsaturated monocyclic ring having 1-3 heteroatoms independently selected from nitrogen, oxygen, and sulfur. In certain embodiments, R is an optionally substituted 6-membered partially unsaturated monocyclic ring having 1-3 heteroatoms independently selected from nitrogen, oxygen, and sulfur. In certain embodiments, R is an optionally substituted 7-membered partially unsaturated monocyclic ring having 1-3 heteroatoms independently selected from nitrogen, oxygen, and sulfur. In some embodiments, R is optionally substituted 3-membered heterocyclic ring having one heteroatom selected from nitrogen, oxygen or sulfur. In some embodiments, R is optionally substituted 4-membered heterocyclic ring having 1-3 heteroatoms independently selected from nitrogen, oxygen, and sulfur. In some embodiments, R is optionally substituted 5-membered heterocyclic ring having 1-3 heteroatoms independently selected from nitrogen, oxygen, and sulfur. In some embodiments, R is optionally substituted 6-membered heterocyclic ring having 1-3 heteroatoms independently selected from nitrogen, oxygen, and sulfur. In some embodiments, R is optionally substituted 7-membered heterocyclic ring having 1-3 heteroatoms independently selected from nitrogen, oxygen, and sulfur.

In some embodiments, R is an optionally substituted 7-10 membered bicyclic saturated or partially unsaturated heterocyclic ring having 1-5 heteroatoms independently selected from nitrogen, oxygen, and sulfur. In some embodiments, R is optionally substituted indolinyl. In some embodiments, R is optionally substituted isoindolinyl. In some embodiments, R is optionally substituted 1, 2, 3, 4-tetrahydroquinolinyl. In some embodiments, R is optionally substituted 1, 2, 3, 4-tetrahydroisoquinolinyl. In some embodiments, R is an optionally substituted azabicyclo[3.2.1]octanyl.

In some embodiments, R is an optionally substituted 8-10 membered bicyclic heteroaryl ring having 1-5 heteroatoms independently selected from nitrogen, oxygen, and sulfur.

In some embodiments, R is an optionally substituted 5,6-fused heteroaryl ring having 1-5 heteroatoms independently selected from nitrogen, oxygen, and sulfur. In some embodiments, R is an optionally substituted 5,6-fused heteroaryl ring having 1-4 heteroatoms independently selected from nitrogen, oxygen, and sulfur. In some embodiments, R is an optionally substituted 5,6-fused heteroaryl ring having 1-3 heteroatoms independently selected from nitrogen, oxygen, and sulfur. In some embodiments, R is an optionally substituted 5,6-fused heteroaryl ring having two heteroatoms independently selected from nitrogen, oxygen, and sulfur. In some embodiments, R is optionally substituted 1,4-dihydropyrrolo[3,2-b]pyrrolyl, 4H-furo[3,2-b]pyrrolyl, 4H-thieno[3,2-b]pyrrolyl, furo[3,2-b]furanyl, thieno[3,2-b]furanyl, thieno[3,2-b]thienyl, 1H-pyrrolo[1,2-a]imidazolyl, pyrrolo[2,1-b]oxazolyl or pyrrolo[2,1-b]thiazolyl. In some embodiments, R is an optionally substituted 5,6-fused heteroaryl ring having three heteroatoms independently selected from nitrogen, oxygen, and sulfur. In some embodiments, R is optionally substituted dihydropyrroloimidazolyl, 1H-furoimidazolyl, 1H-thienoimidazolyl, furooxazolyl, furoisoxazolyl, 4H-pyrrolooxazolyl, 4H-pyrroloisoxazolyl, thienooxazolyl, thienoisoxazolyl, 4H-pyrrolothiazolyl, furothiazolyl, thienothiazolyl, 1H-imidazoimidazolyl, imidazooxazolyl or imidazo[5,1-b]thiazolyl. In some embodiments, R is an optionally substituted 5,6-fused heteroaryl ring having four heteroatoms independently selected from nitrogen, oxygen, and sulfur. In some embodiments, R is an optionally substituted 5,6-fused heteroaryl ring having five heteroatoms independently selected from nitrogen, oxygen, and sulfur.

In some embodiments, R is an optionally substituted 5,6-fused heteroaryl ring having 1-5 heteroatoms independently selected from nitrogen, oxygen, and sulfur. In other embodiments, R is an optionally substituted 5,6-fused heteroaryl ring having 1-2 heteroatoms independently selected from nitrogen, oxygen, and sulfur. In certain embodiments, R is an optionally substituted 5,6-fused heteroaryl ring having one heteroatom independently selected from nitrogen, oxygen, and sulfur. In some embodiments, R is optionally substituted indolyl. In some embodiments, R is optionally substituted benzofuranyl. In some embodiments, R is optionally substituted benzo[b]thienyl. In certain embodiments, R is an optionally substituted 5,6-fused heteroaryl ring having two heteroatoms independently selected from nitrogen, oxygen, and sulfur. In some embodiments, R is optionally substituted azaindolyl. In some embodiments, R is optionally substituted benzimidazolyl. In some embodiments, R is optionally substituted benzothiazolyl. In some embodiments, R is optionally substituted benzoxazolyl. In some embodiments, R is an optionally substituted indazolyl. In certain embodiments, R is an optionally substituted 5,6-fused heteroaryl ring having three heteroatoms independently selected from nitrogen, oxygen, and sulfur. In some embodiments, R is optionally substituted oxazolopyridiyl, thiazolopyridinyl or imidazopyridinyl. In certain embodiments, R is an optionally substituted 5,6-fused heteroaryl ring having four heteroatoms independently selected from nitrogen, oxygen, and sulfur. In some embodiments, R is optionally substituted purinyl, oxazolopyrimidinyl, thiazolopyrimidinyl, oxazolopyrazinyl, thiazolopyrazinyl, imidazopyrazinyl, oxazolopyridazinyl, thiazolopyridazinyl or imidazopyridazinyl. In certain embodiments, R is an optionally substituted 5,6-fused heteroaryl ring having five heteroatoms independently selected from nitrogen, oxygen, and sulfur.

In certain embodiments, R is an optionally substituted 6,6-fused heteroaryl ring having 1-5 heteroatoms independently selected from nitrogen, oxygen, and sulfur. In some embodiments, R is an optionally substituted 6,6-fused heteroaryl ring having 1-2 heteroatoms independently selected from nitrogen, oxygen, and sulfur. In other embodiments, R is an optionally substituted 6,6-fused heteroaryl ring having one heteroatom selected from nitrogen, oxygen, and sulfur. In some embodiments, R is optionally substituted quinolinyl. In some embodiments, R is optionally substituted isoquinolinyl. In some embodiments, R is an optionally substituted 6,6-fused heteroaryl ring having two heteroatoms independently selected from nitrogen, oxygen, and sulfur. In some embodiments, R is optionally substituted quinazolinyl, phthalazinyl, quinoxalinyl or naphthyridinyl. In some embodiments, R is an optionally substituted 6,6-fused heteroaryl ring having three heteroatoms independently selected from nitrogen, oxygen, and sulfur. In some embodiments, R is optionally substituted pyridopyrimidinyl, pyridopyridazinyl, pyridopyrazinyl, or benzotriazinyl. In some embodiments, R is an optionally substituted 6,6-fused heteroaryl ring having four heteroatoms independently selected from nitrogen, oxygen, and sulfur. In some embodiments, R is optionally substituted pyridotriazinyl, pteridinyl, pyrazinopyrazinyl, pyrazinopyridazinyl, pyridazinopyridazinyl, pyrimidopyridazinyl or pyrimidopyrimidinyl. In some embodiments, R is an optionally substituted 6,6-fused heteroaryl ring having five heteroatoms independently selected from nitrogen, oxygen, and sulfur.

In some embodiments, $R^1$, $R^2$, $R^3$ or

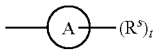

comprises one or more chiral elements, for example, chiral centers. In some embodiments, $R^1$, $R^2$, $R^3$ or

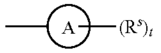

is asymmetric. Phosphoramidites comprising such asymmetric moieties can, among other things, be used for preparing chirally controlled oligonucleotide compositions, such as those described in WO/2014/012081, WO/2015/107425, etc. In some embodiments, when used in oligonucleotide synthesis, such phosphoramidites can deliver diastereoselectivity greater than about 50%, 60%, 70%, 80%, 90%, 91%, 92%, 93%, 94%, 95%, 96%, 97%, 98% or 99% at the newly formed P-chiral center, optionally with greater than about 50%, 60%, 70%, 80%, 90%, 91%, 92%, 93%, 94%, 95%, 96%, 97%, 98% or 99% yield. In some embodiments, diastereoselectivity of a chiral internucleotidic linkage in an oligonucleotide may be measured through a model reaction, e.g. formation of a dimer under essentially the same or comparable conditions wherein the dimer has the same internucleotidic linkage as the chiral internucleotidic linkage, the 5'-nucleoside of the dimer is the same as the nucleoside to the 5'-end of the chiral internucleotidic linkage, and the 3'-nucleoside of the dimer is the same as the nucleoside to the 3'-end of the chiral internucleotidic linkage. For example, diastereoselectivity of the underlined coupling or linkage in NNNNNNNG*SGNNNNNNN can be assessed from coupling two G moieties under the same or comparable conditions, e.g., monomers, chiral auxiliaries, solvents, activators, temperatures, etc.

In some embodiments,

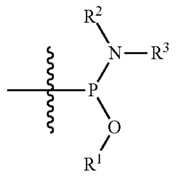

comprises one or more chiral elements and is asymmetric. In some embodiments,

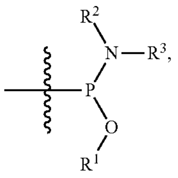
or
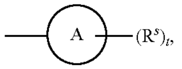

is

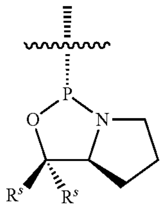
or
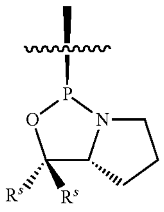
.

In some embodiments,

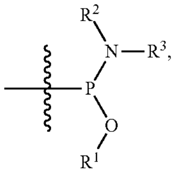
or
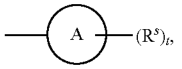

is

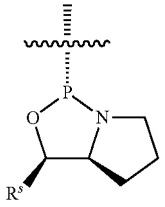
or
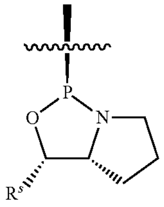
.

In some embodiments, at least one $R^s$ is not hydrogen. In some embodiments, each $R^s$ is not hydrogen. In some embodiments, $R^s$ is optionally substituted phenyl. In some embodiments, $R^s$ is optionally substituted $C_{1-6}$ aliphatic. In some embodiments,

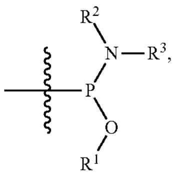
or
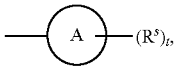

is

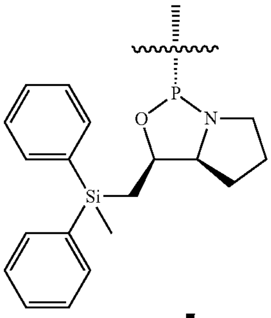
or
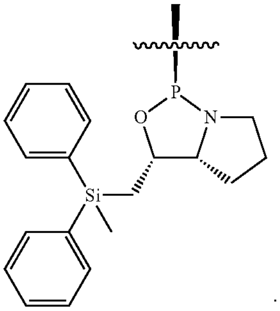
.

In some embodiments,

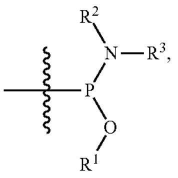
or
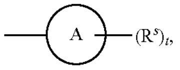

is

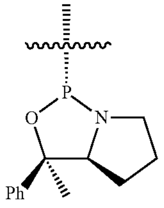
or
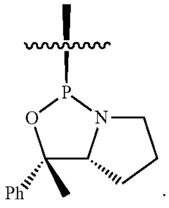
.

As a person of ordinary skill in the art appreciates, phosphoramidites can be prepared from nucleoside and chiral auxiliaries, including those comprising an amino group and a hydroxyl group as illustrated in the examples. Suitable chiral auxiliaries include but are not limited to those described in WO/2011/005761, WO/2013/012758, WO/2014/012081, WO/2015/107425, WO/2010/064146, WO/2014/010250, WO/2011/108682, WO/2012/039448, or WO/2012/073857, the chiral auxiliaries of each of which are hereby incorporated by reference. Among other things, provided technologies have been applied to prepare phosphoramidites using chiral auxiliaries of various structures, for example, those demonstrated in the Examples.

In some embodiments, a phosphoramidite is one described in WO/2011/005761, WO/2013/012758, WO/2014/012081, WO/2015/107425, WO/2010/064146, WO/2014/010250, WO/2011/108682, WO/2012/039448, or WO/2012/073857, the phosphoramidites of each of which are hereby incorporated by reference. In some embodiments, the present disclosure provides a method comprising an oligonucleotide preparation method described in one of these applications, wherein the phosphoramidites are purified using a method described herein.

In some embodiments, a phosphoramidite is:

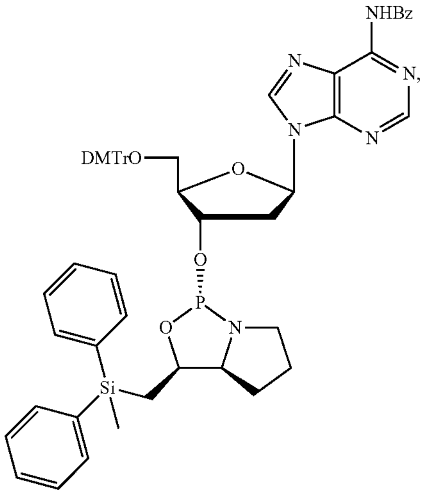

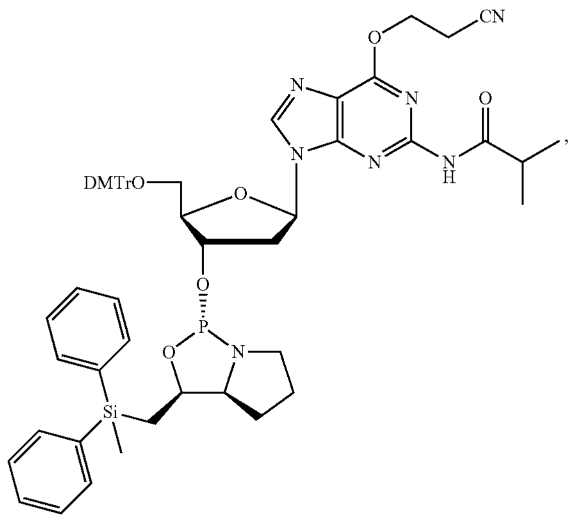

-continued

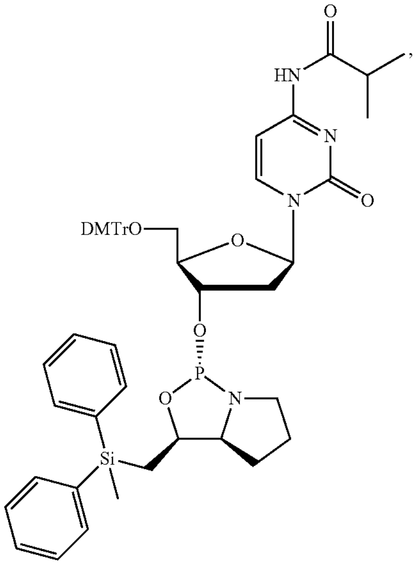

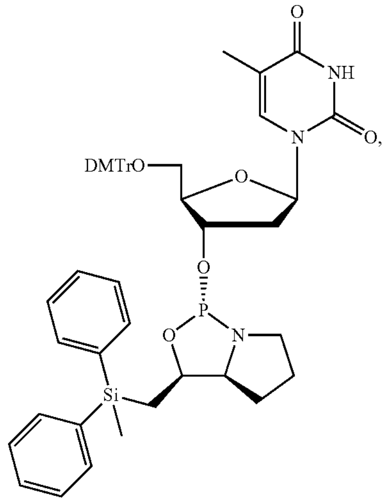

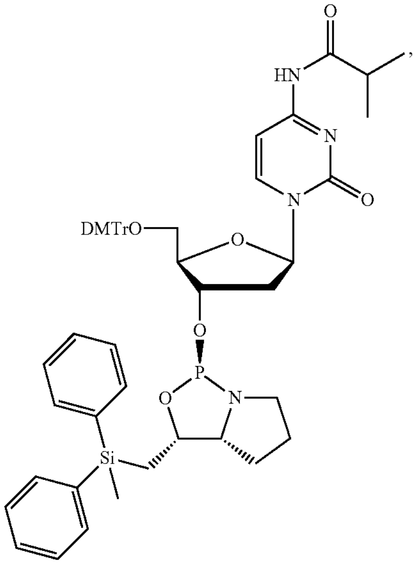

-continued

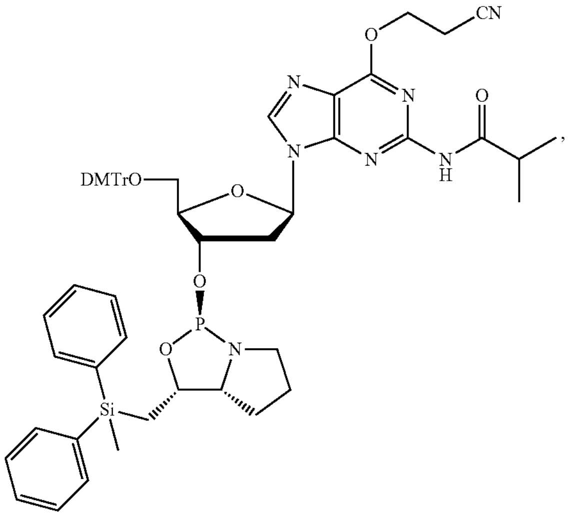

,

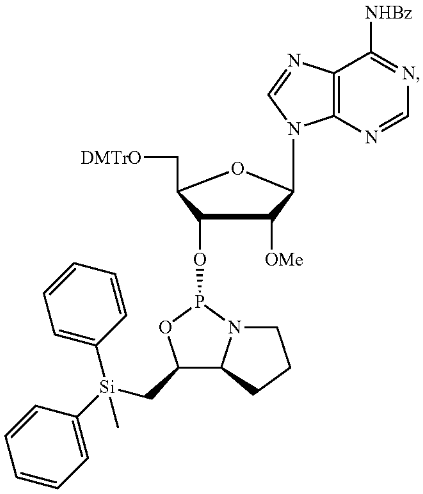

,

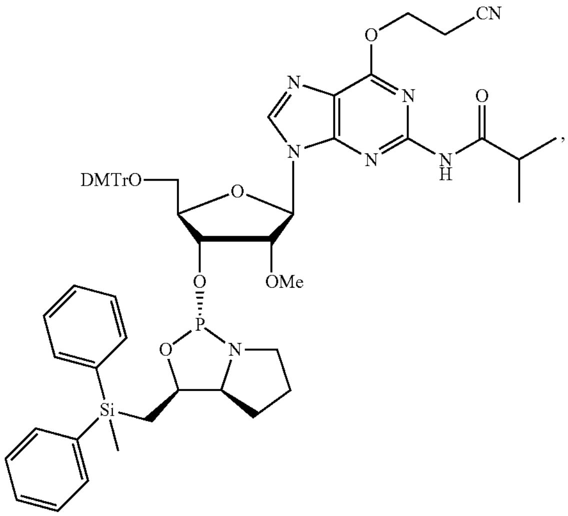

,

-continued

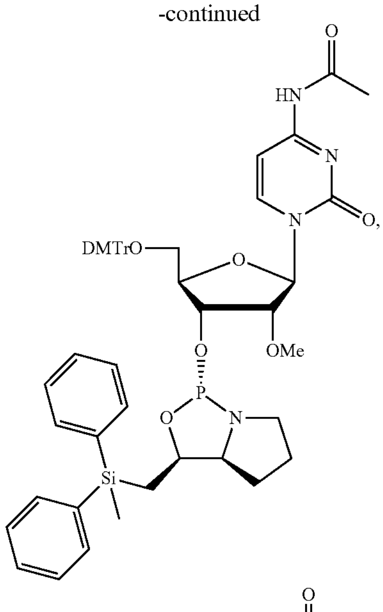

, or

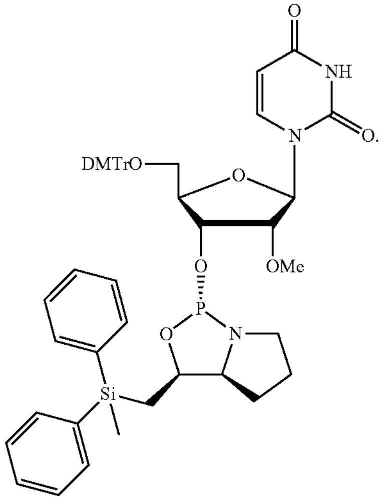

.

In some embodiments, a reaction forming a preparation prior to filtration is a multi-step reaction.

Provided methods may comprise use of a temperature higher and/or lower than room temperature. In some embodiments, provided methods, e.g., in a reaction forming a phosphoramidite, comprise use of a lowered temperature, such as a temperature equal to or lower than about −78, −75, −70, −65, −60, −55, −50, −45, −40, −35, −30, −25, −20, −15, −10, −5, 0, 5, 10, 15, or 20° C. In some embodiments, provided methods, e.g., in a reaction forming a phosphoramidite, comprise use of an elevated temperature, such as a temperature equal to or more than about 25, 30, 35, 40, 45, 50, 55, 60, 65, 70, 75, 80, 85, 90, 95, 100, 110, 120, 130, 140 or 150° C. In some embodiments, provided methods comprise a temperature increase from a lowered temperature to another lowered temperature. In some embodiments, provided methods comprise a temperature increase from a lowered temperature to room temperature. In some embodiments, provided methods comprise a temperature increase from room temperature to an elevated temperature. In some embodiments, provided methods comprise a temperature increase from a lowered temperature to an elevated temperature. In some embodiments, provided methods comprise a temperature decrease from an elevated temperature to another elevated temperature. In some embodiments, provided methods comprise a temperature decrease from an elevated temperature to room temperature. In some embodiments, provided methods comprise a temperature decrease from room temperature to a lowered temperature. In some embodiments, provided methods comprise a temperature decrease from an elevated temperature to a lowered temperature.

Various solvents are suitable for use in provided methods. In some embodiments, reactions for forming phosphoramidites are performed in a solvent comprising ether. In some embodiments, reactions for forming phosphoramidites are performed in a solvent comprising THF. In some embodiments, reactions for forming phosphoramidites are performed in THF. In some embodiments, salts formed when forming phosphoramidites have a lower solubility than phosphoramidites; they precipitate from the preparation and can be removed by filtration as described herein.

In some embodiments, provided methods use water to quench unreacted reagents, for example, phosphorochloridite. In contrast to conventional methods using a material amount of water to wash crude preparations comprising phosphoramidite and reaction byproducts, provided methods use a limited amount of water, and any excess water is optionally removed, for example, through use of one or more desiccants. In some embodiments, a desiccant is $Na_2SO_4$. In some embodiments, a desiccant is $MgSO_4$. In some embodiments, a limited amount is about or less than 1 mole equivalent of phosphoramidites (i.e., molar ratio of water:phosphoramidite is about or less than 1:1). In some embodiments, a limited amount is about or less than 1.1, 1.2, 1.3, 1.4, 1.5, 1.6, 1.7, 1.8, 1.9, or 2 mole equivalents of phosphoramidites.

In some embodiments, a material amount is about or more than 1, 2, 3, 4, 5, 6, 7, 8, 9, 10, 11, 12, 13, 14, 15, 16, 17, 18, 19, 20, 25, 30, 35, 40, 45, 50, 55, 60, 65, 70, 75, 80, 85, 90, 95, 100 mole equivalents of phosphoramidites (i.e., molar ratio of water:phosphoramidite is about or more than 1, 2, 3, 4, 5, 6, 7, 8, 9, 10, 11, 12, 13, 14, 15, 16, 17, 18, 19, 20, 25, 30, 35, 40, 45, 50, 55, 60, 65, 70, 75, 80, 85, 90, 95, 100:1). In some embodiments, a material amount is about or more than 2, 3, 4, 5, 6, 7, 8, 9, 10, 11, 12, 13, 14, 15, 16, 17, 18, 19, 20, 25, 30, 35, 40, 45, 50, 55, 60, 65, 70, 75, 80, 85, 90, 95, 100 mole equivalents of phosphoramidites. In some embodiments, a material amount is about or more than 2 mole equivalents of phosphoramidites. In some embodiments, a material amount is about or more than 3 mole equivalents of phosphoramidites. In some embodiments, a material amount is about or more than 4 mole equivalents of phosphoramidites. In some embodiments, a material amount is about or more than 5 mole equivalents of phosphoramidites. In some embodiments, a material amount is about or more than 6 mole equivalents of phosphoramidites. In some embodiments, a material amount is about or more than 7 mole equivalents of phosphoramidites. In some embodiments, a material amount is about or more than 8 mole equivalents of phosphoramidites. In some embodiments, a material amount is about or more than 9 mole equivalents of phosphoramidites. In some embodiments, a material amount is about or more than 10 mole equivalents of phosphoramidites. In some embodiments, a material amount is about or more than 20 mole equivalents of phosphoramidites. In some embodiments, a material amount is about or more than 50 mole equivalents of phosphoramidites. In some embodiments, a material amount is about or more than 100 mole equivalents of phosphoramidites.

In some embodiments, a material amount is about or more than 0.5%, 1%, 2%, 3%, 4%, 5%, 6%, 7%, 8%, 9% 10%, 15%, 20%, 30%, 40%, 50%, 60%, 70%, 80%, 90%, 100%, 200% or more (v/v) of the volume of a composition, e.g., a solution comprising a phosphoramidite product or a preparation comprising a phosphoramidite product before filtration. In some embodiments, a material amount is about or more than 0.5% (v/v). In some embodiments, a material amount is about or more than 1% (v/v). In some embodiments, a material amount is about or more than 2% (v/v). In some embodiments, a material amount is about or more than 3% (v/v). In some embodiments, a material amount is about or more than 4% (v/v). In some embodiments, a material amount is about or more than 5% (v/v). In some embodiments, a material amount is about or more than 6% (v/v). In some embodiments, a material amount is about or more than 7% (v/v). In some embodiments, a material amount is about or more than 8% (v/v). In some embodiments, a material amount is about or more than 9% (v/v). In some embodiments, a material amount is about or more than 10% (v/v). In some embodiments, a material amount is about or more than 15% (v/v). In some embodiments, a material amount is about or more than 20% (v/v). In some embodiments, a material amount is about or more than 30% (v/v). In some embodiments, a material amount is about or more than 40% (v/v). In some embodiments, a material amount is about or more than 50% (v/v). In some embodiments, a material amount is about or more than 60% (v/v). In some embodiments, a material amount is about or more than 70% (v/v). In some embodiments, a material amount is about or more than 80% (v/v). In some embodiments, a material amount is about or more than 90% (v/v). In some embodiments, a material amount is about or more than 100% (v/v). In some embodiments, a material amount is about or more than 200% (v/v). In some embodiments, a material amount is about or more than 250% (v/v). In some embodiments, a material amount is about or more than 300% (v/v).

In some embodiments, no solution or composition comprising a phosphoramidite product is contacted with water of more than 100, 90, 80, 70, 60, 50, 40, 30, 20, 10, 9, 8, 7, 6, 5, 4, 3, 2, or 1 mole equivalent of the phosphoramidite. In some embodiments, no solution or composition comprising a phosphoramidite product is contacted with water of more than 100, 90, 80, 70, 60, 50, 40, 30, 20, 10, 9, 8, 7, 6, 5, 4, 3, or 2 mole equivalents of the phosphoramidite. In some embodiments, no solution or composition comprising a phosphoramidite product is contacted with water of more than 100, 90, 80, 70, 60, 50, 40, 30, 20, 10, 9, 8, 7, 6, or 5 mole equivalents of the phosphoramidite. In some embodiments, no solution or composition comprising a phosphoramidite product is contacted with water of more than 100, 90, 80, 70, 60, 50, 40, 30, 20, or 10 mole equivalents of the phosphoramidite.

In some embodiments, one or more steps are performed under an inert gas. In some embodiments, formation of phosphoramidites is performed under an inert gas. In some embodiments, filtration is performed under an inert gas. In some embodiments, an inert gas is argon. In some embodiments, an inert gas is nitrogen.

In some embodiments, one or more steps are performed under increased pressure. In some embodiments, one or more steps are performed under vacuum. In some embodiments, filtration is performed under vacuum.

In some embodiments, provided methods do not use any halogenated solvents. In some embodiments, provided methods do not use chloroform.

In some embodiments, provided methods comprise purifying phosphoramidites using chromatography. In some embodiments, a chromatography is HPLC. In some embodiments, a chromatography is silica gel column chromatograph. In some embodiments, silica gel is pre-treated with a hydroscopic solvent. In some embodiments, a hydroscopic solvent is an anhydrous alcohol. In some embodiments, a hydroscopic solvent is anhydrous methanol. In some embodiments, a hydroscopic solvent is anhydrous ethanol. In some embodiments, a hydroscopic solvent is acetonitrile. In some embodiments, a hydroscopic solvent is ethyl acetate. In some embodiments, a mobile phase comprises a base. In some embodiments, a mobile phase comprises 0.1%-10% base. In some embodiments, a mobile phase comprises 1% base. In some embodiments, a mobile phase comprises 5% base. In some embodiments, a base is $N(R)_3$. In some embodiments, a base is $Et_3N$.

In some embodiments, a provided compound, e.g., phosphoramidite, oligonucleotide, etc., has a purity which is about or more than 50%, 60%, 70%, 75%, 80%, 85%, 90%, 91%, 92%, 93%, 94%, 95%, 96%, 97%, 98%, or 99%. In some embodiments, a purity is about 50% or more. In some embodiments, a purity is about 55% or more. In some embodiments, a purity is about 60% or more. In some embodiments, a purity is about 65% or more. In some embodiments, a purity is about 70% or more. In some embodiments, a purity is about 75% or more. In some embodiments, a purity is about 80% or more. In some embodiments, a purity is about 85% or more. In some embodiments, a purity is about 90% or more. In some embodiments, a purity is about 91% or more. In some embodiments, a purity is about 92% or more. In some embodiments, a purity is about 93% or more. In some embodiments, a purity is about 94% or more. In some embodiments, a purity is about 95% or more. In some embodiments, a purity is about 96% or more. In some embodiments, a purity is about 97% or more. In some embodiments, a purity is about 98% or more. In some embodiments, a purity is about 99% or more. In some embodiments, a purity is about 99.5% or more.

As demonstrated herein, provided technologies can surprisingly improve yields and/or purity of phosphoramidites. In some embodiments, the absolute improvement is about 5%, 10%, 15%, 20%, 25%, 30%, 35%, 40%, 45%, 50%, 55%, 60%, 65%, 70%, 75%, 80%, 85%, 90%, 95% or more. In some embodiments, the absolute improvement is greater than about 5%, 10%, 15%, 20%, 25%, 30%, 35%, 40%, 45%, 50%, 55%, 60%, 65%, 70%, 75%, 80%, 85%, 90%, 95% or more. In some embodiments, yield from a provided technology is greater than about 80%, while yield from a corresponding technology without pre-treatment is less than about 60% (corresponding to an absolute improvement of greater than 20%). In some embodiments, the improvement relative to a corresponding technology without pre-treatment is greater than about 5%, 10%, 15%, 20%, 25%, 30%, 35%, 40%, 45%, 50%, 55%, 60%, 65%, 70%, 75%, 80%, 85%, 90%, 95%, 100%, 150%, 200%, 250%, 300%, 400%, 500%, 600%, 700%, 800%, 900% or more.

In some embodiments, a reagent in a provided method is dried before use. Various drying methods in the art can be utilized in accordance with the present disclosure. In some embodiments, a reagent is dried through azeotrope. In some embodiments, a reagent is dried under high vacuum. In some embodiments, a reagent is dried using a desiccant, e.g., $MgSO_4$, $Na_2SO_4$, $CaH_2$, etc. In some embodiments, a reagent is dried by a combination of methods.

In some embodiments, the present disclosure provides methods for preparing an oligonucleotide, comprising providing a provided phosphoramidite. In some embodiments, the present disclosure provides methods for preparing an oligonucleotide composition, comprising providing a provided phosphoramidite. In some embodiments, an oligonucleotide composition is a chirally controlled oligonucleotide composition. In some embodiments, provided phosphoramidites are used to incorporate nucleosides to elongate base sequences. As readily appreciated by a person having ordinary skill in the art, various known oligonucleotide synthesis schemes can use provided phosphoramidites to prepare oligonucleotides and compositions thereof, for example, those described in US 2011/0294124, US 2015/0211006, US 2015/0197540, WO 2015/107425, PCT/US2016/043542, and PCT/US2016/056123, each of which is incorporated herein by reference. In some embodiments, provided methods are used to prepare oligonucleotides and oligonucleotide compositions, including chirally controlled oligonucleotide compositions, described in US 2011/0294124, US 2015/0211006, US 2015/0197540, WO/2011/005761, WO/2013/012758, WO/2014/012081, WO/2015/107425, WO/2010/064146, WO/2014/010250, WO/2011/108682, WO/2012/039448, WO/2012/073857, WO 2015/107425, PCT/US2016/043542, and PCT/US2016/056123, each of which is incorporated herein by reference. In some embodiments, provided methods are used to prepare oligonucleotide compositions comprising WV-1092, WV-2595, WV-2603, WV-1510, WV-2378, WV-2380, WV-2417, WV-2418, WV-2601, WV-2602, WV-2671, WV-3473, WV-2528, WV-2531, WV-3047, or WV-3153. In some embodiments, provided methods are used to prepare oligonucleotide compositions comprising WV-3153. In some embodiments, provided methods are used to prepare oligonucleotide compositions comprising WV-1092. In some embodiments, provided methods are used to prepare oligonucleotide compositions comprising WV-2595. In some embodiments, provided methods are used to prepare oligonucleotide compositions comprising WV-2603. In some embodiments, provided methods are used to prepare oligonucleotide compositions comprising WV-3473. In some embodiments, provided methods are used to prepare oligonucleotide compositions comprising WV-1510. In some embodiments, provided methods are used to prepare oligonucleotide compositions comprising WV-2378. In some embodiments, provided methods are used to prepare oligonucleotide compositions comprising WV-2380. In some embodiments, provided methods are used to prepare oligonucleotide compositions comprising WV-2417. In some embodiments, provided methods are used to prepare oligonucleotide compositions comprising WV-2418. In some embodiments, provided methods are used to prepare oligonucleotide compositions comprising WV-2601. In some embodiments, provided methods are used to prepare oligonucleotide compositions comprising WV-2602. In some embodiments, provided methods are used to prepare oligonucleotide compositions comprising WV-2671. In some embodiments, provided methods are used to prepare oligonucleotide compositions comprising WV-2528. In some embodiments, provided methods are used to prepare oligonucleotide compositions comprising WV-2531. In some embodiments, provided methods are used to prepare oligonucleotide compositions comprising WV-3047. In some embodiments, provided methods are used to prepare oligonucleotide compositions comprising WV-3153. In some embodiments, provided methods are used to prepare oligonucleotide compositions comprising WV-2595. In some embodiments, provided methods are used to prepare chirally controlled oligonucleotide composition of WV-1092, WV-2595, WV-2603, WV-1510, WV-2378, WV-2380, WV-2417, WV-2418, WV-2601, WV-2602, WV-2671, WV-3473, WV-2528, WV-2531, WV-3047, or WV-3153. In some embodiments, provided methods are used to prepare chirally controlled oligonucleotide compositions comprising WV-1092. In some embodiments, provided methods are used to prepare chirally controlled oligonucleotide compositions comprising WV-2595. In some embodiments, provided methods are used to prepare chirally controlled oligonucleotide compositions comprising WV-2603. In some embodiments, provided methods are used to prepare chirally controlled oligonucleotide compositions comprising WV-3473. In some embodiments, provided methods are used to prepare chirally controlled oligonucleotide compositions comprising In some embodiments, provided methods are used to prepare chirally controlled oligonucleotide compositions comprising WV-1510. In some embodiments, provided methods are used to prepare chirally controlled oligonucleotide compositions comprising WV-2378. In some embodiments, provided methods are used to prepare chirally controlled oligonucleotide compositions comprising WV-2380. In some embodiments, provided methods are used to prepare chirally controlled oligonucleotide compositions comprising WV-2417. In some embodiments, provided methods are used to prepare chirally controlled oligonucleotide compositions comprising WV-2418. In some embodiments, provided methods are used to prepare chirally controlled oligonucleotide compositions comprising WV-2601. In some embodiments, provided methods are used to prepare chirally controlled oligonucleotide compositions comprising WV-2602. In some embodiments, provided methods are used to prepare chirally controlled oligonucleotide compositions comprising WV-2671. In some embodiments, provided methods are used to prepare chirally controlled oligonucleotide compositions comprising WV-2528. In some embodiments, provided methods are used to prepare chirally controlled oligonucleotide compositions comprising WV-2531. In some embodiments, provided methods are used to prepare chirally controlled oligonucleotide compositions comprising WV-3047. In some embodiments, provided methods are used to prepare chirally controlled oligonucleotide compositions comprising WV-3153. In some embodiments, provided methods are used to prepare oligonucleotide compositions comprising WV-2602.

WV-1092:
(SEQ ID NO: 1)
mG*SmGmCmAmC*SA*SA*SG*SG*SG*SC*SA*SC*RA*SG*SmAmCm UmU*SmC;

WV-2595:
(SEQ ID NO: 2)
mG*SmGmGmUmC*SC*ST*SC*SC*SC*SC*SA*SC*RA*SG*SmAmGm GmG*SmA

WV-2603:
(SEQ ID NO: 3)
mG*SmUmGmCmA*SC*SA*SC*SA*SG*ST*SA*SG*RA*ST*SmGmAm GmG*SmG;

-continued

WV-3473:
(SEQ ID NO: 4)
fU*SfC*SfA*SfA*SfG*SfG*SmAfA*SmGmA*SfU*SmGmGfC*Sf A*SfU*SfU*SfU*SfC*SfU;

WV-1510:
(SEQ ID NO: 5)
G*SmGmCmAmC*SA*SA*SG*SG*SG*SC*SA*SC*RA*SG*SmAmCm UmU*SC

WV-2378:
(SEQ ID NO: 6)
mG*SmCmAmCmA*SA*SG*SG*SG*SC*SA*SC*RA*SG*SA*SmCmUm UmC*SmC

WV-2380:
(SEQ ID NO: 7)
mC*SmAmCmAmA*SG*SG*SG*SC*SA*SC*RA*SG*SA*SC*SmUmUm CmC*SmA

WV-2417:
(SEQ ID NO: 8)
mA*SmUmAmAmA*ST*ST*SG*ST*SC*RA*ST*SC*SA*SC*SmCmAm GmA*SmA

WV-2418:
(SEQ ID NO: 9)
mA*SmAmUmAmA*SA*ST*ST*SG*ST*SC*RA*ST*SC*SA*SmCmCm AmG*SmA

WV-2601:
(SEQ ID NO: 10)
mG*SmCmAmCmA*SC*SA*SG*ST*SA*SG*RA*ST*SG*SA*SmGmGm GmA*SmG

WV-2602:
(SEQ ID NO: 11)
mU*SmGmCmAmC*SA*SC*SA*SG*ST*SA*SG*RA*ST*SG*SmAmGm GmG*SmA

WV-2671:
(SEQ ID NO: 12)
mG*SmG*SmGmUmC*SC*ST*SC*SC*SC*SC*SA*SC*RA*SG*SmAm GmG*SmG*SmA

WV-3047:
(SEQ ID NO: 13)
fU*fC*fA*fA*fG*fG*mA*mA*mG*mA*fU*mG*mG*fC*fA*fU* fU*fU*fC*fU

WV-2528:
(SEQ ID NO: 14)
fU*SfC*SfA*SfA*SfG*SfG*SfA*SfA*SfG*SmA*RmU*SfG* SfG*SfC*SfA*SfU*SfU*SfU*SfC*SfU

WV-3153:
(SEQ ID NO: 15)
fU*SfC*SfA*SfA*SfG*SfG*SfA*SfA*SmGfA*SmUfG*SmG* SfC*SfA*SfU*SfU*SfU*SfC*SfU

-continued

WV-2531:

(SEQ ID NO: 16)

fU*SfC*SfA*SfA*SfG*SfG*SfA*SfA*SfG*SmAmU*SfG*SfG*SfC*SfA*SfU*SfU*SfU*SfC*SfU wherein *S represents an *Sp* phosphorothioate linkage, *R represents an *Rp* phosphorothioate linkage, each non-labeled linkage is a natural phosphate linkage, m represents a 2'-OMe for a sugar moiety, and f represents a 2'-F for a sugar moiety.

In some embodiments, as readily appreciated by a person having ordinary skill in the art, in provided oligonucleotide compositions oligonucleotides may exist as salts. In some embodiments, provided oligonucleotide compositions are pharmaceutical compositions. In some embodiments, provided oligonucleotides exist as pharmaceutically acceptable salts.

In some embodiments, the present disclosure provides a composition of an oligonucleotide, wherein at least 1%, 2%, 3%, 4%, 5%, 6%, 7%, 8%, 9%, 10%, 15%, 20%, 25%, 30%, 35%, 40%, 45%, 50%, 55%, 60%, 65%, 70%, 75%, 80%, 85%, 90%, 91%, 92%, 93%, 94%, 95%, 96%, 97%, 98%, or 99% of all oligonucleotides within the composition that have the base sequence of the oligonucleotide are the oligonucleotide (or salts thereof). In some embodiments, the present disclosure provides a composition of WV-1092, wherein at least 1%, 2%, 3%, 4%, 5%, 6%, 7%, 8%, 9%, 10%, 15%, 20%, 25%, 30%, 35%, 40%, 45%, 50%, 55%, 60%, 65%, 70%, 75%, 80%, 85%, 90%, 91%, 92%, 93%, 94%, 95%, 96%, 97%, 98%, or 99% of all oligonucleotides within the composition that have the base sequence of WV-1092 are WV-1092 (or salts thereof). In some embodiments, the present disclosure provides a composition of WV-2603, wherein at least 1%, 2%, 3%, 4%, 5%, 6%, 7%, 8%, 9%, 10%, 15%, 20%, 25%, 30%, 35%, 40%, 45%, 50%, 55%, 60%, 65%, 70%, 75%, 80%, 85%, 90%, 91%, 92%, 93%, 94%, 95%, 96%, 97%, 98%, or 99% of all oligonucleotides within the composition that have the base sequence of WV-2603 are WV-2603 (or salts thereof). In some embodiments, the present disclosure provides a composition of WV-3473, wherein at least 1%, 2%, 3%, 4%, 5%, 6%, 7%, 8%, 9%, 10%, 15%, 20%, 25%, 30%, 35%, 40%, 45%, 50%, 55%, 60%, 65%, 70%, 75%, 80%, 85%, 90%, 91%, 92%, 93%, 94%, 95%, 96%, 97%, 98%, or 99% of all oligonucleotides within the composition that have the base sequence of WV-3473 are WV-3473. In some embodiments, the present disclosure provides a composition of WV-1510, wherein at least 1%, 2%, 3%, 4%, 5%, 6%, 7%, 8%, 9%, 10%, 15%, 20%, 25%, 30%, 35%, 40%, 45%, 50%, 55%, 60%, 65%, 70%, 75%, 80%, 85%, 90%, 91%, 92%, 93%, 94%, 95%, 96%, 97%, 98%, or 99% of all oligonucleotides within the composition that have the base sequence of WV-1510 are WV-1510 (or salts thereof). In some embodiments, the present disclosure provides a composition of WV-2378, wherein at least 1%, 2%, 3%, 4%, 5%, 6%, 7%, 8%, 9%, 10%, 15%, 20%, 25%, 30%, 35%, 40%, 45%, 50%, 55%, 60%, 65%, 70%, 75%, 80%, 85%, 90%, 91%, 92%, 93%, 94%, 95%, 96%, 97%, 98%, or 99% of all oligonucleotides within the composition that have the base sequence of WV-2378 are WV-2378 (or salts thereof). In some embodiments, the present disclosure provides a composition of WV-2380, wherein at least 1%, 2%, 3%, 4%, 5%, 6%, 7%, 8%, 9%, 10%, 15%, 20%, 25%, 30%, 35%, 40%, 45%, 50%, 55%, 60%, 65%, 70%, 75%, 80%, 85%, 90%, 91%, 92%, 93%, 94%, 95%, 96%, 97%, 98%, or 99% of all oligonucleotides within the composition that have the base sequence of WV-2380 are WV-2380 (or salts thereof). In some embodiments, the present disclosure provides a composition of WV-2417, wherein at least 1%, 2%, 3%, 4%, 5%, 6%, 7%, 8%, 9%, 10%, 15%, 20%, 25%, 30%, 35%, 40%, 45%, 50%, 55%, 60%, 65%, 70%, 75%, 80%, 85%, 90%, 91%, 92%, 93%, 94%, 95%, 96%, 97%, 98%, or 99% of all oligonucleotides within the composition that have the base sequence of WV-2417 are WV-2417 (or salts thereof). In some embodiments, the present disclosure provides a composition of WV-2418, wherein at least 1%, 2%, 3%, 4%, 5%, 6%, 7%, 8%, 9%, 10%, 15%, 20%, 25%, 30%, 35%, 40%, 45%, 50%, 55%, 60%, 65%, 70%, 75%, 80%, 85%, 90%, 91%, 92%, 93%, 94%, 95%, 96%, 97%, 98%, or 99% of all oligonucleotides within the composition that have the base sequence of WV-2418 are WV-2418 (or salts thereof). In some embodiments, the present disclosure provides a composition of WV-2601, wherein at least 1%, 2%, 3%, 4%, 5%, 6%, 7%, 8%, 9%, 10%, 15%, 20%, 25%, 30%, 35%, 40%, 45%, 50%, 55%, 60%, 65%, 70%, 75%, 80%, 85%, 90%, 91%, 92%, 93%, 94%, 95%, 96%, 97%, 98%, or 99% of all oligonucleotides within the composition that have the base sequence of WV-2601 are WV-2601 (or salts thereof). In some embodiments, the present disclosure provides a composition of WV-2602, wherein at least 1%, 2%, 3%, 4%, 5%, 6%, 7%, 8%, 9%, 10%, 15%, 20%, 25%, 30%, 35%, 40%, 45%, 50%, 55%, 60%, 65%, 70%, 75%, 80%, 85%, 90%, 91%, 92%, 93%, 94%, 95%, 96%, 97%, 98%, or 99% of all oligonucleotides within the composition that have the base sequence of WV-2602 are WV-2602 (or salts thereof). In some embodiments, the present disclosure provides a composition of WV-2671, wherein at least 1%, 2%, 3%, 4%, 5%, 6%, 7%, 8%, 9%, 10%, 15%, 20%, 25%, 30%, 35%, 40%, 45%, 50%, 55%, 60%, 65%, 70%, 75%, 80%, 85%, 90%, 91%, 92%, 93%, 94%, 95%, 96%, 97%, 98%, or 99% of all oligonucleotides within the composition that have the base sequence of WV-2671 are WV-2671 (or salts thereof). In some embodiments, the present disclosure provides a composition of WV-2528, wherein at least 1%, 2%, 3%, 4%, 5%, 6%, 7%, 8%, 9%, 10%, 15%, 20%, 25%, 30%, 35%, 40%, 45%, 50%, 55%, 60%, 65%, 70%, 75%, 80%, 85%, 90%, 91%, 92%, 93%, 94%, 95%, 96%, 97%, 98%, or 99% of all oligonucleotides within the composition that have the base sequence of WV-2528 are WV-2528 (or salts thereof). In some embodiments, the present disclosure provides a composition of WV-2531, wherein at least 1%, 2%, 3%, 4%, 5%, 6%, 7%, 8%, 9%, 10%, 15%, 20%, 25%, 30%, 35%, 40%, 45%, 50%, 55%, 60%, 65%, 70%, 75%, 80%, 85%, 90%, 91%, 92%, 93%, 94%, 95%, 96%, 97%, 98%, or 99% of all oligonucleotides within the composition that have the base sequence of WV-2531 are WV-2531 (or salts thereof). In some embodiments, the present disclosure provides a composition of WV-3047, wherein at least 1%, 2%, 3%, 4%, 5%, 6%, 7%, 8%, 9%, 10%, 15%, 20%, 25%, 30%, 35%, 40%, 45%, 50%, 55%, 60%, 65%, 70%, 75%, 80%, 85%, 90%, 91%, 92%, 93%, 94%, 95%, 96%, 97%, 98%, or 99% of all oligonucleotides within the composition that have the base sequence of WV-3047 are WV-3047 (or salts thereof). In some embodiments, the present disclosure provides a composition of WV-3153, wherein at least 1%, 2%, 3%, 4%, 5%, 6%, 7%, 8%, 9%, 10%, 15%, 20%, 25%, 30%, 35%, 40%, 45%, 50%, 55%, 60%, 65%, 70%, 75%, 80%, 85%, 90%, 91%, 92%, 93%, 94%, 95%, 96%, 97%, 98%, or 99% of all oligonucleotides within the composition that have the base sequence of WV-3153 are WV-3153 (or salts thereof). In some embodiments, the percentage is at least 1%. In some embodiments, the percentage is at least 2%. In some embodiments, the percentage is at least 3%. In some embodiments, the percentage is at least 4%. In some embodiments, the percentage is at least 5%. In some embodiments, the percentage is at least 10%. In some embodiments, the percentage is at least 15%. In some embodiments, the percentage is at least 20%. In some embodiments, the percentage is at least 30%. In some embodiments, the percentage is at least 40%. In some embodiments, the percentage is at least 50%. In some embodiments, the percentage is at least 60%. In some embodiments, the percentage is at least 70%. In some embodiments, the percentage is at least 80%. In some embodiments, the percentage is at least 90%. In some embodiments, the percentage is at least 95%. As appreciated by a person having ordinary skill in the art, percentage of oligonucleotides having a particular linkage stereochemistry pattern of n internucleotidic linkages in a preparation may be calculated as $SE^1*SE^2*SE^3* \ldots SE^n$, wherein $SE^1$, $SE^2$, $SE^3$, . . . , $SE^n$ is independently the stereoselectivity of the $1^{st}$, $2^{nd}$, $3^{rd}$, . . . , and $n^{th}$ chiral internucleotidic linkage; as also appreciated by a person having ordinary skill in the art, stereoselectivity of a chiral internucleotidic linkage in an oligonucleotide may be measured through a model reaction, e.g. formation of a dimer under essentially the same or comparable conditions wherein the dimer has the same internucleotidic linkage as the chiral internucleotidic linkage, the 5'-nucleoside of the dimer is the same as the nucleoside to the 5'-end of the chiral internucleotidic linkage, and the 3'-nucleoside of the dimer is the same as the nucleoside to the 3'-end of the chiral internucleotidic linkage (e.g., for fU*SfU*SfC*SfU, through the dimer of fU*SfC).

In some embodiments, the present disclosure provides new technologies, e.g., compounds, compositions, methods, etc., for preparing a phosphoramidite and/or an oligonucleotide. In some embodiments, the present disclosure provides new technologies for purifying a phosphoramidite. In some embodiments, provided technologies greatly improve efficiency of phosphoramidite synthesis, and/or significantly decrease the cost of phosphoramidite, and oligonucleotides, compositions and medicaments prepared therefrom. Among other things, provided technologies can be utilized to prepare phosphoramidites for a variety of oligonucleotide synthesis methods, including but not limited to those described in WO/2011/005761, WO/2013/012758, WO/2014/012081, WO/2015/107425, WO/2010/064146, WO/2014/010250, WO/2011/108682, WO/2012/039448, or WO/2012/073857, the methods of each of which are hereby incorporated by reference. In some embodiments, methods provided herewith are particularly useful for preparing chirally controlled oligonucleotide compositions, such as those described in WO/2014/012081, WO/2015/107425, etc.

In some embodiments, provided oligonucleotides comprise certain structural features of provided phosphoramidites, for example, protected G phosphoramidites wherein $O^6$ is not protected. In some embodiments, such oligonucleotides also comprise chiral auxiliary residues as those from provided phosphoramidites. In some embodiments, the present disclosure provides a compound or a salt thereof, wherein the compound is an oligonucleotide comprising one or more base moieties BA, wherein BA is optionally protected

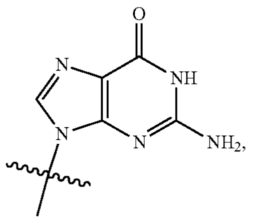

wherein $O^6$ is not protected. In some embodiments, the present disclosure provides a compound or a salt thereof, wherein the compound is an oligonucleotide comprising one or more base moieties BA, wherein BA is optionally substituted

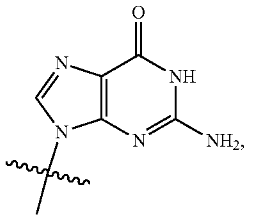

wherein $O^6$ is not substituted. In some embodiments, BA is

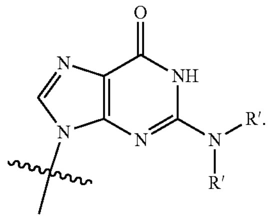

In some embodiments, BA is

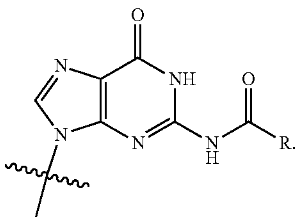

In some embodiments, BA is

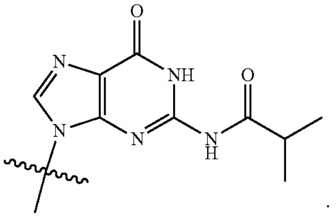 [SMILES: *n1cnc2c(=O)[nH]c(NC(=O)C(C)C)nc21]

In some embodiments, a provided compound is described, for example, in claims 130, 131, and dependent claims thereof. In some embodiments, a provided compound is a product or intermediate oligonucleotide of a provided oligonucleotide synthesis method.

In some embodiments, an oligonucleotide is a polymer or oligomer of nucleotide monomers, containing any combination of nucleotides, modified nucleotides, nucleotide analogs, sugars, modified sugars, phosphate bridges, or modified phosphorus atom bridges (also referred to herein as "internucleotidic linkage", defined further herein). Oligonucleotides can be single-stranded or double-stranded. As used herein, the term "oligonucleotide strand" encompasses a single-stranded oligonucleotide. A single-stranded oligonucleotide can have double-stranded regions and a double-stranded oligonucleotide can have single-stranded regions. Example oligonucleotides include, but are not limited to structural genes, genes including control and termination regions, self-replicating systems such as viral or plasmid DNA, single-stranded and double-stranded siRNAs and other RNA interference reagents (RNAi agents or iRNA agents), shRNA, antisense oligonucleotides, ribozymes, microRNAs, microRNA mimics, supermirs, gapmers, aptamers, antimirs, antagomirs, Ul adaptors, triplex-forming oligonucleotides, G-quadruplex oligonucleotides, RNA activators, immuno-stimulatory oligonucleotides, and decoy oligonucleotides. Double-stranded and single-stranded oligonucleotides that are effective in inducing RNA interference are also referred to as siRNA, RNAi agent, or iRNA agent, herein. In some embodiments, these RNA interference inducing oligonucleotides associate with a cytoplasmic multi-protein complex known as RNAi-induced silencing complex (RISC). In many embodiments, single-stranded and double-stranded RNAi agents are sufficiently long that they can be cleaved by an endogenous molecule, e.g., by Dicer, to produce smaller oligonucleotides that can enter the RISC machinery and participate in RISC mediated cleavage of a target sequence, e.g. a target mRNA. Oligonucleotides of the present disclosure can be of various lengths. In particular embodiments, oligonucleotides can range from about 2 to about 200 nucleotides in length. In various related embodiments, oligonucleotides, single-stranded, double-stranded, and triple-stranded, can range in length from about 4 to about 10 nucleotides, from about 10 to about 50 nucleotides, from about 20 to about 50 nucleotides, from about 15 to about 30 nucleotides, from about 20 to about 30 nucleotides in length. In some embodiments, the oligonucleotide is from about 9 to about 39 nucleotides in length. In some embodiments, the oligonucleotide is at least 4 nucleotides in length. In some embodiments, the oligonucleotide is at least 5 nucleotides in length. In some embodiments, the oligonucleotide is at least 6 nucleotides in length. In some embodiments, the oligonucleotide is at least 7 nucleotides in length. In some embodiments, the oligonucleotide is at least 8 nucleotides in length. In some embodiments, the oligonucleotide is at least 9 nucleotides in length. In some embodiments, the oligonucleotide is at least 10 nucleotides in length. In some embodiments, the oligonucleotide is at least 11 nucleotides in length. In some embodiments, the oligonucleotide is at least 12 nucleotides in length. In some embodiments, the oligonucleotide is at least 15 nucleotides in length. In some embodiments, the oligonucleotide is at least 20 nucleotides in length. In some embodiments, the oligonucleotide is at least 25 nucleotides in length. In some embodiments, the oligonucleotide is at least 30 nucleotides in length. In some embodiments, the oligonucleotide is a duplex of complementary strands of at least 18 nucleotides in length. In some embodiments, the oligonucleotide is a duplex of complementary strands of at least 21 nucleotides in length. In some embodiments, a sequence of a nucleic acid or an oligonucleotide comprises or consists of a common base sequence hybridizes with a transcript of dystrophin, Malat1, myostatin, Factor XI, Huntingtin, a myostatin receptor, c-Myc, ActRIIB, ActRIIA, SMN2, K-Ras, beta-catenin, dystrophia myotonica protein kinase (DMPK), C9orf72, alpha-ENaC, beta-ENaC, ApoE4, ApoC3, FGF23, an epidermal growth factor receptor, Vascular Endothelial Growth Factor Receptor-2 (VEGFR-2), Proprotein convertase subtilisin/kexin type 9 (PCSK9), SMAD7 or KRT14 (Keratin 14), estrogen receptor (ER), ERBB2, calcium signal transducer 2 (TACSTD2) or a mutant thereof. In some embodiments, a provided oligonucleotide is capable of hybridizing with a transcript of Huntingtin. In some embodiments, a provided oligonucleotide is capable of hybridizing with a transcript of mutant Huntingtin. In some embodiments, a provided oligonucleotide is capable of hybridizing with a transcript of mutant Huntingtin which comprises expanded CAG repeats. In some embodiments, a provided oligonucleotide is capable of hybridizing with a transcript of dystrophin. In some embodiments, a provided oligonucleotide is capable of hybridizing with a transcript of mutant dystrophin. In some embodiments, a provided oligonucleotide is capable of hybridizing with a transcript of mutant dystrophin, and causing skipping of one or more exons to produce a protein with higher activity than the protein produced absent skipping of the one or more exons. In some embodiments, a sequence of a nucleic acid or an oligonucleotide comprises or consists of a common base sequence is capable of hybridizing with a transcript of a gene related to Huntington's disease, a cancer, a disease of the circulatory system, a disease of the digestive system, a disease of the nervous system, a disease of the digestive system, spinal muscular atrophy, spinal muscular atrophy type 1, amyotrophic lateral sclerosis, Duchenne muscular dystrophy, myotonic dystrophy, myotonic dystrophy type 1, a genetic disease of the liver, a metabolic disease of the liver, epidermolysis bullosa simplex, a genetic disease of the skin, a genetic disease of the skin, or irritable bowel syndrome, a disease of the musculature, a disease of the eye, a disease of the reproductive system, a disease of the male reproductive system, a disease of the female reproductive system, a disease of the central nervous system, or a genetic disease, or a metabolic disease.

In some embodiments, an oligonucleotide is an antisense oligonucleotide which is antisense to a target nucleic acid or sequence. In some embodiments, a provided oligonucleotide mediates skipping modulation (e.g., increasing beneficial skipping that produces a desired product, and/or decrease deleterious skipping that produces an undesired product, e.g., increasing levels of a desirable or non-disease-associated exon-containing mRNA, and/or decreasing level of an undesirable or disease-associated exon-deleted mRNA). In some embodiments, an oligonucleotide directs RNase H-mediated cleavage of a target nucleic acid. In some embodiments, an oligonucleotide provides benefits and/or activities without directing RNase H-mediated cleavage of a target nucleic acid (or significant levels of this activity). In some embodiments, an oligonucleotide achieves a beneficial effect (e.g., increasing levels of a desirable or non-disease-associated mRNA, or decreasing levels of an undesirable or disease-associated mRNA) via a mechanism which does not involve RNase H, e.g., steric hindrance, splicing modulation, RNA interference, etc.

In some embodiments, an oligonucleotide mediates RNA interference. In some embodiments, an oligonucleotide is a single-stranded siRNA. In some embodiments, an oligonucleotide is a strand comprised in a double-stranded siRNA.

In some embodiments, a complementary nucleotide sequence is a nucleotide sequence that forms Watson-Crick pairs with a target nucleotide sequence. In some embodiments, a complementary nucleotide sequence is a nucleotide sequence that forms one or more Wobble base pairs with a target nucleotide sequence. A Watson-Crick pair typically refers to a pair of nucleobases in which hydrogen bonds are formed between adenine-thymine, adenine-uracil or guanine-cytosine, and Wobble base pair typically refers to a pair of nucleobases in which hydrogen bonds are formed between guanine-uracil, inosine-uracil, inosine-adenine or inosine-cytosine. In some embodiments, a complementary nucleotide sequence is 100% complementary to its target nucleotide sequence. In some embodiments, a complementary nucleotide sequence may contain, for example, 1 to 3, 1 or 2, or one nucleotide non-complementary to a target nucleotide sequence.

In some embodiments, in a sequence or an oligonucleotide complementary to a target sequence, each nucleobase can be independently replaced by another moiety (e.g., another nucleobase or a modified nucleobase) which can form base paring as in Watson-Crick base pairing and/or Wobble base paring to the corresponding nucleobase in the target sequence.

In some embodiments, a nucleobase is replaced by another moiety (e.g., a modified nucleobase) which can perform a function that is the same as the nucleobase. In some embodiments, in a sequence disclosed herein, a nucleobase is replaced by another moiety (e.g., a modified nucleobase) which can perform a function that is the same as the nucleobase. As a non-limiting example, each adenine in a sequence or oligonucleotide can independently be replaced with 2,6-diaminopurine, which like adenine can form hydrogen bonds with thymine or uracil. In some embodiments, in a sequence disclosed herein, a nucleobase is replaced by inosine.

In some embodiments, an oligonucleotide contains increased levels of one or more isotopes. In some embodiments, an oligonucleotide is labeled, e.g., by one or more isotopes of one or more elements, e.g., hydrogen, carbon, nitrogen, etc. In some embodiments, an oligonucleotide comprises base modifications, sugar modifications, and/or internucleotidic linkage modifications, wherein the oligonucleotide contains an enriched level of deuterium. In some embodiments, an oligonucleotide is labeled with deuterium (replacing $—^{1}H$ with $—^{2}H$) at one or more positions. In some embodiments, one or more $^{1}H$ of an oligonucleotide or any moiety conjugated to an oligonucleotide (e.g., a targeting moiety, etc.) is substituted with $^{2}H$. Such oligonucleotides can be used in any compositions or methods described herein.

Unless otherwise stated, structures depicted herein are also meant to include all isomeric (e.g., enantiomeric, diastereomeric, and geometric (or conformational)) forms of the structure; for example, the R and S configurations for each asymmetric center, (Z) and (E) double bond isomers, and (Z) and (E) conformational isomers. Therefore, single stereochemical isomers as well as enantiomeric, diastereomeric, and geometric (or conformational) mixtures of the present compounds are within the scope of the disclosure. Unless otherwise stated, all tautomeric forms of the compounds of the disclosure are within the scope of the disclosure. Additionally, unless otherwise stated, structures depicted herein are also meant to include compounds that differ only in the presence of one or more isotopically enriched atoms. For example, compounds having the present structures except for the replacement of hydrogen by deuterium or tritium, or the replacement of a carbon by a $^{11}C$- or $^{13}C$- or $^{14}C$-enriched carbon are within the scope of this disclosure. Such compounds are useful, for example, as analytical tools or probes in biological assays. Unless otherwise specified, oligonucleotides depicted herein (e.g., WV-1092, WV-2603, WV-3473, WV-1510, WV-2378, WV-2380, WV-2417, WV-2418, WV-2601, WV-2602, WV-2671, WV-2528, WV-2531, WV-3047, WV-3153, etc.) also include salts thereof. In some embodiments, an oligonucleotide is a salt. In some embodiments, an oligonucleotide is a sodium salt. In some embodiments, an oligonucleotide is a sodium salt, wherein each linkage exists in the form of a sodium salt.

As used herein and in the claims, the singular forms "a", "an", and "the" include the plural reference unless the context clearly indicates otherwise. Thus, for example, a reference to "a compound" includes a plurality of such compounds.

EXEMPLIFICATION

Non-limiting examples were provided below. A person of ordinary skill in the art appreciates that other phosphoramidites can similarly be prepared with greatly improved yields and/or purity as illustrated herein.

Scheme 1.

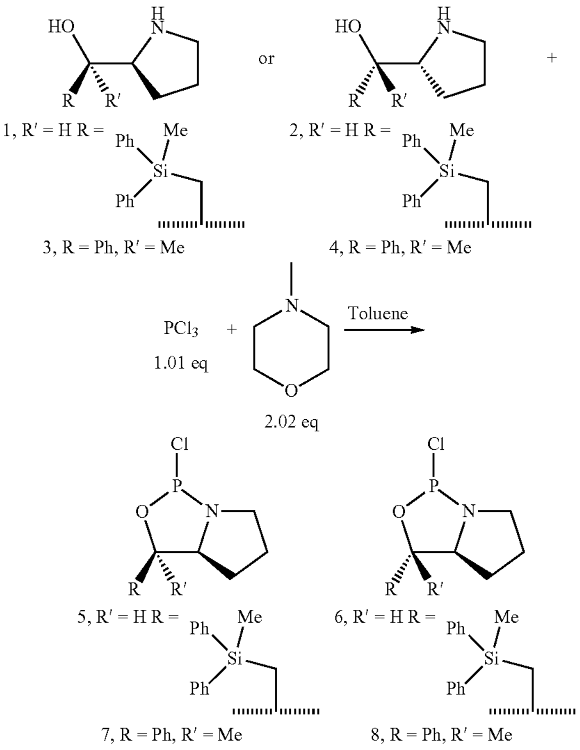

1, R' = H R =
2, R' = H R =
or
+
3, R = Ph, R' = Me
4, R = Ph, R' = Me
5, R' = H R =
6, R' = H R =
7, R = Ph, R' = Me
8, R = Ph, R' = Me

β-Amino alcohol 1-4 (78 g, 250 mmol) was dissolved with toluene (600 mL, 1 L single neck flask, water bath temperature=35° C.), then dried by azeotropic distillation through the removal of approximately 300 mL of toluene. A resulted solution of dried amino alcohol was treated with 4-methylmorpholine (55.5 mL, 505 mmol). This solution was added dropwise via cannula over 30 min to an ice-cold solution of phosphorus trichloride (22.03 mL, 253 mmol) in toluene (200 mL). After warming to room temperature for 1 h, the mixture was filtered carefully under vacuum/argon. The resulting filtrate was concentrated by rotary evaporation (flushing with Ar) then under high vacuum overnight. Crude compound 5-8, isolated as thick oil, which was used in the next step of the reaction without further purification.

Scheme 2.

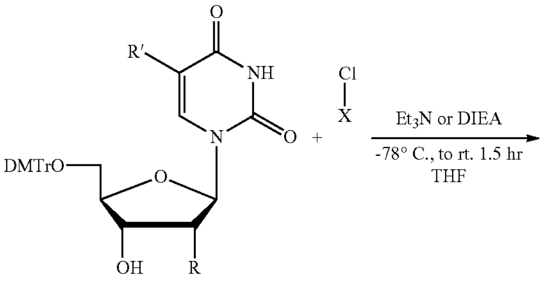

9: R' = H, R = H
10: R' = H, R = OMe
11: R' = H, R = $OCH_2CH_2OMe$
12: R' = H, R = F
13: R' = Me, R = H
14: R' = Me, R = OMe
15: R' = Me, R = $OCH_2CH_2OMe$
16: R' = Me, R = F

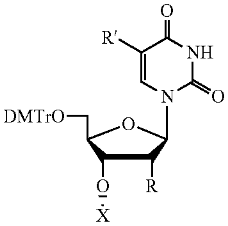

X = 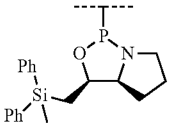

17: R' = H, R = H
18: R' = H, R = OMe
19: R' = H, R = $OCH_2CH_2OMe$
20: R' = H, R = F
21: R' = Me, R = H
22: R' = Me, R = OMe
23: R' = Me, R = $OCH_2CH_2OMe$
24: R' = Me, R = F

X = 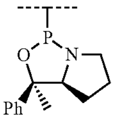

33: R' = H, R = H
34: R' = H, R = OMe
35: R' = H, R = $OCH_2CH_2OMe$
36: R' = H, R = F
37: R' = Me, R = H
38: R' = Me, R = OMe
39: R' = Me, R = $OCH_2CH_2OMe$
40: R' = Me, R = F

-continued

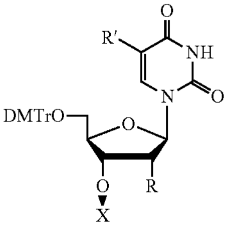

X = 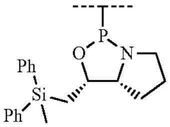

25: R' = H, R = H
26: R' = H, R = OMe
27: R' = H, R = $OCH_2CH_2OMe$
28: R' = H, R = F
29: R' = Me, R = H
30: R' = Me, R = OMe
31: R' = Me, R = $OCH_2CH_2OMe$
32: R' = Me, R = F

X = 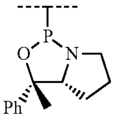

41: R' = H, R = H
42: R' = H, R = OMe
43: R' = H, R = $OCH_2CH_2OMe$
44: R' = H, R = F
45: R' = Me, R = H
46: R' = Me, R = OMe
47: R' = Me, R = $OCH_2CH_2OMe$
48: R' = Me, R = F

Scheme 3.

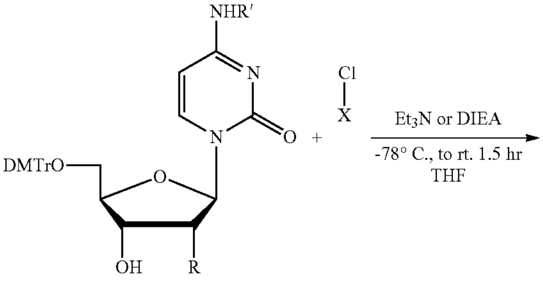

49: R' = Ac, R = H
50: R' = Ac, R = OMe
51: R' = Ac, R = $OCH_2CH_2OMe$
52: R' = Ac, R = F
49a: R' = iBu, R = H
50a: R' = iBu, R = OMe
51a: R' = iBu, R = $OCH_2CH_2OMe$
52a: R' = iBu, R = F

-continued

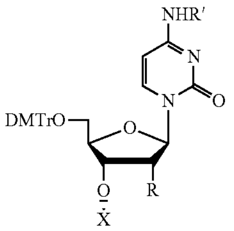

X = 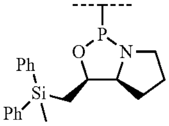

53: R′ = Ac, R = H 53a: R′ = iBu, R = H
54: R′ = Ac, R = OMe 54a: R′ = iBu, R = OMe
55: R′ = Ac, R = $OCH_2CH_2OMe$ 55a: R′ = iBu, R = $OCH_2CH_2OMe$
56: R′ = Ac, R = F 56a: R′ = iBu, R = F

X = 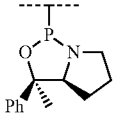

61: R′ = Ac, R = H 61a: R′ = iBu, R = H
62: R′ = Ac, R = OMe 62a: R′ = iBu, R = OMe
63: R′ = Ac, R = $OCH_2CH_2OMe$ 63a: R′ = iBu, R = $OCH_2CH_2OMe$
64: R′ = Ac, R = F 64a: R′ = iBu, R = F

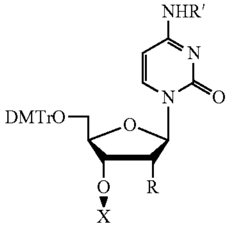

X = 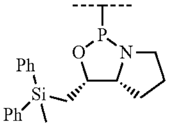

57: R′ = Ac, R = H 57a: R′ = iBu, R = H
58: R′ = Ac, R = OMe 58a: R′ = iBu, R = OMe
59: R′ = Ac, R = $OCH_2CH_2OMe$ 59a: R′ = iBu, R = $OCH_2CH_2OMe$
60: R′ = Ac, R = F 60a: R′ = iBu, R = F

X = 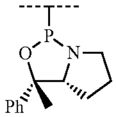

65: R′ = Ac, R = H 65a: R′ = iBu, R = H
66: R′ = Ac, R = OMe 66a: R′ = iBu, R = OMe
67: R′ = Ac, R = $OCH_2CH_2OMe$ 67a: R′ = iBu, R = $OCH_2CH_2OMe$
68: R′ = Ac, R = F 68a: R′ = iBu, R = F

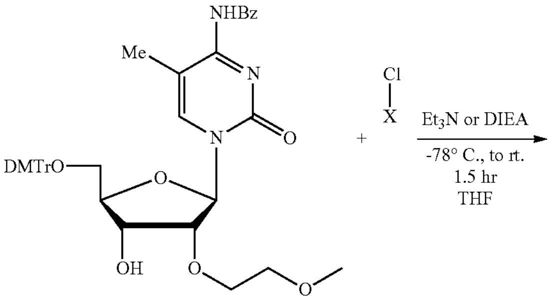

51b

-continued

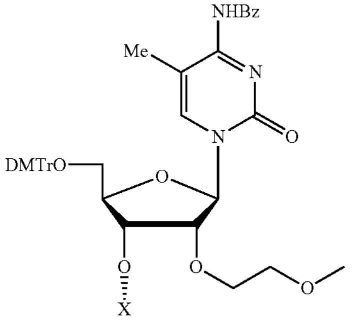

X = 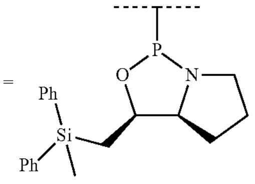

55b

X = 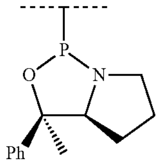

63b

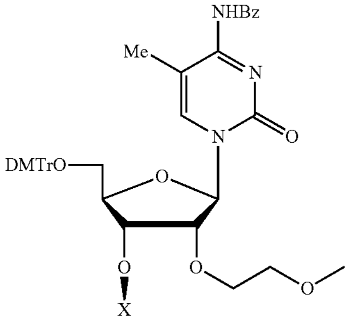

X = 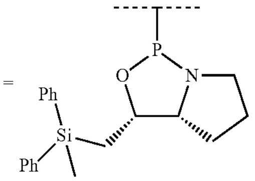

59b

X = 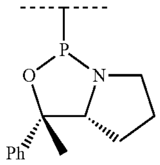

67b

Scheme 4.

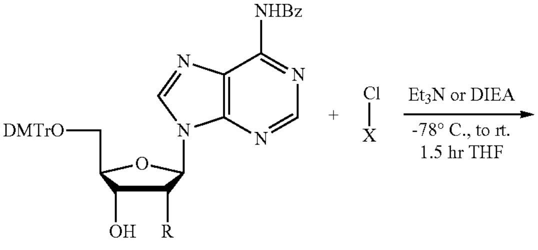

69: R = H
70: R = OMe
71: R = $OCH_2CH_2OMe$
72: R = F

-continued
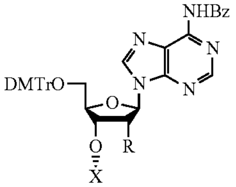
X =
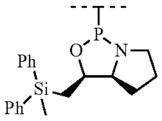
73: R = H
74: R = OMe
75: R = $OCH_2CH_2OMe$
76: R = F
X =
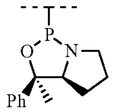
81: R = H
82: R = OMe
83: R = $OCH_2CH_2OMe$
84: R = F
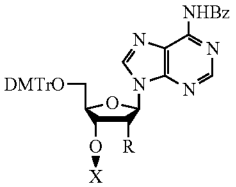
X =
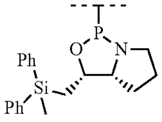
77: R = H
78: R = OMe
79: R = $OCH_2CH_2OMe$
80: R = F
X =
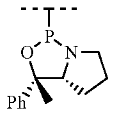
85: R = H
86: R = OMe
87: R = $OCH_2CH_2OMe$
88: R = F
Scheme 5.
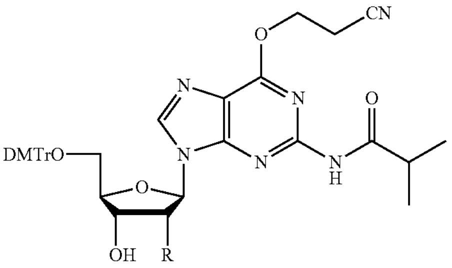
89: R = H
90: R = OMe
91: R = $OCH_2CH_2OMe$
92: R = F
+
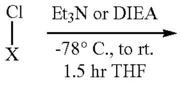
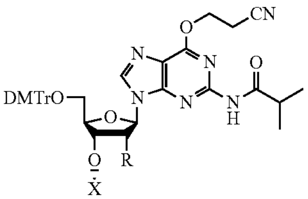
X =
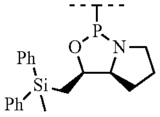
93: R = H
94: R = OMe
95: R = $OCH_2CH_2OMe$
96: R = F
X =
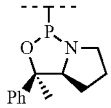
101: R = H
102: R = OMe
103: R = $OCH_2CH_2OMe$
104: R = F -continued

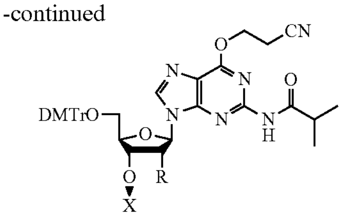

X =

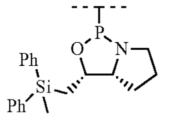

97: R = H

98: R = OMe

99: R = $OCH_2CH_2OMe$

100: R = F

X =

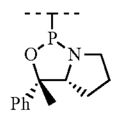

105: R = H

106: R = OMe

107: R = $OCH_2CH_2OMe$

108: R = F

General experimental procedure for chiral amidites 17-48, 53-68, 53a-68a, 73-88 and 93-108:

The nucleoside 9-16, 49-52, 49a-52a, 69-72 and 89-92 (178.5 mmol) was dried in a single neck 2000 mL round bottom flask by azeotropic evaporation by anhydrous toluene (250 mL) and dried under high vacuum for 18 h. This dried compound was dissolved in dry THE (375 mL) and transferred into three neck 2000 mL round bottom flask with magnetic stir bar. Then, triethylamine (125 mL, 898 mmol), dried over $CaH_2$, was added into the reaction mixture, then cooled to ~−10° C. A THF solution (215 mL) of the crude chlorooxazaphospholidine (253 mmol) was added through cannula over −15 min, then, gradually warmed to room temperature over about 1 hr. LCMS showed that the starting material was consumed. The reaction mixture was then treated with water (1.6 mL, 0.09 mol) slowly at ~ 15° C. The reaction mixture was further stirred less than 5 min, 25 g of $MgSO_4$ was added, and then the reaction mixture was filtered carefully under vacuum/argon and the resulting filtrate was reduced to yellow foam by rotary evaporation then dried under high vacuum overnight. Crude mixture was purified by silica gel column (which was pre-deactivated with acetonitrile) chromatography using ethyl acetate (5% TEA) and Hexane (5% TEA) as eluents.

Compound 18: Yield: 84%. $[\alpha]_D^{25}$=31.49 (c=1, $CHCl_3$). $^1$H NMR (500 MHz, Chloroform-d) δ 8.29 (s, 1H), 7.91 (d, J=8.2 Hz, 1H), 7.55-7.44 (m, 4H), 7.42-7.19 (m, 15H), 6.91-6.76 (m, 4H), 5.96 (d, J=3.5 Hz, 1H), 5.19 (d, J=8.1 Hz, 1H), 4.83 (q, J=7.0 Hz, 1H), 4.62 (dt, J=8.8, 5.6 Hz, 1H), 4.03-3.96 (m, 1H), 3.78 (d, J=4.9 Hz, 6H), 3.76-3.72 (m, 1H), 3.58-3.31 (m, 7H), 3.06 (ddt, J=15.4, 10.8, 4.6 Hz, 1H), 1.81 (ddq, J=12.2, 8.0, 4.0 Hz, 1H), 1.62 (ddd, J=28.5, 16.2, 8.3 Hz, 2H), 1.44 (dd, J=14.6, 6.8 Hz, 1H), 1.41-1.32 (m, 1H), 1.32-1.18 (m, 1H), 0.61 (s, 3H). $^{13}$C NMR (126 MHz, $CDCl_3$) δ 163.87, 158.77, 158.73, 150.36, 144.41, 140.28, 136.49, 136.02, 135.34, 135.13, 134.53, 134.48, 134.37, 130.29, 130.24, 129.58, 129.47, 128.28, 128.00, 127.95, 127.87, 127.20, 113.30, 102.15, 87.48, 87.12, 83.56, 83.54, 82.57, 79.40, 79.32, 77.48, 77.22, 76.97, 69.52, 69.45, 67.68, 67.67, 61.32, 58.59, 55.25, 55.24, 46.84, 46.56, 27.16, 26.03, 26.01, 17.88, 17.85, −3.39. $^{31}$P NMR (202 MHz, $CDCl_3$) δ 150.61. P(III) Purity=99.6%. MS calculated for $C_{50}H_{55}N_3O_9PSi$ $[M+H]^+$ 900.34, Observed: 900.3.

Compound 20: Yield: 85%. $[\alpha]_D^{25}$=23.7 (c=1, $CHCl_3$). $^{31}$P NMR ($CDCl_3$, 162 MHz) δ 152.54, 152.59. P(III) Purity=99.2%. MS calculated for $C_{49}H_{52}FN_3O_8PSi$ $[M+H]^+$ 888.32, Observed: 888.4.

Compound 21: Yield: 67%. $[\alpha]_D^{25}$=33.32 (c=1, $CHCl_3$). $^{31}$P NMR ($CDCl_3$, 162 MHz) δ 151.78. P(III) Purity=98.3%. MS calculated for $C_{50}H_{55}N_3O_8PSi$ $[M+H]^+$ 884.35, Observed: 884.4.

Compound 23: Yield: 68%. $[\alpha]_D^{25}$=14.59 (c=1, $CHCl_3$). $^{31}$P NMR ($CDCl_3$, 162 MHz) δ 154.39. P(III) Purity=99.8%. MS calculated for $C_{53}H_{61}N_3O_{10}PSi$ $[M+H]^+$ 958.39, Observed: 958.72.

Compound 28: Yield 59%. $[\alpha]_D^{25}$=−17.61 (c=1, $CHCl_3$). $^{31}$P NMR ($CDCl_3$, 162 MHz) δ 157.77. P(III) Purity=99.6%. MS calculated for $C_{49}H_{52}FN_3O_8PSi$ 888.32 $[M+H]^+$, 888.57.

Compound 29: Yield: 93%. $[\alpha]_D^{25}$=−18.66 (c=1, $CHCl_3$). $^{31}$P NMR ($CDCl_3$, 162 MHz) δ 154.87. P(III) Purity=99.8%. MS calculated for $C_{50}H_{55}N_3O_8PSi$: 884.35 $[M+H]^+$, Observed: 884.78.

Compound 31: Yield: 85%. $[\alpha]_D^{25}$=−14.31 (c=1, $CHCl_3$). $^{31}$P NMR ($CDCl_3$, 202 MHz) δ 154.16. P(III) Purity=99.9%. MS calculated for $C_{53}H_{61}N_3O_{10}PSi$ $[M+H]^+$ 958.39, Observed: 958.4.

Compound 36: Yield: 84%. $^{31}$P NMR ($CDCl_3$, 202 MHz) δ 158.94. MS calculated for $C_{42}H_{43}FN_3O_8PNa$ $[M+Na]^+$ 790.27, Observed: 790.4.

Compound 53: Yield: 70%. $[\alpha]_D^{25}$=72.74 (c=1, $CHCl_3$). $^{31}$P NMR ($CDCl_3$, 162 MHz) δ 156.06. P(III) Purity=98.9%. MS calculated for $C_{51}H_{56}N_4O_8PSi$: 911.36 $[M+H]^+$, Observed: 911.87.

Compound 53a: Yield: 80%. $[\alpha]_D^{25}$=62.20 (c=1, $CHCl_3$) $^{31}$P NMR ($CDCl_3$, 162 MHz) δ 150.15. P(III) Purity=97.8%. MS calculated for $C_{53}H_{60}FN_4O_8PSi$: 939.39 $[M+H]^+$, Observed: 939.

Compound 54: Yield: 77%. $[\alpha]_D^{25}$=41.4 (c=1, $CHCl_3$). $^1$H NMR (500 MHz, Chloroform-d) δ 9.06 (s, 1H), 8.49 (d, J=7.5 Hz, 1H), 7.58-7.44 (m, 4H), 7.40 (d, J=7.4 Hz, 2H), 7.38-7.21 (m, 13H), 6.92 (d, J=7.2 Hz, 1H), 6.90-6.79 (m, 4H), 5.98 (s, 1H), 4.91-4.80 (m, 1H), 4.59 (td, J=8.3, 4.8 Hz, 1H), 4.14 (dd, J=17.8, 7.9 Hz, 1H), 3.79 (d, J=6.0 Hz, 6H), 3.73 (d, J=4.7 Hz, 1H), 3.60-3.39 (m, 6H), 3.36-3.24 (m, 1H), 3.02 (dd, J=8.7, 4.7 Hz, 1H), 2.22 (s, 3H), 1.77 (dd, J=8.2, 4.3 Hz, 1H), 1.70-1.55 (m, 2H), 1.43 (dd, J=14.5, 7.6 Hz, 1H), 1.36-1.17 (m, 2H), 0.59 (s, 3H). $^{13}$C NMR (126 MHz, $CDCl_3$) δ 171.17, 163.35, 158.74, 158.72, 154.89, 144.92, 144.28, 136.39, 136.19, 135.50, 135.21, 134.49, 134.42, 130.26, 130.21, 129.52, 129.45, 128.32, 128.04, 127.95, 127.92, 127.87, 127.19, 113.33, 96.91, 89.03, 87.08, 83.83, 81.84, 79.34, 79.27, 77.48, 77.22, 76.97, 68.64, 68.56, 67.41, 67.39, 60.54, 60.37, 58.69, 55.22, 46.83, 46.54, 27.06, 26.10, 26.08, 24.81, 17.89, 17.86, 14.24, −3.43. $^{31}$P NMR (202 MHz, $CDCl_3$) δ 153.81. MS calculated for $C_{52}H_{58}N_4O_9PSi$ $[M+H]^+$ 941.37, Observed: 941.90.

Compound 55b: Yield: 68%. $[\alpha]_D^{25}$=51.14 (c=1, $CHCl_3$). $^{31}$P NMR ($CDCl_3$, 162 MHz) δ 154.69. P(III) Purity=98.3%. MS calculated for $C_{60}H_{66}N_4O_{10}PSi$ $[M+H]^+$ 1061.43, Observed: 1061.45. MS calculated for $C_{51}H_{55}FN_4O_8PSi$ $[M+H]^+$ 929.35, Observed: 929.05.

Compound 57a: Yield: 89%, $[\alpha]_D^{25}$=−11.21 (c=1, $CHCl_3$). $^{31}$P NMR ($CDCl_3$, 202 MHz) δ 155.76. MS calculated for $C_{53}H_{60}FN_4O_8PSi$ $[M+H]^+$ 939.39, Observed: 939.4.

Compound 58: Yield: 86%, $[\alpha]_D^{25}$=−12.55 (c=1, $CHCl_3$). $^{31}$P NMR ($CDCl_3$, 162 MHz) δ 157.01. P(III) Purity=99.5%. MS calculated for $C_{52}H_{58}N_4O_9PSi$ $[M+H]^+$ 941.37, Observed: 941.85.

Compound 59b: Yield: 86%, $[\alpha]_D^{25}$=28.45 (c=1, $CHCl_3$). $^{31}$P NMR ($CDCl_3$, 162 MHz) δ 155.09. P(III) Purity=99.1%. MS calculated for $C_{60}H_{65}FN_4O_{10}PSi$ $[M+H]^+$ 1061.43, Observed: 1061.46.

Compound 60: Yield 75%. $[\alpha]_D^{25}$=−30.52 (c=1, $CHCl_3$). $^{31}$P NMR ($CDCl_3$, 162 MHz) δ 157.91. P(III) Purity=99.3%. MS calculated for $C_{51}H_{55}FN_4O_8PSi$ $[M+H]^+$ 929.35, Observed 929.93.

Compound 64: Yield: 85%. $^{31}$P NMR ($CDCl_3$, 202 MHz) δ 158.2. MS calculated for $C_{44}H_{47}FN_4O_8P$ $[M+H]^+$ 809.31, Observed: 809.45.

Compound 73: Yield: 75%. $[\alpha]_D^{25}$=18.61 (c=1, $CHCl_3$). $^{31}$P NMR ($CDCl_3$, 202 MHz): 150.68. P(III) Purity=98.6%. MS calculated for $C_{57}H_{58}N_6O_7PSi$ $[M+H]^+$ 997.39, Observed: 997.39.

Compound 74: Yield: 81%. $[\alpha]_D^{25}$=1.73 (c=1, $CHCl_3$). $^{31}$P NMR ($CDCl_3$, 162 MHz) δ 154.18. P(III) Purity=99.0%. MS calculated for $C_{58}H_{60}N_6O_8PSi$ $[M+H]^+$ 1027.40, Observed: 1027.5.

Compound 75: Yield: 79%. $[\alpha]_D^{25}$=−4.95 (c=1, $CHCl_3$). $^{31}$P NMR ($CDCl_3$, 162 MHz) δ 153.89. P(III) Purity=98.8%. MS calculated for $C_{60}H_{64}N_6O_9PSi$ $[M+H]^+$ 1071.42, Observed: 1071.34.

Compound 76: Yield: 81%. $[\alpha]_D^{25}$=1.67 (c=1, $CHCl_3$). $^1$H NMR (400 MHz, Chloroform-d) δ 8.98 (s, 1H), 8.65 (s, 1H), 8.13 (s, 1H), 8.04 (d, J=7.3 Hz, 2H), 7.62 (t, J=7.2 Hz, 1H), 7.54 (t, J=7.3 Hz, 2H), 7.44 (d, J=6.5 Hz, 4H), 7.36 (d, J=7.1 Hz, 2H), 7.32-7.03 (m, 13H), 6.74 (d, J=7.9 Hz, 4H), 6.12 (d, J=17.2 Hz, 1H), 5.24-5.04 (m, 2H), 4.89 (d, J=6.4 Hz, 1H), 4.12 (d, J=6.4 Hz, 1H), 3.74 (s, 6H), 3.56-3.36 (m, 3H), 3.25 (d, J=10.1 Hz, 1H), 2.95 (d, J=8.4 Hz, 1H), 1.84 (s, 1H), 1.68 (d, J=7.5 Hz, 1H), 1.59-1.19 (m, 4H), 0.62 (s, 3H). $^{13}$C NMR (100 MHz, $CDCl_3$) δ 171.07, 164.77, 158.54, 152.33, 151.11, 149.85, 144.61, 142.35, 136.74, 135.86, 135.77, 135.72, 134.55, 134.31, 133.68, 132.81, 130.08, 129.28, 129.14, 128.87, 128.20, 127.93, 127.86, 127.78, 127.67, 126.86, 123.79, 113.11, 92.93, 91.02, 87.63, 87.29, 86.44, 82.41, 79.73, 79.63, 77.51, 77.39, 77.19, 69.30, 69.13, 68.25, 68.22, 62.18, 60.37, 55.21, 46.67, 46.32, 27.47, 25.97, 25.94, 21.04, 17.83, 17.79, 14.24, −3.17. $^{31}$P NMR (162 MHz, $CDCl_3$) δ 149.17, 149.12. P(III) Purity=97.1%. MS calculated for $C_{57}H_{57}FN_6O_7PSi$ $[M+H]^+$ 1015.38, Observed: 1015.44.

Compound 77: Yield: 88%. $[\alpha]_D^{25}$=−27.57 (c=1, $CHCl_3$). $^{31}$P NMR ($CDCl_3$, 162 MHz) δ 156.12. P(III) Purity=99.5%. MS calculated for $C_{57}H_{58}N_6O_7PSi$ $[M+H]^+$ 997.39, Observed: 997.87.

Compound 78: Yield: 87%. $[\alpha]_D^{25}$=−25.18 (c=1, $CHCl_3$). $^{31}$P NMR ($CDCl_3$, 162 MHz) δ 153.29. P(III) Purity=99.6%. MS calculated for $C_{58}H_{60}N_6O_8PSi$ $[M+H]^+$ 1027.40, Observed: 1027.91.

Compound 79: Yield: 88%. $[\alpha]_D^{25}$=−27.11 (c=1, $CHCl_3$). $^{31}$P NMR ($CDCl_3$, 162 MHz) δ 153.24. P(III) Purity=99.1%. MS calculated for $C_{60}H_{64}N_6O_9PSi$ $[M+H]^+$ 1071.42, Observed: 1071.4.

Compound 80: Yield 80%. $[\alpha]_D^{25}$=−31.82 (c=1, $CHCl_3$). $^{31}$P NMR ($CDCl_3$, 162 MHz) δ 156.61. P(III) Purity=99.6%. MS calculated for $C_{57}H_{57}FN_6O_7PSi$ $[M+H]^+$ 1015.38, Observed 1015.97.

Compound 84: Yield: 86%. $^{31}$P NMR ($CDCl_3$, 202 MHz) δ 155.22. MS calculated for $C_{50}H_{49}FN_6O_7P$ $[M+H]^+$ 895.34, Observed: 895.43.

Compound 93: Yield: 65%. $[\alpha]_D^{25}$=21.26 (c=1, $CHCl_3$). $^{31}$P NMR ($CDCl_3$, 162 MHz) δ 151.34. P(III) Purity=98.9%. MS calculated for $C_{57}H_{64}N_7O_8PSi$ $[M+H]^+$ 1032.42, Observed: 1032.95.

Compound 94: Yield: 61%. $[\alpha]_D^{25}$=9.31 (c=1, $CHCl_3$). $^{31}$P NMR ($CDCl_3$, 202 MHz) δ 154.82. P(III) Purity=98.8%. MS calculated for $C_{58}H_{65}N_7O_9PSi$ $[M+H]^+$ 1062.44, Observed: 1062.38.

Compound 97: Yield: 65%. $[\alpha]_D^{25}$=−13.53 (c=1, $CHCl_3$). $^{31}$P NMR ($CDCl_3$, 162 MHz) δ 155.63. P(III) Purity=97.3%. MS calculated for $C_{57}H_{64}N_7O_8PSi$ $[M+H]^+$ 1032.42, Observed: 1032.54.

Scheme 6.

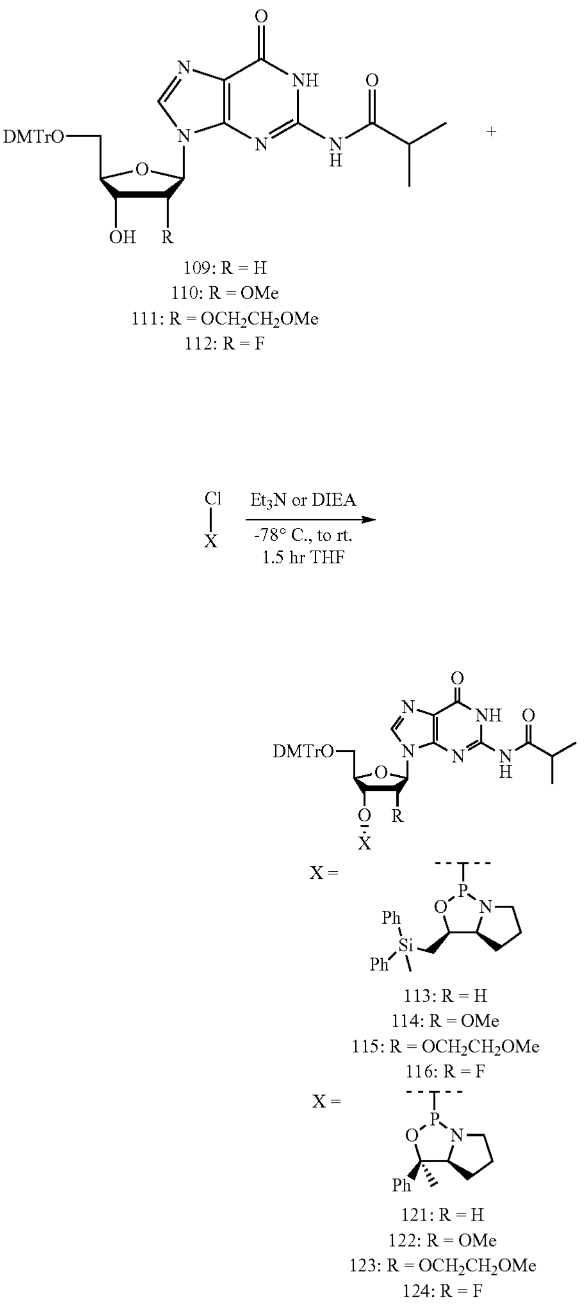

109: R = H
110: R = OMe
111: R = $OCH_2CH_2OMe$
112: R = F

113: R = H
114: R = OMe
115: R = $OCH_2CH_2OMe$
116: R = F

121: R = H
122: R = OMe
123: R = $OCH_2CH_2OMe$
124: R = F

-continued

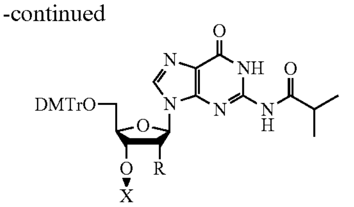

X =

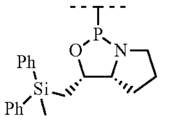

117: R = H
118: R = OMe
119: R = $OCH_2CH_2OMe$
120: R = F

X =

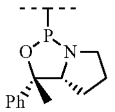

125: R = H
126: R = OMe
127: R = $OCH_2CH_2OMe$
128: R = F

The nucleoside 109-112 (178.5 mmol) was dried in a single neck 2000 mL round bottom flask by azeotropic evaporation by anhydrous toluene (250 mL) and dried under vacuum for 18 h. This dried compound was dissolved in dry THE (375~600 mL) and transferred into three neck 2000 mL round bottom flask with magnetic stir bar. Then, triethylamine (125 mL, 898 mmol), dried over $CaH_2$, was added into the reaction mixture, then cooled to −10~−20° C. Chlorotrimethylsilane (22.6 mL, 179 mmol) was added dropwise over 10 min. A THF solution (215 mL) of the crude chlorooxazaphospholidine (253 mmol) was added through cannula over 15 min then, gradually warmed to room temperature about 1 h. LCMS showed that the starting material was consumed. Then, the reaction mixture was treated with water (2.4 mL, 0.13 mol) and the reaction mixture was further stirred less than 5 min then, 25 g of $MgSO_4$ was added followed by stirring the reaction mixture for another 10 min. Then, it was filtered carefully under vacuum/argon and the resulting filtrate was reduced to yellow foam by rotary evaporation then dried under high vacuum overnight. Crude mixture was purified by silica column (which was pre-deactivated with acetonitrile) chromatography using ethyl acetate (5% TEA) and acetonitrile (5% TEA) as eluents.

As appreciated by those skilled in the art, various silylating reagents can be used in accordance with the present disclosure. In some embodiments, a silylating reagent is chlorotrimethylsilane. In some embodiments, a silylating reagent is chlorotriethylsilane. In some embodiments, a silylating reagent is tert-tutyldimethylsilyl chloride. In some embodiments, a silylating reagent is chloro-decyl-dimethylsilane. In some embodiments, a silylating reagent is chlorodimethylphenethylsilane. In some embodiments, a silylating reagent is chlorotriisopropylsilane.

Compound 113: Yield: 73%. $[\alpha]_D^{25}$=15.29 (c=1, $CHCl_3$). $^{31}$P NMR ($CDCl_3$, 162 MHz) δ 150.39. P(III) Purity=99.5%. MS calculated for $C_{54}H_{60}N_6O_8PSi$ $[M+H]^+$ 979.40, Observed: 979.92.

Compound 114: Yield: 60%. $[\alpha]_D^{25}$=0.26 (c=1, $CHCl_3$). $^1$H NMR (500 MHz, Chloroform-d) δ 11.85 (s, 1H), 7.72 (s, 1H), 7.58 (d, J=7.4 Hz, 2H), 7.43 (t, J=7.2 Hz, 8H), 7.38-7.08 (m, 10H), 6.81 (dd, J=14.1, 8.8 Hz, 4H), 5.75 (d, J=8.1 Hz, 1H), 5.30 (s, 1H), 4.86 (dd, J=8.1, 5.2 Hz, 1H), 4.81-4.71 (m, 1H), 4.67 (dd, J=10.0, 5.1 Hz, 1H), 3.88 (s, 1H), 3.76 (d, J=7.8 Hz, 6H), 3.51 (ddd, J=14.2, 10.4, 7.4 Hz, 1H), 3.34 (s, 3H), 3.22 (dq, J=12.9, 6.0 Hz, 1H), 3.08 (ddt, J=14.9, 10.7, 4.3 Hz, 1H), 2.92 (dd, J=10.7, 2.5 Hz, 1H), 1.83 (dt, J=7.7, 3.8 Hz, 1H), 1.63 (dt, J=19.4, 8.6 Hz, 1H), 1.50 (dd, J=14.7, 9.1 Hz, 1H), 1.39 (dd, J=14.6, 5.5 Hz, 2H), 1.32-1.17 (m, 3H), 0.81 (d, J=6.8 Hz, 3H), 0.61-0.47 (m, 5H). $^{31}$P NMR (202 MHz, $CDCl_3$) δ 154.09. P(III) Purity=97.5%. MS calculated for $C_{55}H_{62}N_6O_9PSi$ $[M+H]^+$ 1009.41, Observed: 1009.95.

Compound 115: Yield: 82%. $[\alpha]_D^{25}$=−7.44 (c 1, $CHCl_3$). $^{31}$P NMR (162 MHz, $CDCl_3$) δ 155.71. P(III) Purity=98.7%. MS calculated for $C_{57}H_{66}N_6O_{10}PSi$ $[M+H]^+$ 1053.45, Observed: 1053.28.

Compound 116: Yield: 81%. $[\alpha]_D^{25}$=11.6 (c=1, $CHCl_3$). $^{13}$C NMR (100 MHz, $CDCl_3$) δ 179.02, 158.82, 155.80, 149.69, 148.30, 147.83, 144.81, 138.03, 136.54, 135.95, 135.90, 135.64, 134.53, 134.50, 134.37, 130.09, 130.07, 129.51, 129.48, 129.42, 128.15, 128.10, 127.97, 127.19, 123.96, 122.20, 113.38, 86.52, 83.31, 79.45, 79.36, 77.59, 77.27, 76.95, 67.86, 67.83, 62.36, 60.44, 55.28, 55.22, 46.96, 46.61, 36.03, 27.20, 25.97, 25.94, 21.10, 18.76, 18.74, 17.66, 17.62, 14.28, −3.29. $^{31}$P NMR (162 MHz, $CDCl_3$) δ 153.65, 153.58. P(III) Purity=99.4%. MS calculated for $C_{54}H_{59}FN_6O_8PSi$ $[M+1]^+$ 997.39, Observed: 997.48.

Compound 117: Yield: 84%. $[\alpha]_D^{25}$=−19.83 (c=1, $CHCl_3$). $^{31}$P NMR (162 MHz, $CDCl_3$) δ 155.10. P(III) Purity=99.8%. MS calculated for $C_{54}H_{60}N_6O_8PSi$ $[M+H]^+$ 979.40, Observed: 979.92.

Compound 119: Yield: 92%. $[\alpha]_D^{25}$=−24.36 (c=1, $CHCl_3$). $^{31}$P NMR (162 MHz, $CDCl_3$) δ 150.80. P(III) Purity=99.5%. MS calculated for $C_{57}H_{66}N_6O_{10}PSi$ $[M+H]^+$ 1053.45, Observed: 1053.47.

Compound 120: Yield: 83%. $[\alpha]_D^{25}$=−17.50 (c=1, $CHCl_3$). $^{31}$P NMR ($CDCl_3$, 162 MHz) δ 155.58. P(III) Purity=99.0%. MS calculated for $C_{54}H_{59}FN_6O_8PSi$ $[M+H]^+$ 997.39, Observed: 997.87.

Compound 124: Yield: 83.9%. $^{31}$P NMR ($CDCl_3$, 202 MHz): δ 157.15, MS calculated for $C_{47}H_{51}FN_6O_8P$ $[M+H]^+$ 877.35, Observed: 877.48.

As extensively described, phosphoramidites with various structural elements, e.g., nucleabases, sugars, chiral auxiliaries, and combinations thereof, can be readily prepared using provided methods in accordance with the present disclosure. Additional examples are provided below.

General Procedure I: Chiral auxiliary (174.54 mmol) was dried by azeotropic evaporation with anhydrous toluene (80 ml×3) at 35° C. in a rota-evaporator and dried under high vacuum for overnight. A solution of this dried chiral auxiliary (174.54 mmol) and 4-methylmorpholine (366.54 mmol) dissolved in anhydrous toluene or THE (170 mL) was added to an ice-cooled (isopropyl alcohol-dry ice bath) solution of trichlorophosphine (16.0 mL, 183.27 mmol) in anhydrous toluene or THE (150 mL) placed in three neck round bottomed flask through cannula under Argon (start Temp: −10.0° C., Max: temp 0° C., 30 min addition) and the reaction mixture was warmed at 15° C. for 1 hr. After that filtered the precipitated white solid by vacuum under argon using airfree filter tube (chemglass: Filter Tube, 24/40 Inner Joints, 80 mm OD Medium Frit, Airfree, Schlenk). The solvent was removed with rota-evaporator under argon at low temperature (25° C.) and the crude semi-solid obtained was dried under vacuum overnight (~15 h) and was used for the next step directly.

General Procedure II: Nucleoside (9.11 mmol) was dried by co-evaporation with 60 mL of anhydrous pyridine at 35° C. followed by anhydrous toluene (60 mL×2) at 35° C. and dried under at high vacuum for overnight. Then dried nucleoside was dissolved in dry THE (78 mL), followed by addition of triethylamine (63.80 mmol) then cooled to −5° C. under Argon (in 2'F-dG case 1 eq of TMS-Cl used). The THF solution of the crude (made from general procedure I, 18.22 mmol) was added through cannula over 3 min then gradually warmed to room temperature. After 1 hr at rt, TLC indicated conversion of SM to product (total reaction time 1 h), the reaction mixture was the quenched with $H_2O$ (9.11 mmol, 0.1 mL) at 0° C., and added anhydrous $MgSO_4$ (9.11 mmol, ~ 1 g) and stirred for 10 min. Then the reaction mixture was filtered under argon using air free filter tube, washed with THF, and dried under rotary evaporation at 26° C. to provide white crude solid product which was dried under high vacuum overnight. The crude product was purified by ISCO-combiflash system (80 g gold rediSep high performance silica column pre-equilibrated with EtOAc) using ethyl acetate/xexane with 5% TEA as a solvent (compound eluted at 60-65% EtOAc/Hexanes/5% $Et_3N$). The column fractions containing purified product were pooled together. After evaporation of the solvent, the product was dried under high vacuum to provide white solid with isolated yield of, e.g., 60-95%.

Scheme 7.

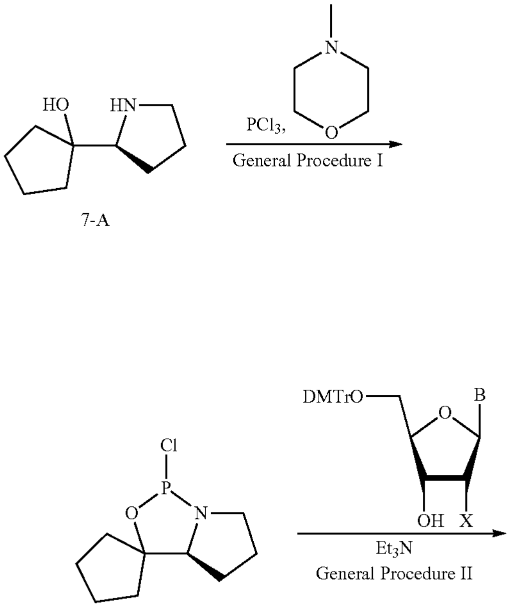

7-A

7-A-Cl

-continued

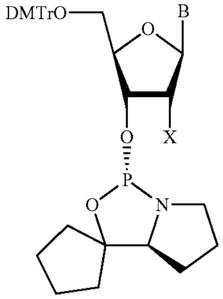

7-A: 1: X = OMe, B = $A^{Bz}$
2: X = F, B = $A^{Bz}$
3: X = F, B = $C^{Ac}$
4: X = F, B = U
5: X = F, B = $G^{iBu}$

Preparation of 7-A-Cl: (3a'S)-1'-chlorotetrahydro-1'H-spiro[cyclopentane-1,3'-pyrrolo[1,2-c][1,3,2]oxazaphosphole]: General Procedure I. $^{31}P$ NMR (162 MHz, Chloroform-d) δ 170.01.

Preparation of 7-A-2'OMe-$dA^{Bz}$ (1): N-(9-((2R,3R,4R,5R)-5-((bis(4-methoxyphenyl)(phenyl)methoxy)methyl)-3-methoxy-4-(((1'S,3a'S)-tetrahydro-1'H-spiro[cyclopentane-1,3'-pyrrolo[1,2-c][1,3,2]oxazaphosphol]-1'-yl)oxy)tetrahydrofuran-2-yl)-4,5-dihydro-9H-purin-6-yl)benzamide. General Procedure II. $[\alpha]_D^{23}$=+1.15 (c 1.92, $CHCl_3$). $^{31}P$ NMR (162 MHz, Chloroform-d) δ 156.24. MS ($ESI^+$) calculated for $C_{48}H_{51}N_6O_8P$ 870.3; found 871.3 ($M+H^+$).

Preparation of 7-A-2'F-$dA^{Bz}$ (2): N-(9-((2R,3R,4R,5R)-5-((bis(4-methoxyphenyl)(phenyl)methoxy)methyl)-3-fluoro-4-(((1'S,3a'S)-tetrahydro-1'H-spiro[cyclopentane-1,3'-pyrrolo[1,2-c][1,3,2]oxazaphosphol]-1'-yl)oxy)tetrahydrofuran-2-yl)-4,5-dihydro-9H-purin-6-yl)benzamide. General Procedure II. $[\alpha]_D^{23}$=+12.49 (c 1.26, $CHCl_3$). $^{31}P$ NMR (162 MHz, Chloroform-d) δ 155.38 (d, J=10.1 Hz). MS ($ESI^+$) calculated for $C_{47}H_{48}FN_6O_7P$ 858.3; found 859.3 ($M+H^+$).

Preparation of 7-A-2'F-$dC^{Ac}$ (3): N-(1-((2R,3R,4R,5R)-5-((bis(4-methoxyphenyl)(phenyl)methoxy)methyl)-3-fluoro-4-(((1'S,3a'S)-tetrahydro-1'H-spiro[cyclopentane-1,3'-pyrrolo[1,2-c][1,3,2]oxazaphosphol]-1'-yl)oxy)tetrahydrofuran-2-yl)-2-oxo-1,2-dihydropyrimidin-4-yl)acetamide. General Procedure II. $[\alpha]_D^{23}$=+55.69 (c 1.33, $CHCl_3$). $^{31}P$ NMR (162 MHz, Chloroform-d) δ 157.82 (d, J=7.8 Hz). MS ($ESI^+$) calculated for $C_{41}H_{46}FN_4O_8P$ 772.3; found 773.2 ($M+H^+$).

Preparation of 7-A-2'F-dU (4): 1-((2R,3R,4R,5R)-5-((bis(4-methoxyphenyl)(phenyl)methoxy)methyl)-3-fluoro-4-(((1'S,3a'S)-tetrahydro-1'H-spiro[cyclopentane-1,3'-pyrrolo[1,2-c][1,3,2]oxazaphosphol]-1'-yl)oxy)tetrahydrofuran-2-yl)pyrimidine-2,4(1H,3H)-dione. General Procedure II. $[\alpha]_D^{23}$=+42.88 (c 1.67, $CHCl_3$). $^{31}P$ NMR (162 MHz, Chloroform-d) δ 157.99 (d, J=9.1 Hz). MS ($ESI^+$) calculated for $C_{39}H_{43}FN_3O_8P$ 731.2; found 754.2 (M+Na*).

Preparation of 7-A-2'F-$dG^{iBu}$ (5): N-(9-((2R,3R,4R,5R)-5-((bis(4-methoxyphenyl)(phenyl)methoxy)methyl)-3-fluoro-4-(((1'S,3a'S)-tetrahydro-1'H-spiro[cyclopentane-1,3'-pyrrolo[1,2-c][1,3,2]oxazaphosphol]-1'-yl)oxy)tetrahydrofuran-2-yl)-6-oxo-4,5,6,9-tetrahydro-1H-purin-2-yl)isobutyramide. General Procedure II. $[\alpha]_D^{23}$=+42.80 (c 1.39, $CHCl_3$). $^{31}P$ NMR (162 MHz, Chloroform-d) δ 156.12 (d, J=11.2 Hz). MS ($ESI^+$) calculated for $C_{44}H_{50}FN_6O_8P$ 840.3; found 841.3 ($M+H^+$).

Scheme 8.

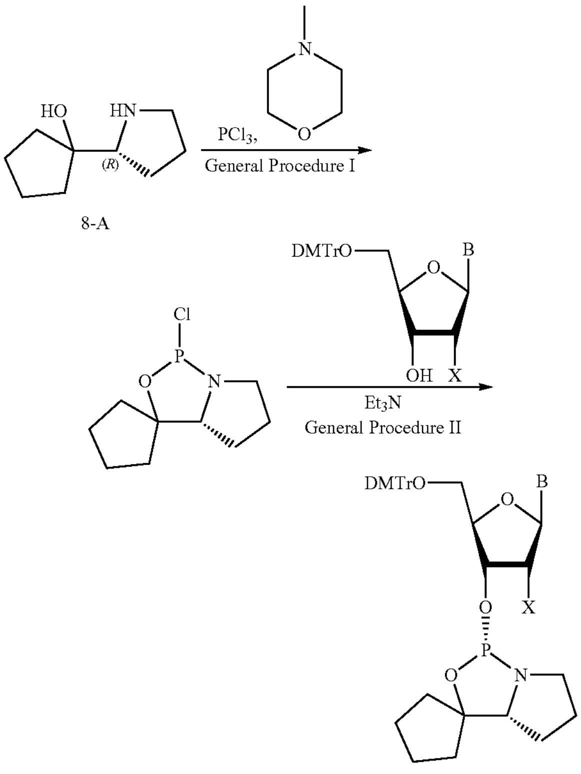

8-A

8-A: 1: X = F, B = $A^{Bz}$
2: X = OMe, B = $A^{Bz}$
3: X = F, B = $C^{Ac}$
4: X = F, B = U
5: X = F, B = $G^{iBu}$

Preparation of 8-A-Cl: (3a'R)-1'-chlorotetrahydro-1'H-spiro[cyclopentane-1,3'-pyrrolo[1,2-c][1,3,2]oxazaphosphole]. General Procedure I. $^{31}P$ NMR (162 MHz, Chloroform-d) δ 169.46.

Preparation of 8-A-2'F-d$A^{Bz}$ (1): N-(9-((2R,3R,4R,5R)-5-((bis(4-methoxyphenyl)(phenyl)methoxy)methyl)-3-fluoro-4-(((1'R,3a'R)-tetrahydro-1'H-spiro[cyclopentane-1,3'-pyrrolo[1,2-c][1,3,2]oxazaphosphol]-1'-yl)oxy)tetrahydrofuran-2-yl)-4,5-dihydro-9H-purin-6-yl)benzamide. General Procedure II. $[\alpha]_D^{23}$=−21.18 (c 1.35, $CHCl_3$). $^{31}P$ NMR (162 MHz, Chloroform-d) δ 155.69 (d, J=7.0 Hz). MS ($ESI^+$) calculated for $C_{47}H_{48}FN_6O_7P$ 858.3; found 859.3 ($M+H^+$).

Preparation of 8-A-2'OMe-d$A^{Bz}$ (2): N-(9-((2R,3R,4R,5R)-5-((bis(4-methoxyphenyl)(phenyl)methoxy)methyl)-3-methoxy-4-(((1'R,3a'R)-tetrahydro-1'H-spiro[cyclopentane-1,3'-pyrrolo[1,2-c][1,3,2]oxazaphosphol]-1'-yl)oxy)tetrahydrofuran-2-yl)-4,5-dihydro-9H-purin-6-yl)benzamide. General Procedure II. $[\alpha]_D^{23}$=−10.52 (c 1.35, $CHCl_3$). $^{31}P$ NMR (162 MHz, Chloroform-d) δ 156.39. MS ($ESI^+$) calculated for $C_{48}H_{51}N_6O_8P$ 870.3; found 871.3 ($M+H^+$).

Preparation of 8-A-2'F-d$C^{Ac}$ (3): N-(1-((2R,3R,4R,5R)-5-((bis(4-methoxyphenyl)(phenyl)methoxy)methyl)-3-fluoro-4-(((1'R,3a'R)-tetrahydro-1'H-spiro[cyclopentane-1,3'-pyrrolo[1,2-c][1,3,2]oxazaphosphol]-1'-yl)oxy)tetrahydrofuran-2-yl)-2-oxo-1,2-dihydropyrimidin-4-yl)acetamide. General Procedure II. $[\alpha]_D^{23}$=+40.37 (c 1.82, $CHCl_3$). $^{31}P$ NMR (162 MHz, Chloroform-d) δ 158.59 (d, J=5.9 Hz). MS ($ESI^+$) calculated for $C_{41}H_{46}FN_4O_8P$ 872.3; found 873.2 ($M+H^+$).

Preparation of 8-A-2'F-dU (4): 1-((2R,3R,4R,5R)-5-((bis(4-methoxyphenyl)(phenyl)methoxy)methyl)-3-fluoro-4-(((1'R,3a'R)-tetrahydro-1'H-spiro[cyclopentane-1,3'-pyrrolo[1,2-c][1,3,2]oxazaphosphol]-1'-yl)oxy)tetrahydrofuran-2-yl)pyrimidine-2,4(1H,3H)-dione. General Procedure II. $[\alpha]_D^{23}$=+20.17 (c 1.52, $CHCl_3$). $^{31}P$ NMR (162 MHz, Chloroform-d) δ 159.35 (d, J=6.3 Hz). MS ($ESI^+$) calculated for $C_{39}H_{43}FN_3O_8P$ 731.2; found 754.2 (M+Na*).

Preparation of 8-A-2'F-d$G^{IBu}$ (5): N-(9-((2R,3R,4R,5R)-5-((bis(4-methoxyphenyl)(phenyl)methoxy)methyl)-3-fluoro-4-(((1'R,3a'R)-tetrahydro-1'H-spiro[cyclopentane-1,3'-pyrrolo[1,2-c][1,3,2]oxazaphosphol]-1'-yl)oxy)tetrahydrofuran-2-yl)-6-oxo-4,5,6,9-tetrahydro-1H-purin-2-yl)isobutyramide. General Procedure II. $[\alpha]_D^{23}$=+5.95 (c 1.48, $CHCl_3$). $^{31}P$ NMR (162 MHz, Chloroform-d) δ 157.29 (d, J=7.0 Hz). MS ($ESI^+$) calculated for $C_{44}H_{50}FN_6O_8P$ 840.3; found 841.3 ($M+H^+$).

Scheme 9.

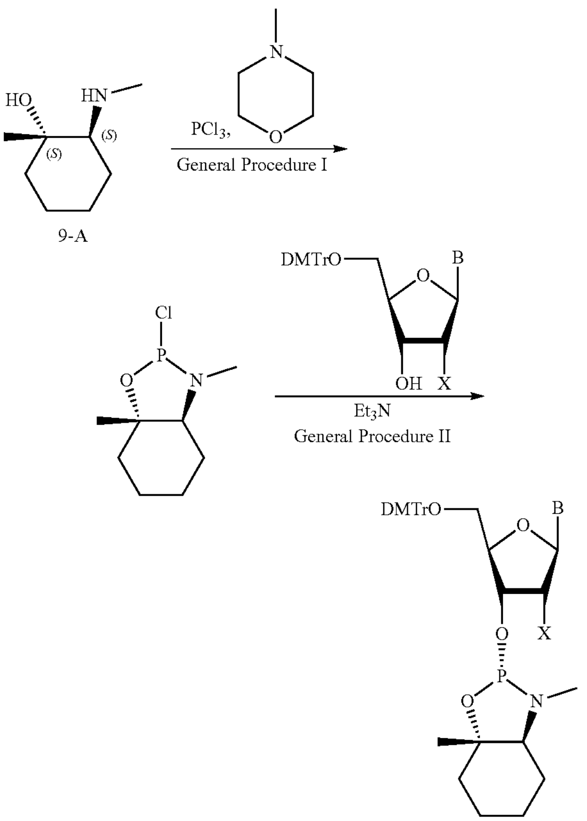

9-A

9-A: 1: X = F, B = $A^{Bz}$
2: X = OMe, B = $A^{Bz}$
3: X = F, B = $C^{Ac}$
4: X = F, B = U
5: X = F, B = $G^{iBu}$

Preparation of 9-A-Cl: (3aS,7aS)-2-chloro-3,7a-dimethyloctahydrobenzo[d][1,3,2]oxazaphosphole. General Procedure I. $^{31}P$ NMR (162 MHz, Chloroform-d) δ 178.44.

Preparation of 9-A-2'F-d$A^{Bz}$ (1): N-(9-((2R,3R,4R,5R)-5-((bis(4-methoxyphenyl)(phenyl)methoxy)methyl)-4-(((2S, 3aS,7aS)-3,7a-dimethylhexahydrobenzo[d][1,3,2]oxazaphosphol-2(3H)-yl)oxy)-3-fluorotetrahydrofuran-2-yl)-9H-purin-6-yl)benzamide. General Procedure II. $[\alpha]_D^{23}$=−31.59 (c 1.17, $CHCl_3$). $^{31}P$ NMR (162 MHz, Chloroform-d) δ 165.37 (d, J=8.3 Hz). MS ($ESI^+$) calculated for $C_{46}H_{58}FN_6O_7P$ 846.3; found 847.3 ($M+H^+$).

Preparation of 9-A-2'OMe-$dA^{Bz}$ (2): N-(9-((2R,3R,4R,5R)-5-((bis(4-methoxyphenyl)(phenyl)methoxy)methyl)-4-(((2S,3aS,7aS)-3,7a-dimethylhexahydrobenzo[d][1,3,2]oxazaphosphol-2(3H)-yl)oxy)-3-methoxytetrahydrofuran-2-yl)-9H-purin-6-yl)benzamide. General Procedure II. $[\alpha]_D^{23}$=−33.76 (c 1.11, $CHCl_3$). $^{31}P$ NMR (162 MHz, Chloroform-d) δ 165.32. MS (ESI*) calculated for $C_{47}H_{51}FN_6O_8P$ 858.3; found 859.2 ($M+H^+$).

Preparation of 9-A-2'OMe-$dC^{Ac}$ (3): N-(1-((2R,3R,4R,5R)-5-((bis(4-methoxyphenyl)(phenyl)methoxy)methyl)-4-(((2S,3aS,7aS)-3,7a-dimethylhexahydrobenzo[d][1,3,2]oxazaphosphol-2(3H)-yl)oxy)-3-fluorotetrahydrofuran-2-yl)-2-oxo-1,2-dihydropyrimidin-4-yl)acetamide. General Procedure II. $[\alpha]_D^{23}$=−19.49 (c 1.31, $CHCl_3$). $^{31}P$ NMR (162 MHz, Chloroform-d) δ 165.19 (d, J=6.7 Hz). MS ($ESI^+$) calculated for $C_{40}H_{46}FN_4O_8P$ 760.3; found 761.3 ($M+H^+$).

Preparation of 9-A-2'F-dU (4): 1-((2R,3R,4R,5R)-5-((bis(4-methoxyphenyl)(phenyl)methoxy)methyl)-4-(((2S,3aS,7aS)-3,7a-dimethylhexahydrobenzo[d][1,3,2]oxazaphosphol-2(3H)-yl)oxy)-3-fluorotetrahydrofuran-2-yl)pyrimidine-2,4(1H,3H)-dione. General Procedure II. $[\alpha]_D^{23}$=−3.76 (c 1.42, $CHCl_3$). $^{31}P$ NMR (162 MHz, Chloroform-d) δ 165.40 (d, J=7.2 Hz). MS ($ESI^+$) calculated for $C_{38}H_{43}FN_3O_8P$ 719.2; found 758.5 (M+K+).

Preparation of 9-A-2'F-$dG^{iBu}$ (5): N-(9-((2R,3R,4R,5R)-5-((bis(4-methoxyphenyl)(phenyl)methoxy)methyl)-4-(((2S,3aS,7aS)-3,7a-dimethylhexahydrobenzo[d][1,3,2]oxazaphosphol-2(3H)-yl)oxy)-3-fluorotetrahydrofuran-2-yl)-6-oxo-6,9-dihydro-1H-purin-2-yl)isobutyramide. General Procedure II. $[\alpha]_D^{23}$=+46.33 (c 1.41, $CHCl_3$). $^{31}P$ NMR (162 MHz, Chloroform-d) δ 165.03 (d, J=8.4 Hz). MS ($ESI^+$) calculated for $C_{43}H_{50}FN_6O_8P$ 828.3; found 829.4 ($M+H^+$).

Scheme 10.

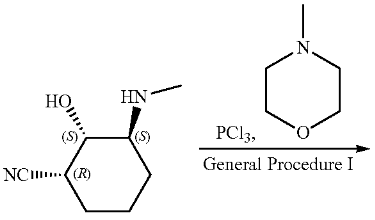

10-A

-continued

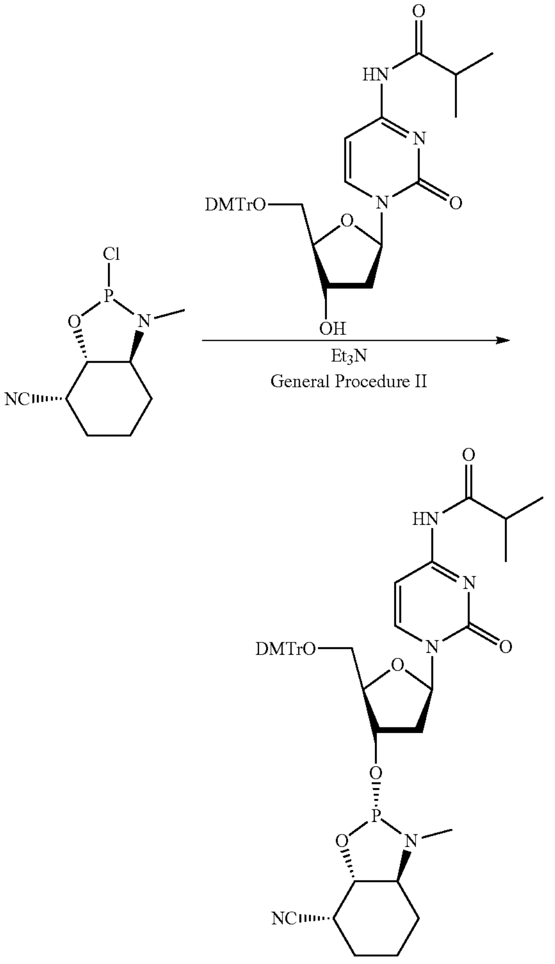

10-A-2'-$dC^{iBu}$

Preparation of 10-A-Cl: (3aS,7R,7aS)-2-chloro-3-methyloctahydrobenzo[d][1,3,2]oxazaphosphole-7-carbonitrile. General Procedure I. $^{31}P$ NMR (162 MHz, Chloroform-d) δ 173.10.

Preparation of 10-A-2-$dC^{iBu}$: N-(1-((2R,4S,5R)-5-((bis(4-methoxyphenyl)(phenyl)methoxy)methyl)-4-(((2R,3aS,7R,7aS)-7-cyano-3-methylhexahydrobenzo[d][1,3,2]oxazaphosphol-2(3H)-yl)oxy)tetrahydrofuran-2-yl)-2-oxo-1,2-dihydropyrimidin-4-yl)isobutyramide. General Procedure II. $[\alpha]_D^{23}$=+70.47 (c 1.38, $CHCl_3$). $^{31}P$ NMR (162 MHz, Chloroform-d) δ 155.12. MS ($ESI^+$) calculated for $C_{42}H_{48}N_5O_8P$ 781.3; found 782.3 ($M+H^+$).

Scheme 11.

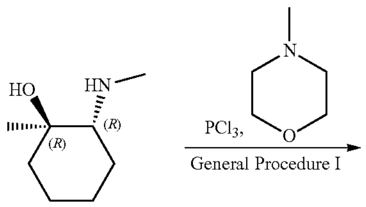

11-A

-continued

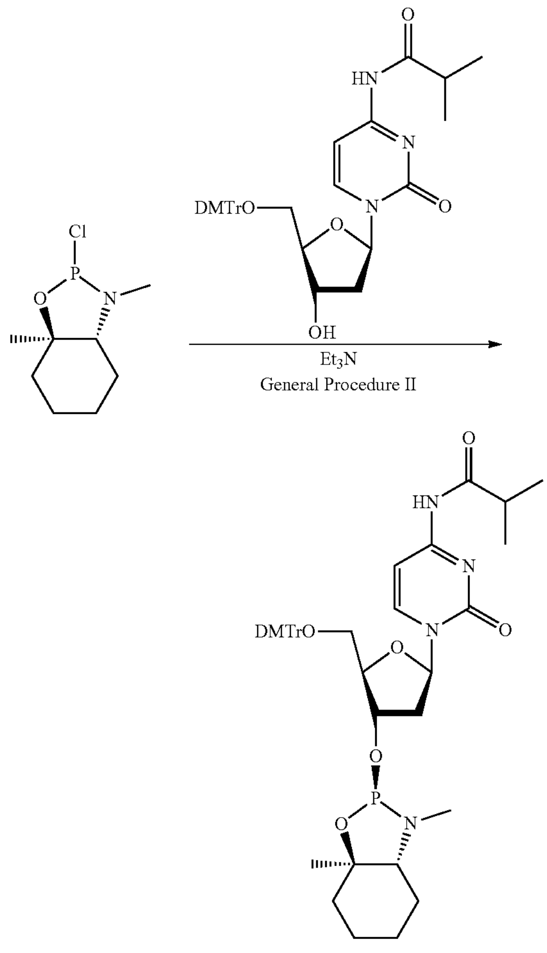

11-A-2'-dC$^{iBu}$

-continued

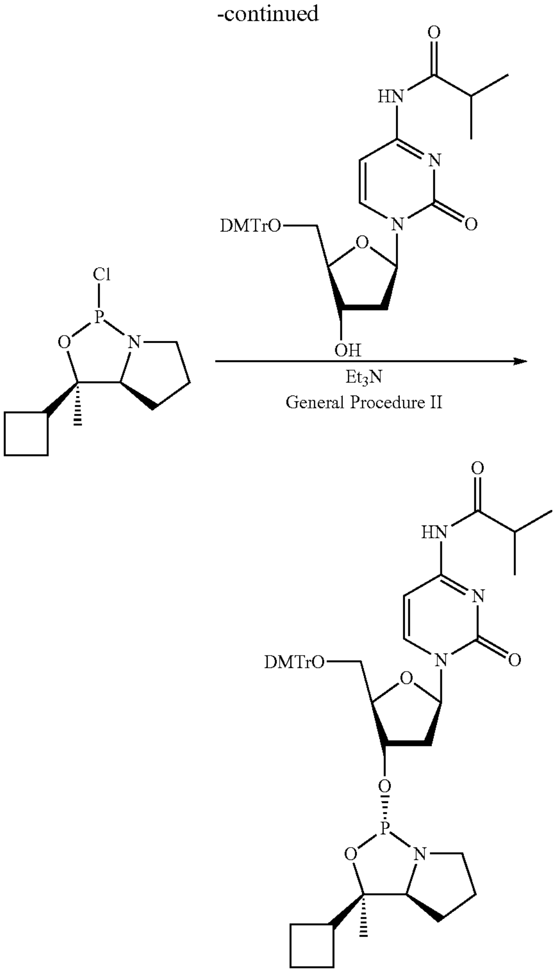

12-A-2'-dC$^{iBu}$

Preparation of 11-A-Cl: (3aR,7aR)-2-chloro-3,7a-dimethyloctahydrobenzo[d][1,3,2]oxazaphosphole. General Procedure I. $^{31}$P NMR (162 MHz, Chloroform-d) δ 178.56.

Preparation of 11-A-2-dC$^{iBu}$: N-(1-((2R,4S,5R)-5-((bis(4-methoxyphenyl)(phenyl)methoxy)methyl)-4-(((2R,3aR,7aR)-3,7a-dimethylhexahydrobenzo[d][1,3,2]oxazaphosphol-2(3H)-yl)oxy)tetrahydrofuran-2-yl)-2-oxo-1,2-dihydropyrimidin-4-yl)isobutyramide. General Procedure II. $[\alpha]_D^{23}$=+75.32 (c 1.15, $CHCl_3$). $^{31}$P NMR (162 MHz, Chloroform-d) δ 163.99. MS (ESI$^+$) calculated for $C_{42}H_{51}N_4O_8P$ 770.3; found 771.3 (M+H$^+$).

Preparation of 12-A-Cl: (3R,3aS)-1-chloro-3-cyclobutyl-3-methyltetrahydro-1H,3H-pyrrolo[1,2-c][1,3,2]oxazaphosphole. General Procedure I. $^{31}$P NMR (162 MHz, Chloroform-d) δ 160.54.

Preparation of 12-A-2-dC$^{iBu}$: N-(1-((2R,4S,5R)-5-((bis(4-methoxyphenyl)(phenyl)methoxy)methyl)-4-(((1S,3R,3aS)-3-cyclobutyl-3-methyltetrahydro-1H,3H-pyrrolo[1,2-c][1,3,2]oxazaphosphol-1-yl)oxy)tetrahydrofuran-2-yl)-2-oxo-1,2-dihydropyrimidin-4-yl)isobutyramide. General Procedure II. $[\alpha]_D^{23}$=+23.39 (c 1.20, $CHCl_3$). $^{31}$P NMR (162 MHz, Chloroform-d) δ 151.94. MS (ESI$^+$) calculated for $C_{44}H_{53}N_4O_8P$ 796.3; found 797.4 (M+H$^+$).

Scheme 12.

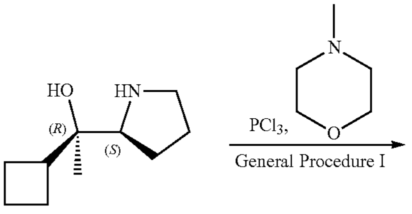

12-A

Scheme 13.

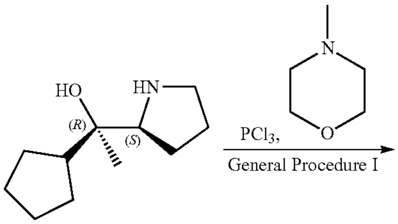

13-A

-continued

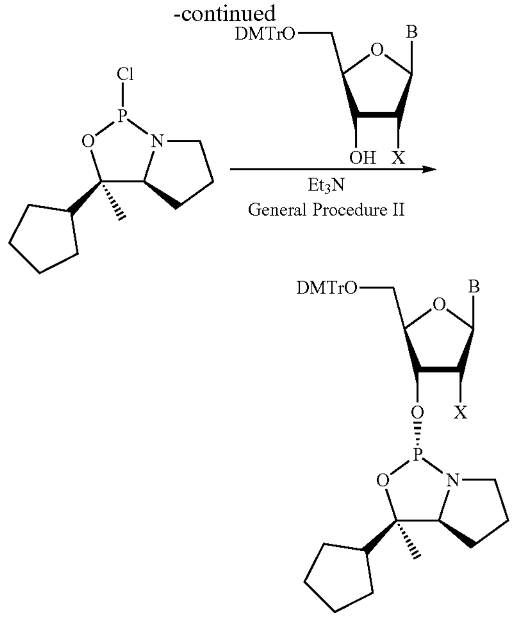

13-A: 1: X = F, B = $A^{Bz}$
2: X = OMe, B = $A^{Bz}$
3: X = F, B = $C^{Ac}$
4: X = F, B = U
5: X = F, B = $G^{iBu}$

Preparation of 13-A-Cl: (3R,3aS)-1-chloro-3-cyclopentyl-3-methyltetrahydro-1H,3H-pyrrolo[1,2-c][1,3,2]oxazaphosphole. General Procedure I. $^{31}P$ NMR (162 MHz, Chloroform-d) δ 161.36, 172.77.

Preparation of 13-A-2'F-$dA^{Bz}$ (1): N-(9-((2R,3R,4R,5R)-5-((bis(4-methoxyphenyl)(phenyl)methoxy)methyl)-4-(((1S,3R,3aS)-3-cyclopentyl-3-methyltetrahydro-1H,3H-pyrrolo[1,2-c][1,3,2]oxazaphosphol-1-yl)oxy)-3-fluorotetrahydrofuran-2-yl)-9H-purin-6-yl)benzamide. General Procedure II. $[\alpha]_D^{23}$=+11.99 (c 1.21, $CHCl_3$). $^{31}P$ NMR (162 MHz, Chloroform-d) δ 156.41 (d, J=12.5 Hz). MS ($ESI^+$) calculated for $C_{49}H_{52}FN_6O_7P$ 886.3; found 887.8 ($M+H^+$).

Preparation of 13-A-2'OMe-$A^{Bz}$ (2): N-(9-((2R,3R,4R,5R)-5-((bis(4-methoxyphenyl)(phenyl)methoxy)methyl)-4-(((1S,3R,3aS)-3-cyclopentyl-3-methyltetrahydro-1H,3H-pyrrolo[1,2-c][1,3,2]oxazaphosphol-1-yl)oxy)-3-methoxytetrahydrofuran-2-yl)-9H-purin-6-yl)benzamide. General Procedure II. $[\alpha]_D^{23}$=+2.95 (c 1.43, $CHCl_3$). $^{31}P$ NMR (162 MHz, Chloroform-d) δ 156.69. MS ($ESI^+$) calculated for $C_{40}H_{55}N_6O_8P$ 898.3; found 899.8 ($M+H^+$).

Preparation of 13-A-2'F-$dC^{Ac}$ (3): N-(1-((2R,3R,4R,5R)-5-((bis(4-methoxyphenyl)(phenyl)methoxy)methyl)-4-(((1S,3R,3aS)-3-cyclopentyl-3-methyltetrahydro-1H,3H-pyrrolo[1,2-c][1,3,2]oxazaphosphol-1-yl)oxy)-3-fluorotetrahydrofuran-2-yl)-2-oxo-1,2-dihydropyrimidin-4-yl)acetamide. General Procedure II. $[\alpha]_D^{23}$=+57.44 (c 1.77, $CHCl_3$). $^{31}P$ NMR (162 MHz, Chloroform-d) δ 157.84 (d, J=8.4 Hz). MS ($ESI^+$) calculated for $C_{43}H_{50}FN_4O_8P$ 801.3; found 801.4 ($M+H^+$).

Preparation of 13-A-2'F-dU (4): 1-((2R,3R,4R,5R)-5-((bis(4-methoxyphenyl)(phenyl)methoxy)methyl)-4-(((1S,3R,3aS)-3-cyclopentyl-3-methyltetrahydro-1H,3H-pyrrolo[1,2-c][1,3,2]oxazaphosphol-1-yl)oxy)-3-fluorotetrahydrofuran-2-yl)pyrimidine-2,4(1H,3H)-dione. General Procedure II. $[\alpha]_D^{23}$=+46.16 (c 1.30, $CHCl_3$). $^{31}P$ NMR (162 MHz, Chloroform-d) δ 159.43 (d, J=6.4 Hz). MS ($ESI^+$) calculated for $C_{41}H_{47}FN_3O_8P$ 782.6; found 801.4 (M+Na*).

Preparation of 13-A-2'F-$dG^{iBu}$ (5): N-(9-((2R,3R,4R,5R)-5-((bis(4-methoxyphenyl)(phenyl)methoxy)methyl)-4-(((1S,3R,3aS)-3-cyclopentyl-3-methyltetrahydro-1H,3H-pyrrolo[1,2-c][1,3,2]oxazaphosphol-1-yl)oxy)-3-fluorotetrahydrofuran-2-yl)-6-oxo-6,9-dihydro-1H-purin-2-yl)isobutyramide. General Procedure II. $^{31}P$ NMR (162 MHz, Chloroform-d) δ 155.64 (d, J=12.6 Hz). MS ($ESI^+$) calculated for $C_{46}H_{54}FN_6O_8P$ 782.6; found 869.8 (M+Na).

Scheme 14.

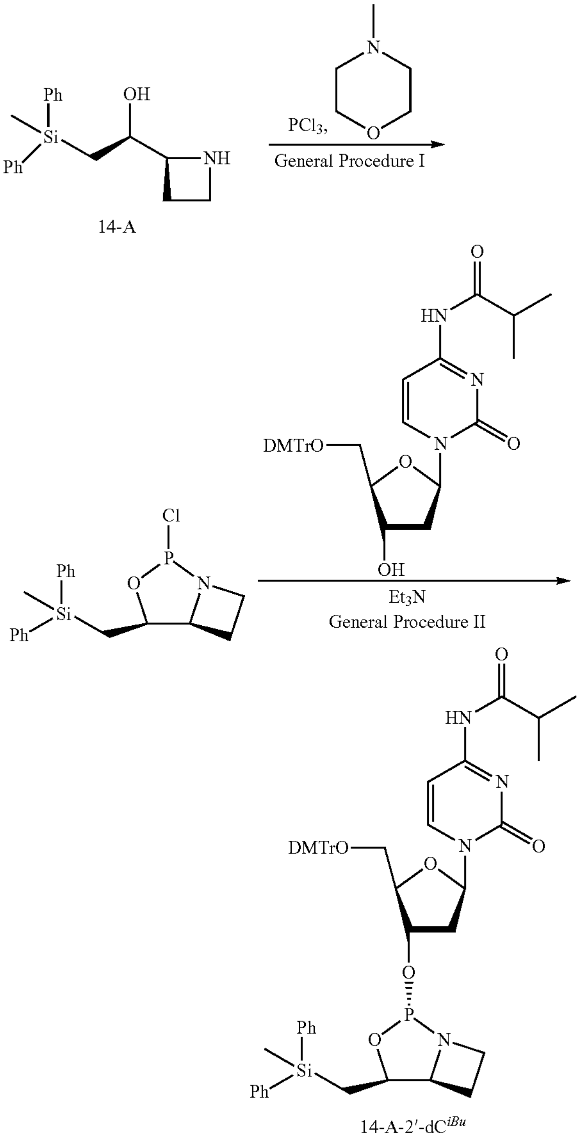

14-A

14-A-2'-$dC^{iBu}$

Preparation of 14-A-Cl: (4S,5S)-2-chloro-4-((methyldiphenylsilyl)methyl)-3-oxa-1-aza-2-phosphabicyclo[3.2.0]heptane. General Procedure I. $^{31}P$ NMR (162 MHz, Chloroform-d) δ 177.31, 181.73.

Preparation of 14-A-2'-$dC^{iBu}$: N-(1-((2R,4S,5R)-5-((bis(4-methoxyphenyl)(phenyl)methoxy)methyl)-4-(((2S,4S,5S)-4-((methyldiphenylsilyl)methyl)-3-oxa-1-aza-2-phosphabicyclo[3.2.0]heptan-2-yl)oxy)tetrahydrofuran-2-yl)-2-oxo-1,2-dihydropyrimidin-4-yl)isobutyramide. General Procedure II. $^{31}P$ NMR (162 MHz, Chloroform-d) δ 155.68. MS ($ESI^+$) calculated for $C_{52}H_{57}N_4O_8PSi$ 924.3; found 925.3 ($M+H^+$).

Provided phosphoramidites were successfully and/or can be employed to prepare chirally controlled oligonucleotide compositions, for example, of WV-1092, WV-2595, WV-2603, WV-1510, WV-2378, WV-2380, WV-2417, WV-2418, WV-2601, WV-2602, WV-2671, WV-3473, WV-2528, WV-2531, WV-3047, WV-3153, etc.

In some embodiments, automated solid-phase synthesis of chirally controlled oligonucleotide composition was performed according to example cycles shown herein.

| step | operation | reagents and solvent | volume | waiting time |
|---|---|---|---|---|
| 1 | detritylation | 3% DCA in toluene | 10 mL | 65 s |
| 2 | coupling | 0.15M monomer in $^iPrCN$ + 0.5M CMIMT in MeCN | 0.5 mL | 5 min |
| 3 | capping | 20% $Ac_2O$, 30% 2,6-lutidine in MeCN + 20% MeIm in MeCN | 1.2 mL | 60 s |
| 4 | oxidation or sulfurization | 1.1M TBHP in DCM-decane or 0.1M POS in MeCN | 1.0 mL | 300 s |

In some embodiments, after synthesis, the resin was treated with 1M TEA-HF in DMF-$H_2O$ (3:1, v/v; 1 mL) for 2 h at 50° C. PS5G support was washed with MeCN, $H_2O$, and add AMA (conc. $NH_3$-40% $MeNH_2$ (1:1, v/v)) (1 mL) for 45 min at 50° C. The mixture was cooled to room temperature and the resin was removed by membrane filtration (washed with $H_2O$ for 2 mL). The filtrate was concentrated under reduced pressure until it becomes about 1 mL. The residue was diluted with 1 mL of $H_2O$ and purified/analyzed by AEX-HPLC and RP-UPLC-MS. Additional cycles and/or conditions, for example, those described in US 2011/0294124, US 2015/0211006, US 2015/0197540, and WO 2015/107425, each of which is incorporated herein by reference, can also be utilized in accordance with the present disclosure to prepare chirally controlled oligonucleotide compositions using one or more provided phosphoramidites.

As demonstrated herein, among other things, the present disclosure identified that aqueous work-ups and/or extractions can lower yields of phosphoramidites. In some embodiments, the present disclosure provides technologies for preparing phosphoramidites without using aqueous work-ups and/or extractions. In some embodiments, provided technologies save time and reduce cost. In some embodiments, by not using extractions, provided technologies reduce wastes, particularly in some cases, completely avoiding toxic and difficult-to-handle chloroform wastes generated from extractions. While not wishing to be bound by theory, Applicant submits that by reducing exposure to air and/or water, provided technologies can reduce degradation of phosphoramidite products, as certain such products can be unstable when exposed to air and/or water. Compared to earlier conventional methods, which usually have yields around 60% or less, provided technologies can consistently provide yields of around 80% or more for many phosphoramidites. As unlimited examples, provided technologies provide greatly improved yields and/or purity for 2'-F-G, 2'-methoxy-U, 2'-methoxy-A, 2'-methoxy-G, etc. As demonstrated herein, provided technologies can surprisingly prepare G phosphoramidites without $O^6$ protection.

While several embodiments of the present disclosure have been described and illustrated herein, those of ordinary skill in the art will readily envision a variety of other means and/or structures for performing the functions and/or obtaining the results and/or one or more of the advantages described herein, and each of such variations and/or modifications is deemed to be within the scope of the present disclosure. More generally, those skilled in the art will readily appreciate that all parameters, dimensions, materials, and configurations described herein are meant to be example and that the actual parameters, dimensions, materials, and/or configurations will depend upon the specific application or applications for which the teachings of the present disclosure is/are used. Those skilled in the art will recognize, or be able to ascertain using no more than routine experimentation, many equivalents to the specific embodiments of the disclosure described herein. It is, therefore, to be understood that the foregoing embodiments are presented by way of example only and that, within the scope of the appended claims and equivalents thereto, the disclosure may be practiced otherwise than as specifically described and claimed. The present disclosure is directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the scope of the present disclosure.

The invention claimed is:

1. A composition comprising a compound having the structure of formula I:

I

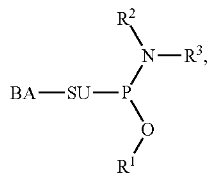

or a salt thereof and a silylating reagent;

BA is

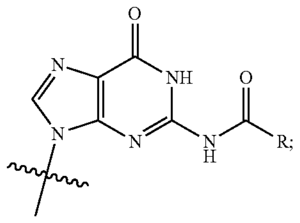

SU is

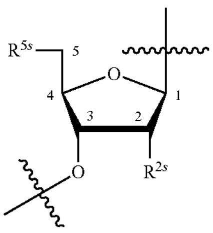

, wherein SU is connected to the phosphorus atom in formula I through the oxygen atom;

$R^{5s}$ is R' or —OR';

$R^{2s}$ is —H, —F, —CN, —$N_3$, —NO, —$NO_2$, —O—($C_{1-10}$ alkyl), or —O-(optionally substituted $C_{1-6}$ alkylene)-OR', or $R^{2s}$ is L connecting C2 with C1, C2, C3, C4 or C5, wherein L is —O—$CH_2$— wherein the —$CH_2$— is optionally substituted;

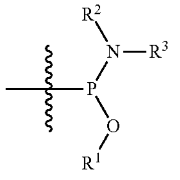 is 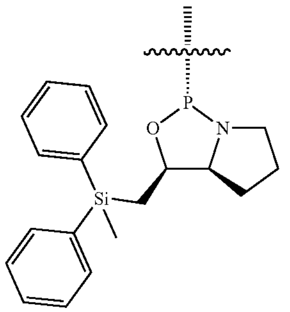 or 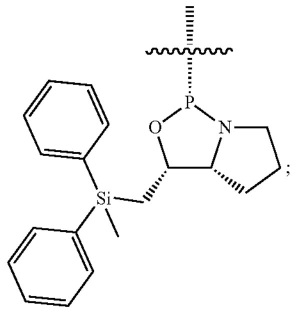 ;

each R' is independently —R, —C(O)R, —$CO_2$R, or —$SO_2$R, or:

two or more R' are taken together with their intervening atoms to form an optionally substituted monocyclic, bicyclic or polycyclic, saturated, partially unsaturated, or aryl 3-30 membered ring having, in addition to the intervening atoms, 0-10 heteroatoms independently selected from oxygen, nitrogen, sulfur, phosphorus and silicon; and each R is independently hydrogen, or an optionally substituted group selected from $C_{1-30}$ aliphatic, $C_{1-30}$ heteroaliphatic having 1-10 heteroatoms independently selected from oxygen, nitrogen, sulfur, phosphorus and silicon, $C_{6-30}$ aryl, a 5-30 membered heteroaryl ring having 1-10 heteroatoms independently selected from oxygen, nitrogen, sulfur, phosphorus and silicon, and a 3-30 membered heterocyclic ring having 1-10 heteroatoms independently selected from oxygen, nitrogen, sulfur, phosphorus and silicon.

2. The compound of claim 1, wherein the composition is selected from:

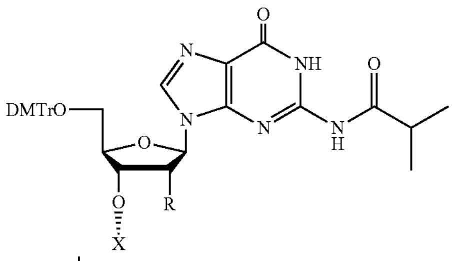

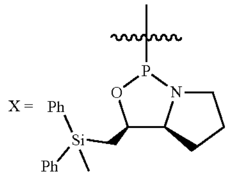

113: R = H
114: R = OMe
115: R = $OCH_2CH_2OMe$
116: R = F

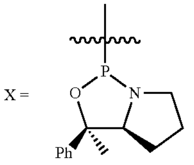

121: R = H
122: R = OMe
123: R = $OCH_2CH_2OMe$
124: R = F

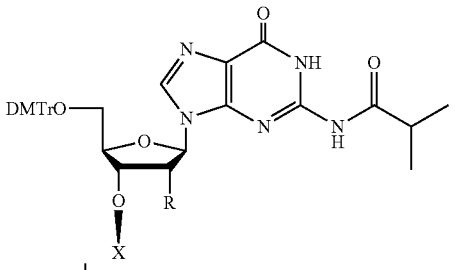

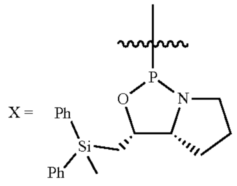

117: R = H
118: R = OMe
119: R = $OCH_2CH_2OMe$
120: R = F

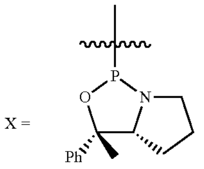

125: R = H
126: R = OMe
127: R = $OCH_2CH_2OMe$
128: R = F .

3. The composition of claim 1, wherein BA is

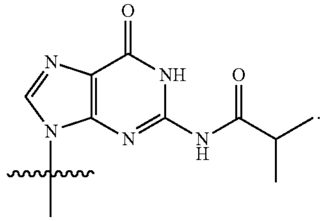 [SMILES: *n1cnc2c(=O)[nH]c(NC(=O)C(C)C)nc21]

4. The composition of claim 1, wherein $R^{5s}$ is DMTrO-.

5. The composition of claim 3, wherein $R^{5s}$ is DMTrO-.

6. The composition of claim 1, wherein $R^{2s}$ is —H, —F, —OMe, —$OCH_2CH_2OMe$, or $R^{2s}$ is L connecting C2 with C4, wherein $R^{2s}$ (C2)-O-(methylene)-(C4) or (C2)-O-(methylmethylene)-(C4).

7. The composition of claim 1, wherein $R^{2s}$ is —H, —F, —OMe, —$OCH_2CH_2OMe$, or $R^{2s}$ is L connecting C2 with C4, wherein $R^{2s}$ (C2)-O-(methylene)-(C4) or (C2)-O-(methylmethylene)-(C4).

8. The composition of claim 4, wherein $R^{2s}$ is —H, —F, —OMe, —$OCH_2CH_2OMe$, or $R^{2s}$ is L connecting C2 with C4, wherein $R^{2s}$ (C2)-O-(methylene)-(C4) or (C2)-O-(methylmethylene)-(C4).

9. The composition of claim 5, wherein $R^{2s}$ is —H, —F, —OMe, —$OCH_2CH_2OMe$, or $R^{2s}$ is L connecting C2 with C4, wherein $R^{2s}$ (C2)-O-(methylene)-(C4) or (C2)-O-(methylmethylene)-(C4).

10. The composition of claim 2, wherein the compound is selected from:

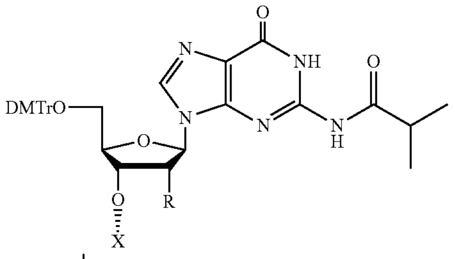

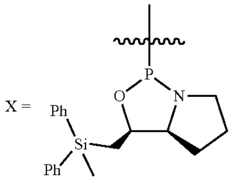

113: R = H
114: R = OMe
115: R = $OCH_2CH_2OMe$
116: R = F

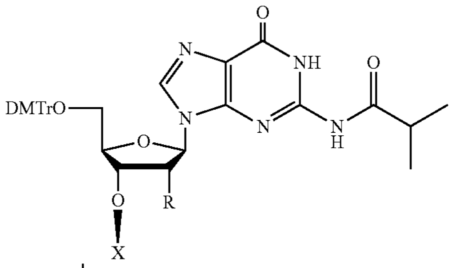

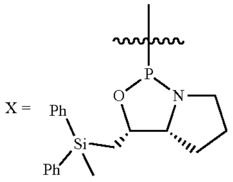

117: R = H
118: R = OMe
119: R = $OCH_2CH_2OMe$
120: R = F .

* * * * *